United States Patent
Llinas-Brunet et al.

(10) Patent No.: US 8,067,438 B2
(45) Date of Patent: *Nov. 29, 2011

(54) HEPATITIS C INHIBITOR COMPOUNDS

(75) Inventors: Montse Llinas-Brunet, Dollard-des-Ormeaux (CA); Murray Douglas Bailey, Pierrefonds (CA); Punit R. Bhardwaj, Laval (CA); Josee Bordeleau, Laval (CA); Pasquale Forgione, Montreal (CA); Elise Ghiro, Laval (CA); Vida J. Gorys, Dollard-des-Ormeaux (CA); Nathalie Goudreau, St-Laurent (CA); Sylvie Goulet, Pierrefonds (CA); Teddy Halmos, Laval (CA); Jean Rancourt, Laval (CA)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/078,225

(22) Filed: Apr. 1, 2011

(65) Prior Publication Data

US 2011/0177030 A1  Jul. 21, 2011

Related U.S. Application Data

(63) Continuation of application No. 11/766,171, filed on Jun. 21, 2007, now Pat. No. 7,939,667, which is a continuation of application No. 10/850,101, filed on May 20, 2004, now Pat. No. 7,585,845.

(60) Provisional application No. 60/472,709, filed on May 21, 2003.

(51) Int. Cl.
  *A61K 31/04* (2006.01)
  *C07D 215/38* (2006.01)
(52) U.S. Cl. ........................ 514/312; 546/153
(58) Field of Classification Search .................. 514/312; 546/153
  See application file for complete search history.

(56) References Cited

U.S. PATENT DOCUMENTS

| | | | |
|---|---|---|---|
| 4,691,007 A | 9/1987 | Dutta et al. | |
| 5,164,402 A | 11/1992 | Brighty | |
| 5,633,388 A | 5/1997 | Diana et al. | |
| 5,962,638 A | 10/1999 | Naumann et al. | |
| 5,994,311 A | 11/1999 | Eichner et al. | |
| 6,143,715 A | 11/2000 | Llinas-Brunet et al. | |
| 6,159,938 A | 12/2000 | Gyorkos et al. | |
| 6,187,905 B1 | 2/2001 | Hurst et al. | |
| 6,277,830 B1 | 8/2001 | Ganguly et al. | |
| 6,323,180 B1 * | 11/2001 | Llinas-Brunet et al. | 514/3.7 |
| 6,329,379 B1 | 12/2001 | Llinas-Brunet et al. | |
| 6,329,417 B1 | 12/2001 | Llinas-Brunet et al. | |
| 6,337,394 B2 | 1/2002 | Karlsson et al. | |
| 6,410,531 B1 | 6/2002 | Llinas-Brunet et al. | |
| 6,420,380 B2 | 7/2002 | Llinas-Brunet et al. | |
| 6,455,571 B1 | 9/2002 | Maring et al. | |
| 6,534,523 B1 | 3/2003 | Bailey et al. | |
| 6,608,027 B1 | 8/2003 | Tsantrizos et al. | |
| 6,642,204 B2 | 11/2003 | Llinas-Brunet et al. | |
| 6,767,991 B1 | 7/2004 | Llinas-Brunet et al. | |
| 6,846,806 B2 | 1/2005 | Priestley | |
| 6,869,964 B2 | 3/2005 | Campbell et al. | |
| 6,872,805 B2 | 3/2005 | Campbell et al. | |
| 6,878,722 B2 | 4/2005 | Campbell et al. | |
| 6,908,901 B2 | 6/2005 | Bailey et al. | |
| 6,919,423 B2 | 7/2005 | Llinas-Brunet | |
| 6,939,854 B2 | 9/2005 | Priestley | |
| 6,995,174 B2 | 2/2006 | Wang et al. | |
| 7,041,698 B2 | 5/2006 | Ripka et al. | |

(Continued)

FOREIGN PATENT DOCUMENTS

CA  2445938  2/2000

(Continued)

OTHER PUBLICATIONS

Smith, et al; Synthesis and Pharmacological Activity of Angiotensin Converting Enzyme Inhibitors: N-(Mercaptoacyl)-4-substituted-(S)-prolines; Journal of Medicinal Chemistry; 1988; vol. 31; pp. 875-885.

Perrone; 2-(Aryloxy)ethylamine Derivatives: Ring Opened Congeners of Long Chain 1-Arylpiperazine with High 5-HT1A Receptor Affinity and Selectivity Versus D2 and a1 Receptors; Medicinal Chemistry Research; 1999; vol. 9; No. 5; pp. 340-353.

Gaucher, et al; Palladium (0) Catalyzed Tandem Alkylation and SN' Cyclization of 1,4-Dichlorobut -2-ene by the N-(Diphenylmethylene) acetonitrile. A Stereoselective Synthesis of 1-Aminocyclo-propanecarboxylic Acids; Tetrahedron Letters; 1995; vol. 36; No. 17; pp. 2979-2982.

(Continued)

*Primary Examiner* — D M Seaman
(74) *Attorney, Agent, or Firm* — Michael P. Morris; Philip I. Datlow

(57) ABSTRACT

Compounds of formula (I):

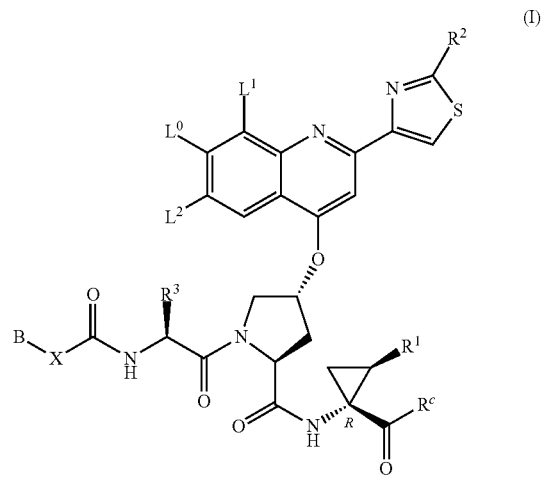

wherein B, X, $R^3$, $L^0$, $L^1$, $L^2$, $R^2$, $R^1$ and $R^C$ are defined herein. The compounds are useful as inhibitors of HCV NS3 protease for the treatment of hepatitis C viral infection.

21 Claims, No Drawings

U.S. PATENT DOCUMENTS

| | | | |
|---|---|---|---|
| 7,091,184 B2 | 8/2006 | Llinas-Brunet et al. | |
| 7,132,504 B2 | 11/2006 | Scola et al. | |
| RE40,525 E | 9/2008 | Llinas-Brunet et al. | |
| 7,585,845 B2* | 9/2009 | Llinas-Brunet et al. | 514/1.1 |
| 7,705,146 B2 | 4/2010 | Bailey et al. | |
| 7,939,667 B2* | 5/2011 | Llinas-Brunet et al. | 546/159 |
| 2002/0111313 A1 | 8/2002 | Campbell et al. | |
| 2003/0186895 A1 | 10/2003 | Llinas-Brunet et al. | |
| 2003/0191067 A1 | 10/2003 | Llinas-Brunet et al. | |
| 2004/0033959 A1 | 2/2004 | Chen et al. | |
| 2004/0072761 A1 | 4/2004 | Campbell et al. | |
| 2004/0077551 A1 | 4/2004 | Campbell et al. | |
| 2004/0106559 A1 | 6/2004 | Wang et al. | |
| 2004/0224900 A1 | 11/2004 | Bailey et al. | |
| 2005/0020503 A1 | 1/2005 | Llinas-Brunet et al. | |
| 2005/0187165 A1 | 8/2005 | Scola et al. | |
| 2006/0019905 A1 | 1/2006 | Bailey et al. | |
| 2006/0046965 A1 | 3/2006 | Bailey et al. | |
| 2006/0258868 A1 | 11/2006 | Bailey et al. | |

FOREIGN PATENT DOCUMENTS

| | | |
|---|---|---|
| CA | 2429359 | 8/2002 |
| CA | 2474156 | 8/2003 |
| CA | 2486308 | 12/2003 |
| DE | 19600034 | 7/1997 |
| GB | 2337262 | 11/1999 |
| JP | 1135478 | 5/1989 |
| JP | 05155827 | 6/1993 |
| JP | 10298151 | 11/1998 |
| JP | 11127861 | 5/1999 |
| JP | 11137252 | 5/1999 |
| JP | 11292840 | 10/1999 |
| JP | 01103993 | 4/2001 |
| WO | 9533763 | 12/1995 |
| WO | 9706804 | 2/1997 |
| WO | 9743310 | 11/1997 |
| WO | 9817679 | 4/1998 |
| WO | 9822496 | 5/1998 |
| WO | 9846597 | 10/1998 |
| WO | 9846630 | 10/1998 |
| WO | 9853814 | 12/1998 |
| WO | 9907733 | 2/1999 |
| WO | 9907734 | 2/1999 |
| WO | 9938888 | 8/1999 |
| WO | 9950230 | 10/1999 |
| WO | 9964442 | 12/1999 |
| WO | 0009543 | 2/2000 |
| WO | 0009558 | 2/2000 |
| WO | 0020400 | 4/2000 |
| WO | 0031129 | 6/2000 |
| WO | 0059929 | 10/2000 |
| WO | 0102424 | 1/2001 |
| WO | 0107407 | 2/2001 |
| WO | 0116357 | 3/2001 |
| WO | 0132691 | 5/2001 |
| WO | 0140262 | 6/2001 |
| WO | 0158929 | 8/2001 |
| WO | 0164678 | 9/2001 |
| WO | 0174768 | 10/2001 |
| WO | 0177113 | 10/2001 |
| WO | 0181325 | 11/2001 |
| WO | 0208187 | 1/2002 |
| WO | 0208198 | 1/2002 |
| WO | 0208244 | 1/2002 |
| WO | 0208251 | 1/2002 |
| WO | 0208256 | 1/2002 |
| WO | 0218369 | 3/2002 |
| WO | 02060926 | 8/2002 |
| WO | 02079234 | 10/2002 |
| WO | 03053349 | 7/2003 |
| WO | 03064416 A1 | 8/2003 |
| WO | 03064455 A2 | 8/2003 |
| WO | 03064456 | 8/2003 |
| WO | 03099274 | 12/2003 |
| WO | 03099316 | 12/2003 |
| WO | 2004032827 | 4/2004 |
| WO | 2004043339 | 5/2004 |
| WO | 2004101602 | 11/2004 |
| WO | 2004101605 | 11/2004 |
| WO | 2004103996 | 12/2004 |
| WO | 2005028501 | 3/2005 |
| WO | 2005046712 | 5/2005 |
| WO | 2006000085 | 1/2006 |
| WO | 2006004455 | 1/2006 |

OTHER PUBLICATIONS

Fliche, et al; Enantioselective synthesis of (1R,2S) and (1S,2S) dehydrocoronamic acids; Synthetic Communications; 1994; vol. 24; No. 20; pp. 2873-2876.

Chen, et al; Chirally selective hydrolysis of D, L amino acid esters by alkaline protease; J. Chem. Soc. Chem. Commun.; 1986; vol. 20; pp. 1514-1516.

Llinas-Brunet; et al; Peptide-based inhibitors of the hepatitis C virus serine protease; Bioorganic & Medicinal Chemistry Letters; 1998; vol. 8; pp. 1713-1718.

Gershonov, et al; 1-Aminocyclobutanecarboxylic acid derivatives as novel structural elements in bioactive peptides: application to tuftsin analogs; Journal of Medicinal Chemistry; 1996; vol. 39; No. 24; pp. 4833-4843.

Chen, et al; Kinetic resolution of esters of amino acids in t-butanol containing 5% water catalyzed by a stable industrial alkaline protease; Chirality; 1994; vol. 6; pp. 572-576.

Ogawa, et al; 2,3-Methanophenylalanine and.Alpha., .Beta.-Dehydrophenylalanine Derivatives as Chymotrypsin Inhibitor; PEPT. Chem. (1990); vol. 27; pp. 379-382.

Llinas-Brunet, et al; Studies on the C-terminal of Hexapeptide Inhibitors of the Hepatitis C Virus Serine Protease; Bioorganic & Medicinal Chemistry Letters; 1998; vol. 8; pp. 2719-2724, 1998.

Huang, et al; Olefin Methathesis-Active Ruthenium Complexes Bearing a Nucleophilic Carbene Ligand; Journal of American Chemical Society; 1999; vol. 121; pp. 2674-2678.

Kingsbury, et al; A Recyclable Ru-Based Methathesis Catalyst; Journal of American Chemical Society; 1999; vol. 121; pp. 791-799.

Krchnak, et al; Polymer-Supported Mitsunobu Ether Formation and its Use in Combinatorial Chemistry; Tetrahedron Letters; 1995; vol. 36; No. 35; pp. 6193-6196.

Lohmann, et al; Replication of Subgenomic Hepatitis C Virus RNAs in a Hepatoma Cell Line; Science; Jul. 2, 1999; vol. 285; pp. 110-113.

Miller, et al; Application of Ring-Closing Methathesis to the Synthesis of Rigidified Amino Acids and Peptides; Journal of American Chemical Society; 1996; vol. 118; pp. 9606-9614.

Nizi, et al; Capped dipeptide phenethylamide inhibitors of the HCV NS3 protease; Bioorganic & Medicinal Chemistry Letters 14: (2004); pp. 2151-2154.

Rano, et al; Solid Phase Synthesis of Aryl Ethers via the Mitsunobu Reaction; Tetrahedron Letters; 1995; vol. 36; No. 22; pp. 3789-3792.

Still, et al; Rapid Chromatographic Technique for Preparative Separations with Moderate Resolution; Journal of Organic Chemistry; 1978; vol. 43; No. 14.

Llinas-Brunet, et al; Peptide-Based Inhibitors of the Hepatitis C Virus Serine Protease; Bioorganic & Medicinal Chemistry Letters; 1998; vol. 8; No. 13; pp. 1713-1718.

Ingallinella, et al; Potent Peptide Inhibitors of Human Hepatitis C Virus NS3 Protease Are Obtained by Optimizing the Cleavage Products; Biochemistry; 1998; vol. 37; pp. 8906-8914.

Landro; Mechanistic Role of an NS4A Peptide Cofactor with the Truncated NS3 Protease of Hepatitis C. Virus: Elucidation of the NS4A Stimulatory Effect via Kinetic Analysis and Inhibitor Mapping; Biochemistry; 1997; vol. 36; pp. 9340-9348.

Mori, et al; The N-Terminal Region of NS3 Serin Proteinase of Hepatitis C Virus Is Important to Maintain Its Enzymatic Integrity; Biochemical and Biophysical Research Communications; 1997; vol. 231; No. 3; pp. 738-742.

Chu, et al; Structure of Sch 68631: A New Hepatitis C Virus Proteinase Inhibitor from *Streptomyces* sp; Tetrahedron Letters; 1996; vol. 37; No. 40; pp. 7229-7232.

Patani et al.; Bioisosterism: A Rational Approach in Drug Design; Chem. Rev.; 1996; vol. 96; pp. 3147-3176.

Slater et al.; Pyrrolidine-5,5-trans-lactams. 4. Incorporation of a P3/P4 Urea Leads to Potent Intracellular Inhibitors of Hepatitis C Virsu NS3/4A Protease; Organic Letters, 5 (24), Jan. 1, 2003, pp. 4627-4630.
Matsumoto, et al; 3D Modeling of HCV Protease and Computer Screening of its Inhibitors; Antiviral Research; 1996; vol. 30; No. 1; pp. A23 (abstract 19).
Steinkuehler; et al; Product Inhibition of the Hepatitis C Virus NS3 Protease; Biochemistry; 1998; vol. 37; pp. 8899-8905.
Derwent Abstract: AN 2001-435746 [47] (JP2001103993).
Derwent Abstract: AN 1999-040664 [04] (JP10298151).
Derwent Abstract: AN 1999-350322 [30] (JP11127861).
Derwent Abstract: AN 2000-018687 [02] (JP11292840).
Derwent Abstract: AN 1999-186214 [16] (JP11035478).
Derwent Abstract: AN 1999-374374 [32] (JP11137252).

Naps and Johns; Optically Active Mono-substituted Succinic Acids and Derivatives; Journal of American Chemical Society; vol. 62; 1940, pp. 2450-2457.
Sibal, et al; Nonhuman Primates: A Critical Role in Current Disease Research; ILAR Journal; 2001; vol. 42; No. 2; pp. 74-84.
Jimenez et al.; Highly Efficient and Stereocontrolled Synthetic Route to Enantiopure ACC Derivatives. Synthesis of (+)-N-Benzyloxycarbonyl-g,d-dehydro-allo-Coronamic Acid Methyl Ester; Tetrahedron Letters; 1994; vol. 35; No. 32; pp. 5945-5948.
Orvieto, et al; Novel, Potent Phenethylamide Inhibitors of the Hepatitis C Virus (HCV) NS3 Protease: Probing the Role of P2 Aryloxyprolines with Hybrid Structures; Bioorganic & Medicinal Chemistry Letters 13; (2003); pp. 2745-2748.

* cited by examiner

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Forward Primer

<400> SEQUENCE: 1
acgcagaaag cgtctagcca tggcgttagt                                    30

<210> SEQ ID NO 2
<211> LENGTH: 30
<212> TYPE: DNA
<213> ORGANISM: Artificial Sequence
<220> FEATURE:
<223> OTHER INFORMATION: Reverse Primer

<400> SEQUENCE: 2
tcccggggca ctcgcaagca ccctatcagg                                    30

<210> SEQ ID NO 3
<211> LENGTH: 26
<212> TYPE: DNA
<213> ORGANISM: Artificial Sequence
<220> FEATURE:
<223> OTHER INFORMATION: PUTR probe

<400> SEQUENCE: 3
tggtctgcgg aaccggtgag tacacc                                        26

HEPATITIS C INHIBITOR COMPOUNDS

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulin treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction (henceforth referred to as NS2/3 protease); the second one is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

More recently, the NS3 protease has been found to potentially have an additional impact by blocking the IFN-mediated cellular antiviral activity in the infected cell (Foy et al., *Science,* 17 Apr. 2003). This lends credence to a hypothesis that the NS3/NS4A protease may represent a dual therapeutic target, the inhibition of which may both block viral replication and restore interferon response of HCV infected cells.

In WO 00/09543, compounds of the formula

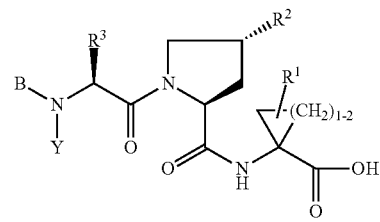

wherein a preferred meaning of $R^2$ is an unsubstituted or mono- or disubstituted quinolinyl residue as defined therein, are described as hepatitis C viral NS3 protease inhibitors, an enzyme essential for the replication of the hepatitis C virus.

The present invention provides tripeptide compounds that have improved potency against the HCV NS3 protease. Furthermore, compounds being highly active in cell culture are provided.

An advantage of one aspect of the present invention resides in the fact that compounds according to this invention specifically inhibit the NS3 protease and do not show significant inhibitory activity against other human serine proteases such as human leukocyte elastase (HLE), or cysteine proteases such as human liver cathepsin B (Cat B).

Compared to the compounds as disclosed in WO 00/09543, compounds as provided by this invention exhibit unexpected advantages. In general they show one or more of the following advantages:
  lower $IC_{50}$ values in a NS3-NS4A protease assay;
  lower $EC_{50}$ values in a cell based HCV RNA replication assay;
  better solubility; and/or
  higher plasma levels when administered orally in the rat.

SUMMARY OF THE INVENTION

Included in the scope of the invention is a racemate, diastereoisomer, or optical isomer of a compound of formula (I):

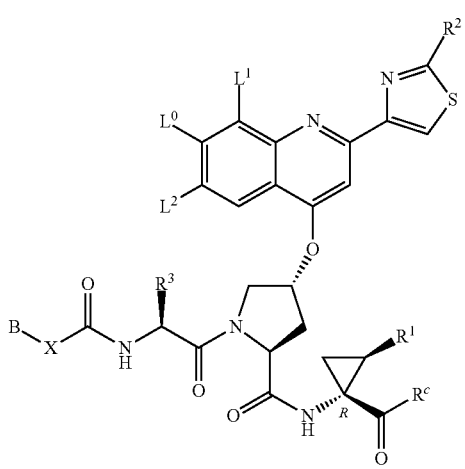

I wherein
B is $(C_{1-10})$alkyl, $(C_{3-7})$cycloalkyl, or $(C_{1-4})$alkyl-$(C_{3-7})$cycloalkyl,
   a) wherein said alkyl, cycloalkyl, and alkyl-cycloalkyl may be mono-, di- or tri-substituted with $(C_{1-3})$alkyl; and
   b) wherein said alkyl, cycloalkyl, and alkyl-cycloalkyl may be mono- or di-substituted with substituents selected from hydroxy and O—$(C_{1-4})$alkyl; and
   c) wherein each of said alkyl groups may be mono-, di- or tri-substituted with halogen; and
   d) wherein each of said cycloalkyl groups being 4-, 5-, 6- or 7-membered having optionally one (for the 4-, 5, 6, or 7-membered) or two (for the 5-, 6- or 7-membered)-$CH_2$-groups not directly linked to each other replaced by —O— such that the O-atom is linked to the group X via at least two C-atoms;
X is O or NH;
$R^3$ is $(C_{2-8})$alkyl, $(C_{3-7})$cycloalkyl or $(C_{1-3})$alkyl-$(C_{3-7})$cycloalkyl, wherein each of said alkyl, cycloalkyl, and alkyl-cycloalkyl groups may be mono-, di- or tri-substituted with $(C_{1-4})$alkyl;
$L^0$ is H, halogen, $(C_{1-4})$alkyl, —OH, —O—$(C_{1-4})$alkyl, —$NH_2$, —NH$(C_{1-4})$alkyl or —N$((C_{1-4})$alkyl$)_2$;
$L^1$, $L^2$ are each independently halogen, cyano, $(C_{1-4})$alkyl, —S—$(C_{1-4})$alkyl, —SO—$(C_{1-4})$alkyl, or —$SO_2$—$(C_{1-4})$alkyl, wherein each of said alkyl groups is optionally substituted with from one to three halogen atoms; and either $L^1$ or $L^2$ (but not both at the same time) may also be H; or
$L^0$ and $L^1$ or
$L^0$ and $L^2$ may be covalently bonded to form, together with the two C-atoms to which they are linked, a 5- or 6-membered carbocyclic ring wherein one or two —$CH_2$-groups not being directly linked to each other may be replaced each independently by —O— or $NR^a$ wherein $R^a$ is H or $(C_{1-4})$alkyl, and wherein said carbo- or heterocyclic ring is optionally mono- or di-substituted with $(C_{1-4})$alkyl;
$R^2$ is $R^{20}$, —$NR^{22}COR^{20}$, —$NR^{22}COOR^{20}$—$NR^{22}R^{21}$ and —$NR^{22}CONR^{21}R^{23}$, wherein
   $R^{20}$ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl;
   $R^{21}$ is H or $R^{20}$ as defined above,
   $R^{22}$ and $R^{23}$ are independently selected from H and methyl,
$R^1$ is ethyl or vinyl;
$R^C$ is hydroxy or $NHSO_2R^S$ wherein $R^S$ is $(C_{1-6})$alkyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; each of which optionally being mono-, di- or tri-substituted with substituents selected from halogen, hydroxy, cyano, $(C_{1-4})$alkyl, O—$(C_{1-6})$alkyl, —CO—$NH_2$, —CO—NH$(C_{1-4}$alkyl, —CO—N$((C_{1-4})$alkyl$)_2$, —$NH_2$, —NH$(C_{1-4})$alkyl and —N$((C_{1-4})$alkyl$)_2$, wherein $(C_{1-4}$alkyl and O—$(C_{1-6})$alkyl are optionally substituted with one to three halogen atoms; and each of which optionally being monosubstituted with nitro;
or $R^S$ is —$N(R^{N2})R^{N1}$), wherein $R^{N1}$ and $R^{N2}$ are independently selected from H, $(C_{1-6})$alkyl, $(C_{3-7})$cycloalkyl, $(C_{1-6})$alkyl-$(C_{3-7})$cycloalkyl, aryl and $(C_{1-6})$alkyl-aryl; wherein said $(C_{1-6})$alkyl, $(C_{3-7})$cycloalkyl, $(C_{1-6})$alkyl-$(C_{3-7})$cycloalkyl, aryl and $(C_{1-6})$alkyl-aryl are optionally substituted with one or more substituents independently selected from halogen, $(C_{1-6})$alkyl, hydroxy, cyano, O—$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl; or
$R^{N2}$ and $R^{N1}$ are linked, together with the nitrogen to which they are bonded, to form a 3- to 7-membered monocyclic saturated or unsaturated heterocycle or a 9- or 10-membered bicyclic saturated or unsaturated heterocycle, each of which optionally containing from one to three further heteroatoms independently selected from N, S and O, and each of which being optionally substituted with one or more substituents independently selected from halogen, $(C_{1-6})$alkyl, hydroxy, cyano, O—$(C_{1-6})$alkyl, —$NH_2$, —NH$(C_{1-4})$alkyl, —N$((C_{1-4})$alkyl$)_2$, —CO—$NH_2$, —CO—NH$(C_{1-4})$alkyl, —CO—N$((C_{1-4})$alkyl$)_2$, —COOH, and —COO$(C_{1-6})$alkyl;
or a pharmaceutically acceptable salt or ester thereof.

Included within the scope of this invention is a pharmaceutical composition comprising an anti-hepatitis C virally effective amount of a compound of formula I, or a pharmaceutically acceptable salt or ester thereof, in admixture with at least one pharmaceutically acceptable carrier medium or auxiliary agent.

According to a further aspect of this embodiment the pharmaceutical composition according to this invention further comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula I, a pharmaceutically acceptable salt or ester thereof, or a composition as described above, alone or in combination with at least one other antiviral agent, administered together or separately.

Also within the scope of this invention is the use of a compound of formula I, or a pharmaceutically acceptable salt or ester thereof, as described herein, for the manufacture of a medicament for the treatment or prevention of hepatitis C viral infection in mammal.

DETAILED DESCRIPTION OF PREFERRED EMBODIMENTS

Definitions

As used herein, the following definitions apply unless otherwise noted:

With reference to the instances where (R) or (S) is used to designate the absolute configuration of a substituent or asymmetric center of a compound of formula I, the designation is done in the context of the whole compound and not in the context of the substituent or asymmetric center alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249-264 (1970)).

As used herein the term "(1R,2S)-vinyl-ACCA" refers to a compound of formula:

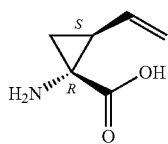

namely, (1R,2S) 1-amino-2-ethenylcyclopropanecarboxylic acid.

The term "$(C_{1-n})$alkyl" as used herein, either alone or in combination with another substituent, means acyclic, straight or branched chain alkyl substituents containing from 1 to n carbon atoms. "$(C_{1-6})$alkyl" includes, but is not limited to, methyl, ethyl, n-propyl, n-butyl, 1-methylethyl (i-propyl), 1-methylpropyl, 2-methylpropyl, 1,1-dimethylethyl (tert-butyl), pentyl and hexyl. The abbreviations Me and Pr denote a methyl group and n-propyl respectively.

The term "$(C_{3-7})$cycloalkyl" as used herein, either alone or in combination with another substituent, means a cycloalkyl substituent containing from 3 to 7 carbon atoms and includes, but is not limited to, cyclopropyl, cyclobutyl, cyclopentyl, cyclohexyl and cycloheptyl.

The term "$(C_{1-n})$alkyl-$(C_{3-7})$cycloalkyl" as used herein means an alkylene radical containing 1 to n carbon atoms to which a cycloalkyl radical containing from 3 to 7 carbon atoms is directly linked; and includes, but is not limited to, cyclopropylmethyl, cyclobutylmethyl, cyclopentylmethyl, 1-cyclopentylethyl, 2-cyclopentylethyl, cyclohexylmethyl, 1-cyclohexylethyl, 2-cyclohexylethyl and cycloheptylpropyl.

The term aryl or "$C_6$ or $C_{10}$ aryl" as used herein interchangeably, either alone or in combination with another radical, means either an aromatic monocyclic group containing 6 carbon atoms or an aromatic bicyclic group containing 10 carbon atoms. Aryl includes, but is not limited to, phenyl, 1-naphthyl or 2-naphthyl.

As used herein, the term "$(C_{1-n})$alkyl-aryl" means an alkyl radical containing from 1 to n carbon atoms to which an aryl is bonded. Examples of $(C_{1-3})$alkyl-aryl include, but are not limited to, benzyl (phenylmethyl), 1-phenylethyl, 2-phenylethyl and phenylpropyl.

The term "O—$(C_{1-n})$alkyl" or "$(C_{1-n})$alkoxy" as used herein, either alone or in combination with another radical, means the radical —O—$(C_{1-n})$alkyl wherein alkyl is as defined above containing from 1 to n carbon atoms, and includes methoxy, ethoxy, propoxy, 1-methylethoxy, butoxy and 1,1-dimethylethoxy. The latter radical is known commonly as tert-butoxy.

The term "halo" or "halogen" as used herein means a halogen substituent selected from fluoro, chloro, bromo or iodo.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

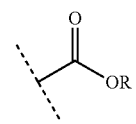

in which the R moiety of the ester is selected from alkyl (including, but not limited to, methyl, ethyl, n-propyl, t-butyl, n-butyl); alkoxyalkyl (including, but not limited to methoxymethyl); alkoxyacyl (including, but not limited to acetoxymethyl); alkyl-aryl (including, but not limited to benzyl); aryloxyalkyl (including, but not limited to phenoxymethyl); aryl (including, but not limited to phenyl), optionally substituted with halogen, $(C_{1-4})$alkyl or $(C_{1-4})$alkoxy. Other suitable prodrug esters can be found in Design of prodrugs, Bundgaard, H. Ed. Elsevier (1985). Such pharmaceutically acceptable esters are usually hydrolyzed in vivo when injected in a mammal and transformed into the acid form of the compound of formula I. With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ-, ω- and τ-interferons, consensus interferons and asialo-interferons), class II interferons (such as γ-interferons) and pegylated forms thereof.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929, WO 03/064416, WO 03/064455, WO 03/064456, WO 02/060926, WO 03/053349, WO 03/099316 or WO 03/099274, and the Vertex pre-development candidate identified as VX-950.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. application No. 60/441,674 filed Jan. 22, 2003, herein incorporated by reference in its entirety (Boehringer Ingelheim), U.S. application No. 60/441,871 filed Jan. 22, 2003, herein incorporated by reference in its entirety (Boehringer Ingelheim), WO 04/005286 (Gilead), WO 04/002977 (Pharmacia), WO 04/002944 (Pharmacia), WO 04/002940 (Pharmacia), WO 03/101993 (Neogenesis), WO 03/099824 (Wyeth), WO 03/099275 (Wyeth), WO 03/099801 (GSK)), WO 03/097646 (GSK), WO 03/095441 (Pfizer), WO 03/090674 (Viropharma), WO 03/084953 (B&C Biopharm), WO 03/082265 (Fujisawa), WO 03/082848 (Pfizer), WO 03/062211 (Merck), WO 03/059356 (GSK), EP 1321463 (Shire), WO 03/040112 (Rigel), WO 03/037893 (GSK), WO 03/037894 (GSK), WO 03/037262 (GSK), WO 03/037895 (GSK), WO 03/026587 (BMS), WO 03/002518 (Dong Wha), WO 03/000254 (Japan Tobacco), WO 02/100846 A1 (Shire), WO 02/100851 A2 (Shire), WO 02/098424 A1 (GSK), WO 02/079187 (Dong Wha), WO 03/02/20497 (Shionogi), WO 02/06246 (Merck), WO 01/47883 (Japan Tobacco), WO 01/85172 A1 (GSK), WO 01/85720 (GSK), WO 01/77091 (Tularik), WO 00/18231 (Viropharma), WO 00/13708 (Viropharma), WO 01/10573 (Viropharma) WO 00/06529 (Merck), EP 1 256 628 A2 (Agouron), WO 02/04425 (Boehringer Ingelheim) WO 03/007945 (Boehringer Ingelheim), WO 03/010140 (Boehringer Ingelheim) and WO 03/010141 (Boehringer Ingelheim). Furthermore other inhibitors of HCV polymerase also include nucleoside analogs, for example, those compounds described in: WO 04/007512 (Merck/Isis), WO 04/003000 (Idenix), WO 04/002999 (Idenix), WO 04/0002422 (Idenix), WO 04/003138 (Merck), WO 03/105770 (Merck), WO 03/105770 (Merck), WO 03/093290 (Genelabs), WO 03/087298 (Biocryst), WO 03/062256 (Ribapharm), WO 03/062255 (Ribapharm), WO 03/061385 (Ribapharm), WO 03/026675 (Idenix), WO 03/026589 (Idenix), WO 03/020222 (Merck), WO 03/000713 (Glaxo), WO 02/100415 (Hoffmann-La Roche), WO 02/1094289 (Hoffmann-La Roche), WO 02/051425 (Mitsubishi), WO 02/18404 (Hoffmann-La Roche), WO 02/069903 (Biocryst Pharmaceuticals Inc.), WO 02/057287 (Merck/Isis), WO 02/057425 (Merck/Isis), WO 01/90121 (Idenix), WO 01/60315 (Shire) and WO 01/32153 (Shire). Specific examples of inhibitors of an HCV polymerase, include JTK-002, JTK-003 and JTK-109 (Japan Tobacco).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from helicase, NS2/3 protease and internal ribosome entry site (IRES). Specific examples of inhibitors of another target in the HCV life cycle include ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Barn 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, δ-, ω- and τ-interferons, consensus interferons, asialo-interferons and pegylated forms thereof.

The term "class II interferon" as used herein means an interferon selected from a group of interferons that all bind to receptor type II. Examples of class II interferons include γ-interferons.

Specific preferred examples of some of these agents are listed below:
  antiviral agents: ribavirin or amantadine;
  immunomodulatory agents: class I interferons, class II interferons or pegylated forms thereof;
  HCV polymerase inhibitors: nucleoside analogs or non-nucleosides;
  inhibitor of another target in the HCV life cycle that inhibits a target selected from: NS3 helicase, NS2/3 protease or internal ribosome entry site (IRES);
  HIV inhibitors: nucleosidic inhibitors, non-nucleosidic inhibitors, protease inhibitors, fusion inhibitors or integrase inhibitors; or
  HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease.

As used herein, the designation whereby a bond to a substituent R is drawn as emanating from the center of a ring, such as, for example,

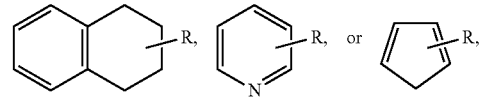

means that the substituent R may be attached to any free position on the ring that would otherwise be substituted with a hydrogen atom, unless specified otherwise.

The following sign - - - or → are used interchangeably in sub-formulas to indicate the bond which is connected to the rest of the molecule as defined.

Preferred Embodiments

In the following preferred embodiments, groups and substituents of the compounds according to this invention are described in detail.

B is preferably selected from $(C_{2-8})$alkyl, $(C_{3-7})$cycloalkyl and $(C_{1-3})$alkyl-$(C_{3-7})$cycloalkyl,
a) wherein said alkyl, cycloalkyl, and alkyl-cycloalkyl may be mono-, di- or tri-substituted with $(C_{1-3})$alkyl; and
b) wherein said alkyl, cycloalkyl and alkyl-cycloalkyl may be mono- or di-substituted with substituents selected from hydroxy and O—$(C_{1-4})$alkyl; and
c) wherein each of said alkyl groups may be mono-, di- or tri-substituted with fluorine or mono-substituted with chlorine or bromine; and
d) wherein in each of said cycloalkyl groups being 5-, 6- or 7-membered, one or two —$CH_2$-groups not being directly linked to each other may be replaced by —O-such that the O-atom is linked to the group X via at least two C-atoms.

More preferably, B is selected from ethyl, n-propyl, i-propyl, n-butyl, 1-methylpropyl, 2-methylpropyl, tert-butyl, cyclopropyl, cyclobutyl, cyclopentyl and cyclohexyl,
a) wherein each of said groups is optionally substituted with 1 to 3 substituents selected from methyl and ethyl;
b) wherein each of said groups is optionally mono- or di-substituted with substituents selected from hydroxy, methoxy and ethoxy; and c) wherein each of said alkyl groups may be mono-, di- or tri-substituted with fluorine or mono-substituted with chlorine or bromine; and d) wherein in each of said cycloalkyl groups being 5-, 6- or 7-membered, one or two —CH$_2$-groups not being directly linked to each other may be replaced by —O-such that the O-atom is linked to the group X via at least two C-atoms.

B is even more preferably selected from ethyl, 1-methylethyl, 1,1-dimethylethyl, propyl, 1-methylpropyl, 2-methylpropyl, 1,1-dimethylpropyl, 1,2-dimethylpropyl, 2,2-dimethylpropyl, 1,1,2-trimethylpropyl, 1,2,2-trimethylpropyl, 1-ethylpropyl, 1-ethyl-2-methylpropyl, 1-(1-methylethyl)-2-methylpropyl, 1-ethyl-2,2-dimethylpropyl, butyl, 1-methylbutyl, 2-methylbutyl, 3-methylbutyl, 1,2-dimethylbutyl, 1,1-dimethylbutyl, 1,3-dimethylbutyl, 2,2-dimethylbutyl, 2,3-dimethylbutyl, 3,3-dimethylbutyl, 1,2,2-trimethylbutyl, 1,2,3-trimethylbutyl, 2,2,3-trimethylbutyl, 2,3,3-trimethylbutyl and 2,2,3-trimethylbutyl, whereby these alkyl-groups may be substituted with chlorine or bromine, or with 1, 2 or 3 fluorine substituents. Examples of preferred fluorinated alkyl groups include, but are not limited to, 2-fluoroethyl, 3-fluoropropyl and 3,3,3-, trifluoropropyl.

In addition, even more preferably, B is cyclopropyl, cyclobutyl, cyclopentyl, or cyclohexyl or is selected from the following formulas, wherein one or two CH$_2$— groups of a cycloalkyl group is replaced by oxygen:

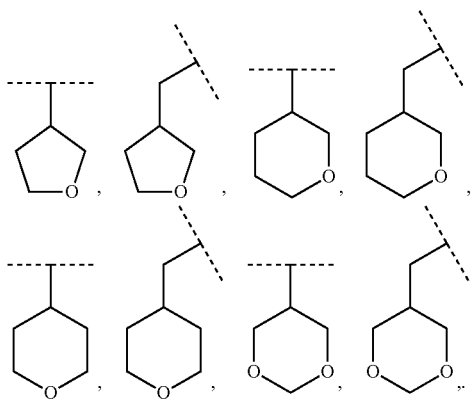

From the above list, cycloalkyl and alkyl-cycloalkyl groups optionally comprising 1 or O-atoms are optionally substituted with 1, 2 or 3 methyl-groups. Especially those cycloalkyl groups, optionally comprising 1 or 2 O-atoms, are preferred, wherein the α-C-atom is substituted with methyl.

Further examples of preferred substituted cyclic groups are

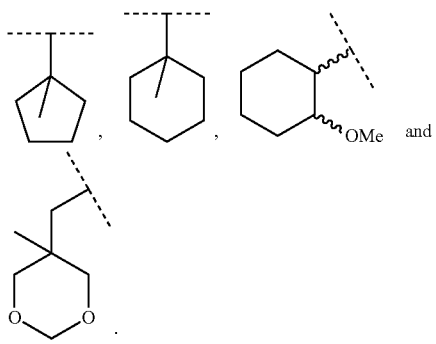

Most preferably B is selected from ethyl, n-propyl, tert-butyl, 2-methylpropyl, 1,2-dimethylpropyl, 1,2,2-trimethylpropyl, 2-fluoroethyl, 3-fluoropropyl, 3,3,3-trifluoropropyl, cyclopropyl, cyclobutyl, cyclopentyl, cyclohexyl, 1-methylcyclopentyl and 1-methylcyclohexyl, and a group selected from:

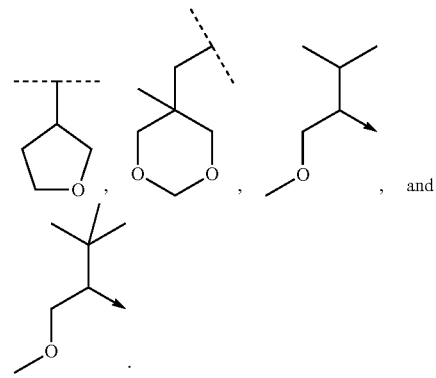

Still, most preferably B is selected from ethyl, n-propyl, tert-butyl, cyclopentyl, 1-methylcyclopentyl, 2-fluoroethyl or 3-fluoropropyl.

According to one embodiment of this invention X is O.

According to another embodiment of this invention X is NH.

R$^3$ is preferably (C$_{2-6}$)alkyl, (C$_{3-7}$)cycloalkyl or (C$_{1-3}$) alkyl-(C$_{3-7}$)cycloalkyl, each of which being optionally substituted with 1 to 3 substituents selected from (C$_{1-4}$)alkyl.

R$^3$ is more preferably selected from ethyl, propyl, butyl, cyclopropyl, cyclobutyl, cyclopentyl, cyclohexyl, cyclopropylmethyl, cyclobutylmethyl, cyclopentylmethyl, or cyclohexylmethyl, each of which optionally being substituted with 1 or 2 substituents selected from methyl, ethyl and propyl.

Even more preferably R$^3$ is selected from 1-methylethyl, 1,1-dimethylethyl, 1-methylpropyl, 2-methylpropyl, 1,1-dimethylpropyl, 1,2-dimethylpropyl, 2,2-dimethylpropyl, cyclopentyl, cyclohexyl, 1-methylcyclopentyl, 1-methylcyclohexyl, cyclopentylmethyl, cyclohexylmethyl, (1-methylcyclopentyl)methyl and (1-methylcyclohexyl)methyl.

R$^3$ is most preferably selected from 1,1-dimethylethyl, cyclopentyl, cyclohexyl and 1-methylcyclohexyl.

Still, R$^3$ is most preferably selected from 1,1-dimethylethyl and cyclohexyl.

L$^0$ is preferably selected from H, halogen, CH$_3$, —OH, —OCH$_3$, —OC$_2$H$_5$, —OC$_3$H$_7$, —OCH(CH$_3$)$_2$, —NHCH$_3$, —NHC$_2$H$_5$, —NHC$_3$H$_7$, —NHCH(CH$_3$)$_2$, —N(CH$_3$)$_2$, —N(CH$_3$)C$_2$H$_5$, —N(CH$_3$)C$_3$H$_7$ and —N(CH$_3$)CH(CH$_3$)$_2$:

Most preferably L$^0$ is selected from H, —OH, —OCH$_3$, halogen and —N(CH$_3$)$_2$.

Even most preferably, L$^0$ is H, —OH or —OCH$_3$.

Still, most preferably, L$^0$ is H or —OCH$_3$.

L$^1$ and L$^2$ are preferably each independently selected from: halogen, —CH$_3$, —C$_2$H$_5$, —OCH$_3$, —OC$_2$H$_5$, —OC$_3$H$_7$, —OCH(CH$_3$)$_2$, CF$_3$, —SMe, —SOMe, and SO$_2$Me whereby either L$^1$ or L$^2$ may be H.

More preferably either one of L$^1$ and L$^2$ is —CH$_3$, —F, —Cl, —Br, —OMe, —SMe, or —SO$_2$Me and the other of L$^1$ and L$^2$ is H.

Most preferably L$^1$ is CH$_3$, —F, —Cl, —Br, —OMe, —SMe, or —SO$_2$Me and L$^2$ is H.

Therefore, preferably L$^0$ is selected from: H, —OH and —OCH$_3$; and either one of L$^1$ and L$^2$ is CH$_3$, —F, —Cl, —Br, —OMe, —SMe, or —SO$_2$Me and the other of L$^1$ and L$^2$ is H.

More preferably $L^0$ is selected from H, —OH and —OCH$_3$; $L^1$ is —CH$_3$, —F, —Cl, —Br, —OMe, —SMe, or —SO$_2$Me; and $L^2$ is H.

Most preferably $L^0$ is H or —OCH$_3$; $L^1$ is —CH$_3$, Cl or Br; and C is H.

In the case $L^0$ and $L^1$ are covalently bonded to form together with the quinoline residue to which they are linked a ring system, this ring system is preferably selected from:

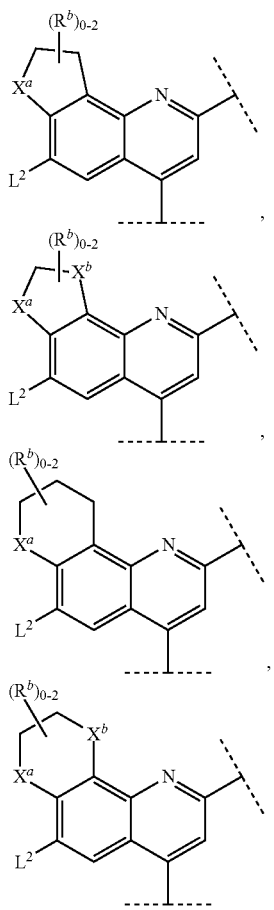

wherein
$X^a$, $X^b$ are independently selected from CH$_2$, O and NR$^a$; most preferably O;
$R^a$ is each independently H or (C$_{1-4}$)alkyl;
$R^b$ is each independently (C$_{1-4}$)alkyl;
$L^2$ is as defined; preferably H or methyl, particularly H.

In the case $L^0$ and $L^2$ are covalently bonded to form together with the quinoline residue to which they are linked a ring system, this ring system is preferably selected from:

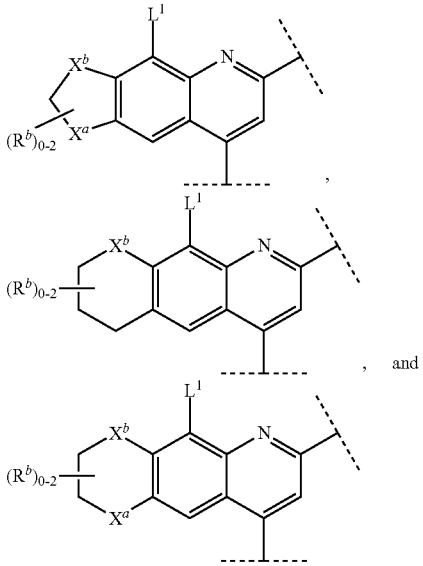

wherein
$X^a$, $X^b$ are independently selected from CH$_2$, O and NR$^a$; most preferably O;
$R^a$ is each independently H or (C$_{1-4}$)alkyl;
$R^b$ is each independently (C$_{1-4}$)alkyl;
$L^1$ is as defined; preferably H or methyl, particularly H.

More preferably, $L^0$ and $L^1$ are covalently bonded to form, together with the quinoline residue to which they are linked, a ring system which is selected from:

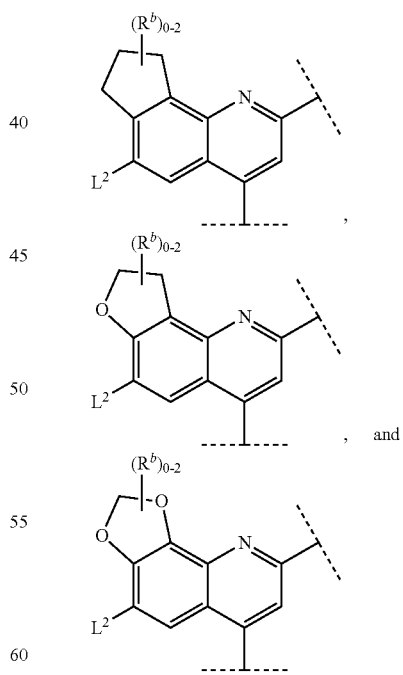

wherein each $R^b$ is independently (C$_{1-4}$)alkyl and $L^2$ is as defined; preferably H or methyl, particularly H.

Most preferably, $L^0$ and $L^1$ are covalently bonded to form together with the quinoline residue to which they are linked a ring system selected from

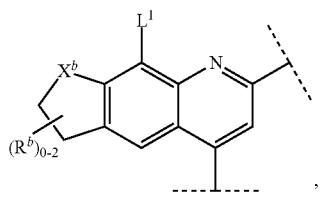

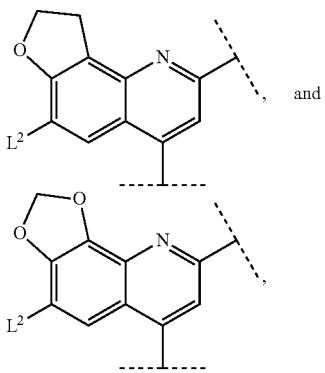

wherein L² is H or —CH₃, preferably H.
R² is preferably R²⁰, —NHCOR²⁰, —NHCOOR²⁰, —NHR²¹ and —NHCONR²¹R²³, wherein
R²⁰ is selected from (C₁₋₈)alkyl, (C₃₋₇)cycloalkyl, (C₁₋₃)alkyl-(C₃₋₇)cycloalkyl, wherein said cycloalkyl and alkyl-cycloalkyl may be mono-, di- or tri-substituted with (C₁₋₃)alkyl; and
R²¹ is H or R²⁰ as defined above; and
R²³ is H or methyl; most preferably H.
More preferably, R² is R²⁰, NHCOR²⁰, —NHCOOR²⁰, —NHR²¹— and —NHCONR²¹R²³, wherein
R²⁰ is selected from methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl, and cyclohexylmethyl, each of said cycloalkyl and alkyl-cycloalkyl groups being optionally substituted with 1 to 3 substituents selected from methyl and ethyl, in particular methyl; and
R²¹ is H or R²⁰ as defined above; and
R²³ is H or methyl; most preferably H.
Preferably, R² is selected from:
a) amino, N-methylamino, N-ethylamino, N-propylamino, N-(1-methylethyl)amino, N-(1,1-dimethylethyl)amino, N-(2-methylpropyl)amino, N-(1-methylpropyl)amino, N-(2,2-dimethylpropyl)amino, N-(1,2-dimethylpropyl)amino, N-(1,1-dimethylpropyl)amino, N-cyclopropylamino, N-cyclobutylamino-, N-cyclopentylamino-, N-cyclohexylamino-, N-(cyclopropylmethyl)amino, N-(cyclobutylmethyl)amino, N-(cyclopentylmethyl)amino, and N-(cyclohexylmethyl)amino;
b) methylcarbonylamino, ethylcarbonylamino, 1-methylethylcarbonylamino, propylcarbonylamino, 2-methylpropylcarbonylamino, 1-methylpropyl-carbonylamino, 2,2-dimethylpropylcarbonylamino, 1,2-dimethylpropylcarbonylamino, 1,1-dimethylpropylcarbonylamino, cyclopropylcarbonylamino, cyclobutylcarbonylamino, cyclopentylcarbonylamino, cyclohexylcarbonylamino, cyclopropylmethylcarbonylamino, cyclobutylmethylcarbonylamino, cyclopentylmethylcarbonylamino, cyclohexylmethylcarbonylamino; and
c) methoxycarbonylamino, ethoxycarbonylamino, 1-methylethoxycarbonylamino, propoxycarbonylamino, tert-butoxycarbonylamino, cyclopropyloxycarbonylamino, cyclobutyloxycarbonylamino, cyclopentyloxycarbonylamino, cyclohexyloxycarbonylamino, cyclopropylmethoxycarbonylamino, cyclobutylmethoxycarbonylamino, cyclopentylmethoxycarbonylamino, cyclohexylmethoxycarbonylamino;
wherein all said cycloalkyl or alkyl-cycloalkyl groups may be mono- or disubstituted with methyl.

Most preferably R² is —NHCOR²⁰, —NHCOOR²⁰, or —NHR²¹, wherein R²⁰ and R²¹ are as defined herein.
Preferably, R²⁰ and R²¹ are independently selected from: methyl, ethyl, n-propyl, propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl, cyclohexylmethyl, each of said cycloalkyl or alkyl-cycloalkyl groups optionally being mono- or di-substituted with methyl or ethyl.
More preferably, R²⁰ and R²¹ are independently selected from: methyl, ethyl, n-propyl, i-propyl, 2,2-dimethylpropyl, cyclopentyl and cyclopentylmethyl.
In the moiety P1 the substituent R¹ and the carbonyl take a syn orientation. Therefore, in the case R¹ is ethyl, the asymmetric carbon atoms in the cyclopropyl group take the R,R configuration according to the subformula:

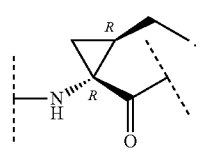

In the case R¹ is vinyl, the asymmetric carbon atoms in the cyclopropyl group take the R,S configuration according to the subformula:

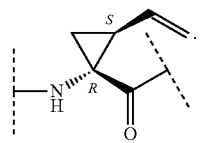

R¹ is preferably vinyl.
R^C is preferably selected from hydroxy or NHSO₂R^S
wherein R^S is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl (benzyl), naphthylmethyl or pyridinylmethyl;
a) each of which optionally being mono-, di- or tri-substituted with substituents selected from fluorine and methyl; and
b) each of which optionally being mono- or disubstituted with substituents selected from hydroxy, trifluoromethyl, methoxy and trifluoromethoxy; and
c) each of which optionally being monosubstituted with substituents selected from chlorine, bromine, cyano, nitro, —CO—NH₂, —CO—NHCH₃, —CO—N(CH₃)₂, —NH₂, —NH(CH₃) and —N(CH₃)₂.
Alternatively preferably, R^C is NHSO₂R^S, wherein R^S is —N(R^{N2})R^{N1}), wherein R^{N1} and R^{N2} are independently selected from H, (C₁₋₄)alkyl, (C₃₋₇)cycloalkyl, (C₁₋₃)alkyl-(C₃₋₇)cycloalkyl, phenyl, and (C₁₋₃)alkyl-phenyl; wherein said (C₁₋₄)alkyl, (C₃₋₇)cycloalkyl, (C₁₋₃)alkyl-(C₃₋₇)cycloalkyl, phenyl and (C₁₋₃)alkyl-phenyl are optionally substituted with one, two or three substituents independently selected from halogen, (C$_{1-6}$)alkyl, hydroxy, cyano, O—(C$_{1-6}$)alkyl, —NH$_2$, —NH(C$_{1-4}$)alkyl, —N((C$_{1-4}$)alkyl)$_2$, —CO—NH$_2$, —CO—N((C$_{1-4}$)alkyl)$_2$, —COOH, and —COO(C$_{1-6}$)alkyl; or R$^{N2}$ and R$^{N1}$ are linked, together with the nitrogen to which they are bonded, to form a 5 or 6-membered monocyclic heterocycle which may be saturated or unsaturated, optionally containing from one to three further heteroatoms independently selected from N, S and O, and optionally substituted with one, two or three substituents independently selected from halogen, (C$_{1-6}$)alkyl, hydroxy, cyano, O—(C$_{1-6}$)alkyl, —NH$_2$, —NH(C$_{1-4}$)alkyl, —N((C$_{1-4}$alkyl)$_2$, —CO—NH$_2$, —CO—NH(C$_{1-4}$)alkyl, —CO—N((C$_{1-4}$)alkyl)$_2$, —COOH, and —COO(C$_{1-6}$)alkyl.

Preferably, the group R$^C$ is hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$—CH$_2$-cyclopropyl, NHSO$_2$-cyclobutyl, NHSO$_2$-cyclopentyl, or NHSO$_2$-phenyl.

More preferably, R$^C$ is hydroxy, or NHSO$_2$-cyclopropyl.

According to a most preferred embodiment, the group R$^C$ is hydroxy. According to an alternative most preferred embodiment, the group R$^C$ is NHSO$_2$-cyclopropyl. According to another alternative most preferred embodiment, the group R$^C$ is NHSO$_2$N(CH$_3$)$_2$.

Also encompassed within the scope of the present invention, are compounds of formula (I) wherein:

B is (C$_{1-10}$)alkyl, (C$_{3-7}$)cycloalkyl, or (C$_{1-4}$)alkyl-(C$_{3-7}$)cycloalkyl,
 a) wherein said cycloalkyl, and alkyl-cycloalkyl may be mono-, di- or tri-substituted with (C$_{1-3}$)alkyl; and
 b) wherein said alkyl, cycloalkyl, and alkyl-cycloalkyl may be mono- or di-substituted with substituents selected from hydroxy and O—(C$_{1-4}$)alkyl; and
 c) wherein all said alkyl-groups may be mono-, di- or tri-substituted with halogen; and
 d) wherein all said cycloalkyl-groups being 4-, 5-, 6- or 7-membered having optionally one (for the 4-, 5, 6, or 7-membered) or two (for the 5-, 6- or 7-membered)- CH$_2$-groups not directly linked to each other replaced by —O-such that the O-atom is linked to the group X via at least two C-atoms;

X is O or NH;

R$^3$ is (C$_{2-8}$)alkyl, (C$_{3-7}$)cycloalkyl or (C$_{1-3}$)alkyl-(C$_{3-7}$)cycloalkyl, wherein said cycloalkyl groups may be mono-, di- or tri-substituted with (C$_{1-4}$)alkyl;

L$^0$ is H, —OH, —O—(C$_{1-4}$)alkyl, —NH$_2$, —NH(C$_{1-4}$)alkyl or —N((C$_{1-4}$)alkyl)$_2$;

L$_1$, L$^2$ are each independently halogen, (C$_{1-4}$)alkyl, —O—(C$_{1-4}$)alkyl or —S—(C$_{1-4}$)alkyl (in any oxidized state such as SO or SO$_2$); and either L$^1$ or L$^2$ (but not both at the same time) may also be H; or L$^0$ and L$^1$ or L$^0$ and L$^2$ may be covalently bonded to form, together with the two C-atoms to which they are linked, a 5- or 6-membered carbocyclic ring wherein one or two —CH$_2$-groups not being directly linked to each other may be replaced each independently by —O— or NR$^a$ wherein R$^a$ is H or (C$_{1-4}$)alkyl, and wherein said carbo- or heterocyclic ring is optionally mono- or di-substituted with (C$_{1-4}$)alkyl;

R$^2$ is R$^{20}$, —NR$^{22}$COR$^{20}$, —NR$^{22}$COOR$^{20}$—NR$^{22}$R$^{21}$ and —NR$^{22}$CONR$^{21}$R$^{23}$, wherein R$^{20}$ is selected from (C$_{1-8}$)alkyl, (C$_{3-7}$)cycloalkyl and (C$_{1-4}$)alkyl-(C$_{3-7}$)cycloalkyl, wherein said cycloalkyl and alkyl-cycloalkyl may be mono-, di- or tri-substituted with (C$_{1-3}$)alkyl;

R$^{21}$ is H or has one of the meanings of R$^{20}$ as defined above,
R$^{22}$ and R$^{23}$ are independently selected from H and methyl,
R$^1$ is ethyl or vinyl;

R$^C$ is hydroxy or NHSO$_2$R$^S$ wherein R$^S$ is (C$_{1-8}$)alkyl, (C$_{3-7}$)cycloalkyl, (C$_{1-8}$)alkyl-(C$_{3-7}$)cycloalkyl, phenyl, naphthyl, pyridinyl, (C$_{1-4}$)alkyl-phenyl, (C$_{1-4}$)alkyl-naphthyl or (C$_{1-4}$)alkyl-pyridinyl; all of which optionally being mono-, di- or tri-substituted with substituents selected from halogen, hydroxy, cyano, (C$_{1-4}$)alkyl, O—(C$_{1-6}$)alkyl, —CO—NH$_2$, —CO—NH(C$_{1-4}$)alkyl, —CO—N((C$_{1-4}$)alkyl)$_2$, —NH$_2$, —NH(C$_{1-4}$)alkyl and —N((C$_{1-4}$)alkyl)$_2$; and all of which optionally being monosubstituted with nitro;

or R$^S$ can be further selected from: —NH(C$_{1-6}$)alkyl, N((C$_{1-6}$)alkyl)$_2$, -Het,

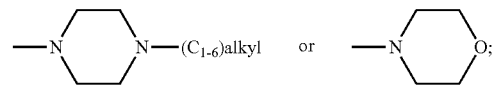

or a pharmaceutically acceptable salt or ester thereof.

Preferably,

B is (C$_{2-8}$)alkyl, (C$_{3-7}$)cycloalkyl or (C$_{1-3}$)alkyl-(C$_{3-7}$)cycloalkyl,
 a) wherein said alkyl, cycloalkyl, and alkyl-cycloalkyl may be mono-, di- or tri-substituted with (C$_{1-3}$)alkyl; and
 b) wherein said alkyl, cycloalkyl, and alkyl-cycloalkyl may be mono- or di-substituted with substituents selected from hydroxy and O—(C$_{1-4}$)alkyl; and
 c) wherein each of said alkyl groups may be mono-, di- or tri-substituted with fluorine or mono-substituted with chlorine or bromine; and
 d) wherein in each of said cycloalkyl groups being 5-, 6- or 7-membered, one or two —CH$_2$-groups not being directly linked to each other may be replaced by —O— such that the O-atom is linked to the group X via at least two C-atoms;

X is O or NH;

R$^3$ is (C$_{2-6}$)alkyl or (C$_{3-7}$)cycloalkyl, both of which being optionally substituted with 1 to 3 substituents selected from (C$_{1-4}$)alkyl;

L$^0$ is H, —OH, —OCH$_3$, halogen or —N(CH$_3$)$_2$;

L$^1$ and L$^2$ are each independently selected from: halogen, —CH$_3$, —C$_2$H$_5$, —OCH$_3$, —OC$_2$H$_5$, —OC$_3$H$_7$, —OCH(CH$_3$)$_2$, CF$_3$, —SMe, —SOMe, and SO$_2$Me, whereby either L$^1$ or L$^2$ may be H;

R$^2$ is R$^{20}$, —NHCOR$^{20}$, —NHCOOR$^{20}$, —NHR$^{21}$ and —NHCONR$^{21}$R$^{23}$, wherein R$^{20}$ is selected from (C$_{1-8}$)alkyl, (C$_{3-7}$)cycloalkyl, (C$_{1-3}$) alkyl-(C$_{3-7}$)cycloalkyl, wherein each of said cycloalkyl and alkyl-cycloalkyl groups may be mono-, di- or tri-substituted with (C$_{1-3}$)alkyl; and R$^{21}$ is H or R$^{20}$ as defined above; and R$^{23}$ is H or methyl;

R$^1$ is ethyl or vinyl; and

R$^C$ is hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$—CH$_2$-cyclopropyl, NHSO$_2$-cyclobutyl, NHSO$_2$-cyclopentyl or NHSO$_2$-phenyl.

More preferably, B is selected from: ethyl, n-propyl, tert-butyl, 2-methylpropyl, 1,2-dimethylpropyl, 1,2,2-trimethylpropyl, 2-fluoroethyl, 3-fluoropropyl, 3,3,3-trifluoropropyl, cyclopropyl, cyclobutyl, cyclopentyl, cyclohexyl, 1-methylcyclopentyl and 1-methylcyclohexyl, and a group selected from:

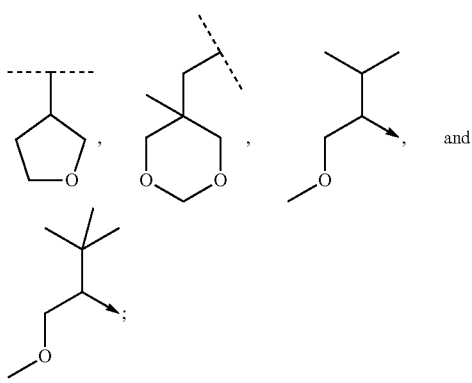

$R^3$ is selected from 1,1-dimethylethyl, cyclopentyl, cyclohexyl and 1-methylcyclohexyl; $L^0$ is H, —OH or —OCH$_3$; $L^1$ is CH$_3$, —F, —Cl, —Br, —OMe, —SMe, or —SO$_2$Me; $L^2$ is H;

$R^2$ is —NHCOR$^{20}$, —NHCOOR$^{20}$ or —NHR$^{21}$, wherein R$^{20}$ and R$^{21}$ are independently selected from methyl, ethyl, n-propyl, i-propyl, 2,2-dimethylpropyl, cyclopentyl and cyclopentylmethyl;

$R^1$ is vinyl; and $R^C$ is hydroxy or NHSO$_2$-cyclopropyl.

Most preferably, B is selected from ethyl, n-propyl, teabutyl, cyclopentyl, 1-methylcyclopentyl, 2-fluoroethyl and 3-fluoropropyl; $R^3$ is selected from 1,1-dimethylethyl and cyclohexyl; $L^0$ is H or —OCH$_3$; $L^1$ is —CH$_3$, —Cl, or —Br; $L^2$ is H; and is hydroxy.

Examples of preferred embodiments according to this invention is each single compound listed in the following Tables 1, 2, 3, 4, 5 and 6.

According to an alternate embodiment, the pharmaceutical composition of this invention may additionally comprise at least one other anti-HCV agent. Examples of anti-HCV agents include, α- (alpha), β- (beta), δ- (delta), γ- (gamma), ω- (omega) or τ- (tau) interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase.

According to yet another alternate embodiment, the pharmaceutical composition of this invention may additionally comprise at least one inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19th Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds, including their pharmaceutically acceptable salts and esters, are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-, β-, δ-, ω-, γ- or τ-interferon, ribavirin, amantadine; other inhibitors of HCV NS3 protease; inhibitors of HCV polymerase; inhibitors of other targets in the HCV life cycle, which include but are not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I, including a pharmaceutically acceptable salt or ester thereof.

In a preferred embodiment, this method is useful in decreasing the NS3 protease activity of the hepatitis C virus infecting a mammal.

As discussed above, combination therapy is contemplated wherein a compound of formula (I), or a pharmaceutically acceptable salt or ester thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

A compound of formula (I), or a pharmaceutically acceptable salt or ester thereof, set forth herein may also be used as a laboratory reagent. Furthermore a compound of this invention, including a pharmaceutically acceptable salt or ester thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt or ester thereof, set forth herein may also be used as a research reagent. A compound of formula (I), including a pharmaceutically acceptable salt or ester thereof, may also be used as positive control to validate surrogate cell-based assays or in vitro or in vivo viral replication assays.

Methodology

Several ways of carrying out the synthesis of compounds of formula I with different quinoline derivatives are disclosed in WO 00/09558. The dipeptide intermediate 15 (Scheme 2) and 2-carbomethoxy-4-hydroxy-7-methoxyquinoline 9 (Scheme 1) were synthesized according to the general methods described in WO 00/09543.

Compounds of formula I wherein $R^C$ is $NHSO_2R^S$ as defined herein are prepared by coupling the corresponding acid of formula I (i.e. $R^C$ is hydroxy) with an appropriate sulfonamide of formula $R^SSO_2NH_2$ in the presence of a coupling agent under standard conditions. Although several commonly used coupling agents can be employed, TBTU and HATU have been found to be practical. The sulfonamides are available commercially or can be prepared by known methods.

The following schemes illustrate two convenient processes using known methods for preparing the compounds of formula I when $R^1$ is vinyl and $R^C$ is OH.

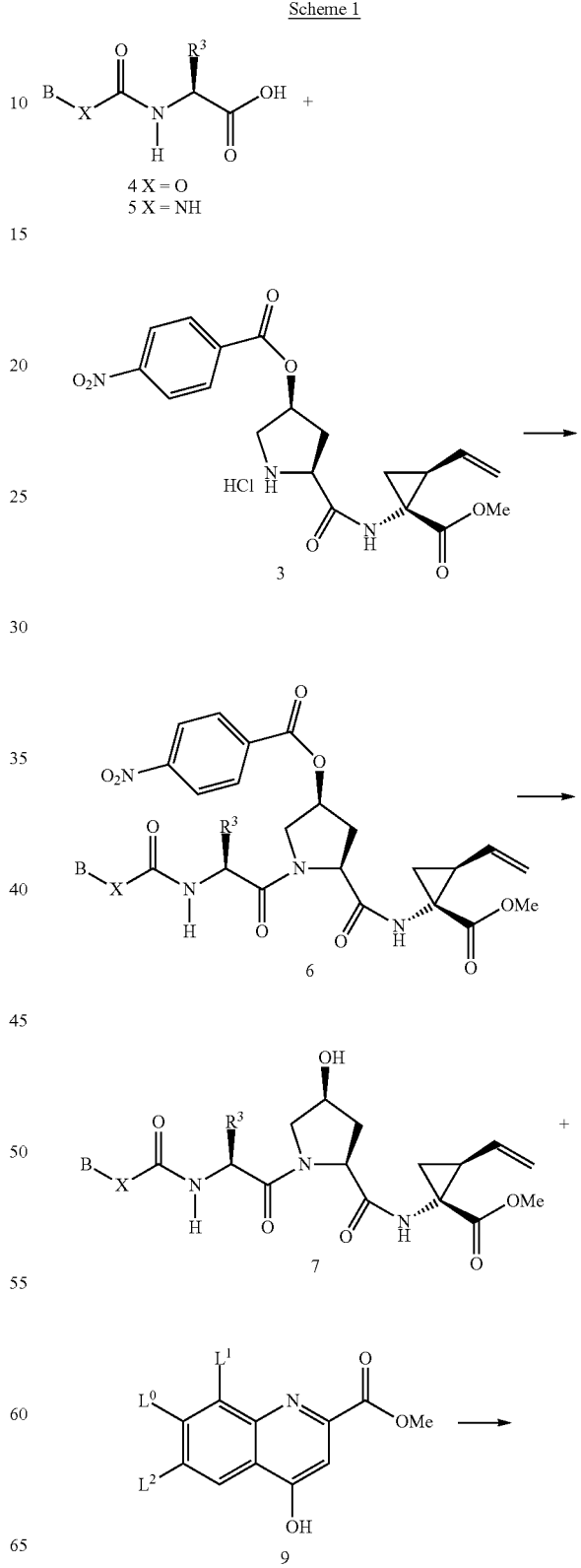

-continued

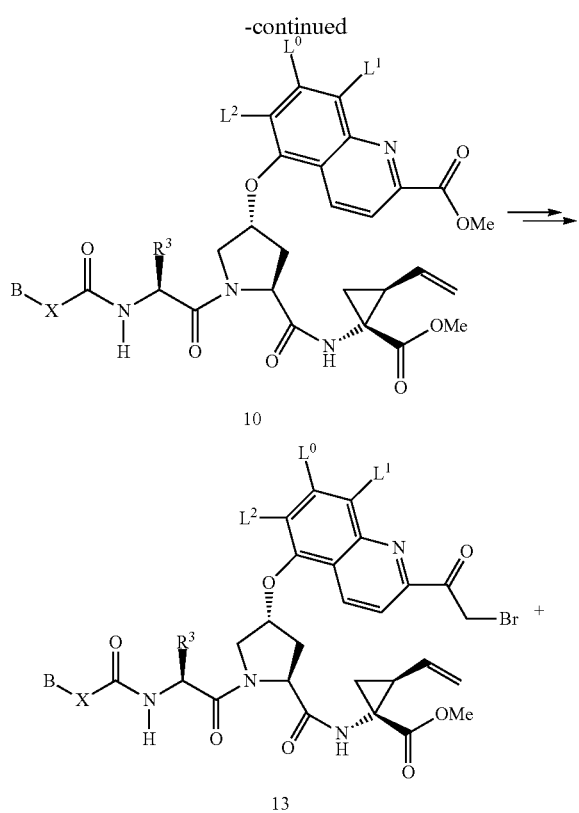

Briefly, the synthesis of dipeptide 3 is carried out by coupling the P1 residue to the properly protected trans-hydroxy proline under standard conditions. The stereochemistry of the hydroxyl group is inverted by the well known Mitsunobu reaction using para-nitrobenzoic acid. Coupling of dipeptide with the P3 moiety (prepared using standard methodology and exemplified in the examples section) yielded tripeptide 6. Introduction of the quinoline moiety to the hydroxyl group of the tripeptide 7 with inversion of stereochemistry can be carried out using either a Mitsunobu reaction or by converting the free hydroxyl group into a good leaving group (such as a brosylate) and displacing it with the hydroxylquinoline derivative 9. For the synthesis of the 2-(2-amino-4-thiazolyl) derivatives, the quinoline used contains a 2-carbomethoxy group as shown in 9. Conversion of the carboxylate group to the aminothiazole derivative is carried out by well known synthetic methodology and is described and exemplified in WO 00/09543 and WO 00/09598. Finally the C-terminal ester is hydrolyzed under basic aqueous conditions.

Scheme 2

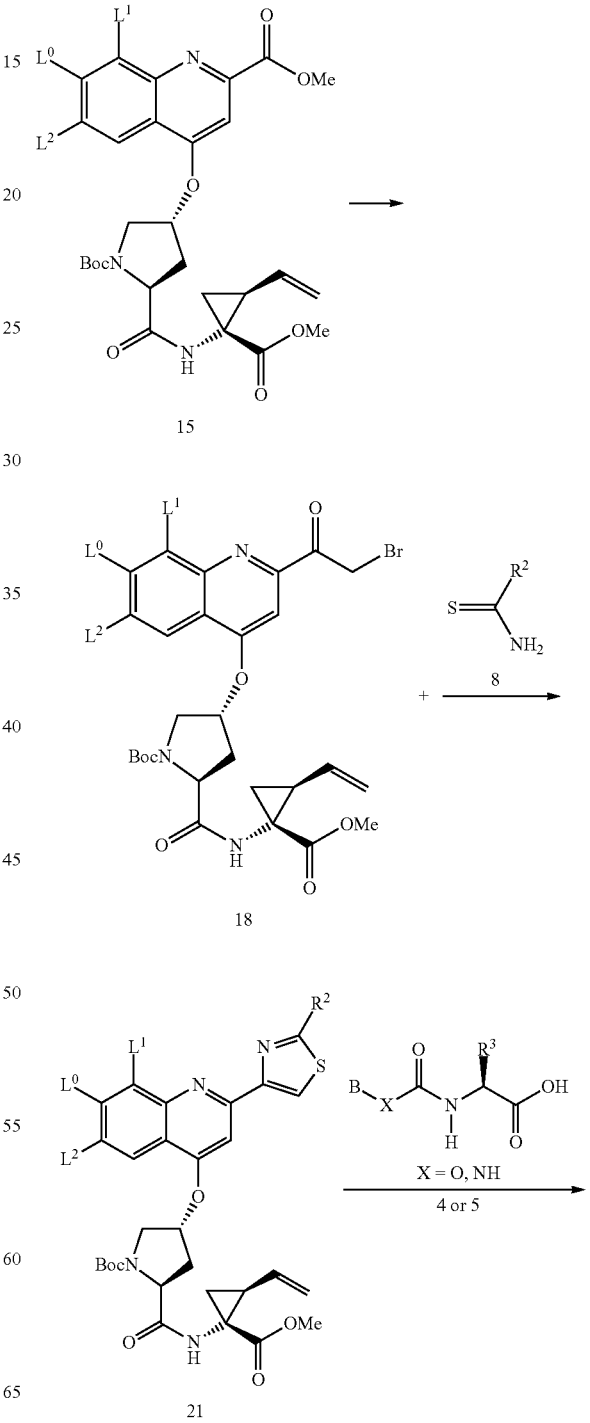

-continued

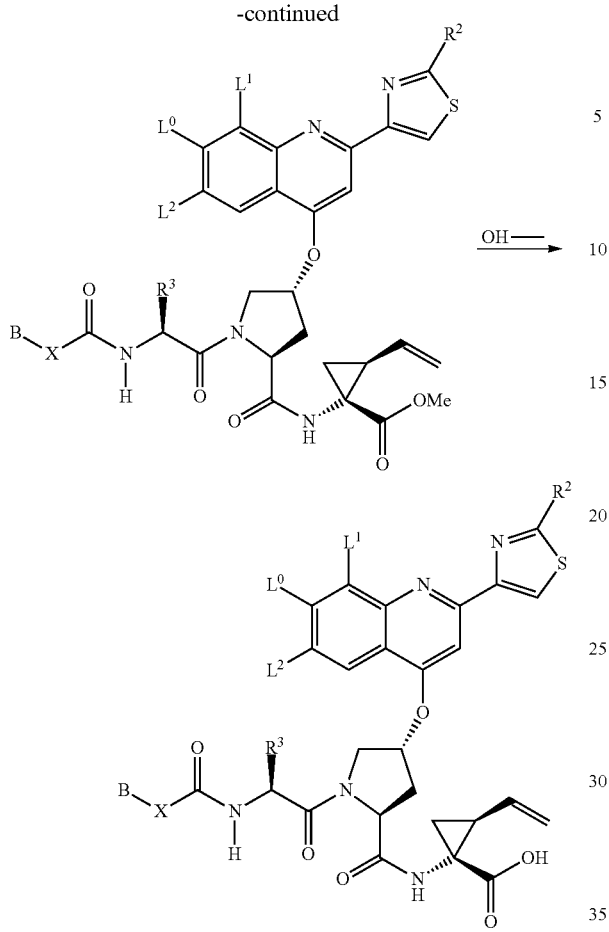

Scheme 2 describes another reaction sequence for making compounds of Formula I. In this case the quinoline moiety is introduced to the dipeptide in a similar way as described in Scheme 1. Finally, the P3 moiety is coupled under standard conditions to the dipeptide 21. Conversion of the resulting tripeptide to the final compound is carried out as described in Scheme 1.

Synthesis of P1 Fragments

P1 moieties of compounds of Formula (I) were prepared using the protocols outlined in WO 00/59929, published Oct. 12, 2000, and WO 00/09543, published on Feb. 24, 2000. In particular, reference is made to pages 33-35, Example 1 of WO00/59929 and Pages 56-69, Example 9-20 of WO00/09543 for the preparation of 1-aminocyclopropanecarboxylic acid P1 moieties.

Synthesis of P2 Substituents

Compounds of formula 9 can be synthesized from commercially available materials using the techniques described in International Patent Applications WO 00/59929, WO 00/09543, WO 00/09558 and U.S. Pat. No. 6,323,180 B1.

Examples of synthesis of different 2-carbomethoxy-4-hydroxyquinoline derivatives were carried out as follows:

Synthesis of 2-carbomethoxy-4-hydroxy-quinoline derivatives was carried out from the corresponding anilines according to the procedure of: Unangst, P. C.; Connor, D. T. *J. Heterocyc. Chem.* 29, 5, 1992, 1097-1100. The procedure is shown in scheme 3 below:

Scheme 3

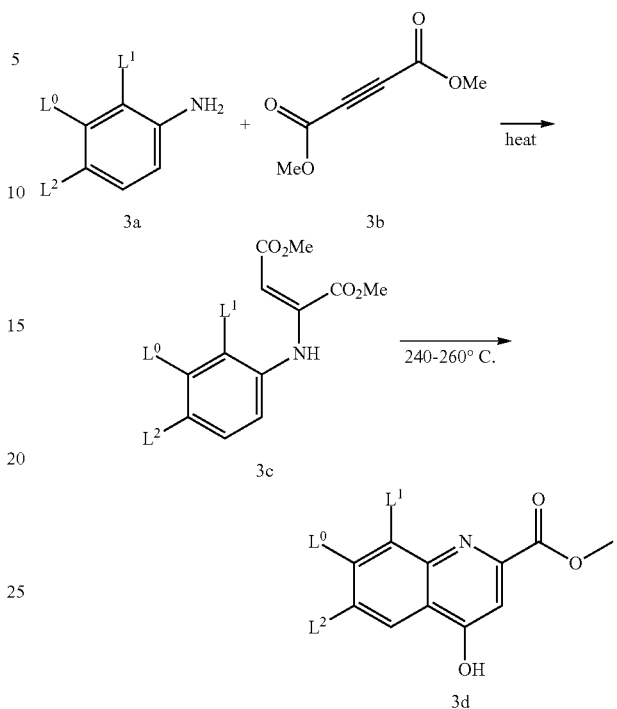

Briefly, properly substituted anilines at the 2, 3 and/or 4 position are allowed to react with dimethyl acetylene dicarboxylate and the resulting enamine is heated at high temperatures to effect the cyclization.

The corresponding anilines are commercially available or may require some well known chemical transformation. For example it can be that the nitro is commercially available and is then converted to the corresponding amine by using a reducing agent. Also when the carboxylic acid is commercially available, it can be transformed into the corresponding amine via a Curtius rearrangement.

Further details of the invention are illustrated in the following examples which are understood to be non-limiting with respect to the appended claims. Other specific ways of synthesis or resolution of the compounds of this invention can be found in WO 00/09543; WO 00/09558 & WO 00/59929 and in co-pending application Ser. No. 09/368,670, all of which are hereby incorporated by reference.

EXAMPLES

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., *J. Org. Chem.*, (1978), 43, 2923).

Abbreviations used in the examples include:
BOC or Boc: tert-butyloxycarbonyl; DBU: 1,8-diazabicyclo[5.4.0]undec-7-ene; DCM: dichloromethane; DIAD: diisopropylazodicarboxylate; DIEA: diisopropylethylamine; DIPEA: diisopropylethyl amine; DMF: N,N-dimethylformamide; DMAP: 4-(dimethylamino)pyridine; DMSO: dimethylsulfoxide; EtOAc: ethyl acetate; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Desorption Ionization-Time of Flight, FAB: Fast Atom Bombardment); Me: methyl; MeOH: methanol; Ph: phenyl; R.T.: room temperature (18 to 22°); tert-butyl or t-butyl: 1,1-dimethylethyl; Tbg: tert-butyl glycine: tert-leucine; TBTU: 2-(1H-benzotriazole-1-yl)-1,1,3,3-tetramethyl uronium tetrafluoroborate; TEA: triethylamine; TFA: trifluoroacetic acid; and THF: tetrahydrofuran.

Example 1

Synthesis of P3 Derivatives

Synthesis of Carbamate 4a

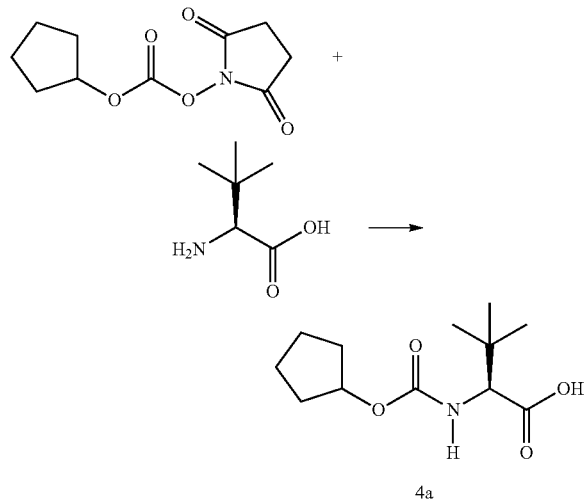

4a

THF (350 mL) was added to a flask containing carbonic acid cyclopentyl ester 2,5-dioxo-pyrrolidin-1-yl ester (9.00 g; 39.6 mmol) and tert-butyl glycine (6.24 g; 47.5 mmol) resulting in a suspension. Distilled water (100 mL) was added with vigorous stirring. A small amount of solid remained undissolved. Triethylamine (16.6 mL; 119 mmol) was then added resulting in a homogenous solution which was stirred at R.T. After 2.5 h, the THF was evaporated and the aqueous residue diluted with water (100 mL): The reaction was rendered basic by the addition of 1 N NaOH (25 mL—final pH>10). The solution was washed with EtOAc (2×200 mL) and the aqueous phase acidified with 1 N HCl (ca. 70 mL—final pH<2). The turbid solution was extracted with EtOAc (200+150 mL). The extract was dried (MgSO₄) and evaporated to give carbamate 4a as a white solid (8.68 g).

Preparation of Ureas 5a

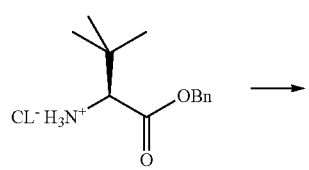

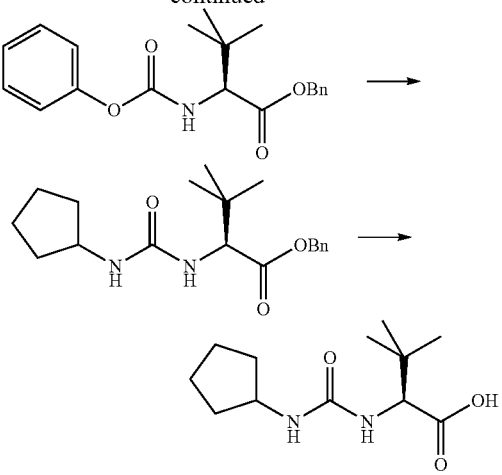

5a

A solution of tert-butyl glycine benzyl ester hydrochloride salt (2.55 g; 9.89 mmol) in THF (20 mL) and pyridine (2.0 mL; 24.73 mmol) was cooled to 0° C. Phenyl chloroformate (1.30 mL; 10.19 mmol) was added dropwise to the cooled solution. The resulting suspension was stirred for 5 min at 0° C., then at R.T. for 1.5 h. The reaction mixture was diluted with EtOAc, washed with 10% citric acid (2×), water (2×), saturated NaHCO₃ (2×), water (2×) and brine (1×), dried (MgSO₄), filtered and evaporated to obtain the crude compound as a nearly colorless oil (3.73 g; >100%; assume 9.89 mmol). The crude product (1.01 g; 2.97 mmol) was dissolved in DMSO (6.5 mL) and cyclopentylamine was added dropwise. The reaction mixture was stirred at R.T. for 45 min and then diluted with EtOAc. The organic phase was washed with 10% citric acid (2×), water (2×), saturated NaHCO₃ (2×), water (2×) and brine (1×), dried (MgSO₄), filtered and evaporated to give the crude cyclopentyl urea -Tbg-OBn product as a nearly colorless oil. The crude material was purified by flash column chromatography with silica using hexane:EtOAc 9:1 to remove the less polar impurities and 7:3 to elute the purified product as a thick colorless oil (936 mg; 95%). The benzyl ester product (936 mg; 2.82 mmol) was deprotected under a hydrogen filled balloon at R.T. in absolute ethanol (15 mL) solution by stirring the solution with 10% Pd/C (93.6 mg) for 5.5 h. The reaction mixture was filtered through a 0.45 micron filter and evaporated to dryness to provide urea 5a as a white solid (669 mg; 98%)

$^1$H NMR (400 MHz, DMSO-d$_6$): δ 12.39 (s, 1H), 6.09 (d, J=7.4 Hz, 1H), 5.93 (d, J=9.4 Hz, 1H), 3.90 (d, J=9.4 Hz, 1H), 3.87-3.77 (m, 1H), 1.84-1.72 (m, 2H), 1.63-1.42 (m, 4H), 1.30-1.19 (m, 2H), 0.89 (s, 9H).

M.S. (electrospray): 241.0 (M−H)⁻ 243.0 (M+H)⁺. Reverse Phase HPLC Homogeneity (0.06% TFA; CH₃CN:H₂O): 99%.

Example 2

Synthesis of Thioureas 8

Synthesis of Thiourea 8a:

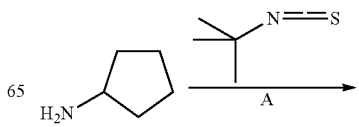

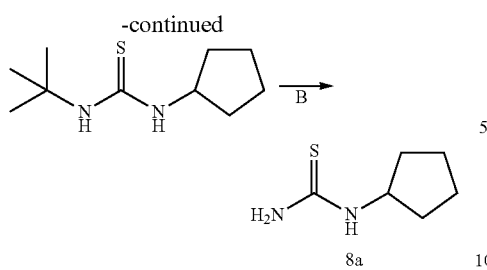

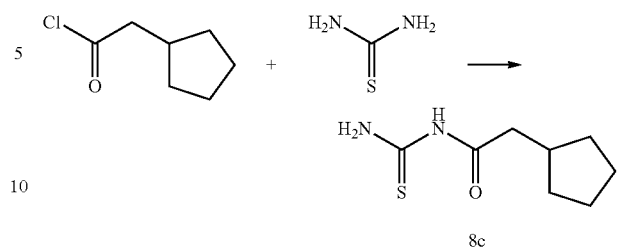

Preparation of Thiourea 8c

To a solution of tert-butyl isothiocyanate (5.0 mL; 39.4 mmoL) in DCM (200 mL) was added cyclopentylamine (4.67 mL; 47.3 mmoL) followed by DIPEA and the reaction mixture was stirred at R.T. for 2 h. The mixture was diluted with EtOAc, and washed with a 10% aqueous solution of citric acid (2×), saturated NaHCO$_3$ (2×), H$_2$O (2×) and brine (1×). The organic layer was dried over anhydrous MgSO$_4$, filtered and evaporated to yield N-tert-butyl-N'-cyclopentylthiourea as a white solid (3.70 g; 47% yield). The N-tert-butyl-N'-cyclopentylthiourea (3.70 g) was dissolved in concentrated HCl (46 mL). The dark yellow solution was heated at a gentle reflux. After 40 min the reaction mixture was allowed to cool to R.T. and thereafter cooled in ice and rendered basic to pH 9.5 with solid and a saturated aqueous solution of NaHCO$_3$. The product was extracted into EtOAc (3×). The combined EtOAc extracts were washed with H$_2$O (2×) and brine (1×). The organic layer was dried (MgSO$_4$), filtered and concentrated to yield a beige solid (2.46 g crude). Trituration of the crude material in hexane/EtOAc 95/5 provided, after filtration, the N-cyclopentythiourea 8a as a white solid (2.38 g; 90% yield).

$^1$H NMR (400 MHz, DMSO-d$_6$): δ 7.58 (bs, 1H), 7.19 (bs, 1H), 6.76 (bs, 1H), 4.34 (bs, 1H), 1.92-1.79 (m, 2H), 1.66-1.55 (m, 2H), 1.55-1.30 (m, 4H). MS; es$^+$ 144.9 (M+H)$^+$, es$^-$: 142.8 (M−H)$^-$.

Preparation of Thiourea 8b

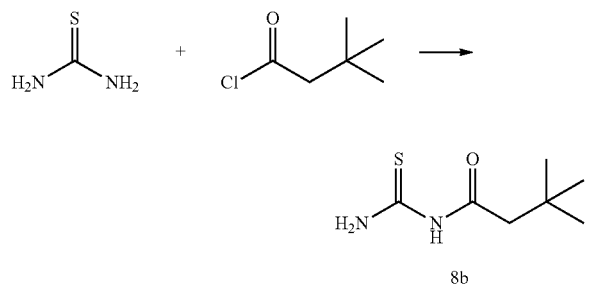

Thiourea (5.0 g, 66 mmol) was dissolved in toluene (50 mL) and tert-butylacetyl chloride (8.88 g, 66 mmol) was added. The mixture was heated at reflux for 14 h to give a yellow solution. The mixture was concentrated to dryness, and the residue partitioned between EtOAc and sat. NaHCO$_3$. The yellow organic phase was dried over MgSO$_4$, filtered and concentrated to give a yellow solid. The solid was dissolved into a minimum amount of EtOAc and triturated with hexane to give 8b as a white solid (8.52 g; 75%). M.S. (electrospray): 173 (M−H)$^-$ 175 (M+H)$^+$. Reverse Phase HPLC Homogeneity (0.06% TFA; CH$_3$CN:H$_2$O): 99%.

Using the procedure described above but using commercially available cyclopentyl acetyl chloride instead of tert-butylacetyl chloride yielded thiourea 8c.

Synthesis of 2-Carbomethoxy-4-Hydroxy Quinoline Derivatives

Example 3A

Synthesis of 2-Carbomethoxy-4-Hydroxy-7-Methoxy-8-Methylquinoline (A5)

Step A

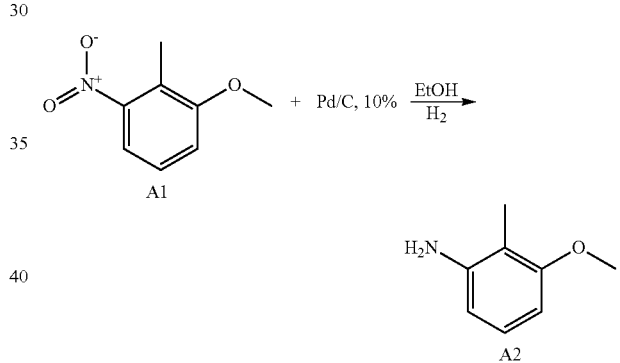

To a solution of 2-methyl-3-nitro anisole A1 (5.1 g; 30.33 mmol; requires ~30 min to dissolve) in absolute ethanol (85 mL) was added 10% Pd/C catalyst (500 mg). The solution was hydrogenated under a hydrogen filled balloon at atmospheric pressure and room temperature for 19 h. The reaction mixture was filtered through a Celite pad, rinsed and evaporated to dryness to obtain 2-methyl-3-methoxyaniline A2 as a deep mauve oil (4.1 g; 29.81 mmol; 98% yield).

MS 137 (MH)$^+$. Reverse Phase HPLC Homogeneity @ 220 nm (0.06% TFA; CH$_3$CN:H$_2$O): 99%.

Step B

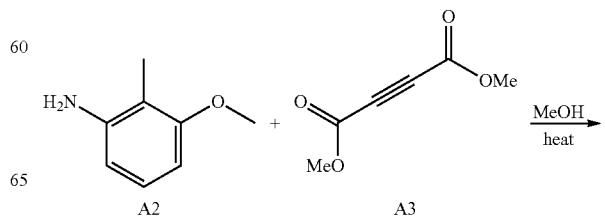

31

-continued

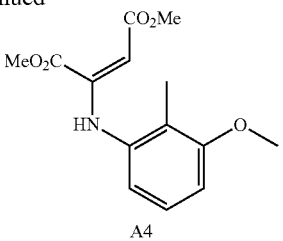

A4

Dimethyl acetylene dicarboxylate A3 (3.6 mL, 29.28 mmol) was added dropwise to a solution of 2-methyl-3-methoxyaniline A2 (3.95 g, 28.79 mmol) in MeOH (100 mL) (reaction is exothermic). The mixture was heated at a gentle reflux for 5 hours cooled and concentrated under vacuum. The crude material was purified by flash column chromatography on silica gel with hexane:EtOAc (95:5) to provide, after evaporation of the pure fractions, the product A4 (6.5 g; 23.27 mmol; 81% yield). Reverse Phase HPLC Homogeneity @ 220 nm (0.06% TFA; $CH_3CN:H_2O$): 95%.

Step C

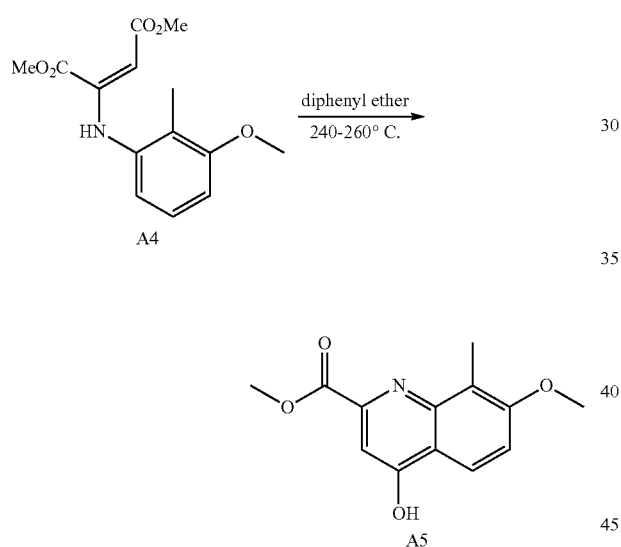

The diester A4 (6.5 g, 23.27 mmol) was dissolved in diphenyl ether (12 mL) and the reaction mixture placed into a pre-heated sand bath at a bath temperature of 350-400° C. Once the reaction mixture attained an internal temperature of 240° C. (observe MeOH evolution at 230-240° C.) a count of six minutes was begun before the bath (temperature end point: 262° C.) was removed and the reaction allowed to cool to room temperature. A solid formed upon cooling which was diluted with ether, filtered and dried to give a tan brown solid (3.48 g crude). The crude material was chromatographed on silica gel column with hexane:EtOAc; 5:5 to remove impurities, then 2:8 and then 100% EtOAc to complete the elution of the product to provide A5, after evaporation, as a pale yellow solid (2.1 g, 37% yield).

MS $(M+H)^+$; 246, and $(M-H)^-$; 248.1. Reverse Phase HPLC Homogeneity @ 220 nm (0.06% TFA; $CH_3CN:H_2O$): 99%.

32

Example 3B

Synthesis of 2-Carbomethoxy-8-Bromo-4-Hydroxy-7-Methoxyquinoline (B6)

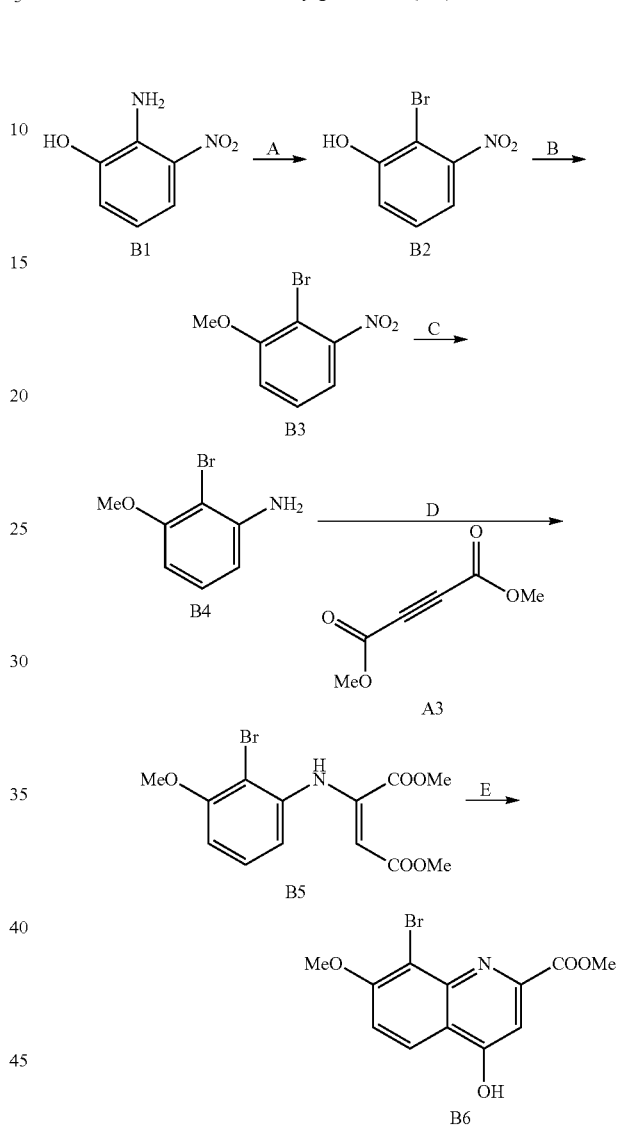

Step A

2-Amino-3-nitrophenol B1 (5 g; 32.4 mmol) was dissolved in $H_2O$ (29.5 mL) and 1,4-dioxane (14.7 mL). The mixture was heated to reflux and hydrobromic acid (48%; 16.7 mL; 147 mmol) was added dropwise over a period of 20 min. Upon completion of the addition, the reflux was maintained an additional 15 min. The reaction was cooled to 0° C. (ice bath), and sodium nitrite (2.23 g; 32.3 mmol) in $H_2O$ (20 mL) was added over a period of 30 min. The stirring was continued for 15 min at 0° C., then the mixture was transferred to a jacketed dropping funnel (0° C.) and added dropwise to a stirred mixture of Cu(I) Br (5.34 g; 37.2 mmol) in $H_2O$ (29.5 mL) and HBr (48%; 16.7 mL; 147 mmol) at 0° C. The reaction was stirred for 15 min at 0° C., warmed to 60° C., stirred for an additional 15 min, cooled to room temperature, and left to stir overnight. The reaction mixture was transferred to a separatory funnel and extracted with ether (3×150 mL). The organic layers were combined, washed with brine (1×), dried (Na₂SO₄), filtered and concentrated to afford the crude product (7.99 g) as a red-brown oil. The crude material was purified by flash column chromatography (1:25 ultra pure silica gel, 230-400 mesh, 40-60 mm, 60 angstroms; CH₂Cl₂ as the solvent) to afford pure 2-bromo-3-nitrophenol B2 (45%; 3.16 g) as an orange-brown solid.

MS 217.8 (MH)⁻. Homogeneity by HPLC (TFA) @ 220 nm: 97%.

Step B

The nitrophenol starting material B2 (3.1 g; 14.2 mmol) was dissolved in DMF (20 mL) and to the solution was added ground cesium carbonate (5.58 g; 17.1 mmol) followed by MeI (2.6 mL; 42.5 mmol). The mixture was stirred at room temperature overnight. The DMF was evaporated, the residue taken up in ether (1×200 mL), washed with water (1×200 mL), brine (4×100 mL), dried (MgSO₄), filtered and evaporated to afford the crude 2-bromo-3-nitroanisole B3 (94%; 3.1 g) as an orange solid.

MS 234 (M+2H)⁺; Homogeneity by HPLC (TFA) @ 220 nm: 98%.

Step C

2-Bromo-3-nitroanisole B3 (1.00 g; 4.31 mmol) was dissolved in glacial acetic acid (11.0 mL) and ethanol (11.0 mL). To this solution was added iron powder (0.98 g; 17.5 mmol). The mixture was stirred at reflux for 3.5 h and worked up. The reaction mixture was diluted with water (35 mL), neutralized with solid Na₂CO₃ and the product extracted with CH₂Cl₂ (3× 50 mL). The extracts were dried (Na₂SO₄), filtered and concentrated in vacuo to afford the crude product, 2-bromo-3 methoxyaniline B4 (91%; 0.79 g) as a pale yellow oil.

MS 201.8 (MH)⁺; Homogeneity by HPLC (TFA) @ 220 nm: 95%.

Step D

To a solution of 2-bromo-3-methoxyaniline B4 (0.79 g; 3.9 mmol) in MeOH (7.6 mL) was added dimethyl acetylene dicarboxylate A3 (0.53 mL; 4.3 mmol) dropwise at 0° C. (caution: reaction is exothermic!). The solution was heated overnight at reflux and worked-up. The MeOH was evaporated and the crude product dried under high vacuum to afford a red gum, purified by flash column chromatography (1:30 ultra pure silica gel, 230-400 mesh, 40-60 mm, 60 angstroms; 4:1 hexane/EtOAc) to afford adduct B5 (86%; 1.16 g) as a pale yellow solid.

MS 344.0 (MH)⁺; Homogeneity by HPLC (TFA) @ 220 nm: 72%.

Step E

To a pre-heated sand bath at about 440° C. (external temperature) was placed the diester adduct B5 (1.1 g; 3.16 mmol) in diphenyl ether (3.6 mL). The reaction was stirred between 230° C.-245° C. (internal temperature; MeOH started evaporating off at about 215° C.) for 7 min and subsequently cooled to room temperature. As the solution cooled the product crystallized from the reaction mixture. The resulting brown solid was filtered, washed with ether and dried under high vacuum to afford the crude bromoquinoline B6 product (74%; 0.74 g) as a brown solid. NMR revealed this product to be a mixture of about 1:1 tautomers.

NMR (DMSO; 400 MHz) ok (1:1 mixture of tautomers); MS 311.9 (MH)⁺;

Homogeneity by HPLC (TFA) @ 220 nm: 96%.

Example 3C

Synthesis of 2-Carbomethoxy-8-Chloro-4-Hydroxy-7-Methoxyquinoline (C6)

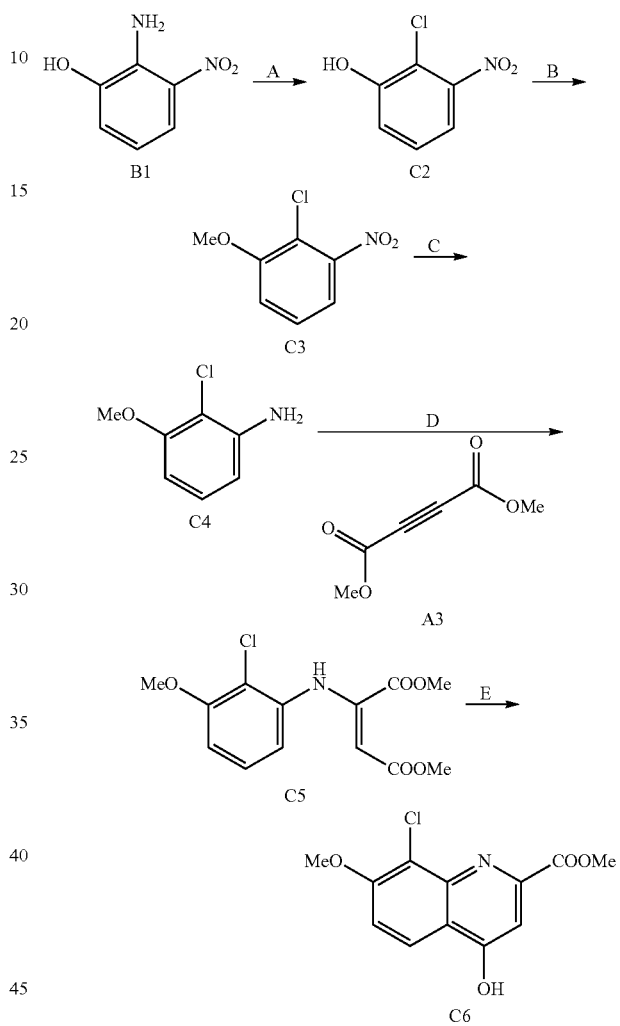

Step A

2-Amino-3-nitrophenol B1 (5 g; 32.4 mmol) was dissolved in concentrated HCl (75 mL) and 1,4-dioxane (14.7 mL). The mixture was heated to 70° C. until most of the solids were in solution. The reaction mixture was cooled to 0° C. (ice bath), and sodium nitrite (2.23 g; 32.3 mmol) in H₂O (5.4 mL) was added over a period of 3 hours to the brown solution. The temperature was maintained below 10° C. during the addition and the stirring was continued for an additional 15 min at 0° C. This diazonium intermediate was poured into a solution of Cu(I)Cl (3.8 g; 38.9 mmol) in H₂O (18.5 mL) and conc. HCl (18.5 mL) at 0° C. The reaction was stirred for 15 min at 0° C., warmed to 60° C., and stirred for an additional 15 min The reaction mixture was then brought to room temperature, and left to stir overnight. The reaction mixture was transferred to a separatory funnel and extracted with ether (3×150 mL). The organic layers were combined, washed with brine (1×), dried (Na₂SO₄), filtered and concentrated to afford the crude product (5.83 g) as a red-brown oil. The crude material was purified by flash column chromatography (1:25 ultra pure silica gel, 230-400 mesh, 40-60 mm, 60 angstroms; 3:1 hexane/EtOAc as the solvent) to afford pure 2-chloro-3-nitrophenol C2 (48%; 2.7 g) as an orange solid. MS 171.8 (MH)⁻: Homogeneity by HPLC (TFA) @ 220 nm: 96%.

Relevant literature for the Sandmeyer Reaction: *J. Med. Chem.*, 1982, 25(4), 446-451.

Step B

The nitrophenol starting material C2 (1.3 g; 7.49 mmol) was dissolved in DMF (10 mL) and to this solution was added ground cesium carbonate (2.92 g; 8.96 mmol), followed by MeI (1.4 mL; 22.5 mmol). The mixture was stirred at room temperature overnight. The DMF was evaporated in vacuo and the residue taken up in ether (150 mL), washed with water (150 mL), brine (4×100 mL), and then dried over (MgSO$_4$). The organic phase was filtered and evaporated to afford the crude 2-chloro-3-nitroanisole C3 (98%; 1.38 g) as an orange solid. Homogeneity by HPLC (TFA) @ 220 nm: 93%.

Step C

2-Chloro-3-nitroanisole C3 (1.38 g; 7.36 mmol) was dissolved in a mixture of glacial acetic acid (19 mL)/ethanol (19 mL). To this solution was added iron powder (1.64 g; 29.4 mmol). The mixture was stirred at reflux for 3.5 hr and worked up. The reaction mixture was diluted with water (70 mL), neutralized with solid Na$_2$CO$_3$ and the product extracted with CH$_2$Cl$_2$ (3×150 mL). The extracts were combined and washed with saturated. brine and then dried over (Na$_2$SO$_4$), filtered and concentrated in vacuo to afford the crude product, 2-chloro-3-methoxyaniline C4 (100%; 1.2 g) as a yellow oil. This material was used as such in the following steps.

MS 157.9 (MH)⁺; Homogeneity by HPLC (TFA) @ 220 nm: 86%.

Step D

To a solution of 2-chloro-3-methoxyaniline C4 (1.2 g; 7.61 mmol) in MeOH (15 mL) was added dimethyl acetylene dicarboxylate A3 (1.0 mL; 8.4 mmol) dropwise at 0° C. (caution: reaction is exothermic!). The solution was heated overnight at reflux and worked-up. The MeOH was evaporated and the crude product dried under high vacuum to afford a red gum which was purified by flash column chromatography (1:30 ultra pure silica gel, 230-400 mesh, 40-60 mm, 60 angstroms; 4:1 hexane/EtOAc) to afford adduct C5 (74%; 1.68 g) as a yellow solid.

MS 300 (MH)⁺; Homogeneity by HPLC (TFA) @ 220 nm: 90%.

Step E

To a pre-heated sand bath at about 440° C. (external temperature) was placed the diester adduct C5 (1.68 g; 5.6 mmol) in diphenyl ether (6.3 mL). The reaction was stirred between 230° C.-245° C. (internal temperature; MeOH started evaporating off at about 215° C.) for 7 min and subsequently cooled to room temperature. As the solution cooled the product crystallized from the reaction mixture. The resulting brownish solid was filtered, washed with ether and dried under high vacuum to afford the quinoline C6 (83%; 1.25 g) as a beige solid. NMR revealed this product to be a mixture of about 1:1 tautomers (keto/phenol forms).

MS 267.9 (MH)⁺; Homogeneity by HPLC (TFA) @ 220 nm: 92%.

Example 3D

Synthesis of 2-Carbomethoxy-8-Fluoro-4-Hydroxy-7-Methoxyquinoline (D5)

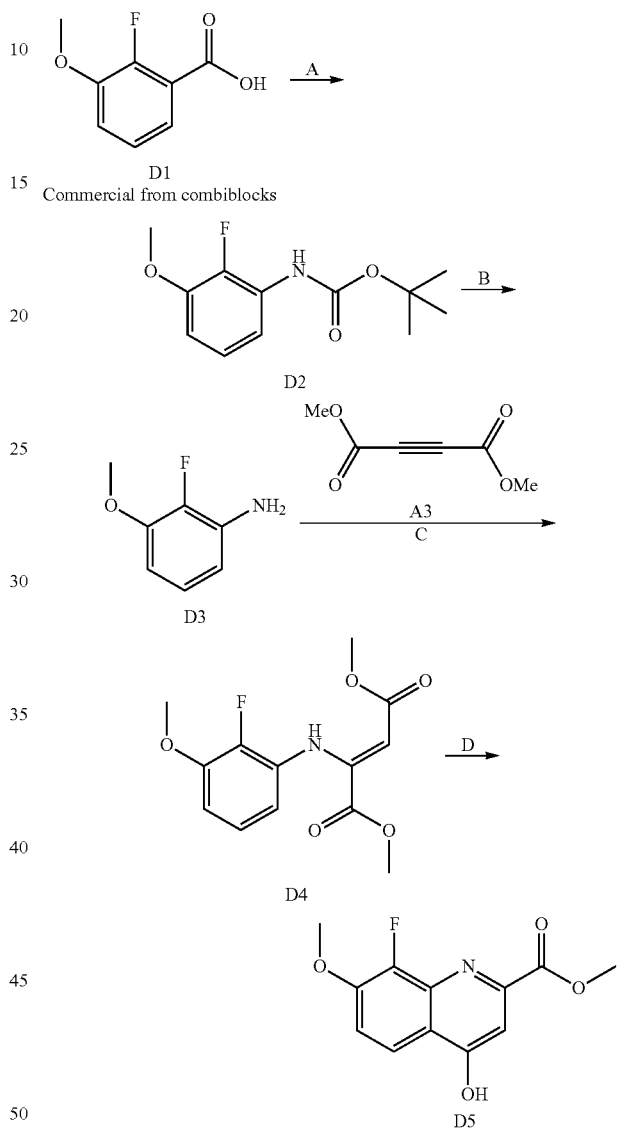

Step A

A solution of 2-fluoro-3-methoxy benzoic acid D1 (1.68 g, 9.87 mmol) and DIPEA (2.07 mL, 11.85 mmol, 1.2 equiv.) in a mixture of toluene (8 mL) and t-BuOH (8 mL) were stirred over activated 4 A molecular sieves for 1 h followed by addition of diphenyl phosphoryl azide (DPPA, 2.55 mL, 11.85 mmol) and this mixture was refluxed overnight. Reaction mixture was filtered and the filtrate was concentrated in vacuo, the residue was taken in EtOAc (50 mL), washed with H$_2$O (2×30 mL) and brine (1×30 mL). The organic phase was dried (MgSO$_4$), filtered and concentrated under reduced pressure. The crude product D2 (2.38 g, 96%) was used as is in the following step. MS analysis shows the loss of Boc group: 141.9 ((M+H)-Boc)⁺, 139.9 ((M−H)-Boc)⁻.

Step B

Compound D2 (2.28 g, 9.45 mmol) was treated with 4N HCl/dioxane solution (from Aldrich) (10 mL, 40 mmol) for 60 min and HPLC analysis showed that the starting material was fully consumed. The reaction mixture was concentrated in vacuo, re-dissolved in EtOAc and washed with water, saturated NaHCO$_3$ (aq), and saturated brine. The organic phase was dried (MgSO$_4$), filtered and concentrated to give 1.18 g (88%) of D3 as a brown oil, which was used as is in the following step. MS: 141.9 (M+H)$^+$, 139.9 (M−H)$^-$.

Step C

Aniline D3 (1.18 g, 8.36 mmol) was combined with dimethylacetylene dicarboxylate A3 (1.45 mL, 10.0 mmol) in methanol (25 mL). The reaction was refluxed for 2 hours before being concentrated to dryness. The crude material was purified by flash chromatography eluting with 9/1 (hexane/EtOAc) to give the Michael adduct D4 as a yellow oil, (1.27 g, 54%).

Step D

The Michael adduct D4 was dissolved in warm diphenyl ether (6 mL) and placed in a sand bath previously heated to ~350° C. The internal temperature of the reaction was monitored and maintained at ~245° C. for about 5 minutes (solution turns brown). After cooling to R.T., the desired 4-hydroxyquinoline crashed out of solution. The brown solid was filtered and washed several times with diethyl ether to give, after drying, quinoline D5 as a brown solid (0.51 g, 45%). MS: 252 (M+H)$^+$, 249.9 (M−H)$^-$. Mixture of 1:1 tautomers, 1H-NMR (DMSO-d6, 400 MHz) 12.04 (s, 1H), 11.02 (s, 1H), 8.0 (d, 1H), 7.88 (d, 1H), 7.65 (m, 1H), 7.39 (s, 1H), 7.32 (m, 1H), 6.5 (s, 1H), 4.0 (s, 3H), 3.98 (s, 3H), 3.95 (s, 3H), 3.91 (s, 3H).

Example 3E

Synthesis of 2-Carbomethoxy-6,8-Dimethyl-4-Hydroxy-7-Methoxyquinoline (E8)

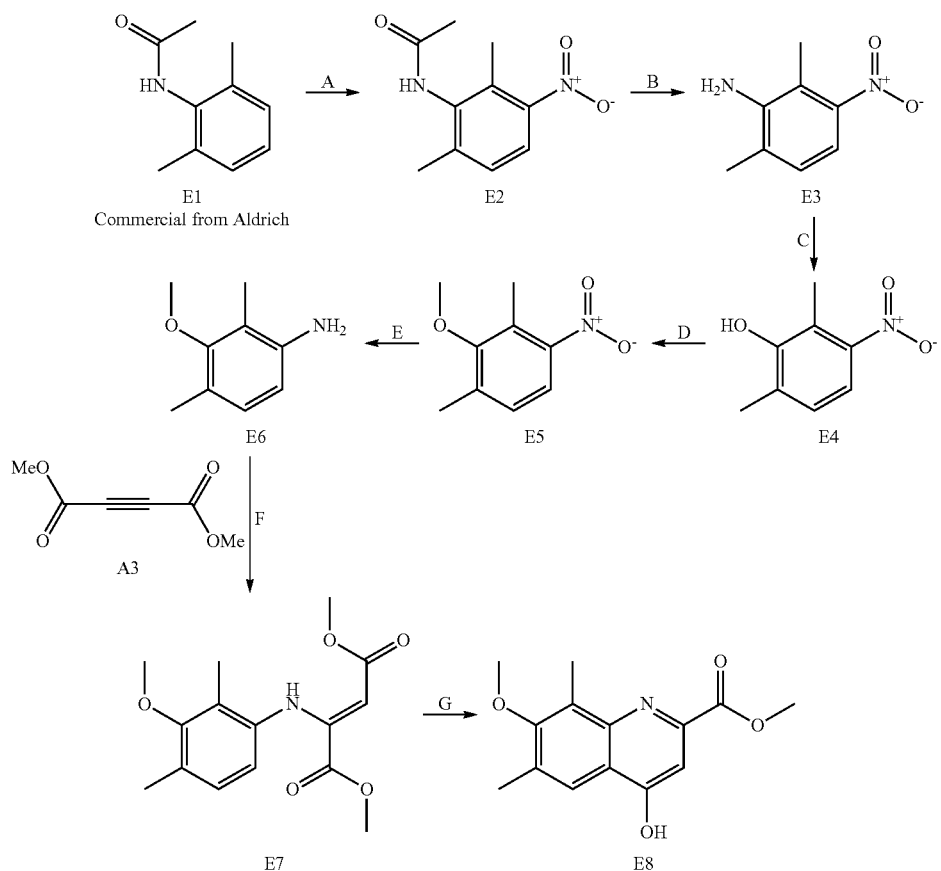

Step A

The amide E1 (5.0 g, 30.63 mmol) was dissolved in a mixture of acetic acid (5 mL) and sulfuric acid (10 mL) and cooled to 0° C. A mixture of nitric acid (70%, 3 mL) and sulfuric acid (2 mL) was added dropwise after which the solution was warmed to R.T. and stirred for 1 h. The reaction mixture was then poured onto crushed ice and filtered (after the ice had melted but the solution was still cold) to yield the desired compound E2 (5.8 g, 91%) which was carried forward to the next reaction without further purification. MS ES$^+$=209.0, ES$^-$=206.9. (Ref: Giumanini, A. G.; Verardo, G.; Polana, M. *J. Prak. Chem.* 1988, 181).

Step B

Compound E2 (5.8 g, 27.86 mmol) was treated with 6M HCl solution (5 mL) in MeOH (10 mL) and heated at reflux for 48 h to yield the desired product E3 (4.6 g, 99%). RP-HPLC indicates full consumption of starting material (R$_t$ (E2)=2.6 min.; R$_t$ (E3)=3.9 min.). The mixture was concentrated and employed in subsequent reaction without further purification.

Step C

Sulfuric acid (18 mL) was added to the solution of aniline E3 (4.20 g, 25.27 mmol) in water (36 mL) at 0° C. followed by the addition of sodium nitrite (2.3 g, 33.33 mmol in water (6 mL). In a separate flask was placed a mixture of water (14 mL) and sulfuric acid (1.5 mL). This solution was brought to reflux and then the initial solution was added dropwise while maintaining a boil. After the addition was complete, boiling was continued for 5 min and the mixture then poured onto ice/sodium carbonate mixture while cooling in an ice bath. The product was extracted with aq. EtOAc and concentrated to yield a dark brown viscous liquid E4 (2.00 g, 47%) which was employed in subsequent reaction without further purification. MS ES$^-$=210.9.

Step D

MeI (1.42 mL, 22.74 mmol) was added to a solution of the starting phenol E4 (1.9 g, 11.37 mmol) and potassium carbonate (2 g) in DMF (25 mL) at R.T. The mixture was heated at 50° C. for 2 h and then cooled to R.T. EtOAc was added and the solution was washed with water (3×) and the aq. layer was then extracted with EtOAc. The combined organic layers were dried, filtered and concentrated to yield the desired methyl ether E5 (2.0 g, 97%). $^1$H-NMR (CDCl$_3$, 400 MHz) 7.62 (d, J=8.4 Hz, 1H), 7.13 (d, J=8.4 Hz, 1H), 3.74 (s, 3H), 2.48 (s, 3H), 2.36 (s, 3H).

Step E

Ten percent (10%) Pd/C (200 mg) was added to a solution of nitro starting material E5 (2.0 g, 11.04 mmol) in EtOH and placed on a Parr shaker under 40 psi H$_2$ atmosphere for 2 h. The solution was filtered through a pad of silica/Celite, rinsed with MeOH and concentrated to yield the desired aniline E6 (1.5 g, 90%) which was employed without further purification.

Step F

Aniline E6 (1.9 g, 12.65 mmol) was combined with dimethylacetylene dicarboxylate A3 (2.32 mL, 18.85 mmol) in methanol (3 mL). The reaction was heated at reflux for 2 h before being concentrated to dryness. The crude material was purified by flash chromatography (9:1 hexane/EtOAc) to give the Michael adduct E7 as a yellow oil (2.8 g, 76%). $^1$H-NMR (CDCl$_3$, 400 MHz) 9.48, (s, br, 1H), 6.89 (d, J=7.9 Hz, 1H), 6.47 (d, J=7.9 Hz, 1H), 5.35 (s, 1H), 3.74 (s, 3H), 3.70 (s, 3H), 3.65 (s, 3H) 2.27 (s, 3H), 2.24 (s, 3H).

Step G

The Michael adduct E7 was dissolved in warm diphenyl ether (10 mL) and placed in a sand bath previously heated to ~350° C. The internal temperature of the reaction was monitored, maintained at ~245° C. for about 5 minutes (solution turns brown) and cooled to R.T. at which time the desired 4-hydroxyquinoline precipitated out of solution. The brown solid was filtered and washed several times with diethyl ether to give quinoline E8 as a yellow-brown solid after drying (1.10 g, 88%). $^1$H-NMR (CHCl$_3$, 400 MHz) 8.80, (s, br, 1H), 8.06 (s, 1H), 7.26 (s, 1H), 6.93 (s, 1H), 4.04 (s, 3H), 3.80 (s, 3H), 2.45 (s, 3H) 2.39 (s, 3H).

Example 3F

Synthesis of 2-Carbomethoxy-4-Hydroxy-7-Methoxy-6-Methyl Quinoline (F4)

Step A

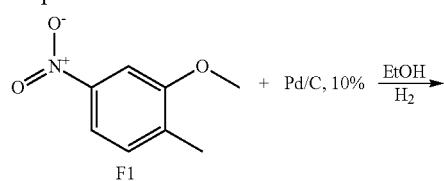

-continued

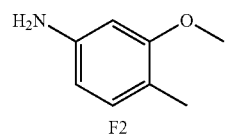

To a suspension of 2-methyl-5-nitroanisole F1 (1.54 g; 9.21 mmol) in absolute ethanol (15 mL) was added 10% Pd/C catalyst (249 mg). The suspension was hydrogenated under a hydrogen filled balloon at atmospheric pressure and room temperature for 6.5 h. The reaction mixture was filtered through a Millex 0.45 micron filter and evaporated to dryness to provide 4-methyl-m-anisidine F2 (1.22 g; 8.89 mmol; 97% yield)

Step B

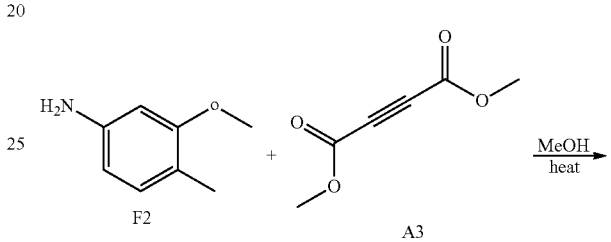

Dimethyl acetylene dicarboxylate A3 (1.1 mL, 8.95 mmol) was added dropwise to a solution of 4-methyl-m-anisidine F2 (1.22 g, 8.89 mmol) in MeOH (20 mL). Caution the reaction is exothermic. The mixture was heated at a gentle reflux for 4 hours, cooled and concentrated under vacuum. The crude material was purified by flash column chromatography on silica gel with hexane:EtOAc (92.5:7.5) to provide, after evaporation of the pure fractions, the diester adduct F3 (1.8 g; 6.44 mmol; 73% yield).

Step C

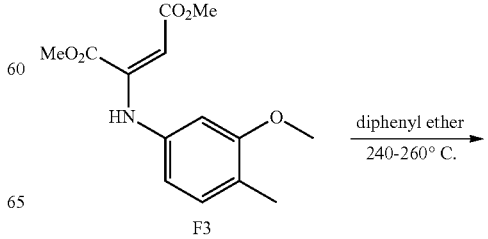

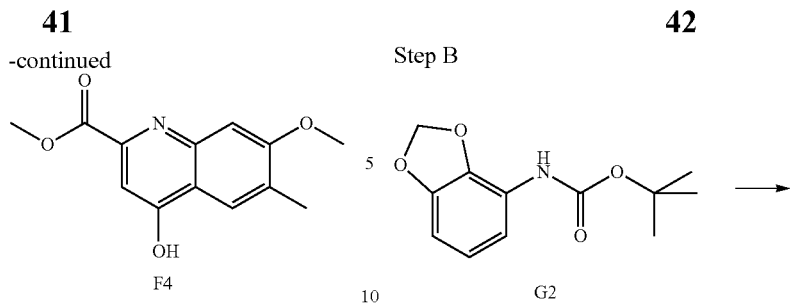

The diester F3 (1.8 g, 6.44 mmol) was dissolved in diphenyl ether (5 mL) and the reaction mixture placed into a preheated sand bath at a bath temperature of 350-400° C. Once the reaction mixture attained an internal temperature of 240° C., a count of five minutes was begun before the bath was removed and the reaction allowed to cool to room temperature overnight. A solid formed upon cooling which was diluted with ether, filtered and dried to give a brown solid (0.97 g crude) containing both regioisomers in almost equal proportions. The crude material was triturated with MeOH and EtOAc, filtered and dried to provide the correct regioisomer of the methylquinoline product F4 as a yellow solid (245 mg, 15% yield). Homogeneity by HPLC (TFA) @ 220 nm: 90%.

Example 3G

Synthesis of 2-Carbomethoxy-4-Hydroxy-[1,3]Dioxolo[4,5-h]Quinoline (G5)

Step A

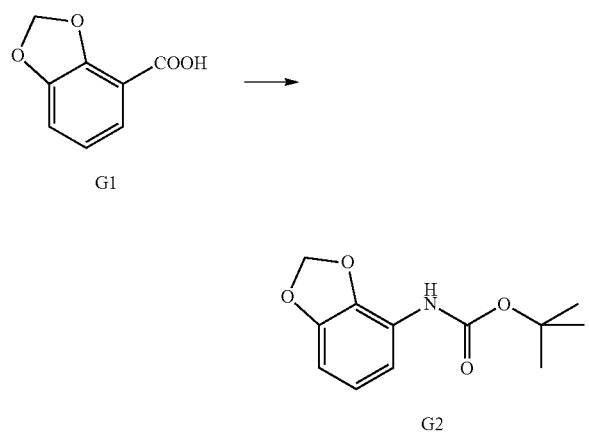

To a refluxing solution of commercially available 2,3-methylenedioxybenzoic acid G1 (485 mg; 2.92 mmol) in 1,4-dioxane (8.0 mL) and t-butanol (2.5 mL) was added TEA (430 □L; 3.08 mmol) and diphenylphosphoryl azide (DPPA, 630 □L; 2.92 mmol) and refluxed for 10 h. The mixture was evaporated, diluted with chloroform, washed with 5% citric acid (3×), water, saturated sodium bicarbonate and brine, dried (MgSO₄), filtered and evaporated to provide the crude product. Flash column purification on silica gel with hexane: EtOAc (75:25) provided the pure Boc-amino compound G2 (257 mg; 37%).

Step B

The Boc starting material G2 (257 mg; 1.08 mmol) was dissolved in 4M HCl/dioxane (5.0 mL) and stirred at room temperature for 1 hr. The solvent was evaporated and the residue diluted with saturated sodium bicarbonate (few mL) and 1 M NaOH (1 mL), extracted with EtOAc (2×), dried (MgSO₄), filtered and evaporated to dryness to provide the crude 2,3-methylene dioxyaniline G3 (158 mg; 106%).

Step C

Dimethyl acetylene dicarboxylate A3 (130 µL, 1.06 mmol) was added dropwise to a solution of crude 2,3-methylene dioxyaniline G3 (148 mg, 1.08 mmol) in MeOH (2.5 mL). Caution the reaction is exothermic. The mixture was heated at a gentle reflux for 3 hours, cooled and concentrated under vacuum. The crude material was purified by flash column chromatography on silica gel with hexane:EtOAc (9:1) to provide, after evaporation of the pure fractions, the diester adduct G4 (185 mg; 0.662 mmol; 61% yield).

Step D

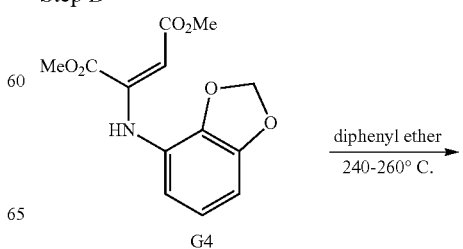

43

-continued

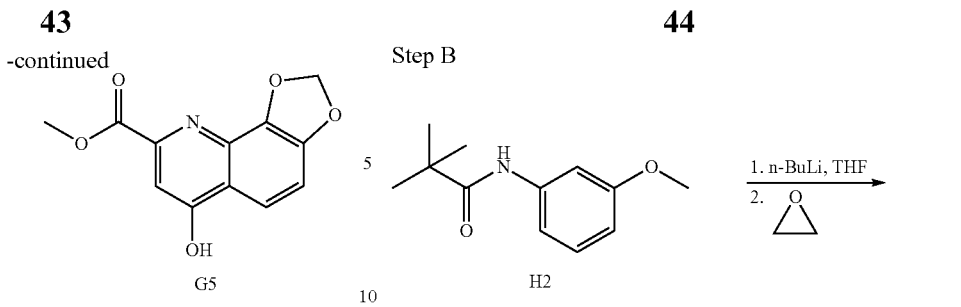

The diester G4 (180 mg, 0.645 mmol) was dissolved in diphenyl ether (2.5 mL) and the reaction mixture placed into a pre-heated sand bath at a bath temperature of 350-400° C. Once the reaction mixture attained an internal temperature of 250° C. (observe MeOH evolution at 220-230° C.) a count of six minutes was begun before the bath (temperature end point: 262° C.) was removed and the reaction allowed to cool to room temperature. A solid formed upon cooling which was diluted with ether, filtered and dried to give the crude dioxo-quinoline G5 (125 mg; 78%). Purification was not required and the material was used as such in the following reactions.

MS (M+H)$^+$; 246, and (M–H)$^-$; 248.1. Homogeneity by HPLC (TFA) @ 220 nm: 88%.

Example 3H

Synthesis of 2-Carbomethoxy-4-Hydroxy-8,9-Dihydro-Furo[2,3-h]Quinoline (H7)

Step A

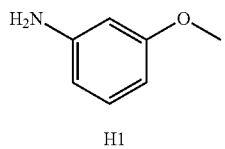

H1

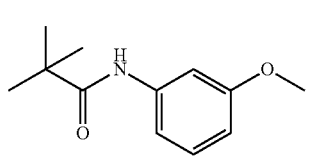

H2

Triethylamine (5.0 mL, 35.6 mmol) was added to a flask containing the amine H1 (2.0 mL, 17.8 mmol) and dichloromethane (100 mL) under an atmosphere of nitrogen. The contents were cooled in an ice bath and trimethylacetylchloride (3.3 mL, 26.7 mmol) was added dropwise. The reaction was allowed to warm slowly to R.T. and stirred for 14 h. at this temperature. The reaction was quenched with NaHCO$_3$ saturated solution and extracted with EtOAc. The combined organic layers were dried, filtered and concentrated followed by flash column chromatography (4:1 to 1:1 hexane:EtOAc) to yield the desired product H2 as an off-white solid (3.7 g, 97% yield).

44

Step B

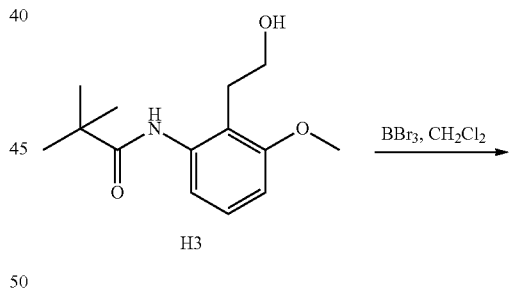

n-BuLi (15.9 mL, 1.6M, 25.5 mmol) was added dropwise to a flame dried flask containing a solution of the starting amide H2 (1.6 g, 7.72 mmol) in THF at 0° C. under argon. Solution turned slight yellow/orange color when n-BuLi was added. The solution was allowed to warm slowly to R.T. and stirred for 24 h. The solution was again cooled to 0° C. and ethylene oxide (0.46 mL, 9.26 mmol) was added dropwise. The solution was allowed to slowly warm to 23° C., quenched with NaHCO$_3$ saturated solution, extracted with EtOAc, dried, filtered and concentrated followed by flash column chromatography (4:1 to 1:1 hexane:ethyl acetate) to obtain the desired product H3 (1.94 g, 5.01 mmol, 65% yield) Homogeneity by HPLC (TFA) @ 220 nm: 99%.

Step C

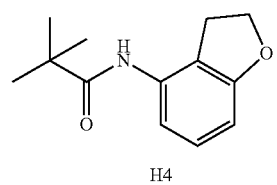

A BBr$_3$ solution (26 mL, 1.0 M, 26.0 mmol) was added dropwise to methyl-ether H3 in CH$_2$Cl$_2$ at 0° C. The solution was slowly warmed to 23° C. and stirred for 14 h at R.T. The reaction was quenched with 1M NaOH solution and extracted with EtOAc and CH$_2$Cl$_2$ to obtain a mixture of desired product H4 and some uncyclized diol. Homogeneity by HPLC (TFA) @ 220 nm: 99%.

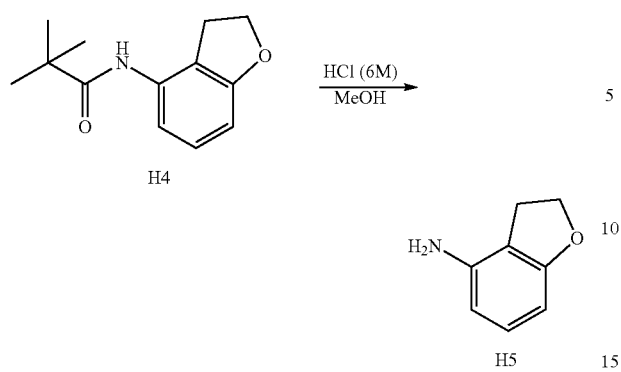

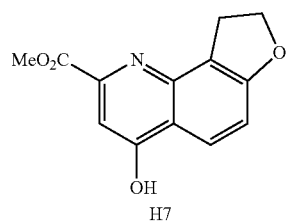

H7

A flask containing starting olefin H6 (0.29 g, 1.04 mmol) in diphenyl ether (2.0 mL) was lowered into a pre-heated sand bath (350° C.). When the internal temperature of the reaction reached 225° C., the flask was heated for 6-7 minutes during which time the internal temperature rose to 240° C. The reaction mixture was then removed from the sand bath and allowed to slowly cool to R.T. A precipitate formed upon standing. Diethyl ether was added and the solution was filtered and rinsed with additional diethyl ether to yield a light-brown solid H7 (0.20 g, 77%). MS 246.0 (MH)$^+$.

Step D

HCl (4.0 mL, 6.0M) was added to a solution of amide H4 (0.27 g, 1.22 mmol) in MeOH (4.0 mL) at 23° C. The reaction was then heated to reflux for 48 h, NaHCO$_3$ (saturated, aq) was added and was extracted with EtOAc. The combined organic layers were dried, filtered and concentrated to obtain the desired aniline H5 which was of sufficient purity to employ in further transformations.

Step E

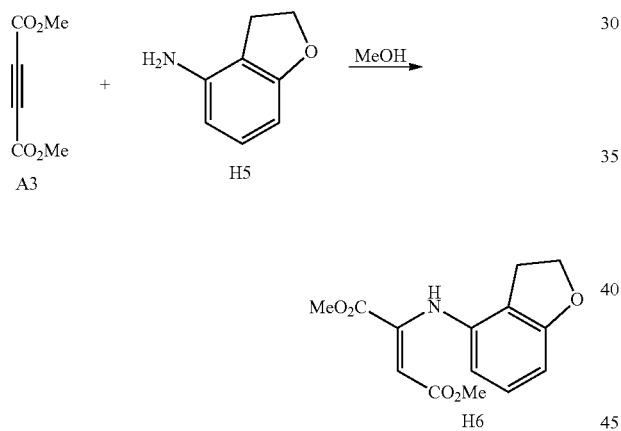

Dimethyl acetylene dicarboxylate A3 (0.16 mL, 1.33 mmol) was added to solution of aniline H5 (0.18 g, 1.33 mmol) in MeOH (3.0 mL) at R.T. The solution was heated at reflux for 3 h., cooled to R.T. and a saturated NaCl solution was added. The mixture was extracted with EtOAc (3×) and the combined organic layers were then dried, filtered and concentrated followed by purification by flash column chromatography (9:1 to 1:1 hex:EtOAc) to afford the desired olefin H6 (0.29 g, 78%).

Step F

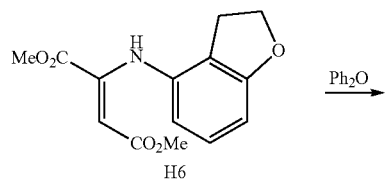

Example 3J

Synthesis of 2-Carbomethoxy-4-Hydroxy-8-Methylthioquinoline (J3)

Step A

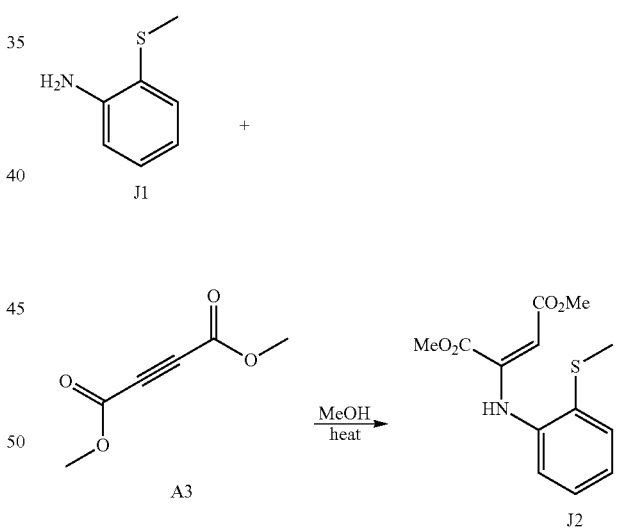

Dimethyl acetylene dicarboxylate A3 (5.21 mL, 35.91 mmol) was added dropwise to a solution of 2-methylmercaptoaniline J1 (5.0 g, 35.91 mmol) in MeOH (100 mL). Caution the reaction is exothermic. The mixture was heated at a gentle reflux for 2 hours, cooled and concentrated under vacuum. The crude material was purified by flash column chromatography with hexane:EtOAc (90:10) to provide, after evaporation of the pure fractions, the diester adduct J2 (10.53 g; 37.43 mmol; 99% yield).

Homogeneity by HPLC (TFA) @ 220 nm: 85%.

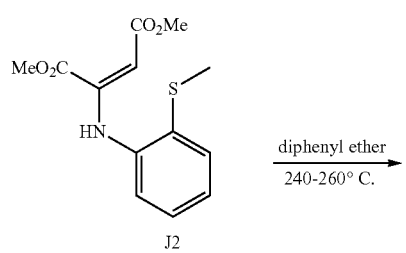

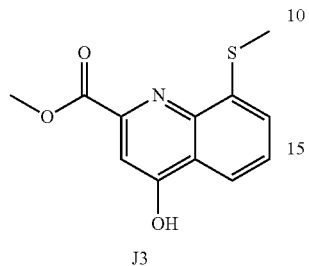

Step B

The diester J2 (10.53 g, 37.43 mmol) was dissolved in diphenyl ether (35 mL) and the reaction mixture placed into a pre-heated sand bath at a bath temperature of 350-400° C. Once the reaction mixture attained an internal temperature of 245° C., a count of six minutes was begun before the bath was removed and the reaction allowed to cool to room temperature. A precipitate formed. which was suspended in ether, filtered and washed again with ether to provide the C8-SMe quinoline product J3 (6.15 g; 66%). MS (M+H)$^+$; 250 Homogeneity by HPLC (TFA) @ 220 nm: 99%.

Example 3K

Synthesis of 7-Tert-Butyloxy-2-Carbomethoxy-4-Hydroxy-8-Methylquinoline (K6)

Step 1:

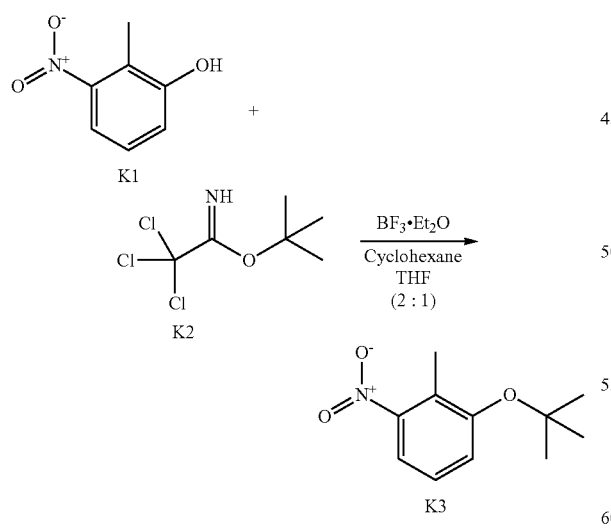

To a solution of 2-methyl-3-nitrophenol K1 (1.1 g; 7.18 mmol) in THF (13 mL) was added cyclohexane (27 mL; a solution was maintained). tert-Butyl trichloroacetimidate K2 (5.36 mL; 28.73 mmol) was added followed by a catalytic amount of boron trifluoride etherate (143.8 □L; 1.14 mmol) and the reaction was stirred at room temperature for 15 h. The reaction was incomplete (by analytical HPLC) and an additional amount of tert-butyl trichloroacetimidate (1.4 mL; 7.51 mmol) was added (reaction remains in solution). The reaction was complete after stirring at room temperature for 5 h. Solid sodium bicarbonate was added, and the mixture was filtered, rinsed with dichlormethane and evaporated to dryness to provide a white solid. The solid was triturated with dichloromethane, the white solid filtered and discarded (=trichloroacetimide). The filtrate was concentrated and loaded onto a flash column for purification (hexane:EtOAc 9:1) to provide the pure 2-methyl-3-tert-butoxynitrobenzene K3 (1.17 g; 78%). Homogeneity by HPLC (TFA) @ 220 nm: 96%

Step 2:

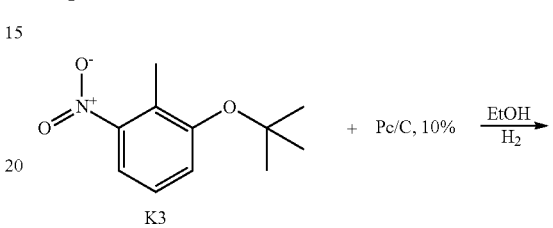

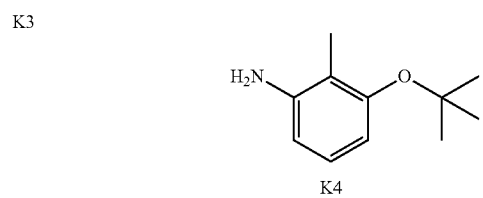

To a solution of 2-methyl-3-tert-butoxynitrobenzene K3 (1.31 g; 6.26 mmol) in absolute ethanol (30 mL) was added 10% Pd/C catalyst (130 mg). The solution was hydrogenated under a hydrogen filled balloon at atmospheric pressure and room temperature for 63 h. The reaction mixture was filtered through a Celite pad, rinsed with absolute EtOH and evaporated to dryness to provide 2-methyl-3-tert-butoxyaniline K4 (1.1 g; 6.14 mmol; 98% yield). M.S. 180 (M+H)+. Homogeneity by HPLC (TFA) @220 nm: 96%

Step 3:

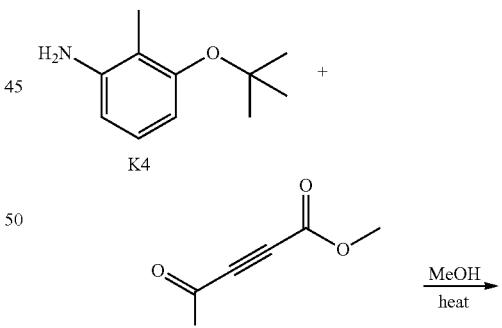

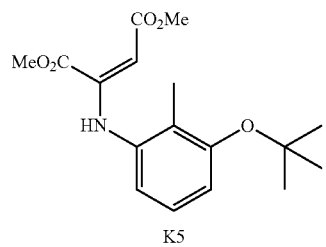

Dimethyl acetylene dicarboxylate A3 (749 μL, 5.97 mmol) was added dropwise to a solution of 2-methyl-3-tert-butoxyaniline K4 (1.07, 5.97 mmol) in MeOH (14 mL). The mixture was heated at a gentle reflux for 2 hours, cooled and concentrated under vacuum. The crude material was purified by flash column chromatography with hexane:EtOAc (95:5) to provide, after evaporation of the pure fractions, the diester adduct (1.13 g; 3.52 mmol; 59% yield). M.S. 320.0 (M−H)⁻ 322.1 (M+H)⁺. Homogeneity by HPLC (TFA) @ 220 nm: 92%.

Step 4:

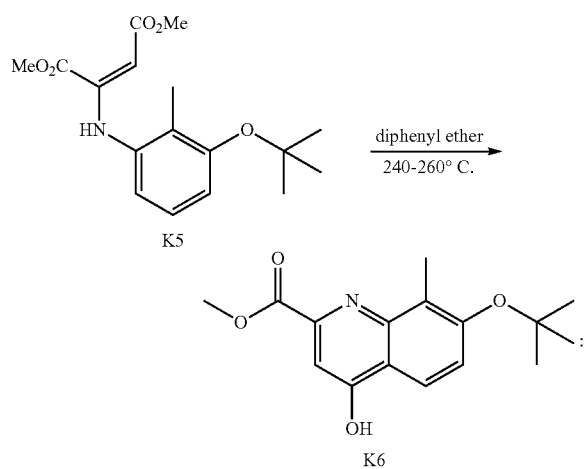

The diester K5 (1.13 g, 3.52 mmol) was dissolved in diphenyl ether (3.0 mL) and the reaction mixture placed into a pre-heated sand bath at a bath temperature of 400-440° C. Once the reaction mixture attained an internal temperature of 230° C. (observe MeOH evolution at 220° C.) a count of six minutes was begun before the bath (temperature end point: 242° C.) was removed and the reaction allowed to cool to room temperature. No solid formed upon cooling, therefore the crude mixture was flash purified with hexane:EtOAc (8:2 to remove the diphenyl ether, then, 4:6 to complete elution of the product) to provide the C7-O-tert-Bu, C8-Me quinoline K6 as a beige solid (838 mg; 82%). MS 288.0 (M−H)⁻ 290.0 (M+H)⁺. Homogeneity by HPLC (TFA) @ 220 nm: 99%.

This quinoline moiety was used for the synthesis of compounds 1032 and 1033 of table 1. For the synthesis of compounds 1034, 1035, 1057 and 1058, also of table 1, quinoline K6 was used. Conversion of the C7-tert-butyl-ether group to an hydroxyl group was done by treatment of the final compound with 50% TFA in dichloromethane for 30 min. at 0° C. then for 30 min. at R.T., evaporated to dryness, diluted with water and lyophilized.

Example 3L

Synthesis of 2-Carbomethoxy-4-Hydroxy-8-Methoxyquinoline (L3)

Step A

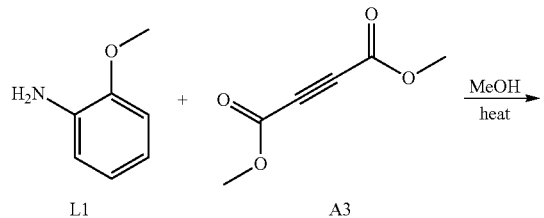

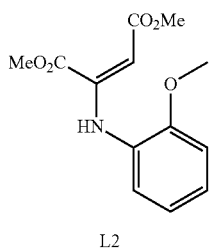

Dimethyl acetylene dicarboxylate A3 (5.5 mL, 44.74 mmol) was added dropwise to a solution of o-anisidine L1 (5.0 mL, 44.33 mmol) in MeOH (100 mL). Caution the reaction is exothermic. The mixture was heated at a gentle reflux for 5 hours, cooled and concentrated under vacuum. The crude material was purified by flash column chromatography with hexane:EtOAc (95:5 to 90:10) to provide, after evaporation of the pure fractions, the diester adduct L2 (10 g; 37.70 mmol; 85% yield). Homogeneity by HPLC (TFA) @ 220 nm: 82%.

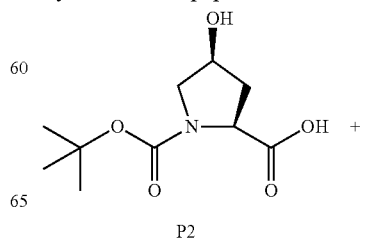

Step B

The diester L2 (10 g, 37.70 mmol) was dissolved in diphenyl ether (15 mL) and the reaction mixture placed into a pre-heated sand bath at a bath temperature of 350-400° C. Once the reaction mixture attained an internal temperature of 240° C., a count of six minutes was begun before the bath was removed and the reaction allowed to cool to room temperature. No solid formed upon cooling, therefore, the crude mixture was flash column purified with hexane:EtOAc (6:4 to 5:5 to remove impurities, then, 2:8 to complete elution) to provide the C8-OMe quinoline product L3 (4.56 g; 52%). MS (M−H)⁻; 231.9 Homogeneity by HPLC (TFA) @ 220 nm: 99%.

Example 4

Preparation of Dipeptides

Synthesis of Dipeptide 1

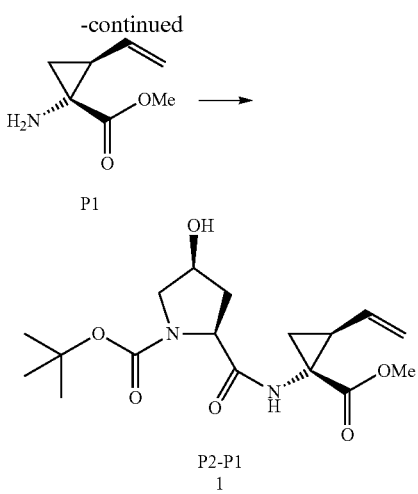

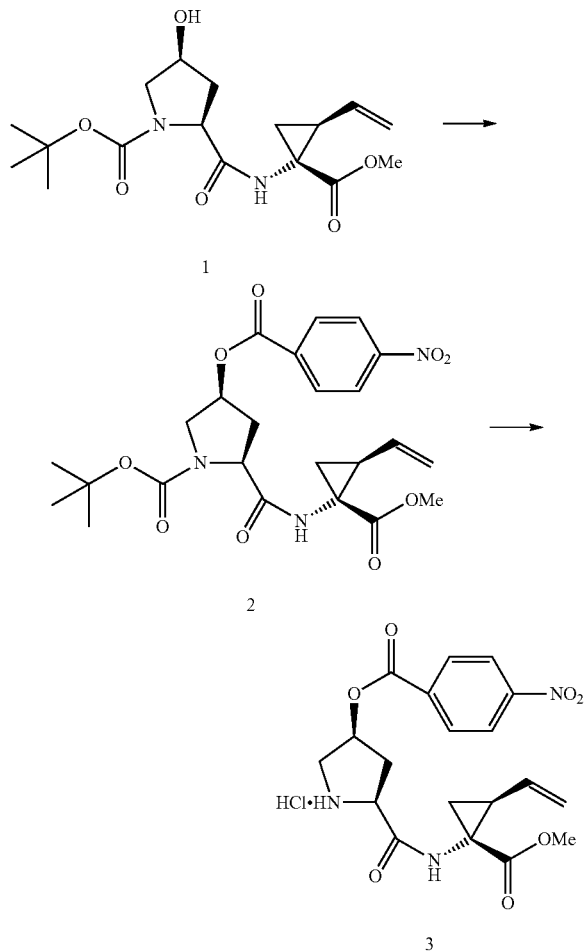

A mixture of Boc-hydroxyproline P2 (50.0 g, 216 mmol), vinyl-ACCA methyl ester P1 (42.25 g, 238 mmol, 1.1 equiv.), TBTU (76.36 g, 238 mmol, 1.1 equiv.) and DIPEA (113 mL, 649 mmol, 3 equiv.) in DMF (800 mL) was stirred at R.T. under a nitrogen atmosphere. After 3.5 h, the solvent was evaporated and the residue extracted with EtOAc. The extract was washed with hydrochloric acid (10%), saturated sodium bicarbonate and brine. The organic phase was then dried over magnesium sulfate, filtered and evaporated to afford an oil. After drying overnight under high vacuum, dipeptide 1 was obtained as a yellow foam (72.0 g, 94%, purity >95% by HPLC).

Preparation of Dipeptide 3

Dipeptide 1 (72.0 g, 203 mmol), triphenylphosphine (63.94 g, 243.8 mmol, 1.2 equiv.) and 4-nitrobenzoic acid (41.08 g, 245.8 mmol, 1.2 equiv) were dissolved in dry THF (1.4 L) The stirred solution was cooled to 0° C. under a nitrogen atmosphere. Diethyl azodicarboxylate (38.4 mL, 244 mmol, 1.2 equiv.) was then added dropwise over 45 min and the reaction allowed to warm to R.T. After 4 h, the solvent was evaporated. The residue was divided into four portions. Each of these was purified by chromatography over fine silica gel (10-40 μm mesh, column diameter 12 cm, column length 16 cm) using a gradient of 2:1 hexane/EtOAc to 1:1 hexane/EtOAc to pure EtOAc. In this manner, the Boc-dipeptide ester 2 was obtained as an amorphous white solid after evaporation of the solvents and drying of the residues under high vacuum at 70° C. for 1 h (108.1 g, quantitative). A solution of 4N hydrogen chloride in dioxane was added to the Boc-dipeptide ester 2 (108 g, 243 mmol) resulting in a colorless solution. The solution was stirred at R.T. for 1 h. The solvent was evaporated and the residue placed under high vacuum for 3 h affording the hydrochloride salt of compound 3 as an amorphous solid. The solid was used as such.

Example 5

Preparation of Tripeptides

Synthesis of tripeptide 6a

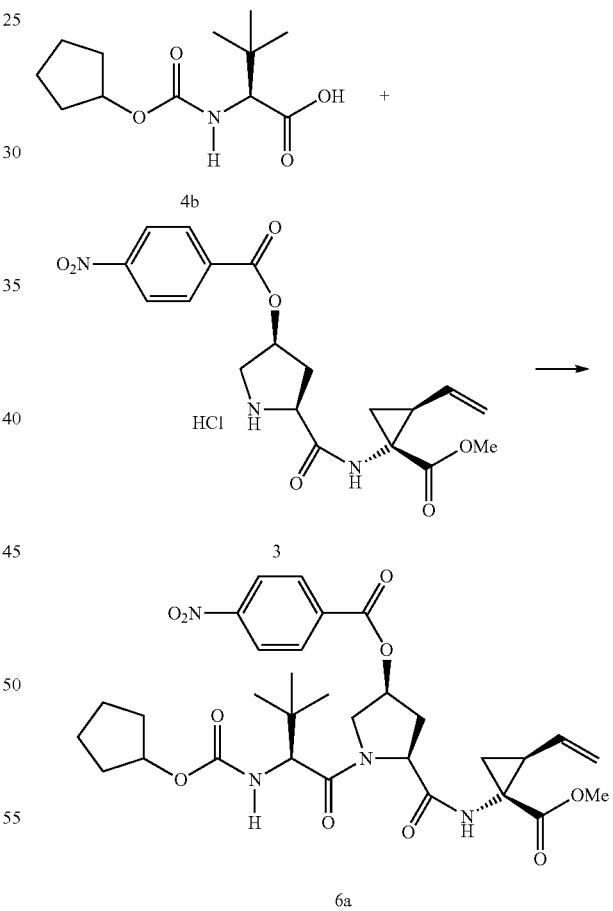

Carbamate 4b (6.15 g, 22.5 mmol) and TBTU (7.72 g, 24.7 mmol) were suspended in DCM and the suspension was stirred rapidly. DIPEA (3.92 mL, 22.5 mmol) was added at R.T. and after 10 min, the reaction was nearly homogeneous. A solution of dipeptide 3 (10.39 g, 23.6 mmol) in anhydrous DCM (100 mL) containing DIPEA (4.11 mL, 23.62 mmol) was then poured into the reaction. The resulting yellow solution was allowed to stir for 14 h. The solvent was then evaporated yielding a yellow syrup which was extracted with EtOAc (300+150 mL) and washed with 0.05N HCl (2×200 mL), saturated Na₂CO₃ (300 mL) and brine (150 mL). The combined extracts were dried over MgSO₄ and evaporated to yield the tripeptide 6a as a pale yellow foam (15.68 g, quantitative).

Synthesis of Tripeptide 7a:

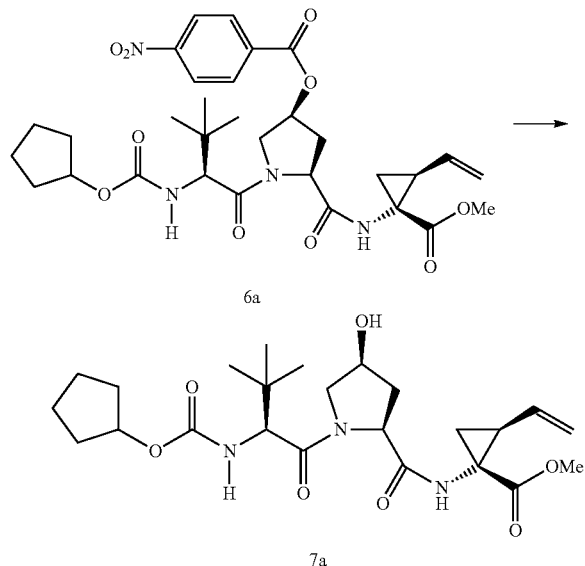

The tripeptide 6a (15.68 g) was dissolved in THF (200 mL) and water (30 mL) was added. The resulting solution was cooled to 0° C. and a solution of lithium hydroxide monohydrate (1.18 g, 28.12 mmol) was added over 3 min with vigorous stirring. After 3 h at 0° C., the excess base was neutralized with 1N HCl (final pH ca. 6) and the THF evaporated, resulting in an aqueous suspension (yellow gum). The mixture was extracted with EtOAc (2×200 mL) and washed with saturated NaHCO₃ (2×300 mL). The combined extracts were dried over MgSO₄ and evaporated to yield a pale yellow foam. Flash chromatography of the foam over silica gel using EtOAc as eluent afforded 7a as a white amorphous solid (9.77 g, 91%).

Synthesis of Tripeptide 6b

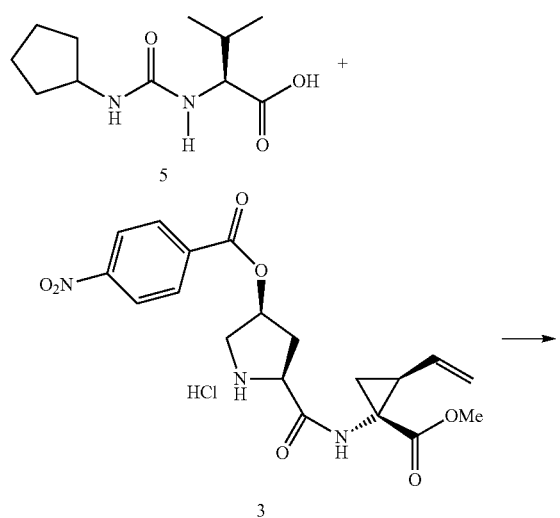

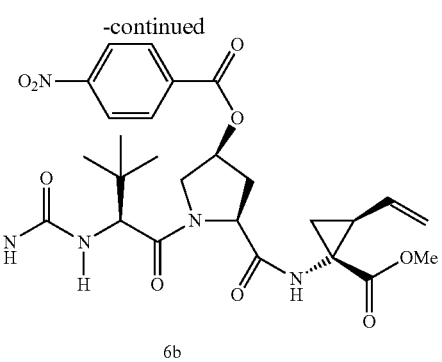

The cyclopentylurea-Tbg 5 (2.21 g, 9.10 mmol) and TBTU (3.12 g, 10.0 mmol) were dissolved/suspended in anhydrous dichloromethane (40 mL) and DIPEA (1 equiv.) was added. The reaction was stirred at ambient temperature under a nitrogen atmosphere until the solution became nearly homogeneous (ca. 10 min). A solution of P1-P2 dipeptide (4.20 g, 9.56 mmol) in anhydrous dichloromethane (35 mL containing 1 equiv. DIPEA) was then added to the reaction and the resulting yellow solution allowed to stir for 14 h after the reaction was rendered basic by the addition of DIPEA (ca. 1.5 mL). The solvent was evaporated yielding a yellow syrup which was extracted with ethyl acetate (150+50 mL) and washed with 0.1N HCl (150 mL), water (100 mL, emulsion broken with brine), saturated Na₂CO₃ (150 mL) and brine (100 mL). The combined extracts were then dried over MgSO₄ and evaporated to a pale yellow solid 6b (6.21 g, HPLC purity 95%).

Synthesis of Tripeptide 7b

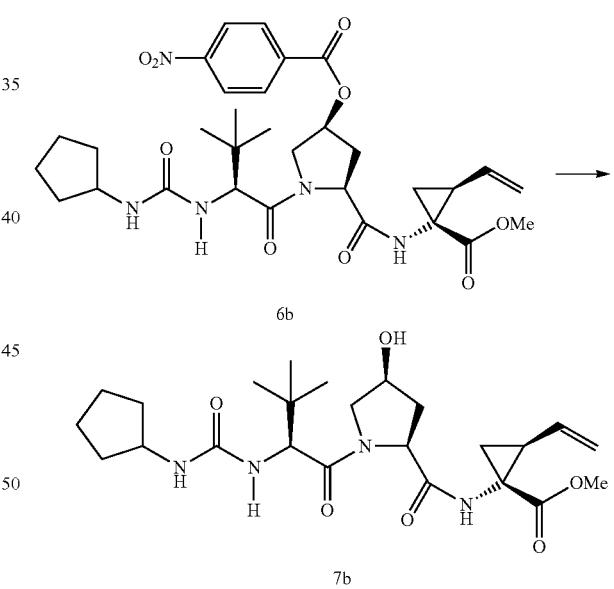

The crude pNBz ester 6b prepared above was dissolved in THF (90 mL) and methanol (40 mL) added. 1.0N sodium hydroxide solution (12.0 mL; 12.0 mmol) was then added with vigorous stirring over 10 min (dropping funnel) and the hydrolysis allowed to proceed at ambient temperature. After 2 h, the excess base was neutralized by the careful addition of 1 N HCl (ca. 1.5 mL, added dropwise until the yellow color faded; final pH ca. 6). The organic solvents were evaporated and the aqueous residue was extracted with ethyl acetate (150+50 mL) and washed with saturated sodium bicarbonate (3×150 mL) and brine (100 mL). The combined extracts were dried over MgSO₄ and evaporated to a pale yellow, amorphous solid which was dried under high vacuum 7b (4.11 g, 87% from the P3-urea, HPLC purity 93%).

Synthesis of Brosylate Derivative 7aBrs

Example 6

Introduction of Quinoline Moieties into the Tripeptides

Synthesis of Intermediate 10a via Brosylate Displacement:

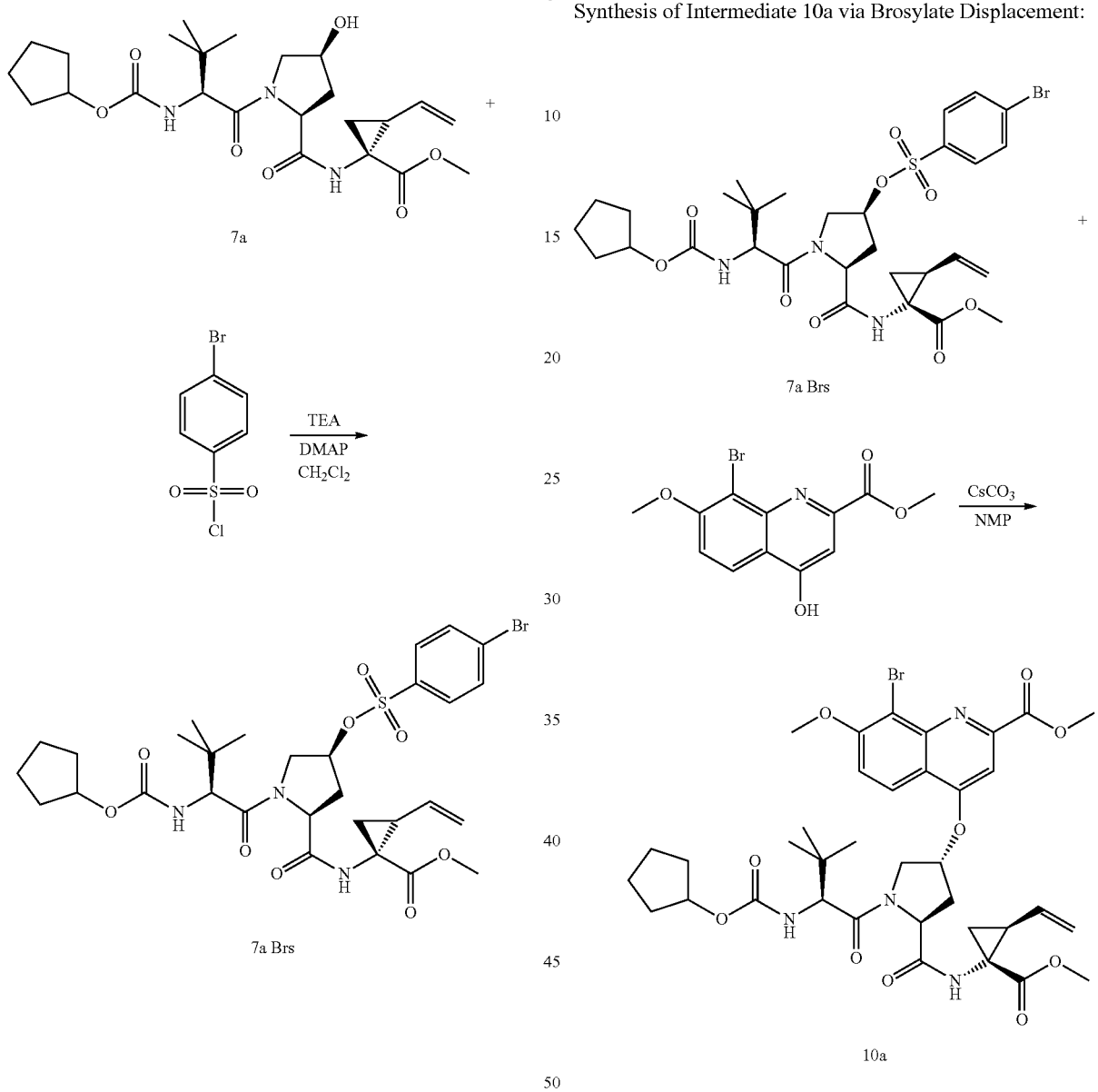

To a cooled solution (0° C.) of the tripeptide (10 g; 20.85 mmol), brosyl chloride (11.19 g; 43.79 mmol) and dimethylaminopyridine (254 mg; 2.09 mmol) dissolved in dichloromethane (75 mL), triethylamine (10.2 mL; 72.98 mmol) was added dropwise. The yellow solution was stirred 1 hour at 0° C., then was slowly allowed to warm to room temperature and stirred 60 hours at room temperature. The reaction mixture was concentrated to dryness, diluted with EtOAc, washed with saturated sodium bicarbonate solution, water and brine, dried (MgSO$_4$), filtered and evaporated to dryness to obtain the crude product The crude material was purified by flash column chromatography with hexane:EtOAc; 60:40 to 50:50 to provide the pure product 7aBrs as a white foam (11.66 g; 80%).

M.S. 698 (M+H)$^+$; 700.2 (MH+2)$^+$. Homogeneity by HPLC (TFA) @ 220 nm: 99%.

The brosylate 7aBrs (0.5 g; 0.71 mmol), bromoquinoline B6 (234 mg; 0.75 mmol) and ground cesium carbonate (56 mg; 0.78 mmol) were all dissolved in 1-methyl-2-pyrrolidinone (7.6 mL), and the solution was heated to 70° C. and stirred for 7 h. The solution was subsequently cooled to room temperature and worked-up. The reaction mixture was poured into EtOAc, washed with H$_2$O (1×), NaHCO$_3$ (saturated; 2×), brine (5×), dried, filtered and concentrated to afford the crude product (0.565 g) as an off white solid. Purification by flash column chromatography (1:30 silica gel; 7:3 EtOAc/hexane) afforded pure product 10a (77%; 0.429 g) as a white solid. MS 775.2 (M+2H)$^+$. Homogeneity by HPLC (TFA) @ 220 nm: 96%.

Synthesis of Intermediate 10b via Mitsunobu Reaction:

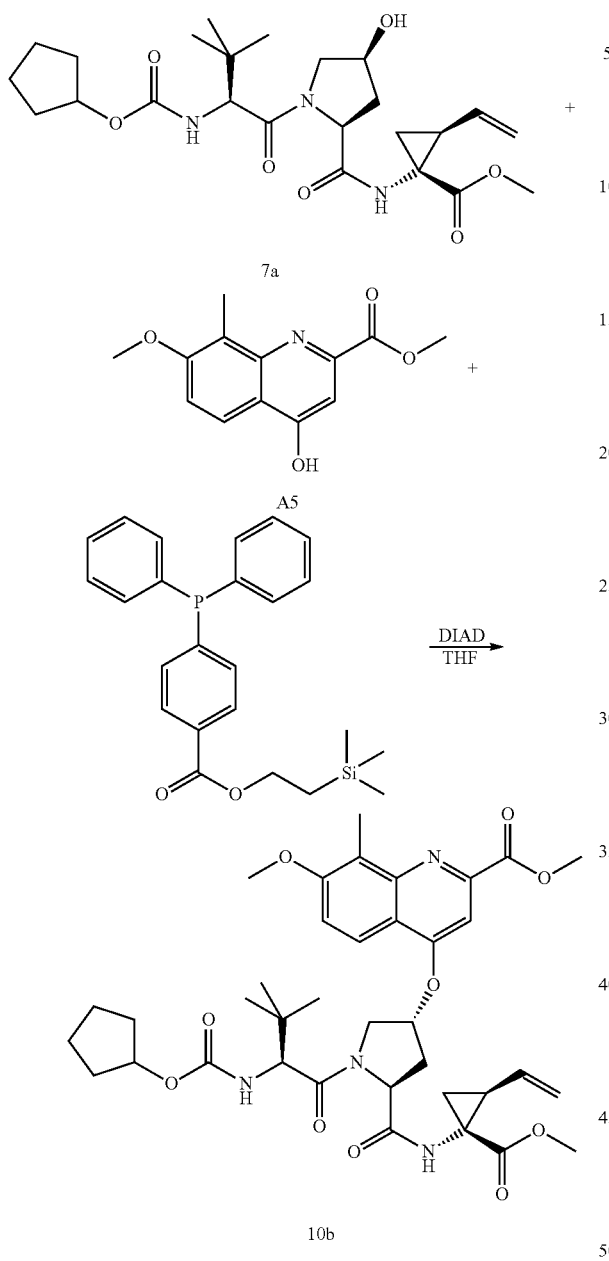

To the tripeptide 7a (1.55 g; 3.23 mmol) dissolved in THF (30 mL), the hydroxyquinoline A5 (1.08 g; 4.37 mmol) was added followed by 0.5 m triphenylphosphine silyl ester in THF (13 mL; 6.46 mmol). To the yellow suspension, was added dropwise the DIAD reagent (1.27 mL; 6.46 mmol) and stirred at room temperature for 2 hours, worked-up by dropwise addition of 1M TBAF/THF solution (11.3 mL; 11.31 mmol) and stirred at room temperature overnight. By analytical HPLC, it is evident that the cleavage of the formed phosphine oxide by-product (to a water soluble moiety) is complete. The reaction was diluted with EtOAc, washed with saturated sodium bicarbonate solution (2×), water (2×), cold 1N NaOH (2×; removes excess quinoline), water (2×) and brine (1×), dried (MgSO$_4$), filtered and evaporated to obtain a beige solid. The crude material was flash column purified with hexane:EtOAc (8:2) to obtain the product 10b as an ivory solid (1.92 g; 84%).

M.S. 707.4 (M−H)⁻ 709.4 (M+H)⁺. Homogeneity by HPLC (TFA) @ 220 nm: 94%.

Example 7

Synthesis of Compound 1007

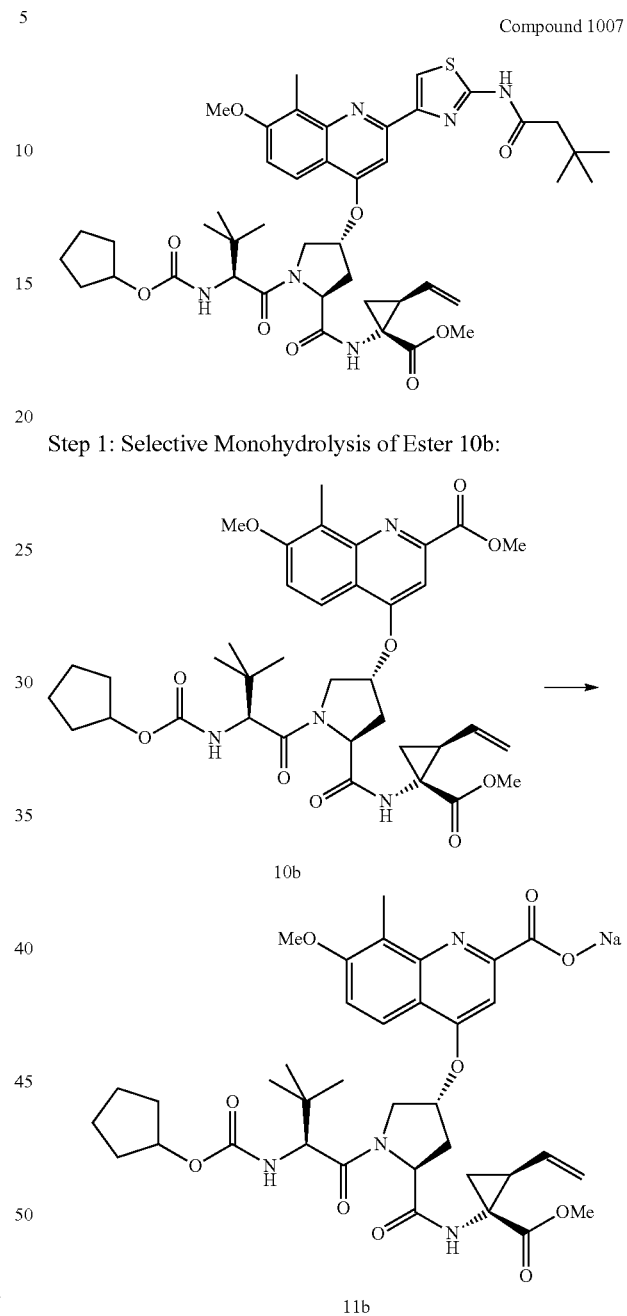

Step 1: Selective Monohydrolysis of Ester 10b:

Tripeptide 10b (149 mg, 0.210 mmol), in 5 mL of a 1:1 mixture of THF-MeOH, was cooled to 0° C. for the addition of a 1N NaOH aqueous solution (0.24 mL, 0.240 mmol). The resulting solution was stirred 15 min at 0° C., 1.5 h at R.T. and found to be incomplete by analytical HPLC. Additional 1N NaOH (0.05 mL, 0.05 mmol) was added and the reaction stirred for an additional hour. The mixture was quenched with 1 M HCl, evaporated to near dryness, diluted with water, frozen and lyophilized to provide the acid 11b (crude material used for next step; assume 0.210 mmol).

Reverse Phase HPLC Homogeneity (0.06% TFA; CH$_3$CN: H$_2$O): 89%.

Step 2: Synthesis of Diazoketone 12b:

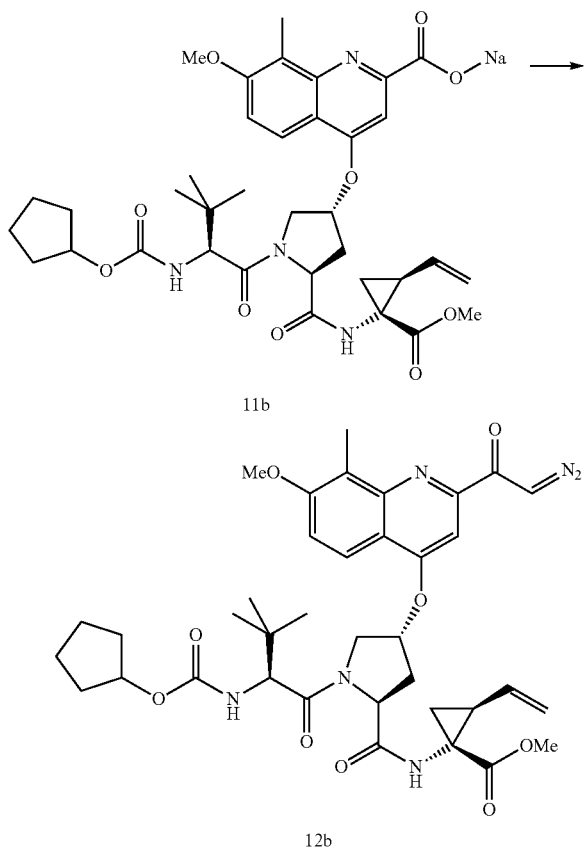

Step 3: Synthesis of Bromoketone 13b:

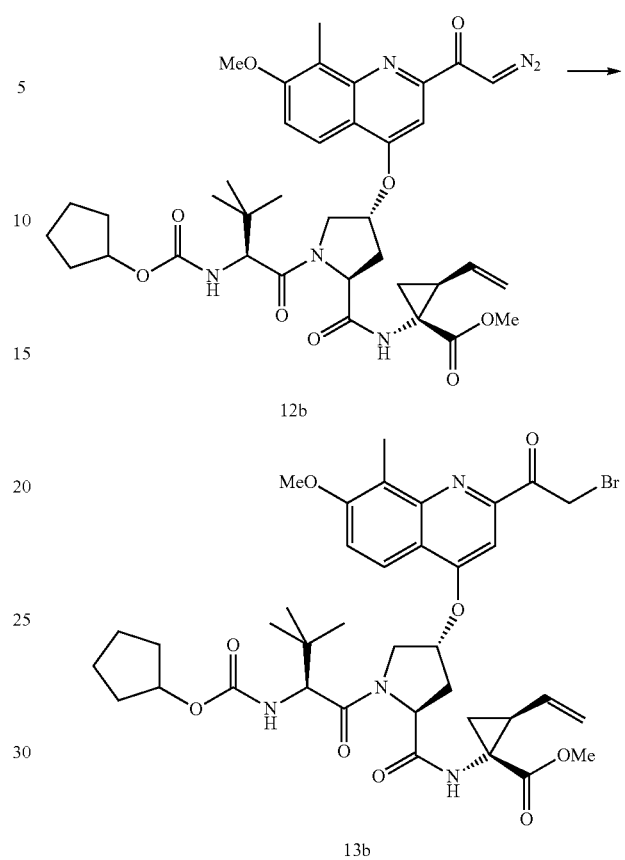

Sodium salt 11b (assume 0.210 mmol) was dissolved in THF (5 mL), triethylamine (75 µL; 0.538 mmol) was added and the solution cooled to 0° C.

Isobutylchloroformate (45 µL; 0.346 mmol) was added dropwise and the white suspension was stirred at 0° C. for 1 hour, followed by the addition of a solution of diazomethane (1M in diethyl ether; 1 mL; 0.999 mmol). The reaction mixture was stirred 15 min at 0° C., 1 hour at R.T. and evaporated to provide a thick suspension. This suspension was dissolved in EtOAc, washed with saturated NaHCO$_3$ (2×), brine (1×), dried (MgSO$_4$), filtered and evaporated to give the crude diazoketone product 12b (145 mg, 95%).

M.S. (electrospray): 717.4 (M−H)$^-$ 719.4 (M+H)$^+$. Reverse Phase HPLC Homogeneity (0.06% TFA; CH$_3$CN: H$_2$O): 85%.

At 0° C., to a solution of diazoketone 12b (145 mg, 0.201 mmol) in THF (4 mL) was added dropwise an HBr solution (48% aq., 0.1 mL) and the mixture was stirred for 1.25 h. The mixture was quenched with a saturated NaHCO$_3$ solution, then the THF was evaporated. The residue was diluted with EtOAc, washed with a saturated NaHCO$_3$ solution (2×), brine (1×), dried (MgSO$_4$), filtered and evaporated to provide the crude bromoketone 13b (139 mg, 89%).

M.S. (electrospray): 773.3 (MH+2)$^+$ 771.3 (M+H)$^+$ 769 (M−H)$^-$.

Step 4: Synthesis of Thiazolyl Tripeptide 14b:

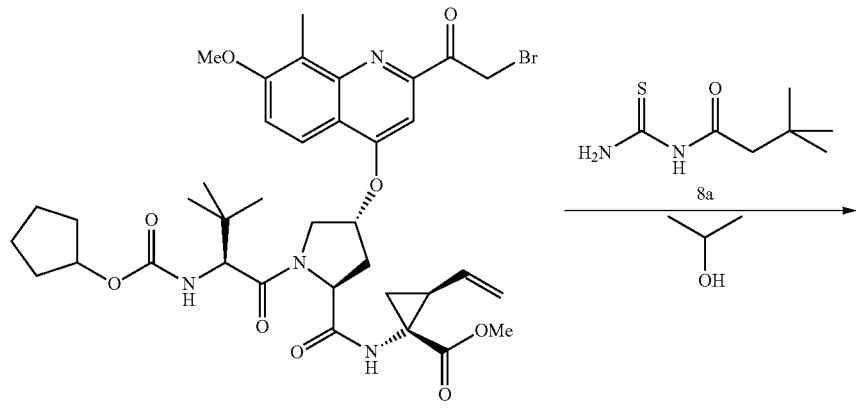

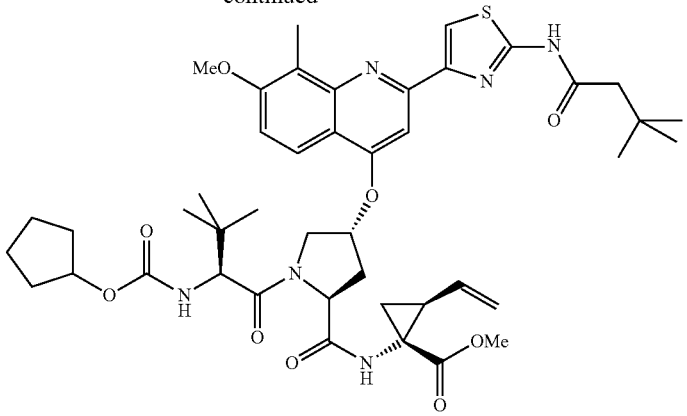

14b

α-Bromoketone 13b (49 mg, 0.0635 mmol) and N-neopentylthiourea 8a (12 mg; 0.0688 mmol) were dissolved in isopropanol (3 mL) and the yellow solution was heated at 75° C. for 1 hour. The solution was allowed to cool to R.T. and evaporated to dryness. This crude material 14b was used for next step (assume 0.0635 mmol).

M.S. (electrospray): 845.5 (M–H)⁻ 847.5 (M+H)⁺.

Reverse Phase HPLC Homogeneity (0.06% TFA; CH₃CN: H₂O): 69% (contain 16% of starting thiourea).

Step 5: Hydrolysis of Ester 14b:

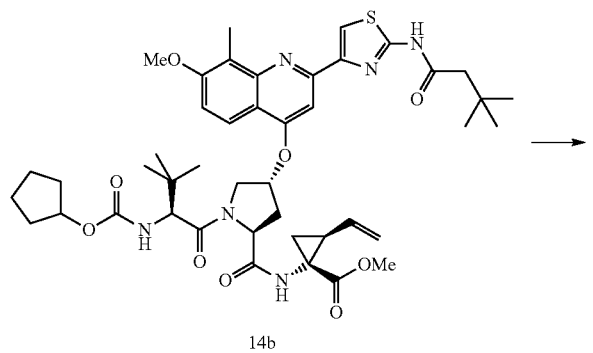

14b

Compound 1007

To a solution of methyl ester 14b (53 mg, 0.0626 mmol), in a 3.5 mL mixture of THF:H₂O (2.5:1), was added solid LiOH-monohydrate (27 mg, 0.643 mmol). 0.5 mL of MeOH was required to obtain an homogeneous solution. The resulting reaction was stirred at room temperature overnight. The organic solution was quenched with acetic acid and concentrated to provide an off white suspension. The crude material was purified by preparatory HPLC (YMC Combiscreen ODS-AQ, 50×20 mm ID S-5 micron, 120 A; ☐☐220 nm) using a linear gradient and 0.06% TFA CH₃CN/H₂O. The pure fractions were combined, concentrated and lyophilized to provide the product 1007 as the TF salt (21 mg; 40% yield).

¹H NMR (400 MHz, DMSO-d₆): ca. 85:15 mixture of rotamers, major rotamer description; ☐12.31 (br s, 1H), 8.56 (s, 1H), 8.20-8.08 (m, 1H), 8.05 (d, J=9.2 Hz, 1H), 7.46 (br s, 1H), 7.30 (d, J=9.0 Hz, 1H), 6.99 (d, J=8.6 Hz, 1H), 5.79-5.66 (m, 1H), 5.50-5.40 (m, 1H), 5.23-5.14 (m, 1H), 5.10-5.02 (m, 1H), 4.70-4.61 (m, 1H), 4.48-4.33 (m, 2H), 4.16-4.08 (m, 1H), 4.04-3.93 (m, 1H), 3.95 (s, 3H), 2.60 (s, 3H), 2.58-2.49 (m, 1H), 2.40 (br s, 2H), 2.32-2.21 (m, 1H), 2.08-1.98 (m, 1H), 1.80-1.22 (m, 10H), 1.04 (m, 9H), 0.97 (s, 9H).

M.S. (electrospray): 831.5 (M–H)⁻ 833.5 (M+H)⁺. Reverse Phase HPLC Homogeneity (0.06% TFA; CH₃CN: H₂O): 99%.

Example 8

Synthesis of Compound 5005

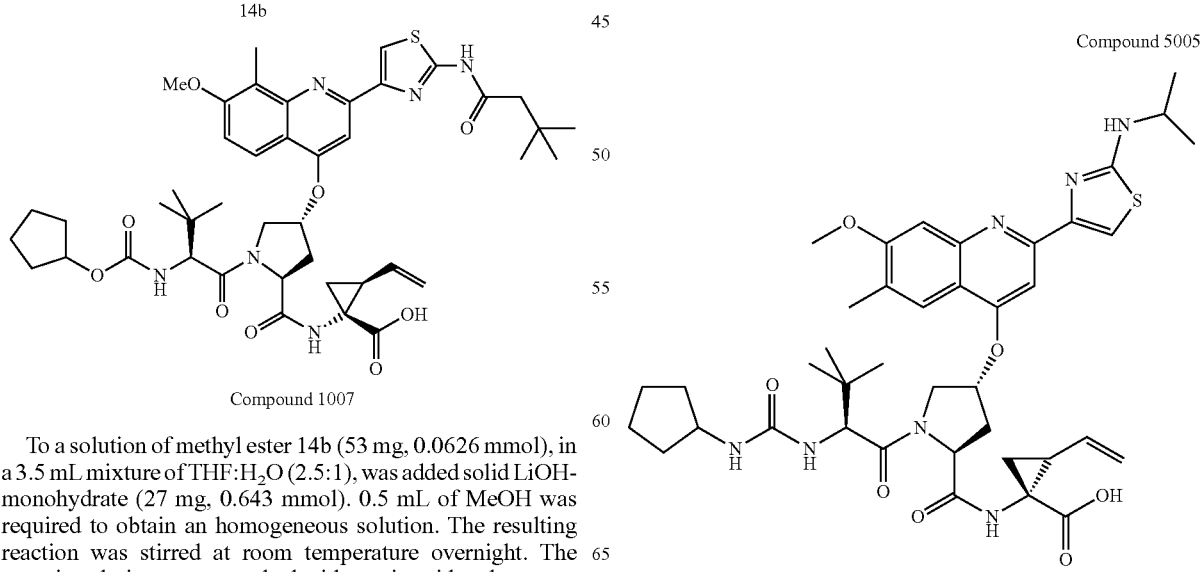

Compound 5005

Step 1:

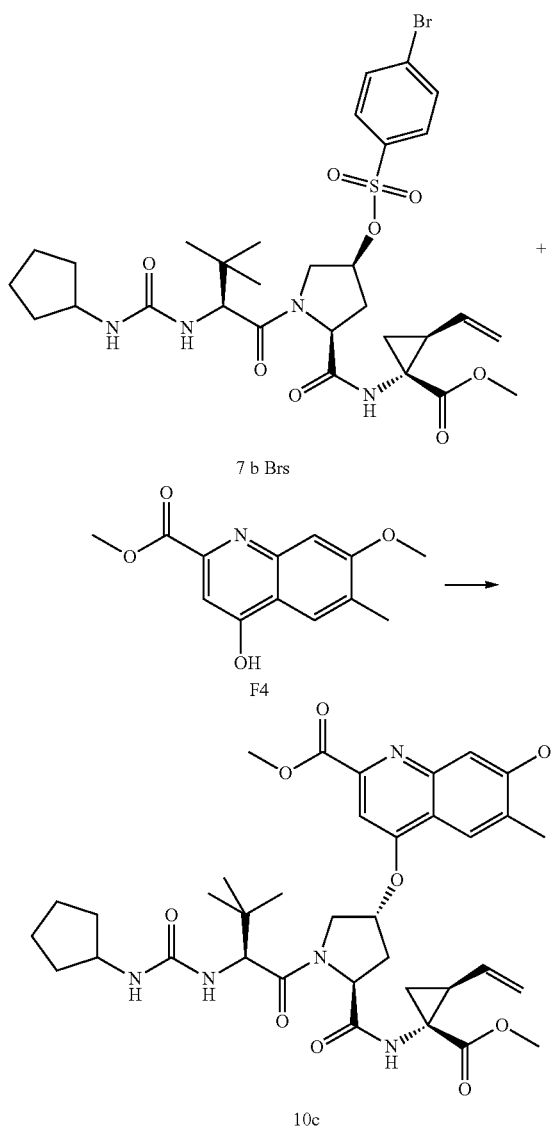

Step 1:
To a solution of the brosylate 7b Brs (1.89 g, 2.71 mmol) and quinoline F4 (670 mg, 2.71 mmol) in 1-methyl-2-pyrrolidinone (26 mL) was added cesium carbonate (971 mg, 2.98 mmol) at ambient temperature. The reaction mixture was heated at 70° C. for 12 hours, cooled to ambient temperature and diluted with EtOAc (100 mL), washed with water (2×50 mL), saturated NaHCO$_3$ solution containing 1M NaOH (⅕ of the volume) (50 mL) and brine (50 mL). The organic phase was dried over MgSO$_4$, filtered and concentrated to afford the crude product as a yellow oil, which was purified by flash chromatography over silica gel column (250-400 Mesh), eluting with EtOAc/hexanes (13:7), to afford 1.27 g of a pale yellow solid (contaminated with 20% of starting quinoline). The solid was dissolved in THF (15 mL) and the suspension was treated with CH$_2$N$_2$ (5 mL) at R.T. for 12 hours, then concentrated. The residue was purified by flash chromatography over silica gel column (250-400 mesh) eluting with EtOAc/CHCl$_3$ (12:6) to afford 0.9 g of pure 10c as a pale yellow foam (48%).

Step 2:
The conversion of the 2-carbomethoxy group of 10c into the 2-(1-oxo-2-bromo)ethyl group of 13c was done using the reaction sequence described in example 7, steps 1, 2 and 3.

Step 3:
Reaction with Thiourea Derivative and Final Hydrolysis:

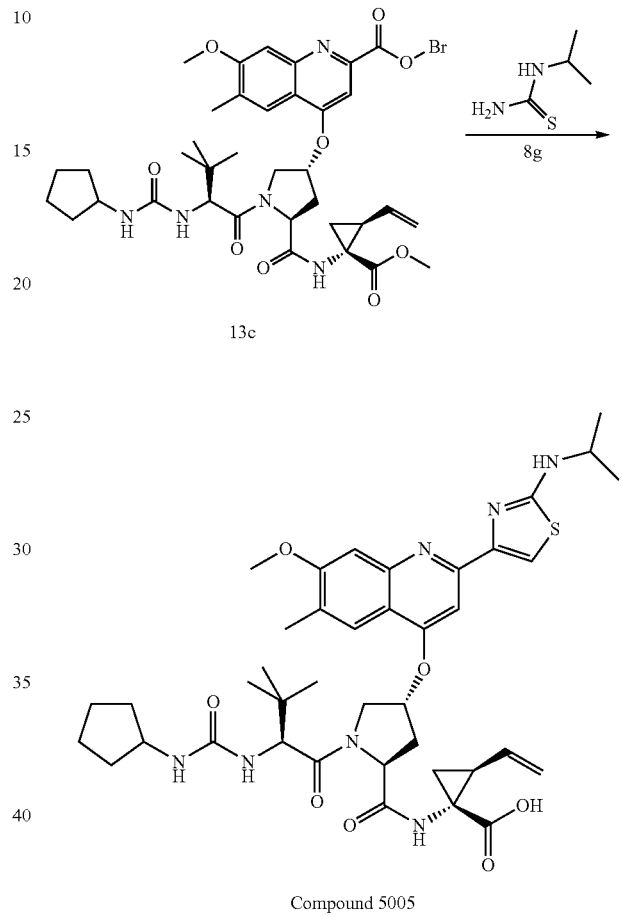

To the solution of 13c (50 mg, 0.065 mmol) in isopropanol (3 mL) was added isopropylthiourea 8g (10 mg, 0.085 mmol). The reaction mixture was stirred at 70° C. for 45 minutes. HPLC revealed complete consumption of the starting material. Cooled to ambient temperature and diluted with THF (2 mL) and 1.0N sodium hydroxide solution (0.325 mL). Stirred at ambient temperature for 12 hours, the reaction mixture was concentrated to dryness. The residue was dissolved in DMSO (2 mL) and the solution was injected onto a Combi-Prep HPLC column. The pure fractions were pooled and lyophilized to yield 26.1 mg of Compound 5005 as an amorphous yellow solid (trifluoroacetate salt) (50% yield).

$^1$H-NMR (400 MHz, DMSO-d$_6$): δ 8.60 and 8.82 (two s, 1H), 8.01-8.11 (m, 1H), 7.98 (s, 1H), 7.86 (s, 1H), 7.72 and 7.75 (two s, 1H), 5.90-6.03 (m, 1H), 5.80-5.90 (d, J=16 Hz, 1H), 5.62-5.79 (m, 2H), 5.15-5.26 (m, 1H), 4.96-5.13 (m, 1H), 4.44-4.61 (m, 2H), 4.16-4.23 (m, 2H), 4.08-4.13 (m, 2H), 3.98-4.01 (two s, 6H), 3.27-3.38 (m, 1H), 2.53-2.70 (m, 1H), 2.32 and 2.36 (two s, 3H), 1.96-2.09 (q, J=9 Hz, 17 Hz, 1H), 1.31-1.67 (m, 7H), 1.23-1.30 (m, 7H), 1.02-1.13 (m, 1H), 0.87 and 0.94 (two s, 9H).

Example 9

Synthesis of Compound 4004

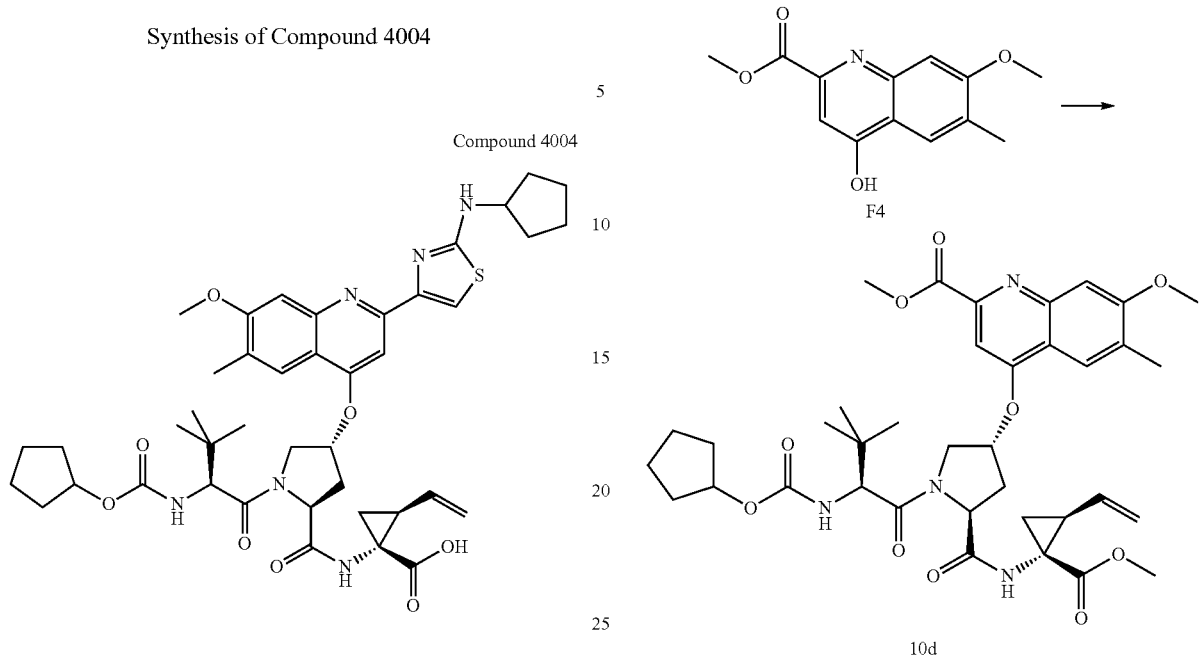

Step 1:

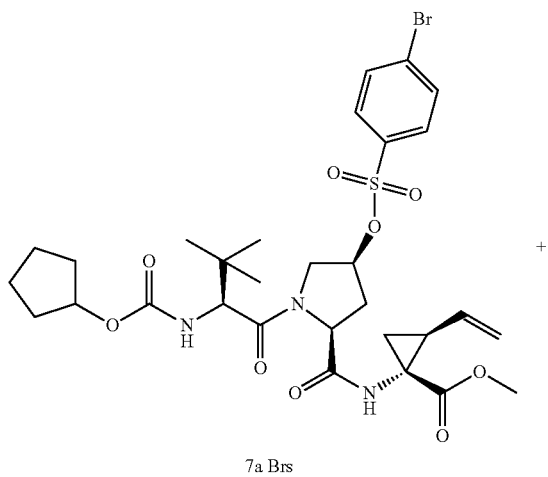

To a solution of brosylate 7a Brs (0.14 g, 0.20 mmol) and F4 (0.06 g, 0.24 mmol) in 1-methyl-2-pyrrolidinone (4 mL) was added cesium carbonate (0.08 g, 0.26 mmol). The mixture was heated to 70° C. and stirred for 7 hr. The reaction mixture was cooled, poured into EtOAc (30 mL), washed with H$_2$O (2×50 mL), sat. NaHCO$_3$ (2×50 mL), and brine (3×50 mL). The organic phase was dried, filtered and concentrated to a yellow oil. This material was purified by flash chromatography on a silica gel column (250-400 mesh) eluting with EtOAc/hexane (2:8), to afford 56 mg (40% yield) of the product 10d as a pale yellow semi-solid.

Step 2:

The conversion of the 2-carbomethoxy group of 10d into the 2-(1-oxo-2-bromo)ethyl group of 13d was done using the reaction sequence described in Example 7, steps 1, 2 and 3.

Step 3:

Reaction with Thiourea Derivative and Final Hydrolysis:

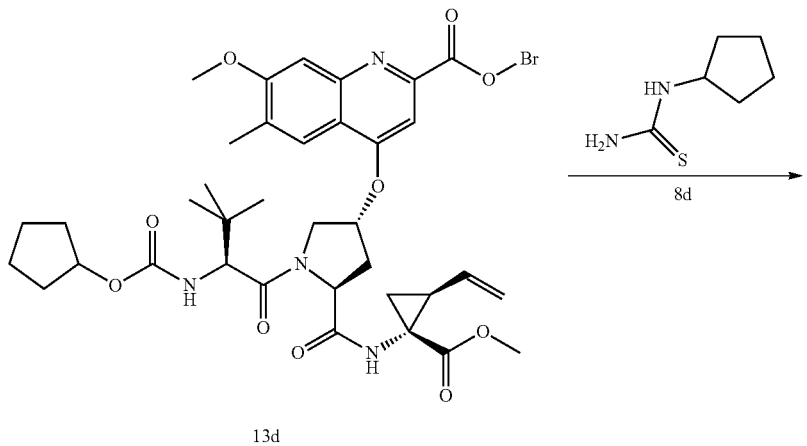

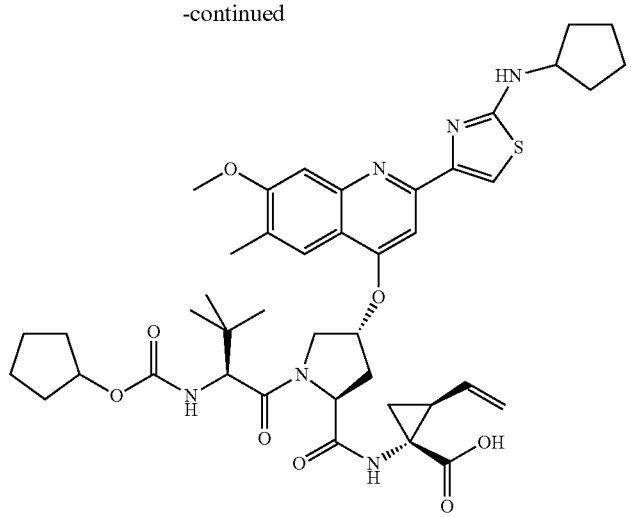

Compound 4004

To a solution of bromoketone 13d (34 mg, 0.045 mmol) in isopropanol (2 mL) was added cyclopentylthiourea 8d (8.4 mg, 0.06 mmol). The reaction mixture was stirred at 70° C. for 45 min, then concentrated to dryness and the residue was dissolved in a mixture of THF (1.5 mL) and methanol (0.3 mL). Water (0.45 mL) was added to this solution slowly with stirring, followed by LiOH (10.3 mg, 0.24 mmol). The reaction mixture was stirred at R.T. for 16 h. HPLC revealed that the reaction has proceeded to completion. The reaction mixture was concentrated, the residue was dissolved in DMSO and the solution was injected on to a Combi-prep HPLC column. The pure fractions were pooled and lyophilized to yield 16.5 mg (42% yield) of compound 4004 as an amorphous white solid (trifluoroacetic acid salt).

$^1$H NMR (400 MHz, DMSO-$d_6$) (mixture of rotamers; 8:2): δ 8.59 and 8.71 (2 s, 1H), 8.13 (m, 2H), 7.83-7.69 (m, 2H), 7.1 (d, J=8.2 Hz, 0.8H), 6.46 (d, J=8.2 Hz, 0.2H), 5.76-5.67 (m, 2H), 5.21 and 5.17 (2 s, 1H). 5.05 (d, J=11 Hz, 1H), 4.53-4.49 (m, 2H), 4.25 (br.s, 1H), 4.04-3.99 (m, 5H), 2.66-2.53 (m, 1H), 2.34 (s, 4H), 2.07-1.98 (m, 3H), 1.76-1.25 (m, 16H), 0.95 and 0.87 (2 s, 9H).

Example 10

Preparation of Dipeptides

Synthesis of Dipeptide 3:

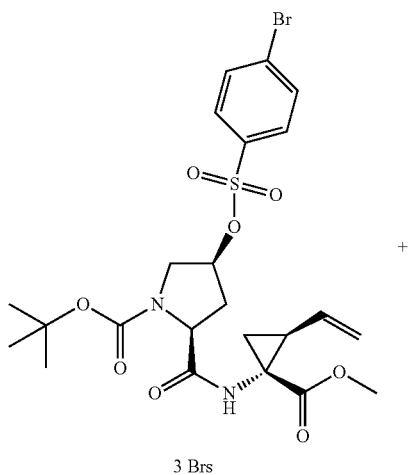

3 Brs

+

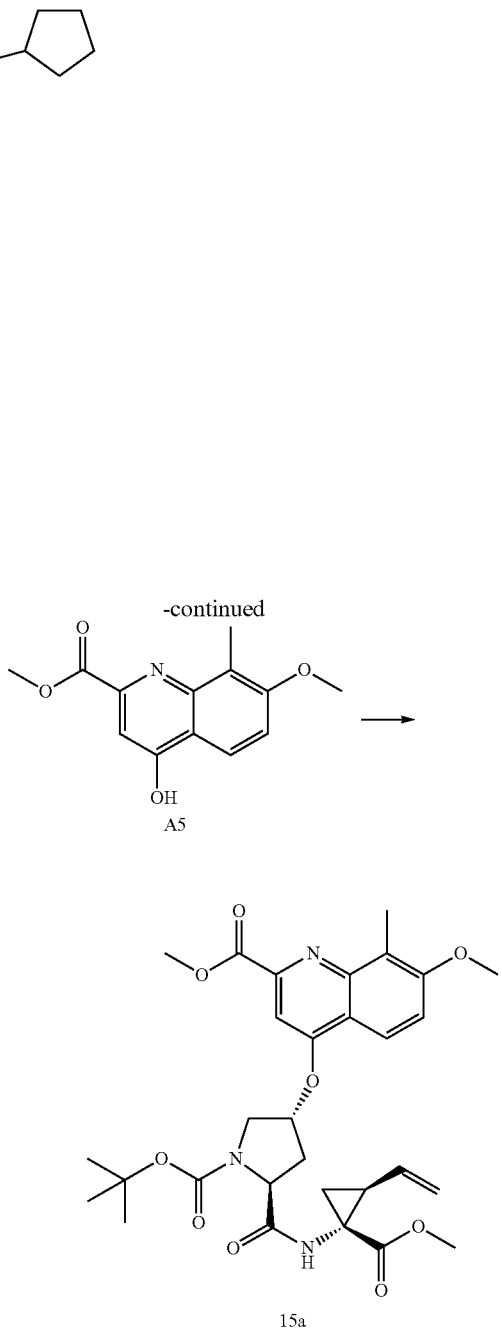

To a solution of the brosylate 3 Brs (4.2 g, 7.32 mmol) and the quinoline A5 (1.45 g, 5.86 mmol) in 1-methyl-2-pyrrolidinone (25 mL) was added cesium carbonate (3.1 g, 9.5 mmol). The mixture was heated to 70° C. for 12 h. The reaction mixture was poured into EtOAc (150 mL), washed with H$_2$O (2×150 mL), saturated solution of NaHCO$_3$ (2×150 mL) and brine (2×150 mL). The organic phase was separated, dried over Na$_2$SO$_4$, filtered and concentrated to afford the crude product as a yellow oil. This material was purified by flash chromatography over silica gel column (250-400 Mesh) eluting with 65% EtOAc in hexane to afford 15a (1.8 g, 42%) as a white solid.

Example 11

Synthesis of Compound 2015

The synthesis was done according to the following sequence:

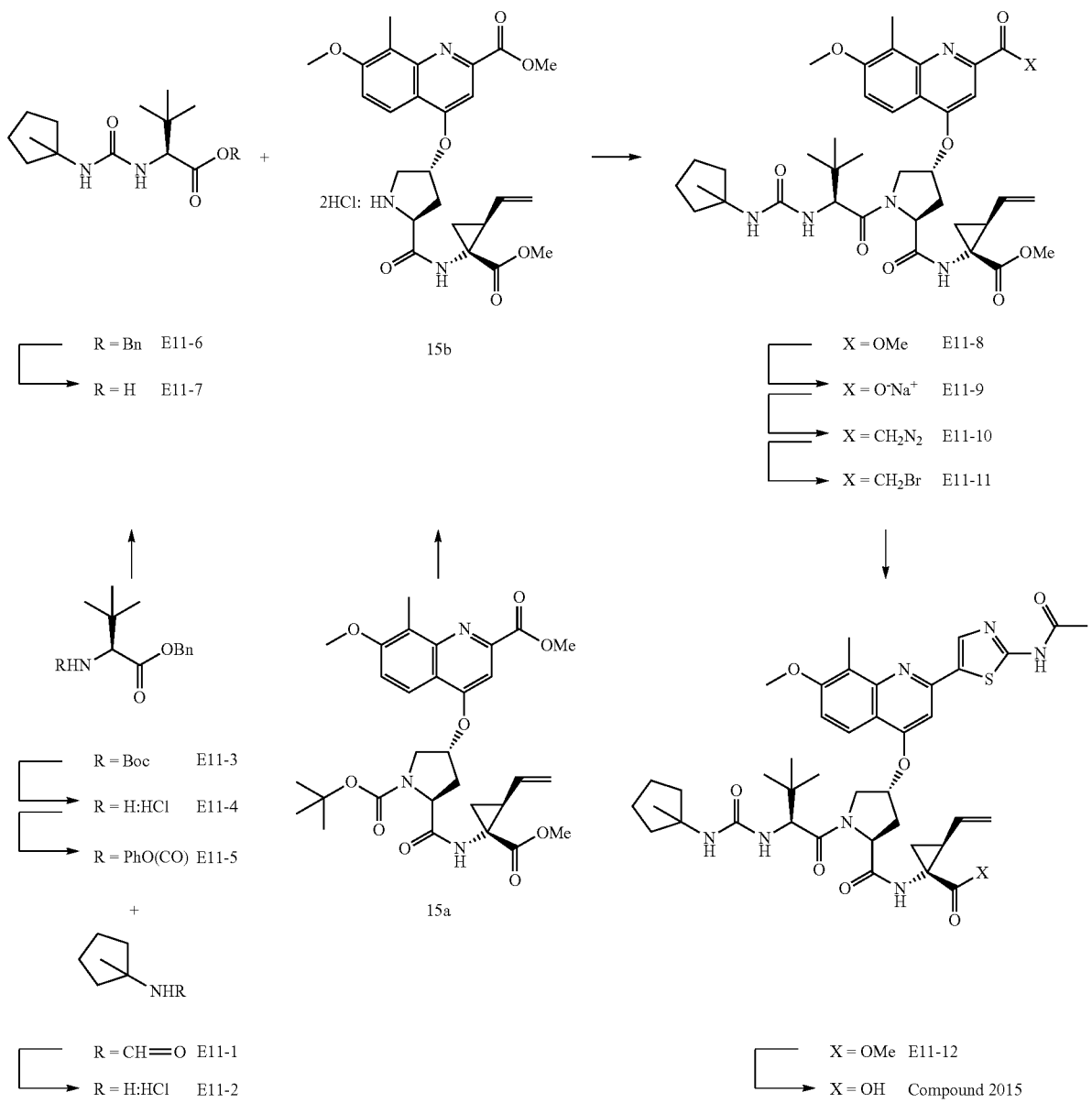

E11-1: Potassium cyanide (1.43 g, 22.0 mmol) was added to a stirred solution of methylcyclopentanol (2.00 g, 20.0 mmol) in glacial acetic acid (1.00 mL) resulting in a thick slurry. To this was added, dropwise, sulfuric acid (3 mL, caution: exothermic) at a rate at which the temperature was maintained at ca. 30-35° C. Additional acetic acid (1 mL) was added to facilitate stirring of the thick paste. The mixture was then heated to 55-60° C. for 30 min followed by stirring at ambient temperature for 16 h. Ice cold water (35 mL) was then added, the mixture extracted with ethyl ether (2×40 mL) and the combined organic phases washed with 5% NaHCO$_3$ (5×30 mL), dried over MgSO$_4$ and the solvent evaporated to yield a pale brown oil (1.16 g). The pH of the combined aqueous washings was then raised to pH 11 by the addition of solid K$_2$CO$_3$ and the resulting solids filtered and washed with ethyl ether (3×40 mL). The filtrate was extracted with ethyl ether (2×40 mL), the combined extracts dried over MgSO$_4$ and the solvent evaporated to yield additional product (0.355 g) which was combined with the above obtained oil (1.52 g, 60%).

E11-2: 5N Hydrochloric acid (8 mL) was added to a solution of E11-1 (1.50 g, 11.8 mmol) in dioxane (8.0 mL) resulting in some precipitation. Ethanol (4 mL) was then added and the solution heated to reflux for 4 h. The reaction was then cooled, the organic solvents evaporated and the aqueous residue washed with hexane (40 mL). The aqueous layer was then evaporated to dryness (ethanol was used to azeotrope the last traces of water) and the resulting solid was dried under high vacuum to yield the methylcyclopentylamine hydrochloride as a beige solid (1.38 g, 86%).

E11-3: To a stirred, ice cold solution of Boc-Tbg-OH (5.00 g, 21.6 mmol) in acetonitrile (75 mL) was added benzyl bromide (2.83 mL, 23.8 mmol) under an argon atmosphere. DBU (3.88 mL, 25.9 mmol) was then added in small portions over ca. 5 min. The resulting suspension was stirred at 0° C. for a further 30 min then allowed to warm to ambient temperature. After 3 h, the solvent was evaporated and the residue extracted with ethyl acetate (50 mL), washed with 1N HCl (2×25 mL), 5% aq NaHCO$_3$ (3×25 mL) and brine (25 mL), and then dried over MgSO$_4$ and the solvent evaporated to yield the benzyl ester as a colorless oil (6.83 g, 98%).

E11-4: The E11-3 (6.80 g, 21.2 mmol) was dissolved in dioxane (4 mL) and a solution of 4N HCl in dioxane (30 mL, 120 mmol) added. After stirring at ambient temperature for 2 h, the solvent was evaporated and the residue allowed to stand under a stream of nitrogen resulting in slow solidification. This material was then triturated with hexane (2×50 mL), filtered, air dried for 30 min then placed under high vacuum for 5 days to afford the hydrochloride salt as a white solid (4.86 g, 89%).

E11-5: To a stirred, ice cold solution of E11-4 (4.85 g, 18.8 mmol) in tetrahydrofuran (75 mL) was added diisopropylethylamine (8.20 mL, 47.0 mmol) followed by the dropwise addition of phenylchloroformate (2.60 mL, 20.7 mmol) under an argon atmosphere. A thick precipitate formed which, upon vigorous stirring, became a fine suspension. After 4.5 h, the mixture was concentrated to a third of its original volume and then extracted with ethyl acetate (50 mL) and washed with water (40 mL), 0.5 M KHSO$_4$ (40 mL), 5% NaHCO$_3$ (2×40 mL) and brine (50 mL). The organic phase was dried over MgSO$_4$ and evaporated to yield the phenyl carbamate as a colorless oil which slowly crystallized over a period of days (6.63 g, quantitative).

E11-6: To a solution of E11-5 (1.00 g, 2.93 mmol) in DMSO (2.00 mL) containing acetonitrile (1.00 mL) was added diisopropylethylamine (817 □L) followed by the amine E11-2 (477 mg, 3.52 mmol). The reaction was stirred at ambient temperature for 2 h and then heated to 70° C. for 45 min The solution was then diluted with ethyl acetate (30 mL), washed with 5% aq K$_2$CO$_3$ (4×50 mL) and brine (50 mL). The organic phase was dried over MgSO$_4$, the solvent evaporated and the residue purified by flash chromatography over TLC grade silica gel using 10:1 to 5:1 (gradient) hexane/ethyl acetate as eluent which afforded the urea E11-6 as a white crystalline solid (798 mg, 79%).

E11-7: To solution of urea E11-6 (780 mg, 2.25 mmol) in absolute ethanol (10 mL) under an argon atmosphere was added 10% Pd—C catalyst (100 mg). The system was purged three times with H$_2$ and then stirred vigorously under a hydrogen-balloon. After 3 h, the catalyst was filtered over Celite and the filtrate evaporated. The residue was then dissolved in methanol (ca. 10 mL), filtered through a Millipore Millex 0.45 uM filter and then evaporated to yield the acid E11-7 as a white solid (539 mg, 93%).

15b: The Boc-dipeptide 15a (1.23 g, 2.11 mmol) was dissolved in dry dioxane (2 mL) and a solution of 4N HCl in dioxane (10 mL, 40 mmol) added, resulting in a bright yellow solution which was allowed to stand at ambient temperature. After 3 h, the solvent was evaporated resulting in a gummy yellow solid which was triturated with dichloromethane (ca. 10 mL) and evaporated to a canary yellow powder which was dried under high vacuum (1.23 g, quantitative).

E11-8: The urea E11-7 (239 mg, 0.932 mmol) and TBTU (3.06 mg, 0.979 mmol) were dissolved/suspended in anhydrous dichloromethane (4 mL) and diisopropylethylamine (157 E1, 0.900 mmol) added. The reaction was stirred at ambient temperature under a nitrogen atmosphere until the solution became nearly homogeneous (ca. 5 min). A solution of dipeptide 15b (494 mg, 0.888 mmol) in dichloromethane containing diisopropylethylamine (314 □L, 1.8 mmol) was then added and the resulting solution allowed to stir for 3 h after the reaction was rendered basic by the addition of additional diisopropylethylamine (ca. 0.15 mL). The solvent was evaporated yielding a yellow syrup which was extracted with ethyl acetate (2×50 mL) and washed with saturated NaHCO$_3$ (2×50 mL) and brine (30 mL). The combined extracts were then dried over MgSO$_4$ and evaporated to afford the tripeptide E11-8 as a fibrous white solid (650 mg, 97%).

E11-9: The ester E11-8 (645 mg, 0.894 mmol) was dissolved in tetrahydrofuran (16 mL) containing methanol (8 mL) and 1.0N aqueous sodium hydroxide solution (900 mL, 0.900 mmol) then added dropwise with vigorous stirring at ambient temperature. After 5 h, the solution was evaporated (keeping the bath temperature below 30° C.) and then placed under high vacuum overnight to afford the carboxylate salt as a pale yellow solid (725 mg, quantitative) which was used without further purification (ca. 10% of diacid present).

E11-10: To a stirred, ice cold suspension of sodium salt E11-9 (0.894 mmol) in tetrahydrofuran (10 mL) under an argon atmosphere was added triethylamine (240 □L, 1.72 mmol) followed by the dropwise addition of isobutyl chloroformate (174 □L, 1.34 mmol). The resulting suspension was stirred at 0° C. for 3 h and a solution of diazomethane in ethyl ether (0.7M, 10 mL, 7 mmol) then added. The yellow suspension was stirred for 30 min at 0° C. and then allowed to warm to ambient temperature. After 1 h, nitrogen was bubbled through the suspension for 15 min. to remove the excess diazomethane and the solvent evaporated. The residue was extracted with ethyl acetate (20 mL) and washed with 5% aqueous NaHCO$_3$ (20 mL) and brine (20 mL). The organic phase was dried over MgSO$_4$ and evaporated to yield the diazoketone E11-10 as a yellow solid (626 mg (96%):

E11-11: To a stirred, ice cold solution of diazoketone E11-10 (620 mg, 0.850 mmol) in tetrahydrofuran (2 mL) was added dropwise 48% aqueous hydrobromic acid (144 □L, 0.850 mmol) and the reaction stirred for 30 min The solution was then diluted and extracted with ethyl acetate (30 mL) and washed with 5% aqueous NaHCO$_3$ (2×20 mL) and brine (20 mL). The organic phase was dried over MgSO$_4$ and evaporated to afford the bromoketone E11-11 as a yellow solid (611 mg, 92%).

E11-12: To a solution of bromoketone E11-11 (75 mg, 0.10 mmol) in isopropanol (0.30 mL) was added diisopropylethylamine (87 □L, 0.50 mmol) and N-acetylthiourea (18 mg, 0.15 mmol). The stirred mixture was heated to 70° C. for 1 h and then extracted with ethyl acetate (30 mL) and washed with 5% aqueous NaHCO$_3$ (20 mL) and brine (20 mL). The organic phase was dried over MgSO$_4$ and evaporated to yield the crude aminothiazole as a yellow solid which was used without further purification.

Compound 2015: The ester E11-12 (0.10 mmol) was dissolved in tetrahydrofuran (0.80 mL) and methanol (0.25 mL) and 1.0 N lithium hydroxide (800 □L, 0.80 mmol) added. After stirring at ambient temperature for 2.5, the organic solvents were evaporated and the resulting aqueous residue was diluted with DMSO (1 mL) and acetic acid (0.7 mL) and the solution injected onto a Combi-Prep HPLC column. The pure fractions were pooled and lyophilized to yield the final inhibitor 2015 as an amorphous yellow solid (trifluoroacetate salt, 16 mg, 20%): $^1$H-NMR (400 MHz, DMSO-d$_6$): δ 0.87 and 0.96 (two s, 9H), 1.19 and 1.28 (two s, 3H), 1.24-1.90 (m, 9H), 2.03 (app q4, Japp=8.8 Hz, 1H), 2.20 (s, 3H), 2.2-2.28 (m, 1H), 2.60 (s, 3H), 3.83-4.05 (m, 2H), 3.93 (s, 3H), 4.19-4.23 (m, 2H), 4.36-4.46 (m, 3H), 4.81 (app t, Japp=7 Hz, 0.2H), 5.03-5.07 (two sets of overlapping dd, 1H), 5.16-5.24 (two sets of overlapping dd, 1H), 5.38 and 5.42 (two br. s, 1H), 5.67-5.83 (m, 1H), 5.95-6.04 (m, 2H), 7.26 (d, J=9.4 Hz, 0.8H), 7.40 (d, J=9.4 Hz, 0.2H), 7.43-7.55 (br. m, 1H), 7.89 (d, J=9.2 Hz, 0.2H), 8.04 (d, J=9.2 Hz, 0.8H), 8.08 (br. s, 1H), 8.54 (s, 0.8H), 8.87 (s, 0.2H), 12.37 and 12.42 (two br. s, 1H).

Example 12

Synthesis of Compound 1038

Compound 1038

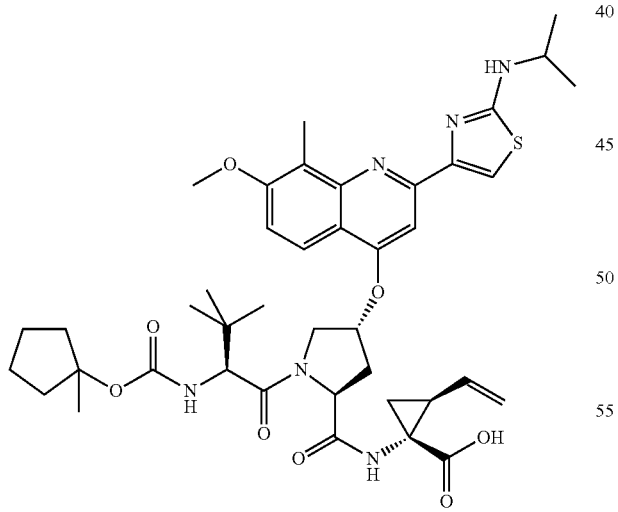

Using a reaction sequence similar to the one described in the last six steps of Example 11, but using carbamate 4c (Example 15) instead of urea 11-7, the following carbamate bromoketone E12-1 was prepared:

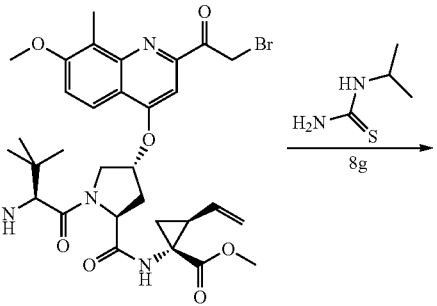

E12-1

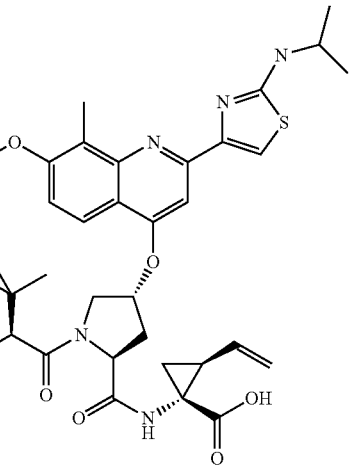

Compound 1038

Conversion of the bromoketone to final compound was done as follows: To a solution of the bromoketone E12-1 (60 mg, 0.076 mmol) in isopropanol (3 mL) was added isopropylthiourea 8g (11.7 mg, 0.99 mmol). The reaction mixture was heated at 70° C. for 45 minutes. HPLC revealed complete consumption of the starting material. The reaction mixture was cooled to ambient temperature, diluted with THF (3 mL) and 1.0N sodium hydroxide solution (1 mL) was added. After stirring at ambient temperature for 12 hours, the reaction mixture was concentrated to dryness. The residue was dissolved in DMSO (2 mL) and the solution was injected onto a Combi-Prep HPLC column. The pure fractions were pooled and lyophilized to yield 9 mg of Compound 1038 as an amorphous yellow solid (trifluoroacetate salt) (15% yield).

$^1$H-NMR 400 MHz, DMSO-d$_6$): δ 12.35 (br s, 1H), 8.56 and 8.76 (two s, 1H), 7.72-8.27 (m, 2H), 7.23-7.68 (m, 2H), 6.68-6.95 (d, J=9 Hz, 0.8H), 6.18-6.34 (d, J=9 Hz, 0.2H), 5.61-5.81 (m, 1H), 5.52 (broad s, 1H), 5.13-5.27 (m, 1H), 4.96-5.13 (m, 1H), 4.31-4.50 (m, 3H), 3.74-4.17 (m, 8H), 2.53-2.60 (m, 3H), 2.20-2.36 (m, 1H), 1.95-2.09 (m, 1H), 1.70-1.91 (m, 2H), 1.95-2.09 (m, 1H), 1.37-1.61, (m, 6H), 1.18-1.32 (m, 9H), 0.87 and 0.96 (two s, 9H).

Example 13

Synthesis of Compound 2013

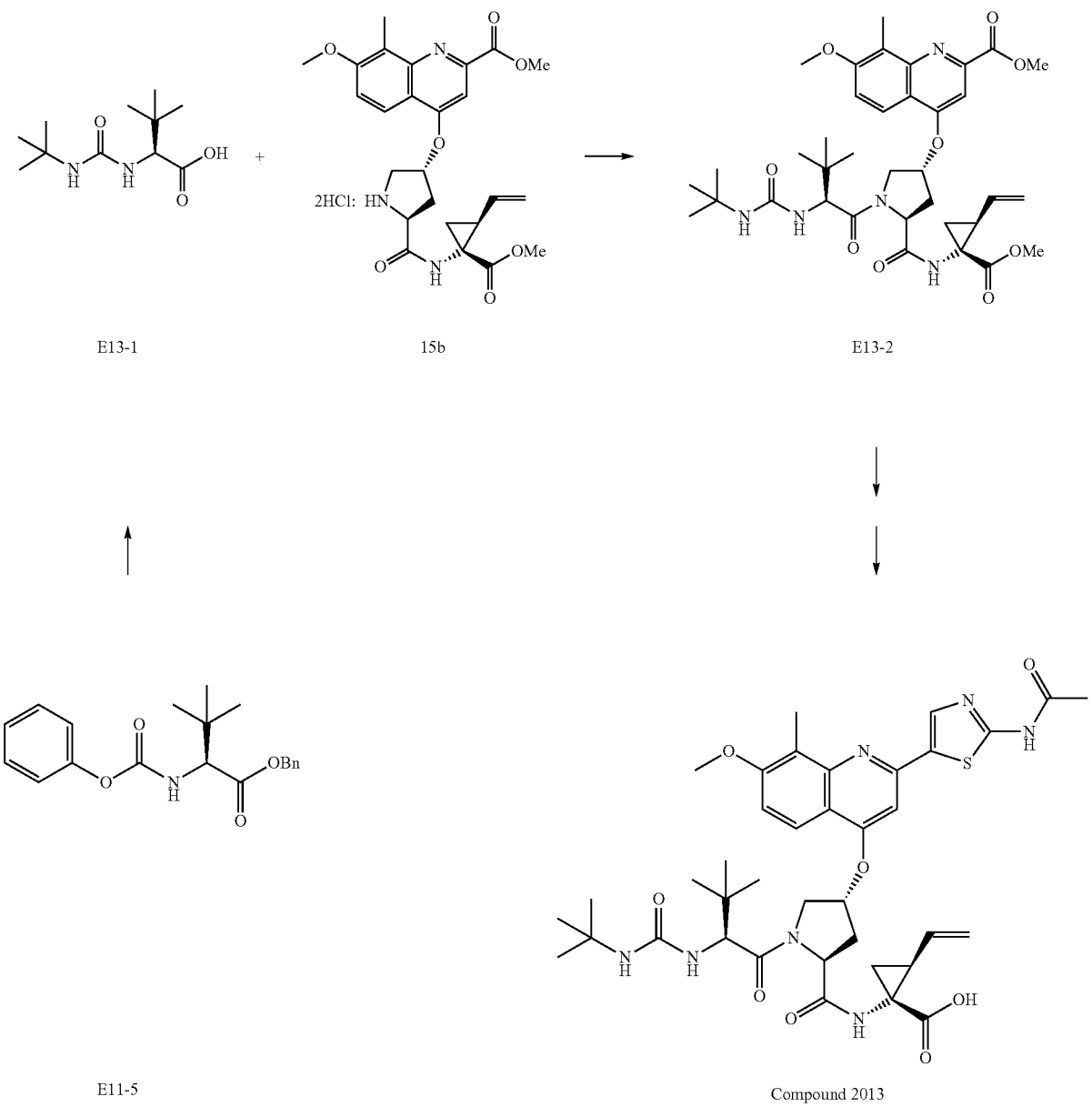

Urea Acid E13-1: The urea-P3 acid was prepared from tert-butylamine and E11-5 by the same sequence of reactions as described in Example 11.

Tripeptide ester E13-2: The urea-P3 acid was coupled with the P1-P2 fragment 15b as described in Example 11.

Compound 2013: The final inhibitor was prepared from E13-2 by a sequence of steps identical to that described in Example 11. The product of the final saponification was isolated as an amorphous yellow powder (trifluoroacetate salt, 21 mg, 28%). $^1$H-NMR (400 MHz, DMSO-$d_6$): δ 0.91 and 0.96 (two s, 9H), 1.15 and 1.21 (two s, 9H), 1.26 (dd, J=5.0, 9.4 Hz, 0.8H), 1.53 (dd, J=5.0, 7.8 Hz, 0.8H), 1.58 (dd, J=4.3, 9.2 Hz, 0.2H), 2.03 (app q4, Japp=8.8 Hz, 1H), 2.20 (s, 3H), 2.2-2.28 (m, 1H), 2.58 (s, 3H), 3.80-4.04 (m, 2H), 3.93 and 3.96 (two s, 3H), 4.18-4.20 (m, 2H), 4.35-4.45 (m, 3H), 4.83 (app t, Japp=7 Hz, 0.2H), 5.03-5.07 (two sets of overlapping dd, 1H), 5.17-5.24 (two sets of overlapping dd, 1H), 5.36 and 5.42 (two br. s, 1H), 5.66-5.80 (m, 1H), 5.86-6.04 (br. m, 2H), 7.25 (d, J=9.2 Hz, 0.8H), 7.40 (d, J=9.2 Hz, 0.2H), 7.4-7.50 (br. m, 1H), 7.88 (d, J=9.0 Hz, 0.2H), 8.03-8.15 (br. m, 1.8H), 8.54 (s, 0.8H), 8.89 (s, 0.2H), 12.38 and 12.42 (two br. s, 1H).

Example 14

Synthesis of Compound 2018

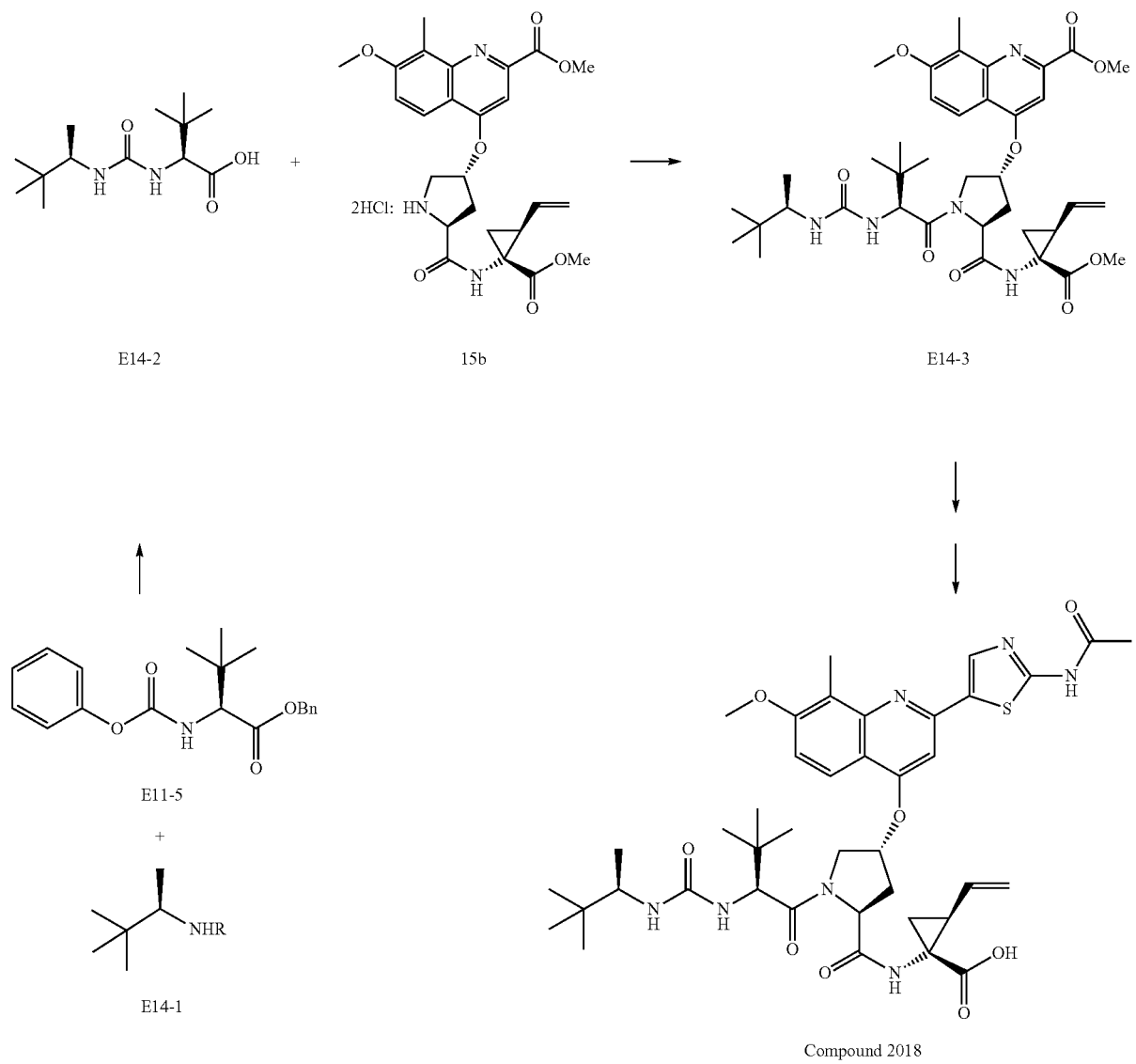

E14-2: The urea-P3 acid E14-2 was prepared from E11-5 and amine E14-1 by the same sequence of reactions as described in Example 11.

E14-3: The urea-P3 acid was coupled with the P1-P2 fragment 15b as described in Example 11.

The final inhibitor was prepared from E14-3 by a sequence of steps identical to that described on Example 11. The product of the final saponification was isolated as an amorphous yellow powder (trifluoroacetate salt, 10 mg, 21%).

$^1$H-NMR (400 MHz, DMSO-d$_6$): δ 0.74-0.97 (m, 21H), 1.25 (dd, J=5, 9 Hz, 1H), 1.47 (dd, J=8, 4 Hz, 0.2H), 1.53 (dd, J=8, 5 Hz, 0.8H), 2.02 (app q$^4$, J$_{app}$=8 Hz, 0.8H), 2.19 (s, 3H), 2.2-2.27 (m, 1H), 2.59 (s, 3H), 3.31-3.43 (m, 1H), 3.93 and 3.95 (two s, 3H), 3.98-4.02* (m), 4.22-4.26* (m), 4.35-4.39* (m), 4.82 (app t, J$_{app}$=7Hz, 0.2H), 5.01-5.06 (two sets of overlapping dd, 1H), 5.16-5.23 (two sets of overlapping dd, 1H), 5.35 and 5.41 (two br. s, 1H), 5.67-5.79 (m, 1H), 5.87 (d, J=9.4 Hz, 0.8H), 5.91 (d, J=9.4 Hz, 0.2H), 6.07 (d, J=8.6 Hz, 0.8H), 6.14 (d, J=9.2 Hz, 0.2H), 7.24-7.5 (m, 2H), 7.89 (d, J=9.2 Hz, 0.2H), 8.04-8.12 (m, 1.8H), 8.54 (s, 0.8H), 8.87 (s, 0.2H), 12.37 and 12.41 (two s, 1H). *obscured by HOD signal.

Example 15

Permutation Library

Both bromo ketones 18a and 18b were used in a permutation library for the parallel synthesis of compounds as shown in the following scheme:

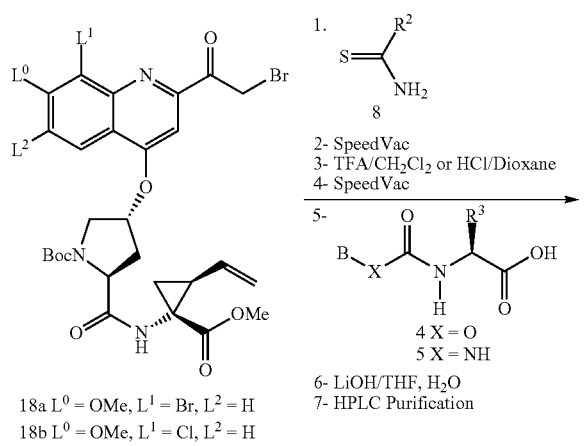

18a L⁰ = OMe, L¹ = Br, L² = H
18b L⁰ = OMe, L¹ = Cl, L² = H

2- SpeedVac
3- TFA/CH₂Cl₂ or HCl/Dioxane
4- SpeedVac
5-

4 X = O
5 X = NH

6- LiOH/THF, H₂O
7- HPLC Purification

Step 1: Formation of the Aminothiazole Ring

A series of 8-mL vials were disposed in a reaction block from an ACT496 synthesizer (from Advanced Chemtech). In each vial was added the thio-derivative (8) of interest (0.0688 mmole), the bromoketone (0.0625 mmole) and isopropanol (500 μL). The closed vials were heated at 70° C. for 1 h. The solvent was then evaporated using a vacuum centrifuge (SpeedVac) and was co-evaporated with 1,2-dichloroethane. The crude products were dried under high vacuum overnight.

Step 2: Removal of the Boc Protecting Group

All the vials were treated with 30% TFA in DCM (500 μL) for 1 h. All vials were transferred on a vacuum centrifuge to remove the volatile material.

Step 3: Coupling

In each vial was added the corresponding carbamate (21c to 21g) and carbamate acid (4b to 4k) (0.0875 mmole), HATU (0.0875 mmole, 33.27 mg) and DIPEA (0.313 mmole, 55 μL) in 500 μL of DMSO and the reaction mixture was allowed to proceed overnight.

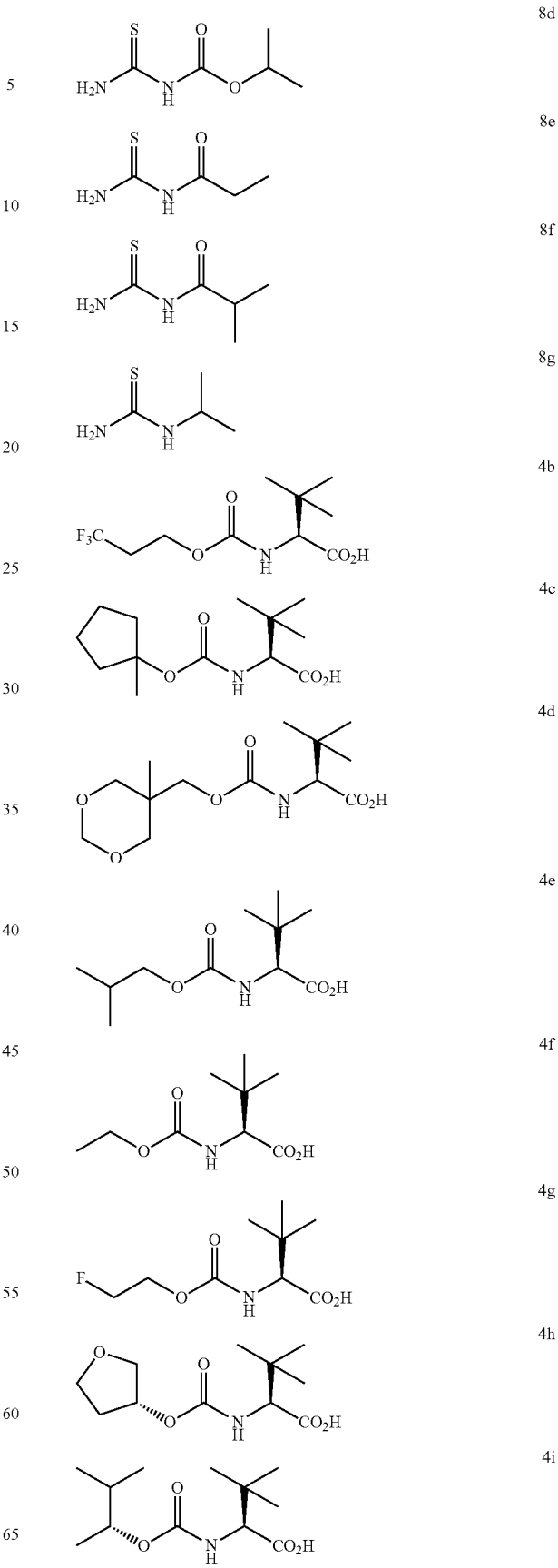

-continued

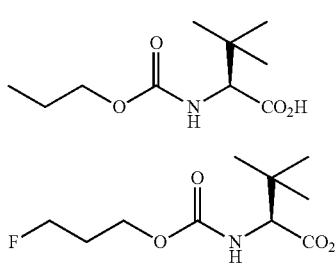

4j

4k

Step 4: Saponification and Purification

All reactions were diluted with 400 μL of DMSO and 200 μL THF. A solution of 500 μL of 2N aq LiOH (1 mmol) was added to each vial and allowed to proceed overnight after which time, the mixture was neutralized by the addition of 400 μL of AcOH. All compounds were purified by semi-prep reversed-phase HPLC (Symmetry column 5 cm×19 cm, $CH_3CN/H_2O$ 0.06% TFA gradient).

Example 16

The following compounds were prepared using reaction sequences and methodologies as described in the above examples:

Compounds from Table 1

Compound 1006

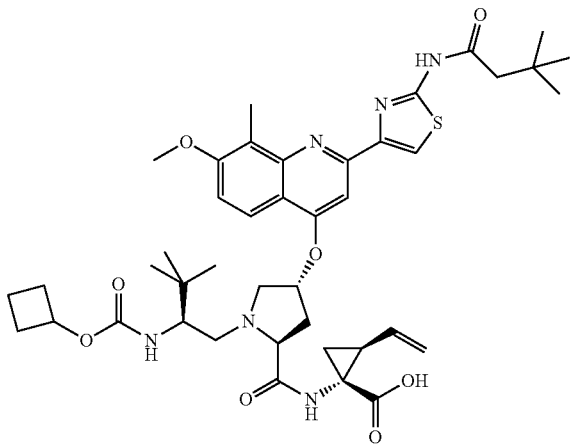

Compound 1006:

$^1$H NMR (400 MHz, DMSO-$d_6$): ca, 85:15 mixture of rotamers, major rotamer description; □12.31 (br s, 1H), 8.56 (s, 1H), 8.14 (br s, 1H), 8.06 (d, J=9.0 Hz, 1H), 7.47 (br s, 1H), 7.34 (d, J=9.0 Hz, 1H), 7.11 (d, J=8.4 Hz, 1H), 5.79-5.66 (m, 1H), 5.51-5.41 (m, 1H), 5.24-5.15 (m, 1H), 5.11-5.03 (m, 1H), 4.53-4.40 (m, 2H), 4.40-4.32 (m, 1H), 4.07 (d, J=8.6 Hz, 1H), 4.04-3.92 (m, 1H), 3.96 (s, 3H), 2.61 (s, 3H), 2.58-2.50 (m, 1H), 2.40 (br s, 2H), 2.31-2.17 (m, 1H), 2.12-1.95 (m, 3H), 1.91-1.76 (m, 2H), 1.71-1.39 (m, 3H), 1.31-1.23 (m, 1H), 1.04 (m, 9H), 0.97 (s, 9H).

M.S. (electrospray): 817.4 (M−H)$^−$ 819.5 (M+H)$^+$. Reverse Phase HPLC Homogeneity (0.06% TFA; $CH_3CN$:$H_2O$): 99

Compound 1030

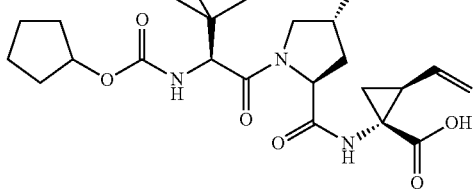

Compound 1030:

$^1$H NMR (400 MHz, DMSO-$d_6$): ca, 85:15 mixture of rotamers, major rotamer description; □8.56 (s, 1H), 8.14 (d, J=9.0 Hz, 1H), 8.00-7.78 (m, 1H), 7.73-7.56 (m, 1H), 7.52 (s, 1H), 7.37 (d, J=9.2 Hz, 1H), 6.97 (d, J=8.6 Hz, 1H), 5.78-5.65 (m, 1H), 5.52-5.45 (m, 1H), 5.23-5.15 (m, 1H), 5.13-5.03 (m, 1H), 4.58-4.50 (m, 1H), 4.50-4.42 (m, 1H), 4.39-4.31 (m, 1H), 4.10-4.03 (m, 1H), 4.01 (s, 3H), 3.99-3.70 (m, under H2O, 2H), 2.34-2.23 (m, 1H), 2.07-1.98 (m, 1H), 1.70-1.37 (m, 9H), 1.34-1.23 (m, 2H), 1.26 (br d, J=6.4 Hz, 6H), 0.96 (s, 9H).

M.S. (electrospray): 839 (M−H)$^−$ 841.3 (M−H+2)$^−$ 841.3 (M+H)$^+$ 843.3 (MH+2)$^+$. Reverse Phase HPLC Homogeneity (0.06% TFA; $CH_3CN$:$H_2O$): 98%

Compound 1015

Compound 1015:

$^1$H NMR (400 MHz, DMSO-$d_6$): ca, 85:15 mixture of rotamers, major rotamer description; □12.32 (br s, 1H), 8.57 (s, 1H), 8.15-8.03 (m, 1H), 8.04 (d, J=9.2 Hz, 1H), 7.47-7.37 (m, 1H), 7.29 (d, J=8.8 Hz, 1H), 7.03 (d, J=8.6 Hz, 1H), 5.78-5.65 (m, 1H), 5.45-5.38 (m, 1H), 5.23-5.14 (m, 1H), 5.09-5.02 (m, 1H), 4.72-4.62 (m, 1H), 4.46-4.32 (m, 2H), 4.16-4.08 (m, 1H), 4.03-3.90 (m, 1H), 3.94 (s, 3H), 2.60 (s, 3H), 2.30-2.19 (m, 1H), 2.20 (s, 3H), 2.06-1.97 (m, 1H), 1.81-1.21 (m, 11H), 0.97 (s, 9H).

M.S. (electrospray): 775.4 (M–H)⁻ 777.5 (M+H)⁺.
Reverse Phase HPLC Homogeneity (0.06% TFA; CH₃CN: H₂O): 99%

(m, 3H), 2.36-2.23 (m, 1H), 1.90-1.79 (m, 1H), 1.34 (m, 9H), 1.37-1.14 (m, 2H), 1.03 (s, 9H), 0.98 (s, 9H).

M.S. (electrospray): 835.4 (M–H)⁻ 837.3 (M+H)⁺.
Reverse Phase HPLC Homogeneity (0.06% TFA; CH₃CN: H₂O): 99%

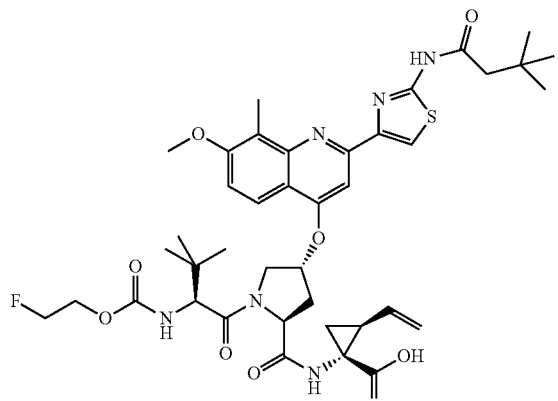

Compound 1024

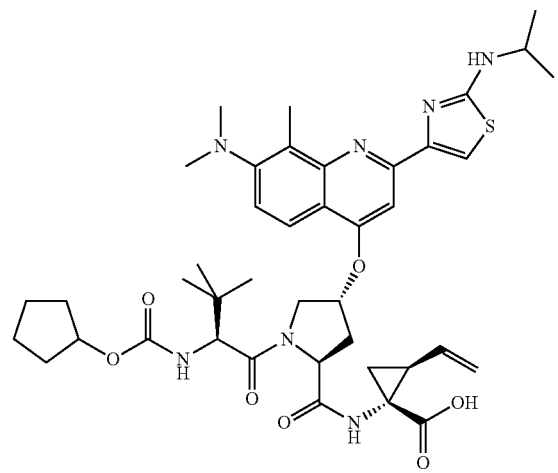

Compound 1011

Compound 1024:
¹H NMR (400 MHz, DMSO-d₆): ca, 85:15 mixture of rotamers, major rotamer description; □12.31 (s, 1H), 8.55 (s, 1H), 8.20-8.05 (m, 1H), 8.03 (d, J=9.2 Hz, 1H), 7.54-7.40 (m, 1H), 7.38 (d, J=8.6 Hz, 1H), 7.33 (d, J=9.4 Hz, 1H), 5.79-5.66 (m, 1H), 5.49-5.41 (m, 1H), 5.23-5.15 (m, 1H), 5.09-5.02 (m, 1H), 4.77-3.85 (m, 8H), 3.95 (s, 3H), 2.60 (s, 3H), 2.58-2.47 (m, 1H), 2.43-2.36 (m, 2H), 2.31-2.20 (m, 1H), 2.07-1.98 (m, 1H), 1.57-1.51 (m, 1H), 1.31-1.23 (m, 1H), 1.04 (s, 9H), 1.00 (s, 9H).

M.S. (electrospray): 809.4 (M–H)⁻ 811.4 (M+H)⁺.
Reverse Phase HPLC Homogeneity (0.06% TFA; CH₃CN: H₂O): 98%

Compound 1011:
¹H NMR (400 MHz, DMSO-d₆): ca, 85:15 mixture of rotamers, major rotamer description; □8.53 (s, 1H), 7.92 (d, J=8.8 Hz, 1H), 7.69 (d, J=7.4 Hz, 1H), 7.46 (s, 1H), 7.39 (s, 1H), 7.25 (d, J=9.0 Hz, 1H), 6.99 (d, J=8.8 Hz, 1H), 5.79-5.64 (m, 1H), 5.44-5.33 (m, 1H), 5.23-5.13 (m, 1H), 5.10-5.00 (m, 1H), 4.81-4.70 (m, 1H), 4.45-4.27 (m, 2H), 4.19-4.11 (m, 1H), 4.04-3.91 (m, 1H), 3.87-3.72 (m, 1H), 2.75 (s, 6H), 2.66 (s, 3H), 2.56-2.42 (m, 1H), 2.29-2.17 (m, 1H), 2.07-1.97 (m, 1H), 1.80-1.21 (m, 10H), 1.25 (br d, J=6.5 Hz, 6H), 0.97 (s, 9H).

M.S. (electrospray): 788.4 (M–H)⁻ 790.5 (M+H)⁺.
Reverse Phase HPLC Homogeneity (0.06% TFA; CH₃CN: H₂O): 95%

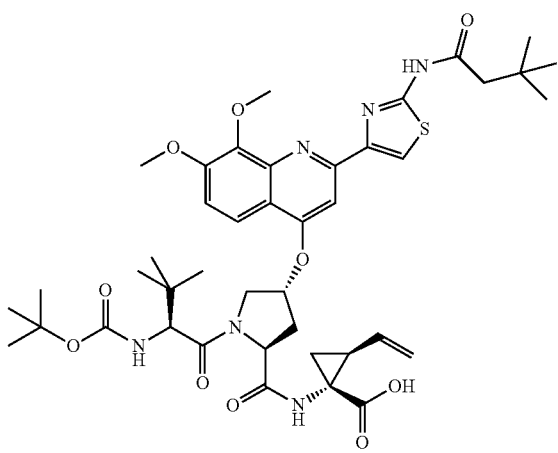

Compound 1001

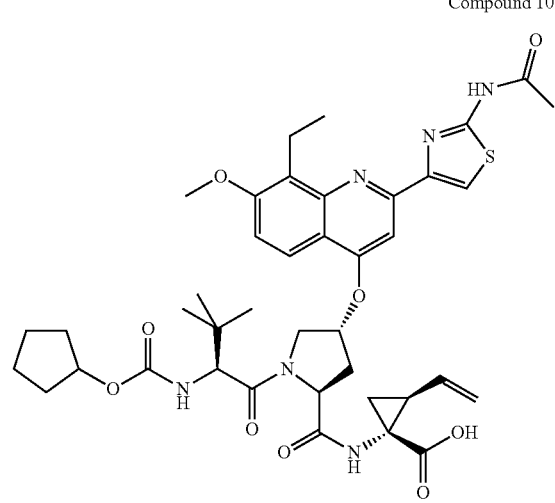

Compound 1023

Compound 1001:
¹H NMR (400 MHz, DMSO-d₆): ca, 7:3 mixture of rotamers, major rotamer description; □8.01 (br s, 1H), 7.92 (s, 1H), 7.90-7.77 (m, 2H), 7.70 (br s, 1H), 7.31 (d, J=9.4 Hz, 1H), 6.72 (d, J=8.8 Hz, 1H), 6.28-6.10 (m, 1H), 5.53-5.33 (m, 1H), 5.03-5.92 (m, 1H), 4.85-4.71 (m, 1H), 4.49-4.40 (m, 1H), 4.19-4.02 (m, 3H), 4.03 (s, 3H), 3.93 (s, 3H), 2.82-2.45

Compound 1023:
¹H NMR (400 MHz, DMSO-d₆): ca, 85:15 mixture of rotamers, major rotamer description; □12.36 (s, 1H), 8.55 (s, 1H), 8.09-7.97 (m, 2H), 7.42 (br s, 1H), 7.29 (d, J=9.2 Hz, 1H), 6.99 (d, J=8.6 Hz, 1H), 5.79-5.66 (m, 1H), 5.45-5.38 (m, 1H), 5.23-5.15 (m, 1H), 5.09-5.02 (m, 1H), 4.75-4.66 (m, 1H), 4.47-4.31 (m, 2H), 4.16-4.09 (m, 1H), 4.03-3.91 (m, 1H), 3.94 (s, 3H), 3.29-3.18 (m, 2H), 2.60-2.43 (m, 1H), 2.30-2.18 (m, 1H), 2.20 (s, 3H), 2.07-1.97 (m, 1H), 1.81-1.33 (m, 9H), 1.31-1.23 (m, 1H), 1.18 (t, J=7.3 Hz, 3H), 0.97 (s, 9H).

M.S. (electrospray): 789.3 (M−H)⁻ 791.4 (M+H)⁺.
Reverse Phase HPLC Homogeneity (0.06% TFA; CH₃CN:H₂O): 98

Compound 1033

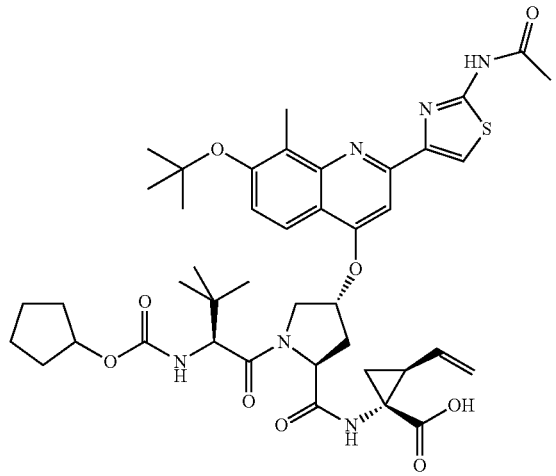

Compound 1033:
¹H NMR (400 MHz, DMSO-d₆): ca, 85:15 mixture of rotamers, major rotamer description; ☐12.36 (s, 1H), 8.53 (s, 1H), 8.05 (s, 1H), 7.98 (d, J=9.0 Hz, 1H), 7.46 (s, 1H), 7.20 (d, J=9.0 Hz, 1H), 7.04 (d, J=8.4 Hz, 1H), 5.80-5.65 (m, 1H), 5.44-5.37 (m, 1H), 5.24-5.14 (m, 1H), 5.10-5.01 (m, 1H), 4.85-4.76 (m, 1H), 4.45-4.34 (m, 2H), 4.21-4.10 (m, 1H), 4.04-3.89 (m, 1H), 2.62 (s, 3H), 2.58-2.47 (m, 1H), 2.28-2.18 (m, 1H), 2.20 (s, 3H), 2.06-1.96 (m, 1H), 1.81-1.38 (m, 9H), 1.39 (s, 9H), 1.29-1.22 (m, 1H), 0.99 (s, 9H).

M.S. (electrospray): 817.4 (M−H)⁻ 819.4 (M+H)⁺.
Reverse Phase HPLC Homogeneity (0.06% TFA; CH₃CN:H₂O): 98%

Compound 1037

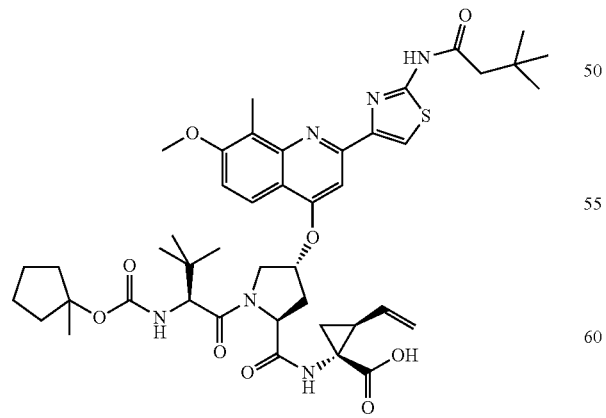

Compound 1037:
¹H NMR (400 MHz, DMSO-d₆): ca, 85:15 mixture of rotamers, major rotamer description; ☐12.29 (s, 1H), 8.54 (s,
1H), 8.19-8.01 (m, 1H), 8.04 (d, J=9.0 Hz, 1H), 7.44 (s, 1H), 7.25 (d, J=9.2 Hz, 1H), 6.79 (d, J=8.4 Hz, 1H), 5.78-5.65 (m, 1H), 5.47-5.37 (m, 1H), 5.22-5.13 (m, 1H), 5.08-5.02 (m, 1H), 4.45-4.33 (m, 2H), 4.13-4.06 (m, 1H), 3.98-3.90 (m, 1H), 3.92 (s, 3H), 2.59 (s, 3H), 2.56-2.46 (m, 1H), 2.41-2.36 (m, 2H), 2.28-2.18 (m, 1H), 2.05-1.96 (m, 1H), 1.93-1.43 (m, 9H), 1.33 (br s, 3H), 1.29-1.22 (m, 1H), 1.03 (s, 9H), 0.97 (s, 9H).

M.S. (electrospray): 845.5 (M−H)⁻ 847.5 (M+H)⁺.
Reverse Phase HPLC Homogeneity (0.06% TFA; CH₃CN:H₂O): 96%

Compound 1051

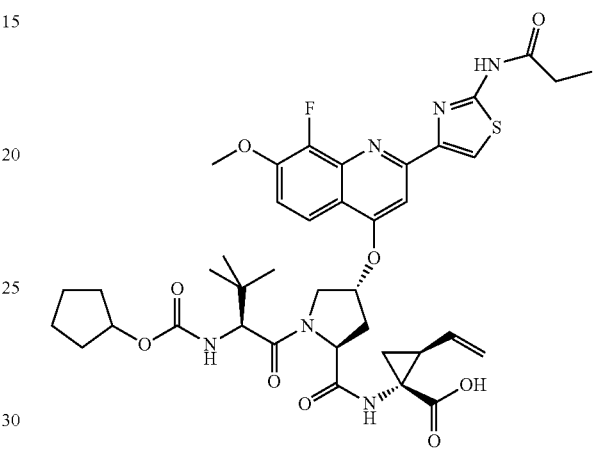

Compound 1051:
¹H NMR (400 MHz, DMSO-d₆): ca, 85:15 mixture of rotamers, major rotamer description; ☐12.35 (s, 1H), 8.54 (s, 1H), 8.03 (s, 1H), 7.92 (d, J=9.2 Hz, 1H), 7.47 (s, 1H), 7.38 (t, J=8.3 Hz, 1H), 6.98 (d, J=8.7 Hz, 1H), 5.78-5.65 (m, 1H), 5.47-5.38 (m, 1H), 5.23-5.13 (m, 1H), 5.09-5.00 (m, 1H), 4.69-4.60 (m, 1H), 4.48-4.30 (m, 2H), 4.14-3.90 (m, 2H), 3.98 (s, 3H), 2.60-2.39 (m, 3H), 2.30-2.20 (m, 1H), 2.06-1.97 (m, 1H), 1.80-1.37 (m, 8H), 1.37-1.20 (m, 2H), 1.12 (t, J=7.5 Hz, 3H), 0.96 (s, 9H).

M.S. (electrospray): 793.3 (M−H)⁻ 795.3 (M+H)⁺.
Reverse Phase HPLC Homogeneity (0.06% TFA; CH₃CN:H₂O): 98%

Compound 1053

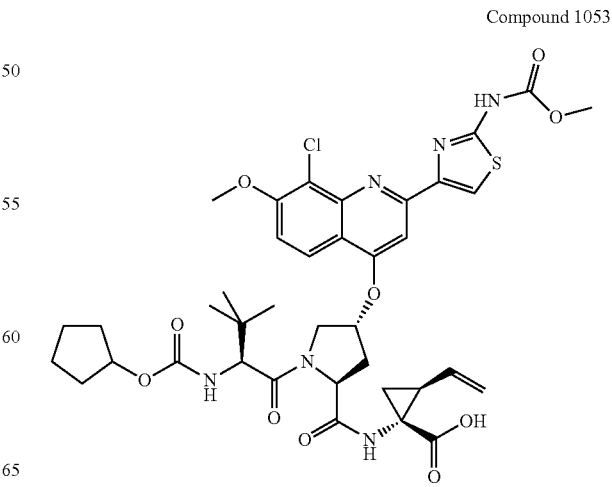

Compound 1053:

¹H NMR (400 MHz, DMSO-d₆): ca, 85:15 mixture of rotamers, major rotamer description; □12.06 (br s, 1H), 8.55 (s, 1H), 8.12 (d, J=9.2 Hz, 1H), 8.05 (s, 1H), 7.46 (m, 1H), 7.39 (d, J=9.3 Hz, 1H), 6.98 (d, J=8.6 Hz, 1H), 5.78-5.66 (m, 1H), 5.44-5.38 (m, 1H), 5.23-5.15 (m, 1H), 5.09-5.02 (m, 1H), 4.65-4.52 (m, 1H), 4.49-4.32 (m, 2H), 4.12-4.05 (m, 1H), 4.01 (s, 3H), 3.99-3.91 (m, 1H), 3.78 (s, 3H), 2.60-2.45 (m, 1H), 2.31-2.20 (m, 1H), 2.07-1.97 (m, 1H), 1.81-1.37 (m, 8H), 1.37-1.22 (m, 2H), 0.96 (s, 9H).

M.S. (electrospray): 811.1 (M−H)⁻ 813.2 (M+H)⁺.
Reverse Phase HPLC Homogeneity (0.06% TFA; CH₃CN: H₂O): 96%

Compound 1041:

¹H NMR (400 MHz, DMSO-d₆): ca, 85:15 mixture of rotamers, major rotamer description; 12.33 (br s, 1H), 8.55 (s, 1H), 8.15-8.02 (m, 1H), 8.04 (d, J=9.0 Hz, 1H), 7.49-7.38 (m, 1H), 7.29 (d, J=9.2 Hz, 1H), 6.99 (d, J=8.8 Hz, 1H), 5.78-5.66 (m, 1H), 5.46-5.39 (m, 1H), 5.23-5.14 (m, 1H), 5.09-5.02 (m, 1H), 4.71-4.62 (m, 1H), 4.47-4.32 (m, 2H), 4.15-4.09 (m, 1H), 4.03-3.92 (m, 1H), 3.94 (s, 3H), 2.60 (s, 3H), 2.58-2.40 (m, 2H), 2.30-2.20 (m, 1H), 2.07-1.97 (m, 1H), 1.80-1.21 (m, 11H), 1.13 (t, J=7.5 Hz, 3H), 0.97 (s, 9H).

M.S. (electrospray): 789.4 (M−H)⁻ 791.4 (M+H)⁺.
Reverse Phase HPLC Homogeneity (0.06% TFA; CH₃CN: H₂O): 98%.

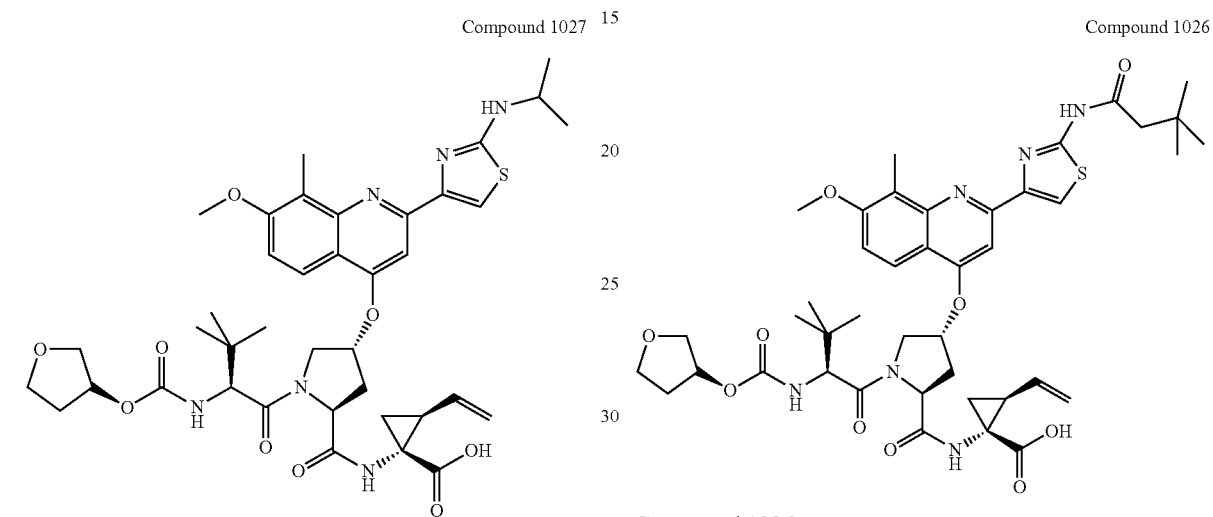

Compound 1027:

¹HNMR (400 MHz, DMSO-d₆): □ 8.58 (s, 1H), 8.06 (d, J=9 Hz, 1H), 7.91, 7.89 (2 s, 1H), 7.57 (brs, 1H), 7.40, 7.38 (2 s, 1H), 7.25 (d, J=9 Hz, 1H), 5.57-5.68 (m, 1H), 5.55 (brs, 1H), 5.20 (d, J=16 Hz, 1H), 5.06 (d, J=11 Hz, 1H)), 4.69 (brs, 1H), 4.47 (t, J=9 Hz, 1H), 4.30-4.35 (m, 1H), 4.08 (d, J=9 Hz, 2H), 4.05-3.96 (m, 2H), 3.97 (s, 3H), 3.66-3.40 (m, 8H), 2.56 (s, 3H), 2.35-2.25 (m, 1H), 2.08-1.98 (m, 1H), 1.60-1.50 (m, 2H), 1.28, 1.26 (2 s, 6H), 0.97 (s, 9H).

EIMS: (M+H)=779.3, (M−H)=777.3

Reverse Phase HPLC Homogeneity (0.06% TFA; CH₃CN: H₂O): 99%.

Compound 1026:

¹H NMR (400 MHz, DMSO-d₆): ca, 85:15 mixture of rotamers major rotamer description; □12.30 (s, 1H), 8.56 (s, 1H), 8.09 (br s, 1H), 8.02 (d, J=9.0 Hz, 1H), 7.44 (br s, 1H), 7.32 (d, J=9.2 Hz, 1H), 7.24 (d, J=8.6 Hz, 1H), 5.78-5.66 (m, 1H), 5.47-5.39 (m, 1H), 5.23-5.15 (m, 1H), 5.10-5.03 (m, 1H), 4.80-4.72 (m, 1H), 4.49-4.41 (m, 1H), 4.37-4.29 (m, 1H), 4.15-4.08 (m, 1H), 4.05-3.95 (m, 1H), 3.95 (s, 3H), 3.80-3.51 (m, under H2O, 4H), 2.60 (s, 3H), 2.57-2.48 (m, 1H), 2.41-2.37 (m, 2H), 2.31-2.21 (m, 1H), 2.07-1.98 (m, 1H), 1.95-1.83 (m, 1H), 1.62-1.46 (m, 2H), 1.31-1.22 (m, 1H), 1.04 (s, 9H), 0.97 (s, 9H). M.S. (electrospray): 833.3 (M−H)⁻ 835.4 (M+H)⁺. Reverse Phase HPLC Homogeneity (0.06% TFA; CH₃CN:H₂O): 99

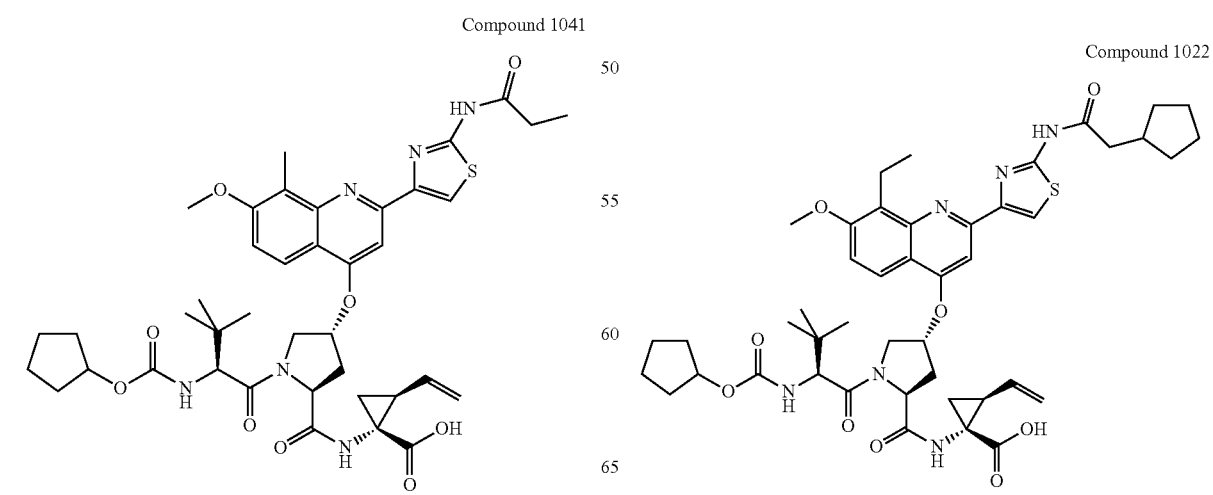

Compound 1022:
¹H NMR (400 MHz, DMSO-d₆): ca, 85:15 mixture of rotamers, major rotamer description; ☐12.32 (s, 1H), 8.55 (s, 1H), 8.08-7.97 (m, 2H), 7.42 (br s, 1H), 7.29 (d, J=9.2 Hz, 1H), 6.99 (d, J=8.8 Hz, 1H), 5.79-5.66 (m, 1H), 5.44-5.37 (m, 1H), 5.24-5.15 (m, 1H), 5.09-5.02 (m, 1H), 4.75-4.67 (m, 1H), 4.43-4.32 (m, 2H), 4.16-3.95 (m, 2H), 3.94 (s, 3H), 3.29-3.18 (m, 2H), 2.59-2.48 (m, 1H), 2.34-2.20 (m, 3H), 2.06-1.98 (m, 1H), 1.81-1.16 (m, 19H), 1.18 (t, J=7.2 Hz, 3H), 0.97 (s, 9H).

M.S. (electrospray): 857.4 (M–H)⁻ 859.5 (M+H)⁺.
Reverse Phase HPLC Homogeneity (0.06% TFA; CH₃CN: H₂O): 98%

Compound 1036:
¹H NMR (400 MHz, DMSO-d₆): ca, 85:15 mixture of rotamers, major rotamer description; ☐12.35 (s, 1H), 8.53 (s, 1H), 8.12-7.98 (m, 2H), 7.41 (s, 1H), 7.24 (d, J=9.2 Hz, 1H), 6.79 (d, J=8.4 Hz, 1H), 5.78-5.64 (m, 1H), 5.44-5.34 (m, 1H), 5.22-5.13 (m, 1H), 5.08-5.01 (m, 1H), 4.46-4.33 (m, 2H), 4.15-4.06 (m, 1H), 4.04-3.95 (m, 1H), 3.92 (s, 3H), 2.59 (s, 3H), 2.57-2.47 (m, 1H), 2.28-2.17 (m, 1H), 2.19 (s, 3H), 2.06-1.96 (m, 1H), 1.94-1.77 (m, 2H), 1.72-1.43 (m, 7H), 1.34 (s, 3H), 1.29-1.21 (m, 1H), 0.97 (s, 9H).

M.S. (electrospray): 789.4 (M–H)⁻ 791.4 (M+H)⁺.
Reverse Phase HPLC Homogeneity (0.06% TFA; CH₃CN: H₂O): 95%

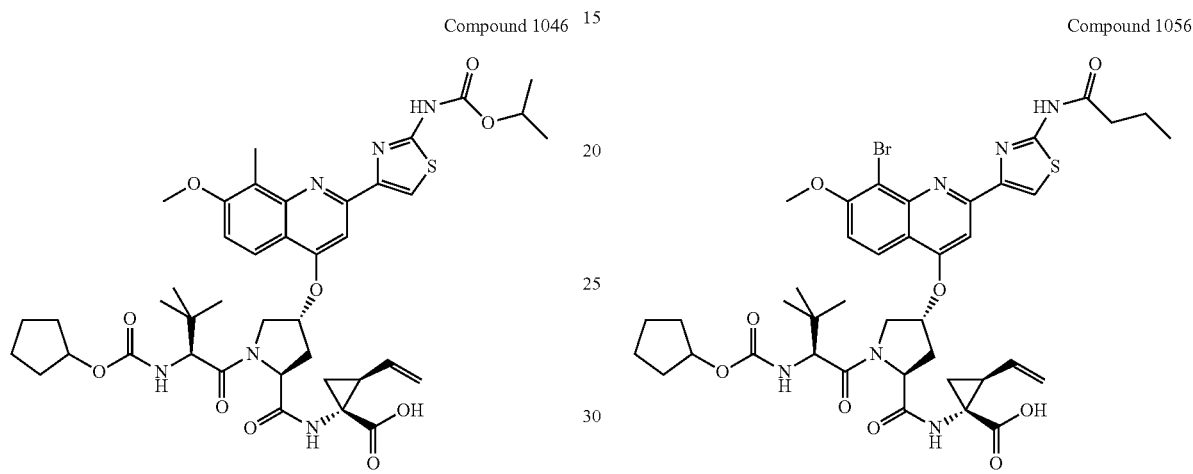

Compound 1046

Compound 1056

Compound 1046:
¹H NMR (400 MHz, DMSO-d₆): ca, 85:15 mixture of rotamers, major rotamer description; ☐11.91 (br s, 1H), 8.56 (s, 1H), 8.08 (br s, 1H), 8.04 (d, J=9.2 Hz, 1H), 7.43 (s, 1H), 7.30 (d, J=9.0 Hz, 1H), 6.99 (d, J=8.8 Hz, 1H), 5.78-5.66 (m, 1H), 5.46-5.38 (m, 1H), 5.23-5.15 (m, 1H), 5.09-5.03 (m, 1H), 5.03-4.93 (m, 1H), 4.71-4.62 (m, 1H), 4.47-4.32 (m, 2H), 4.15-4.08 (m, 1H), 4.05-3.95 (m, 1H), 3.94 (s, 3H), 2.59 (s, 3H), 2.58-2.47 (m, 1H), 2.31-2.20 (m, 1H), 2.07-1.97 (m, 1H), 1.81-1.22 (m, 10H), 1.29 (d, J=6.3 Hz, 6H), 0.97 (s, 9H).

M.S. (electrospray): 819.4 (M–H)⁻ 821.4 (M+H)⁺.
Reverse Phase HPLC Homogeneity (0.06% TFA; CH₃CN: H₂O): 99%

Compound 1056:
¹H NMR (400 MHz, DMSO-d₆): ca, 85:15 mixture of rotamers, major rotamer description; ☐12.35 (s, 1H), 8.55 (s, 1H), 8.17 (d, J=9.2 Hz, 1H), 8.05 (s, 1H), 7.47 (s, 1H), 7.35 (d, J=9.4 Hz, 1H), 6.98 (d, J=8.6 Hz, 1H), 5.78-5.66 (m, 1H), 5.46-5.40 (m, 1H), 5.23-5.15 (m, 1H), 5.09-5.03 (m, 1H), 4.63-4.56 (m, 1H), 4.49-4.34 (m, 2H), 4.13-3.90 (m, under H2O, 2H), 4.01 (s, 3H), 2.60-2.51 (m, 1H), 2.49-2.43 (m, 2H), 2.32-2.21 (m, 1H), 2.07-1.98 (m, 1H), 1.81-1.37 (m, 9H), 1.36-1.16 (m, 3H), 0.96 (s, 9H), 0.93 (t, J=7.4 Hz, 3H).

M.S. (electrospray): 869.1 (M–H)⁻ 871.1 (M+H)⁺.
Reverse Phase HPLC Homogeneity (0.06% TFA; CH₃CN: H₂O): 98%

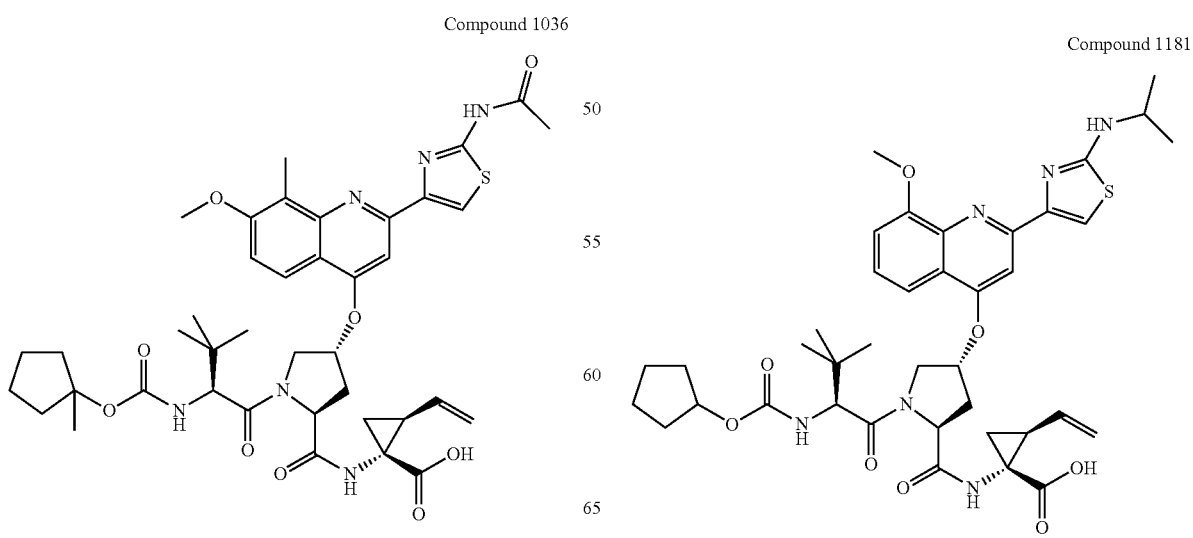

Compound 1036

Compound 1181

Compound 1181:

¹H NMR (400 MHz, DMSO-d₆): ☐ 8.57 (s, 1H), 8.2-7.96 (m, 1H), 7.88-7.70 (m, 2H), 7.62-7.35 (m, 2H), 7.02 (d, J=7.2 Hz, 1H), 5.78-5.65 (m, 1H), 5.65-5.55 (m, 1H), 5.19 (d, J=17.2 Hz, 1H), 5.065 (d, J=11.9 Hz, 1H), 4.63-4.52 (m, 1H), 4.50-4.40 (m, 1H), 4.13-4.08 (m, 2H), 4.06 (s, 3H), 3.98 (bd, J=10 Hz, 1H), 3.92-3.80 (m, 1H), 2.62-2.53 (m, 1H), 2.38-2.27 (m, 1H), 2.02 (dd, J=8.6, 8.6 Hz, 1H), 1.69-1.52 (m, 6H), 1.51-1.41 (m, 3H), 1.40-1.31 (m, 1H), 1.27 (d, J=6.5 Hz, 6H), 0.97 (s, 9H).

MS (electrospray): (M+H)⁺; 763.4 and (M−H)⁻ 761.3.
Reverse Phase HPLC Homogeneity (0.06% TFA; CH₃CN:H₂O): 99%.

Compounds from Table 2

Compound 2012:

¹H NMR (400 MHz, DMSO-d₆): ca, 8:2 mixture of rotamers, major rotamer description; ☐12.29 (s, 1H), 8.54 (s, 1H), 8.08 (br s, 1H), 8.04 (d, J=9.0 Hz, 1H), 7.44 (br s, 1H), 7.25 (d, J=9.2 Hz, 1H), 6.08-5.90 (m, 2H), 5.80-5.65 (m, 1H), 5.45-5.37 (m, 1H), 5.22-5.13 (m, 1H), 5.09-5.02 (m, 1H), 4.48-4.34 (m, 2H), 4.26-4.19 (m, 1H), 4.04-3.90 (m, 1H), 3.93 (s, 3H), 2.60 (s, 3H), 2.68-2.57 (m, 1H), 2.42-2.35 (m, 2H), 2.28-2.18 (m, 1H), 2.08-1.98 (m, 1H), 1.81-1.21 (m, 10H), 1.19 (s, 3H), 1.04 (s, 9H), 0.96 (s, 9H).

M.S. (electrospray): 844.5 (M−H)⁻ 846.5 (M+H)⁺.
Reverse Phase HPLC Homogeneity (0.06% TFA; CH₃CN:H₂O): 99

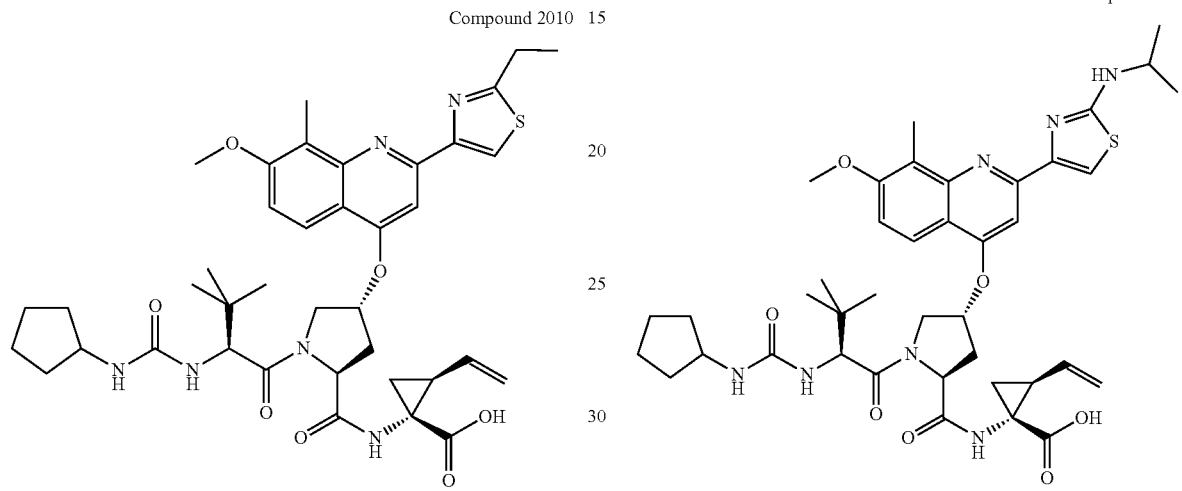

Compound 2010

Compound 2002

Compound 2010:

¹H NMR (400 MHz, DMSO-d₆): ca, 8:2 mixture of rotamers, major rotamer description; ☐8.56 (s, 1H), 8.41 (br s, 1H), 8.04 (d, J=9.2 Hz, 1H), 7.55 (s, 1H), 7.29 (d, J=9.2 Hz, 1H), 6.09-5.99 (m, 1H), 5.97-5.88 (m, 1H), 5.78-5.65 (m, 1H), 5.54-5.48 (m, 1H), 5.23-5.15 (m, 1H), 5.09-5.02 (m, 1H), 4.47-4.33 (m, 2H), 4.27-4.20 (m, 1H), 4.19-3.85 (m, under H2O, 2H), 3.94 (s, 3H), 3.13 (q, J=7.5 Hz, 2H), 2.60 (s, 3H), 2.55-2.42 (m, 1H), 2.34-2.23 (m, 1H), 2.09-2.00 (m, 1H), 1.80-1.37 (m, 7H), 1.40 (t, J=7.5 Hz, 3H), 1.31-1.05 (m, 3H), 0.96 (s, 9H).

M.S. (electrospray): 745.4 (M−H) 747.4 (M+H)⁺. Reverse Phase HPLC Homogeneity (0.06% TFA; CH₃CN:H₂O): 96%

Compound 2002:

¹H NMR (400 MHz, DMSO-d₆): ca, 8:2 mixture of rotamers, major rotamer description; ☐8.57 (s, 1H), 8.28-7.77 (m, 3H), 7.66-7.30 (m, 2H), 6.09-5.98 (m, 1H), 5.96-5.86 (m, 1H), 5.78-5.66 (m, 1H), 5.61-5.48 (m, 1H), 5.26-5.15 (m, 1H), 5.11-5.03 (m, 1H), 4.53-4.39 (m, 2H), 4.25-4.15 (m, 1H), 4.05-3.93 (m, 1H), 3.97 (s, 3H), 3.92-3.50 (m, under H2O, 2H), 2.55 (s, 3H), 2.59-2.42 (m, 1H), 2.36-2.26 (m, 1H), 2.18-1.99 (m, 1H), 1.80-1.36 (m, 7H), 1.27 (d, J=6.3 Hz, 6H), 1.31-1.05 (m, 3H), 0.95 (s, 9H).

M.S. (electrospray): 774.4 (M−H)⁻ 776.5 (M+H)⁺.
Reverse Phase HPLC Homogeneity (0.06% TFA; CH₃CN:H₂O): 94%

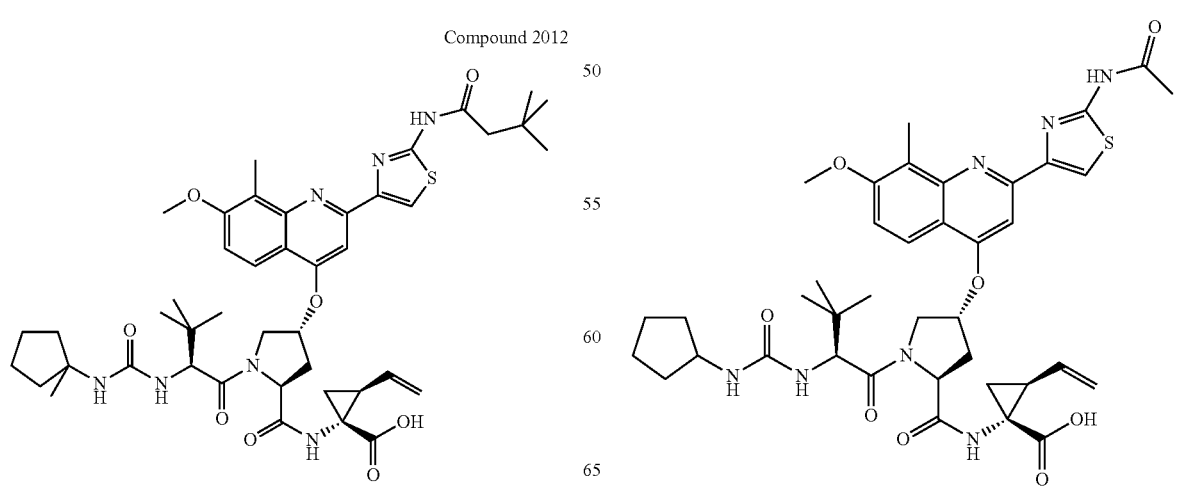

Compound 2012

Compound 2007

Compound 2007:

¹H NMR (400 MHz, DMSO-d₆): ca, 8:2 mixture of rotamers, major rotamer description; ☐12.38 (s, 1H), 8.55 (s, 1H), 8.09 (br s, 1H), 8.06 (d, J=9.2 Hz, 1H), 7.44 (s, 1H), 7.28 (d, J=9.2 Hz, 1H), 6.12-6.01 (m, 1H), 5.98-5.89 (m, 1H), 5.78-5.66 (m, 1H), 5.46-5.38 (m, 1H), 5.23-5.15 (m, 1H), 5.10-5.01 (m, 1H), 4.47-4.36 (m, 2H), 4.28-4.20 (m, 1H), 4.04-3.92 (m, 1H), 3.94 (s, 3H), 3.90-3.50 (m, under H2O, 1H), 2.60 (s, 3H), 2.55-2.47 (m, 1H), 2.31-2.22 (m, 1H), 2.20 (s, 3H), 2.08-1.99 (m, 1H), 1.81-1.38 (m, 7H), 1.31-1.09 (m, 3H), 0.96 (s, 9H).

M.S. (electrospray): 774.4 (M−H)⁻ 776.4 (M+H)⁺. Reverse Phase HPLC Homogeneity (0.06% TFA; CH₃CN:H₂O): 94%

Compound 3002:

¹H NMR (400 MHz, DMSO-d₆): ca, 85:15 mixture of rotamers, major rotamer description; ☐12.33 (s, 1H), 8.55 (s, 1H), 7.98 (s, 1H), 7.75 (d, J=8.6 Hz, 1H), 7.40 (s, 1H), 7.19 (d, J=8.8 Hz, 1H), 6.99 (d, J=8.6 Hz, 1H), 6.26 (s, 2H), 5.79-5.66 (m, 1H), 5.46-5.38 (m, 1H), 5.23-5.14 (m, 1H), 5.10-5.01 (m, 1H), 4.76-4.67 (m, 1H), 4.47-4.30 (m, 2H), 4.11 (d, J=8.8 Hz, 1H), 4.00-3.91 (m, 1H), 2.41-2.36 (m, 2H), 2.29-2.19 (m, 1H), 2.08-1.97 (m, 1H), 1.82-1.22 (m, 11H), 1.03 (s, 9H), 0.96 (s, 9H).

M.S. (electrospray): 831.5 (M−H)⁻ 833.6 (M+H)⁺. Reverse Phase HPLC Homogeneity (0.06% TFA; CH₃CN:H₂O): 99%

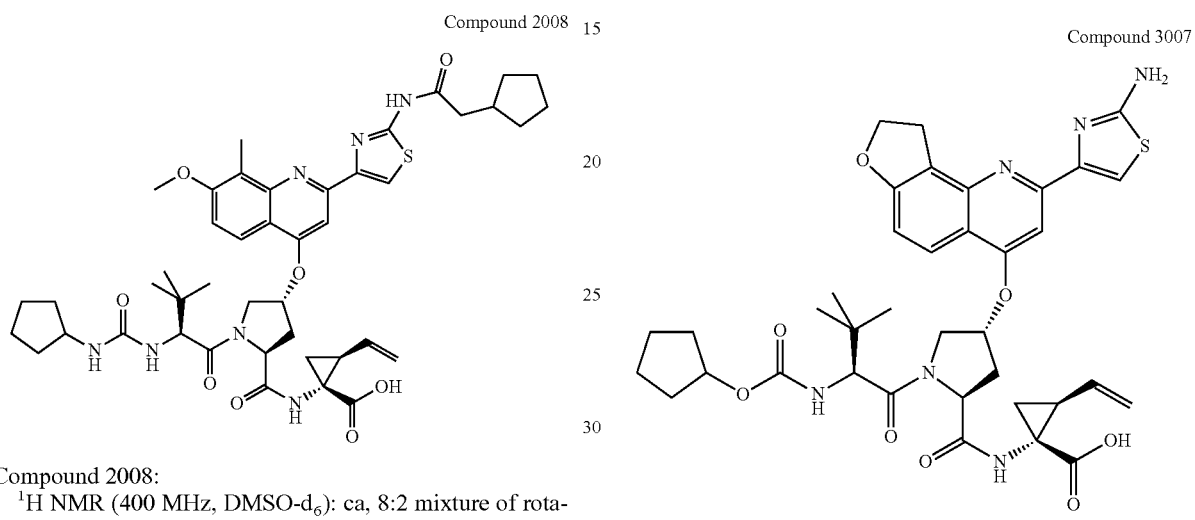

Compound 2008

Compound 3007

Compound 2008:

¹H NMR (400 MHz, DMSO-d₆): ca, 8:2 mixture of rotamers, major rotamer description; ☐12.34 (br s, 1H), 8.55 (s, 1H), 8.17-8.05 (m, 1H), 8.07 (d, J=9.2 Hz, 1H), 7.50-7.42 (m, 1H), 7.28 (d, J=9.2 Hz, 1H), 6.11-6.01 (m, 1H), 5.98-5.88 (m, 1H), 5.78-5.66 (m, 1H), 5.46-5.38 (m, 1H), 5.24-5.14 (m, 1H), 5.10-5.01 (m, 1H), 4.48-4.36 (m, 2H), 4.28-4.20 (m, 1H), 4.07-3.95 (m, 1H), 3.94 (s, 3H), 3.80-3.65 (m, under H2O, 1H), 2.60 (s, 3H), 2.60-2.50 (m, 1H), 2.31-2.20 (m, 2H), 2.08-1.98 (m, 1H), 1.82-1.37 (m, 15H), 1.31-1.07 (m, 5H), 0.96 (s, 9H).

M.S. (electrospray): 842.5 (M−H)⁻ 844.5 (M+H)⁺. Reverse Phase HPLC Homogeneity (0.06% TFA; CH₃CN:H₂O): 97%

Compounds from Table 3

Compound 3007:

¹H NMR (400 MHz, DMSO-d₆): ca, 85:15 mixture of rotamers, major rotamer description; ☐8.56 (s, 1H), 8.04 (d, J=8.8 Hz, 1H), 7.94-7.64 (m, 3H), 7.49-7.37 (m, 1H), 7.09 (d, J=8.4 Hz, 1H), 7.00 (d, J=8.6 Hz, 1H), 5.80-5.66 (m, 1H), 5.58-5.46 (m, 1H), 5.24-5.14 (m, 1H), 5.11-5.01 (m, 1H), 4.85-4.70 (m, 2H), 4.69-4.58 (m, 1H), 4.49-4.81 (m, 2H), 4.09 (d, J=8.6 Hz, 1H), 4.00-3.88 (m, 1H), 3.75-3.30 (m, under H2O, 2H), 2.35-2.22 (m, 1H), 2.07-1.97 (m, 1H), 1.81-1.20 (m, 11H), 0.97 (s, 9H).

M.S. (electrospray): 731.3 (M−H)⁻ 733.3 (M+H)⁺. Reverse Phase HPLC Homogeneity (0.06% TFA; CH₃CN:H₂O): 94%

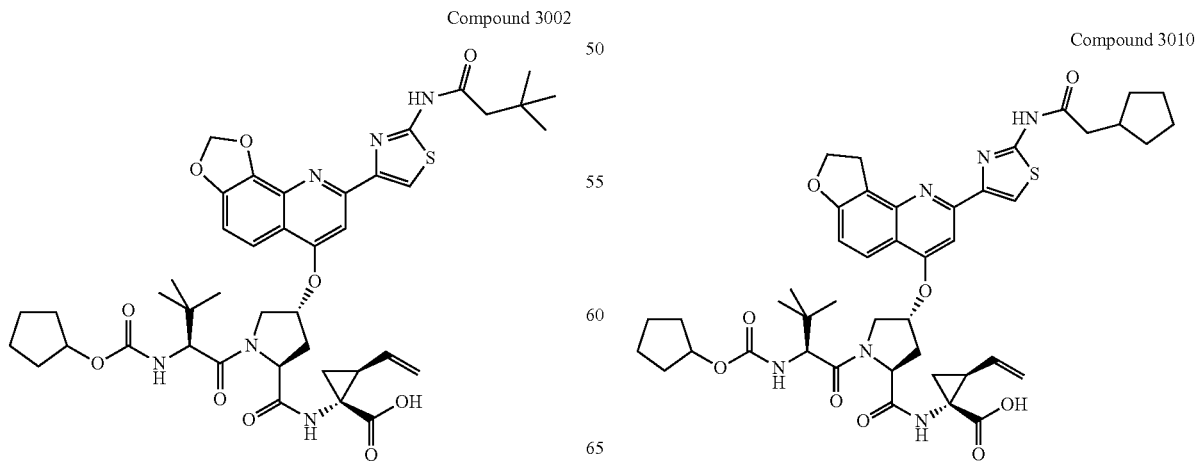

Compound 3002

Compound 3010

Compound 3010:

¹H NMR (400 MHz, DMSO-d₆): ca, 85:15 mixture of rotamers, major rotamer description; ☐12.37 (s, 1H), 8.56 (s, 1H), 8.13-7.96 (m, 2H), 7.43 (s, 1H), 7.05 (d, J=8.8 Hz, 1H), 7.00 (d, J=8.6 Hz, 1H), 5.80-5.64 (m, 1H), 5.50-5.37 (m, 1H), 5.24-5.11 (m, 1H), 5.10-4.98 (m, 1H), 4.83-4.63 (m, 3H), 4.47-4.30 (m, 2H), 4.19-4.05 (m, 1H), 4.04-3.86 (m, 1H), 3.75-3.30 (m, under H2O, 2H), 2.34-2.19 (m, 3H), 2.07-1.97 (m, 1H), 1.82-1.13 (m, 20H), 0.97 (s, 9H).

M.S. (electrospray): 841.3 (M–H)⁻ 843.4 (M+H)⁺. Reverse Phase HPLC Homogeneity (0.06% TFA; CH₃CN: H₂O): 99

Compound 3004:

Mixture of rotamers (approx. 85:15), ¹H NMR of major rotamer given (400 MHz, DMSO-d₆): ☐8.57 (s, 1H); 8.10-8.13 (m, 1H); 8.08 (d, J=8.8 Hz, 1H) 7.86-7.88 (m, 2H); 7.53 (s, 1H); 7.14 (d, J=8.5 Hz, 1H); 7.00 (d, J=8.5, 1H); 5.68-5.78 (m, 1H); 5.57 (s, 1H); 5.19 (d, J=17.0 Hz, 1H); 5.07 (d, J=11.9 Hz, 1H); 4.78-4.82 (m, 2H); 4.58-4.63 (m, 1H); 4.35-4.47 (m, 2H); 3.87-4.08 (m, 8H); 3.58-3.62 (m, 2H); 2.53-2.56 (m, 1H); 2.27-2.33 (m, 1H); 1.99-2.04 (m, 1H); 1.43-1.65 (m, 4H); 1.28-1.30 (m, 1H); 1.26 (d, J=6.2 Hz, 6H); 0.96 (s, 9H).

M.S. (electrospray): 775.4 (M+H)⁺, 773.4 (M–H)⁻.

Homogeneity (0.06% TFA; CH₃CN:H₂O): 98.8%

Compounds from Table 4

Compound 3001

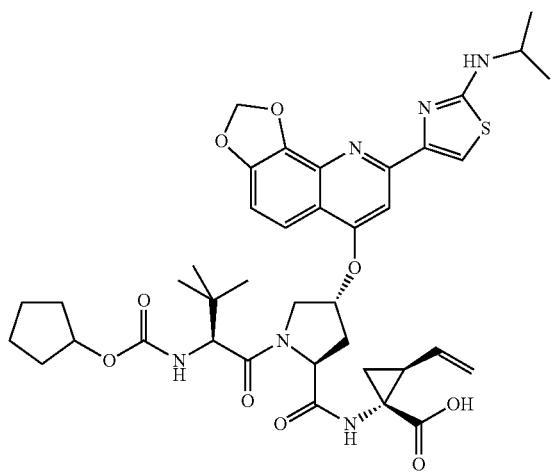

Compound 4005

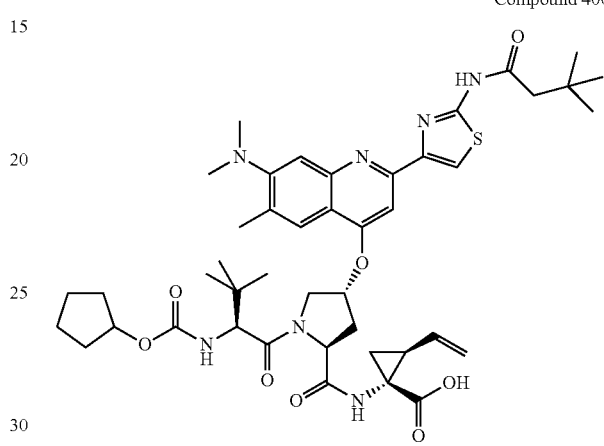

Compound 3001:

¹H NMR (400 MHz, DMSO-d₆): ca, 85:15 mixture of rotamers, major rotamer description; ☐8.55 (s, 1H), 7.95-7.76 (m, 1H), 7.72 (d, J=8.8 Hz, 1H), 7.49 (s, 1H), 7.41 (s, 1H), 7.18 (d, J=8.6 Hz, 1H), 6.98 (d, J=8.6 Hz, 1H), 6.25 (s, 2H), 5.80-5.65 (m, 1H), 5.52-5.46 (m, 1H), 5.24-5.14 (m, 1H), 5.10-5.01 (m, 1H), 4.75-4.66 (m, 1H), 4.48-4.39 (m, 1H), 4.37-4.27 (m, 1H), 4.17-4.07 (m, 1H), 4.01-3.92 (m, 1H), 3.90-3.75 (m, 1H), 2.62-2.44 (m, 1H), 2.31-2.20 (m, 1H), 2.09-1.97 (m, 1H), 1.81-1.20 (m, 10H), 1.25 (br d, J=6.4 Hz, 6H), 0.96 (s, 9H).

M.S. (electrospray): 775.5 (M–H)⁻ 777.6 (M+H)'. Reverse Phase HPLC Homogeneity (0.06% TFA; CH₃CN: H₂O): 99%

Compound 4005:

¹H NMR (400 MHz, DMSO-d₆): ca, 85:15 mixture of rotamers, major rotamer description; ☐12.36 (br s, 1H), 8.57 (s, 1H), 8.60-8.20 (m, 1H), 7.90 (s, 1H), 7.68-7.45 (m, 2H), 6.99 (d, J=8.3 Hz, 1H), 5.78-5.66 (m, 1H), 5.66-5.83 (m, 1H), 5.80-5.50 (m, 1H), 5.23-5.14 (m, 1H), 5.10-5.01 (m, 1H), 4.62-4.36 (m, 3H), 4.11-3.92 (m, 1H), 2.88 (s, 6H), 2.62-2.51 (m, 1H), 2.47 (s, 3H), 2.44-2.38 (m, 2H), 2.36-2.19 (m, 1H), 2.08-1.96 (m, 1H), 1.81-1.20 (m, 10H), 1.03 (s, 9H), 0.96 (s, 9H).

M.S. (electrospray): 844.4 (M–H)⁻ 846.5 (M+H)⁺. Reverse Phase HPLC Homogeneity (0.06% TFA; CH₃CN: H₂O): 99%

Compound 3004

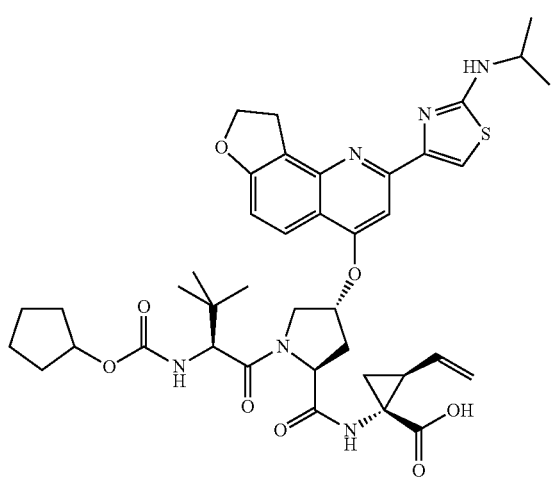

Compound 4007

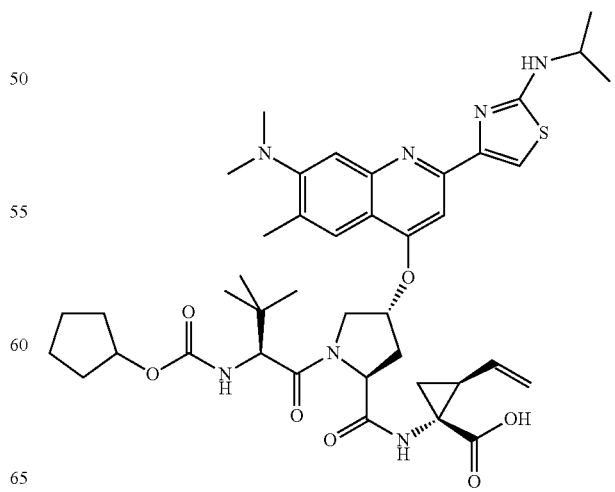

Compound 4007:
¹H NMR (400 MHz, DMSO-d₆): ca, 85:15 mixture of rotamers, major rotamer description; ☐8.59 (s, 1H), 8.27-8.12 (m, 1H), 8.06-7.97 (m, 1H), 7.89 (s, 1H), 7.73 (s, 1H), 7.64 (s, 1H), 6.99 (d, J=8.5 Hz, 1H), 5.79-5.64 (m, 2H), 5.24-5.14 (m, 1H), 5.10-5.01 (m, 1H), 4.54-4.38 (m, 2H), 4.23-4.08 (m, 1H), 4.02 (d, J=8.4 Hz, 1H), 4.00-3.91 (m, 1H), 3.70-3.30 (m, under H2O, 1H), 2.90 (s, 6H), 2.64-2.52 (m, 1H), 2.46 (s, 3H), 2.38-2.26 (m, 1H), 2.07-1.96 (m, 1H), 1.81-1.20 (m, 10H), 1.24 (br d, J=6.5 Hz, 6H), 0.95 (s, 9H).
M.S. (electrospray): 788.4 (M–H)⁻ 790.5 (M+H)⁺.
Reverse Phase HPLC Homogeneity (0.06% TFA; CH₃CN: H₂O): 98%

Compound 4001:
¹H NMR (400 MHz, DMSO-d₆): ca, 85:15 mixture of rotamers, major rotamer description; ☐12.40 (s, 1H), 8.58 (s, 1H), 8.50-8.20 (m, 1H), 7.95 (br s, 1H), 7.72-7.44 (m, 2H), 7.00 (d, J=8.2 Hz, 1H), 5.80-5.67 (m, 1H), 5.67-5.51 (m, 1H), 5.24-5.14 (m, 1H), 5.12-5.02 (m, 1H), 4.63-4.45 (m, 2H), 4.45-4.36 (m, 1H), 4.14-3.93 (m, 2H), 3.99 (s, 3H), 2.64-2.46 (m, 1H), 2.45-2.39 (m, 2H), 2.35 (s, 3H), 2.39-2.28 (m, 1H), 2.08-1.98 (m, 1H), 1.82-1.23 (m, 10H), 1.04 (s, 9H), 0.97 (s, 9H).
M.S. (electrospray): 831.4 (M–H)⁻ 833.5 (M+H)⁺.
Reverse Phase HPLC Homogeneity (0.06% TFA; CH₃CN: H₂O): 99%

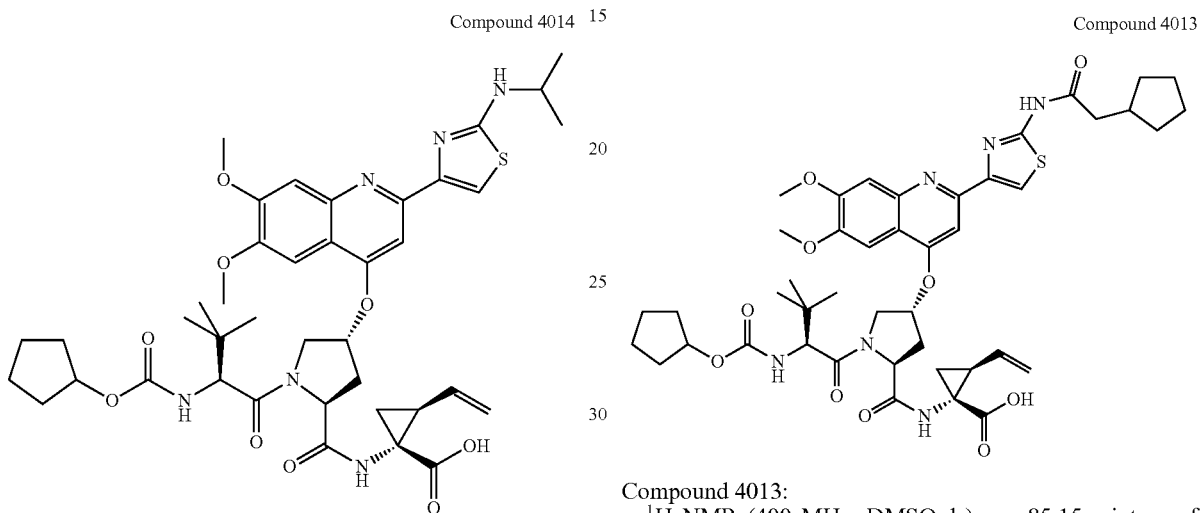

Compound 4014

Compound 4013

Compound 4014:
¹H NMR (400 MHz, DMSO-d₆): ca, 85:15 mixture of rotamers, major rotamer description; ☐8.61 (s, 1H), 8.33-7.60 (m, 4H), 7.33 (s, 1H), 6.95 (d, J=8.4 Hz, 1H), 5.79-5.67 (m, 2H), 5.24-5.16 (m, 1H), 5.10-5.03 (m, 1H), 4.57-4.32 (m, 2H), 4.20-3.88 (m, 3H), 3.99 (s, 3H), 3.93 (s, 3H), 3.65-3.30 (m, under H2O, 1H), 2.65-2.55 (m, 1H), 2.40-2.28 (m, 1H), 2.08-1.98 (m, 1H), 1.81-1.21 (m, 10H), 1.25 (br d, J=6.5 Hz, 6H), 0.95 (s, 9H).
M.S. (electrospray): 791.3 (M–H)⁻ 793.4 (M+H)⁺.
Reverse Phase HPLC Homogeneity (0.06% TFA; CH₃CN: H₂O): 86%

Compound 4013:
¹H NMR (400 MHz, DMSO-d₆): ca, 85:15 mixture of rotamers, major rotamer description; ☐12.36 (s, 1H), 8.59 (s, 1H), 8.36-7.96 (m, 1H), 7.70-7.42 (m, 2H), 7.32 (s, 1H), 6.94 (d, J=8.2 Hz, 1H), 5.79-5.66 (m, 1H), 5.63-5.50 (m, 1H), 5.23-5.15 (m, 1H), 5.10-5.02 (m, 1H), 4.58-4.45 (m, 2H), 4.38-4.28 (m, 1H), 4.12-3.90 (m, 2H), 3.97 (s, 3H), 3.91 (s, 3H), 2.62-2.52 (m, 1H), 2.37-2.21 (m, 3H), 2.08-1.98 (m, 1H), 1.77-1.14 (m, 19H), 0.97 (s, 9H).
M.S. (electrospray): 859.4 (M–H)⁻ 861.4 (M+H)⁺.
Reverse Phase HPLC Homogeneity (0.06% TFA; CH₃CN: H₂O): 92%

Compounds from Table 5

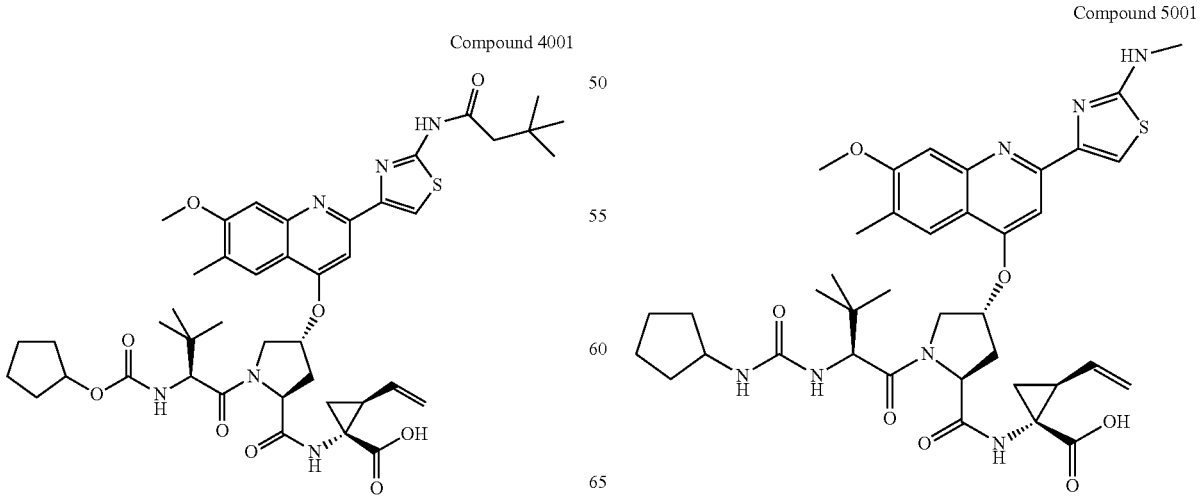

Compound 4001

Compound 5001

Compound 5001:

¹H NMR (400 MHz, DMSO-d₆): ca, 85:15 mixture of rotamers, major rotamer description; □8.60 (s, 1H), 8.34-8.19 (m, 1H), 8.04-7.98 (m, 1H), 7.97 (s, 1H), 7.91-7.81 (m, 1H), 7.73 (s, 1H), 5.99-5.91 (m, 1H), 5.90-5.83 (m, 1H), 5.78-5.66 (m, 2H), 5.25-5.15 (m, 1H), 5.11-5.04 (m, 1H), 4.58-4.46 (m, 2H), 4.15-4.07 (m, 1H), 4.00 (s, 3H), 4.03-3.94 (m, 1H), 3.60-3.15 (m, under H2O, 1H), 3.05 (d, J=4.3 Hz, 3H), 2.63-2.55 (m, 1H), 2.42-2.30 (m, 1H), 2.35 (m, 3H), 2.08-1.99 (m, 1H), 1.80-1.22 (m, 9H), 1.13-1.03 (m, 1H), 0.94 (s, 9H). M.S. (electrospray): 746.3 (M−H)⁻ 748.4 (M+H)⁺. Reverse Phase HPLC Homogeneity (0.06% TFA; CH₃CN:H₂O): 99%

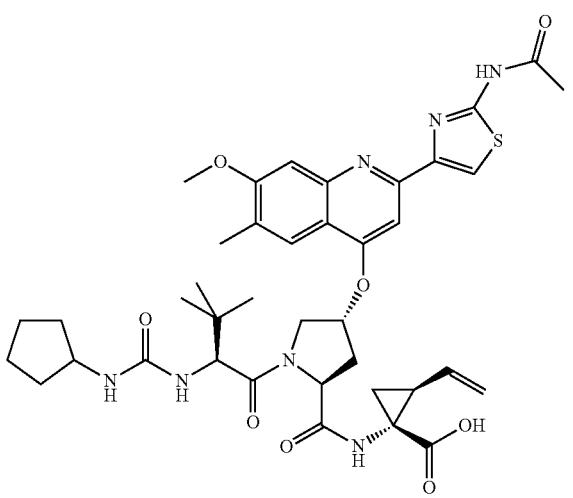

Compound 5002

Compound 5002:

¹H NMR (400 MHz, DMSO-d₆): ca, 8:2 mixture of rotamers major rotamer description; □12.44 (s, 1H), 8.59 (s, 1H), 8.52-8.25 (m, 1H), 7.97 (s, 1H), 7.70-7.46 (m, 2H), 6.03-5.96 (m, 1H), 5.90 (d, J=9.2 Hz, 1H), 5.79-5.66 (m, 1H), 5.64-5.54 (m, 1H), 5.24-5.16 (m, 1H), 5.11-5.04 (m, 1H), 4.55-4.43 (m, 2H), 4.19-4.12 (m, 1H), 4.05-3.94 (m, 1H), 3.99 (s, 3H), 3.80-3.30 (m, under H2O, 1H), 2.68-2.54 (m, 1H), 2.39-2.28 (m, 1H), 2.35 (s, 3H), 2.23 (s, 3H), 2.08-1.99 (m, 1H), 1.80-1.21 (m, 8H), 1.17-1.07 (m, 1H), 1.06-0.95 (m, 1H), 0.95 (s, 9H).

M.S. (electrospray): 774.4 (M−H)⁻ 776.4 (M+H)⁺. Reverse Phase HPLC Homogeneity (0.06% TFA; CH₃CN:H₂O): 99

Compound 5004

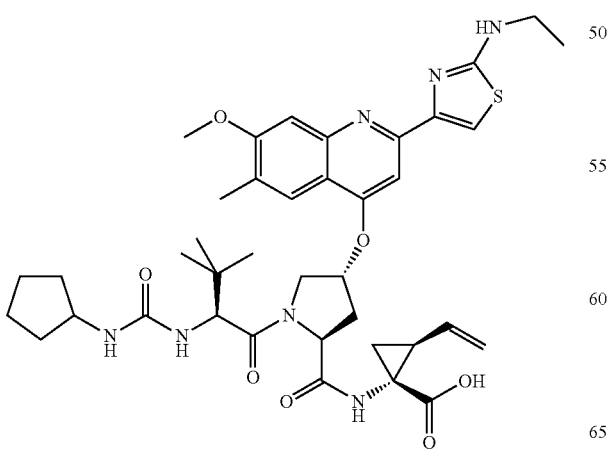

Compound 5004:

¹H NMR (400 MHz, DMSO-d₆): ca, 85:15 mixture of rotamers, major rotamer description; □8.60 (s, 1H), 8.31-8.16 (m, 1H), 8.11-8.02 (m, 1H), 7.97 (s, 1H), 7.89-7.78 (m, 1H), 7.75-7.67 (m, 1H), 6.00-5.92 (m, 1H), 5.90-5.83 (m, 1H), 5.80-5.65 (m, 2H), 5.26-5.16 (m, 1H), 5.11-5.04 (m, 1H), 4.58-4.46 (m, 2H), 4.11 (d, J=9.2 Hz, 1H), 4.05-3.94 (m, 1H), 4.00 (s, 3H), 3.65-3.15 (m, under H2O, 3H), 2.69-2.54 (m, 1H), 2.42-2.30 (m, 1H), 2.35 (s, 3H), 2.08-1.99 (m, 1H), 1.80-1.21 (m, 8H), 1.24 (t, J=7.0 Hz, 3H), 1.14-1.02 (m, 1H), 1.00-0.87 (m, 1H), 0.94 (s, 9H).

M.S. (electrospray): 760.4 (M−H)⁻ 762.4 (M+H)⁺. Reverse Phase HPLC Homogeneity (0.06% TFA; CH₃CN:H₂O): 96%

Compounds from Table 6

Compound 6016

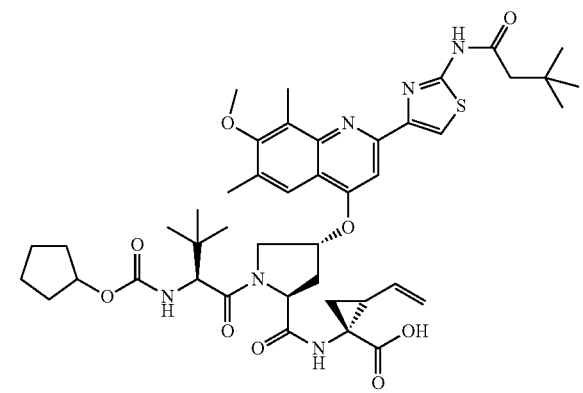

Compound 6016:

¹H NMR (400 MHz, DMSO-d₆): ca, 85:15 mixture of rotamers, major rotamer description; □12.28 (s, 2H); 8.56 (s, 1H); 8.04 (s, 1H) 7.79 (s, 1H); 7.46 (s, 1H); 6.96-7.00 (m, 1H); 5.68-5.75 (m, 1H); 5.40 (s, br, 1H); 5.19 (d, J=17.0 Hz, 1H); 5.06 (d, J=10.1 Hz, 1H); 4.71-4.76 (m, 2H); 4.43 (t, J=8.3, 1H); 4.32-4.34 (m, 1H); 4.13 (d, J=8.3 Hz, 1H); 3.96-4.03 (m, 1H); 3.77 (s, 3H); 2.67 (s, 3H); 2.40 (d, J=4.1 Hz, 3H); 2.24-2.36 (m, 3H); 2.03 (q, J=8.6 Hz, 1H); 1.17-1.75 (m, 10H); 1.04 (s, 9H); 0.98 (s, 9H).

M.S. (electrospray): 845.4 (M−H)⁻ 847.5 (M+H)⁺. Reverse Phase HPLC Homogeneity (0.06% TFA; CH₃CN:H₂O): 96.7%

Synthesis of Compounds of Formula I wherein $R^C$ is $NHSO_2R^S$

Example 17A

Synthesis of Compound 7001

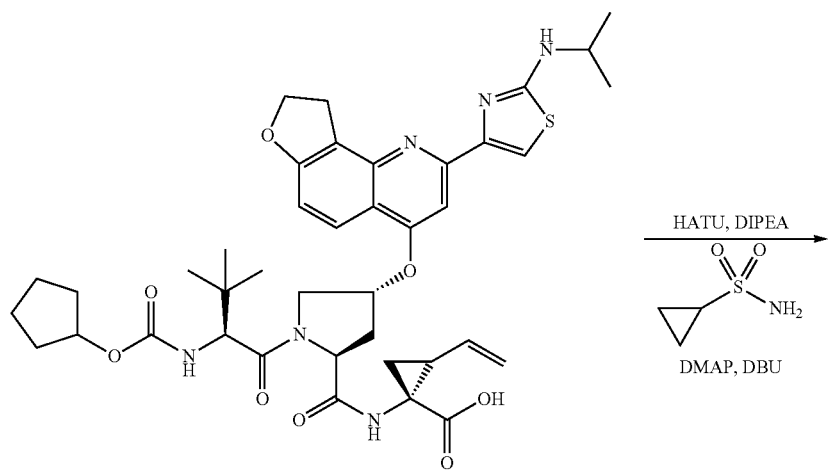

17A1

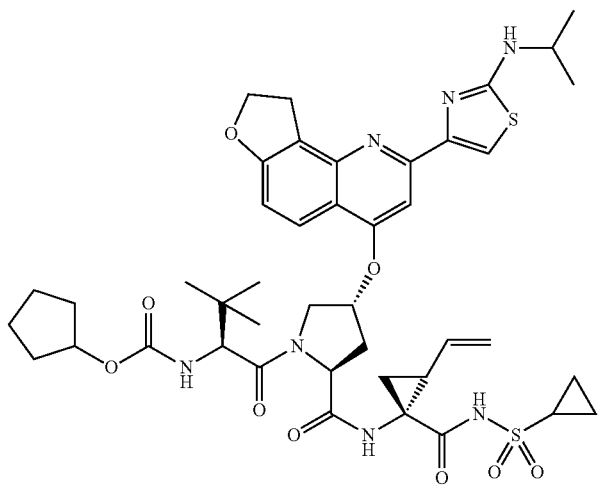

17A2

HATU (20 mg, 0.05 mmol) was added to a solution of compound 17A1 (Compound 3004, Table 3; 20 mg, 0.03 mmol) and DIPEA (0.03 mL, 0.16 mmol) in DMF (1.5 mL) at RT. The solution was stirred for 1 h followed by the addition of DMAP (16 mg, 0.13 mmol) and cyclopropanesulfonamide (7.0 mg, 0.06 mmol). After addition was complete, the mixture was allowed to stir for 15 min and DBU (0.02 mL, 0.14 mmol) was added dropwise. The resulting solution was stirred for 16 h at 23° C., then diluted with DMSO to 2.5 mL total volume and purified by prep HPLC (H$_2$O/CH$_3$CN+ 0.06% TFA). The fractions containing the pure product were combined and the solvents removed by lyophilization to yield 17A2 as a yellow solid (Compound 7001, table 7, 5.4 mg, 23%).

Reverse Phase HPLC Homogeneity (0.06% TFA; CH$_3$CN: H$_2$O): 98.9% (220 nm). MS: 878.8 (M+H)$^+$, 876.4 (M−H)$^−$. $^1$H NMR (400 MHz, DMSO-d$_6$): ☐10.47 (s, 1H); 8.82 (s, 1H); 8.06 (s, br, 1H); 7.52 (s, br, 1H); 7.15 (m, 1H); 7.03 (d, J=8.0 Hz, 1H); 5.58 (m, 2H); 5.20 (d, J=17.0 Hz, 1H); 5.09 (d, J=11.5, 1H); 4.79 (m, 2H); 4.64 (m, 1H); 4.36-4.52 (m, 2H); 4.06 (d, J=8.0 Hz, 1H); 4.00-4.03 (m, 1H); 2.88-2.96 (m, 1H); 2.54-2.57 (m, 1H); 2.10-2.20 (m, 2H); 1.32-1.71 (m, 11H); 1.24 (dd, J=6.3, 1.2 Hz, 6H); 1.00-1.08 (m, 8H); 0.97 (s, 9H).

Example 17B
Synthesis of Compound 7002
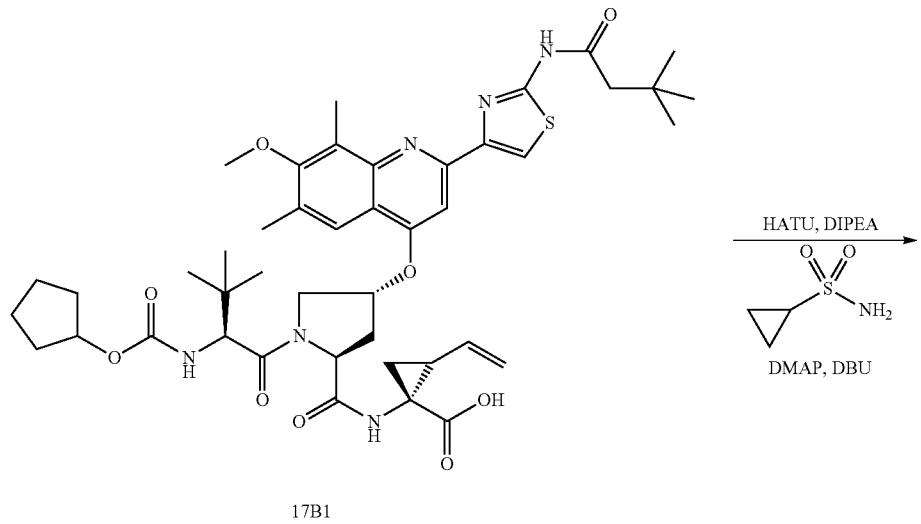
17B1
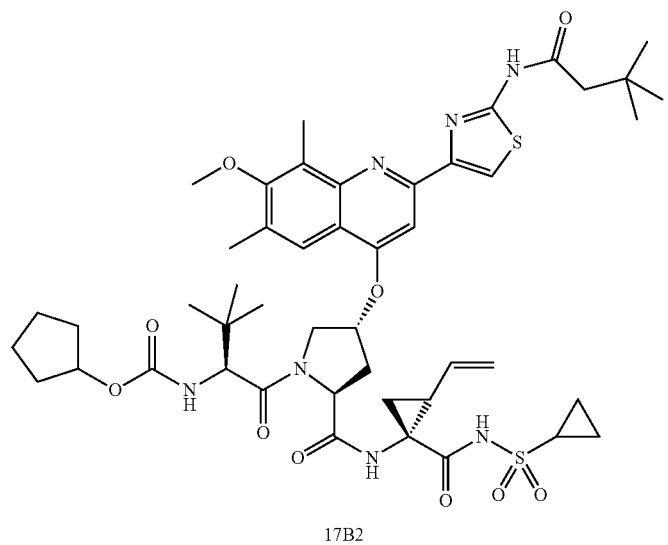
17B2
Using the procedure of Example 17A but starting with compound 17B1 (Compound 6016, Table 6), compound 17B2 (Compound 7002, Table 7) was prepared as a light yellow solid (5.4 mg, 16% yield).
Reverse Phase HPLC Homogeneity (0.06% TFA; CH₃CN: H₂O): 93.1% (220 nm).
MS: 950.4 (M+H)⁺, 948.4 (M−H)⁻. $^1$H NMR (400 MHz, DMSO-d$_6$): □12.26 (s, 1H); 10.48 (s, 1H); 8.83 (s, 1H); 8.02 (s, 1H); 7.79 (s, 1H); 7.45 (s, 1H); 6.94-7.00 (m, 1H); 5.56-5.65 (m, 1H); 5.40 (s, 1H); 5.19 (d, J=16.9, 1H); 5.07 (d, J=11.4, 1H); 4.77 (s, 1H); 4.33-4.42 (m, 2H); 4.11 (d, J=8.0 Hz, 1H); 3.97 (d, J=9.6, 1H); 3.76 (s, 3H); 3.76 (s, 3H); 2.88-2.96 (m, 1H); 2.66 (s, 3H); 2.53-2.60 (m, 1H); 2.31-2.33 (m, 1H); 2.11-2.19 (m, 2H); 1.33-1.70 (m, 12H); 1.22 (s, br, 1H); 1.05-1.08 (m, 2H); 1.02 (s, 9H); 0.98 (s, 9H).

Example 17C

Synthesis of Compound 7003

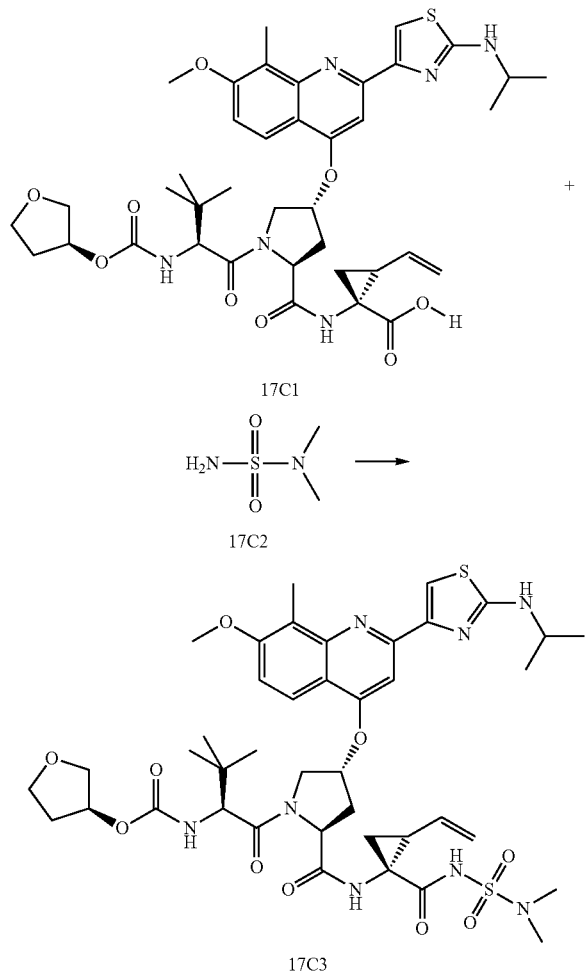

Compound 17C1 (Compound 1027, Table 1; 35 mg, 0.045 mmol), N,N-dimethylsulfamide 17C2 (22.3 mg, 0.180 mmol) DIPEA (39.3 □l, 0.225 mmol) and DMAP (22 mg, 0.180 mmol) were dissolved in DMF (2.5 mL) and to the mixture was added DBU (28.5 □l, 0.203 mmol). The reaction mixture was stirred for 5 min, then HATU (18.8 mg, 0.05 mmol) was added. Stirring was continued for 12 h and the residue was filtered through Millex filter and purified by Prep HPLC (Combiscreen ODS-AQ, 20×50 mm). The pure fractions were pooled together and lyophilized to afford 14 mg (yield, 35%) of compound 17C3 (Compound 7003, Table 7) as a yellow solid.

$^1$HNMR (400 MHz, DMSO-$d_6$): □10.23 (s, 1H), 8.74 (s, 1H), 8.07 (d, J=8 Hz, 1H), 7.59 (s, 1H), 7.45-7.30 (m, 1H), 7.27 (d, J=8 Hz, 1H), 5.53-5.49 (m, 2H), 5.20 (d, J=17 Hz, 1H), 5.10 (d, J=12 Hz, 1H), 4.70 (bs, 1H), 4.50-4.30 (m, 3H), 4.15-4.05 (m, 2H), 3.97 (s, 3H), 2.76 (s, 6H), 2.55 (s, 3H), 2.38-2.32 (m, 1H), 2.23-2.08 (m, 2H), 1.97-1.81 (m, 1H), 1.75-1.45 (m, 4H), 1.32-1.14 (m, 9H), 1.04-0.86 (m, 11H).

EIMS: (M+H)=885.4, (M−H)=883.4

Example 18

NS3-NS4A Protease Assay

The enzymatic assay used to evaluate the present compound is described in WO 00/09543 and WO 00/59929.

Example 19

Cell Based HCV RNA Replication Assay

Cell Culture

Huh7 cells that stably maintain a subgenomic HCV replicon were established as previously described (Lohman et al., 1999. Science 285: 110-113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50, 000 cells/mL in Standard Medium. 200 µL (10, 000 cells) are distributed into each well of a 96-well plate. The plate was then incubated at 37° C. with 5% $CO_2$ until the next day.

Reagents and Materials:

| Product | Company | Catalog # | Storage |
|---|---|---|---|
| DMEM | Wisent Inc. | 10013CV | 4° C. |
| DMSO | Sigma | D-2650 | R.T. |
| Dulbecco's PBS | Gibco-BRL | 14190-136 | R.T. |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | R.T. |
| PVDF 0.22 µm Filter Unit | Millipore | SLGV025LS | R.T. |
| Deep-Well Titer Plate Polypropylene | Beckman | 267007 | R.T. |

Preparation of Test Compound

10 µL of test compound (in 100% DMSO) was added to 2 mL of Assay Medium for a final DMSO concentration of 0.5% and the solution was sonicated for 15 min and filtered through a 0.22 µM Millipore Filter Unit. 900 µl was transferred into row A of a Polypropylene Deep-Well Titer Plate. Rows B to H contain 400 µL aliquots of Assay Medium (containing 0.5% DMSO), and are used to prepare serial dilutions (1/2) by transferring 400 µL from row to row (no compound was included in row H).

Application of Test Compound to Cells

Cell culture medium was aspirated from the 96-well plate containing the S22.3 cells. 175 µL of assay medium with the appropriate dilution of test compound was transferred from each well of the compound plate to the corresponding well of the cell culture plate (row H was used as the "No inhibition control"). The cell culture plate was incubated at 37° C. with 5% $CO_2$ for 72 h.

Extraction of Total Cellular RNA

Following the 72 h incubation period, the total cellular RNA was extracted from the S22.3 cells of the 96-well plate using the RNeasy 96 kit (Qiagen®, RNeasy Handbook. 1999). Briefly, assay medium was completely removed from cells and 100 µL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 mL of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 mL of Buffer RPE (Qiagen® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 mL of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 μl of RNase-free water to each well, sealing plate with a new piece of tape and incubated for 1 min at room temperature. The plate was then centrifuged at 6000 rpm for 4 min at room temperature. The elution step was repeated with a second volume of 50 μL RNase-free water. The microtubes with total cellular RNA are stored at −70°.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 μL of reagent was diluted in 10 mL TE. A Standard Curve of ribosomal RNA was diluted in TE to 2 μg/mL and pre-determined amounts (100, 50, 40, 20, 10, 5, 2 and 0 μL) of the ribosomal RNA solution are then transferred in a new 96-well plate (COSTAR #3997) and the volume was completed to 100 μL with TE. Generally, column 1 of the 96-well plate was used for the standard curve and the other wells are used for the RNA samples to be quantified. 10 μL of each RNA sample that was to be quantified, was transferred to the corresponding well of the 96-well plate and 90 μl of TE was added. One volume (100 μL) of diluted RiboGreen reagent was added to each well of the 96-wells plate and incubated for 2 to 5 minutes at room temperature, protected from light (a 10 μL RNA sample in a 200 μL final volume generates a 20× dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20× dilution.

Reagents and Materials:

| Product | Company | Catalog # | Storage |
|---|---|---|---|
| DEPC | Sigma | D5758 | 4° C. |
| EDTA | Sigma | E5134 | R.T. |
| Trizma-Base | Sigma | T8524 | R.T. |
| Trizma-HCl | Sigma | T7149 | R.T. |
| Collection Tube Strips | Qiagen | 19562 | R.T. |
| Ribogreen RNA Quantitation Kit | Molecular Probe | R11490 | −20° C. |
| Rneasy 96 Kit | Qiagen | 74183 | R.T. |
| Square-Well Blocks | Qiagen | 19573 | R.T. |

Real-Time R.T.-PCR

The Real-Time R.T.-PCR was performed on the ABI Prism 7700 Sequence Detection System using the TaqMan EZ R.T.-PCR Kit from (Perkin-Elmer Applied Biosystems®). R.T.-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327-332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each R.T.-PCR plate. HCV Replicon RNA was synthesized (by T7 transcription) in vitro, purified and quantified by $OD_{260}$. Considering that 1 μg of this RNA=$2.15 \times 10^{11}$ RNA copies, dilutions are made in order to have $10^8$, $10^7$, $10^6$, $10^5$, $10^4$, $10^3$ or $10^2$ genomic RNA copies/5 Total cellular Huh-7 RNA was also incorporated with each dilution (50 ng/5 μL). 5 μL of each reference standard (HCV Replicon+Huh-7 RNA) was combined with 45 μL of Reagent Mix, and used in the Real-Time R.T.-PCR reaction.

The Real-Time R.T.-PCR reaction was set-up for the experimental samples that were purified on RNeasy 96-well plates by combining 5 μL of each total cellular RNA sample with 45 μl of Reagent Mix.

Reagents and Materials:

| Product | COMPANY | Catalog # | Storage |
|---|---|---|---|
| TaqMan EZ R.T.-PCR Kit | PE Applied Biosystems | N808-0236 | −20° C. |
| MicroAmp Optical Caps | PE Applied Biosystems | N801-0935 | R.T. |

-continued

| Product | COMPANY | Catalog # | Storage |
|---|---|---|---|
| MicroAmp Optical 96-Well Reaction Plate | PE Applied Biosystems | N801-0560 | R.T. |

Reagent Mix Preparation:

| Component | Volume for one sample (μL) | Volume for One Plate (μL) (91 samples + Dead Volume) | Final conc. |
|---|---|---|---|
| Rnase-free water | 16.5 | 1617 | |
| 5× TaqMan EZ buffer | 10 | 980 | 1X |
| Mn(OAc)$_2$ (25 mM) | 6 | 588 | 3 mM |
| dATP (10 mM) | 1.5 | 147 | 300 μM |
| dCTP (10 mM) | 1.5 | 147 | 300 μM |
| dGTP (10 mM) | 1.5 | 147 | 300 μM |
| dUTP (20 mM) | 1.5 | 147 | 600 μM |
| Forward Primer (10 μM) | 1 | 98 | 200 nM |
| Reverse Primer (10 μM) | 1 | 98 | 200 nM |
| PUTR probe (5 μM) | 2 | 196 | 200 nM |
| rTth DNA polymerase (2.5 U/μL) | 2 | 196 | 0.1 U/μL |
| AmpErase UNG (1 U/μL) | 0.5 | 49 | 0.01 U/μL |
| Total Volume | 45 | 4410 | |

```
Forward Primer Sequence (SEQ ID. 1):
5'- ACG CAG AAA GCG TCT AGC CAT GGC GTT
AGT -3'

Reverse Primer Sequence (SEQ ID NO. 2):
5'- TCC CGG GGC ACT CGC AAG CAC CCT ATC
AGG -3'
```

Note: Those primers amplify a region of 256-nt present within the 5' untranslated region of HCV.

```
PUTR Probe Sequence (SEQ ID NO. 3):
6FAM- TGG TCT GCG GAA CCG GTG AGT ACA
CC - TAMRA
```

No Template Controls (NTC): On each plate, 4 wells are used as "NTC". For these controls, 5 μL of water are added to the well in place of RNA.

Thermal Cycling Conditions:

| | | |
|---|---|---|
| 50° C. | 2 min | |
| 60° C. | 30 min | |
| 95° C. | 5 min | |
| 95° C. | 15 sec | } for 2 cycles |
| 60° C. | 1 min | |
| 90° C. | 15 sec | } for 40 cycles |
| 60° C. | 1 min | |

Following the termination of the R.T.-PCR reaction the data analysis requires setting of threshold fluorescence signal for the PCR plate and a standard curve was constructed by plotting the $C_T$ value versus RNA copy number used in each reference reaction. The $C_T$ values obtained for the assay samples are used to interpolate an RNA copy number based on the standard curve.

Finally, the RNA copy number was normalized (based on the RiboGreen RNA quantification of the total RNA extracted from the cell culture well) and expressed as genome equivalents/μg of total RNA [g.e./μg].

The RNA copy number [g.e./μg] from each well of the cell culture plate was a measure of the amount of replicating HCV RNA in the presence of various concentrations of inhibitor. The % inhibition was calculated with the following equation:

$$100-[(g.e./\mu g\ inh)/(g.e./\mu g\ ctl) \times 100].$$

A non-linear curve fit with the Hill model was applied to the inhibition-concentration data, and the 50% effective concentration ($EC_{50}$) was calculated by the use of SAS software (Statistical Software System; SAS Institute, Inc. Cary, N.C.).

When the compounds of this invention are evaluated in the preceding enzymatic and cell based assays, the compounds are found to be highly active.

Example 20

Specificity Assays

The specificity assays used to evaluate the selectivity of this compound are described in WO 00/09543.

When the compounds were evaluated in the specificity assays, the compounds of formula I were found to be selective in that they do not show significant inhibition (no measurable activity at concentrations up to 30 μM) in the Human Leukocyte Elastase and Cathepsin B assays.

Example 21

Pharmacokinetic Properties

The present invention comprises compounds that show pharmacokinetic properties such as detectable plasma levels in the rat at 1 hour and 2 h after an oral dose of 5 mg/kg.

More explicitly, the following assay, an in vivo oral absorption screen, is used to determine plasma levels of test compounds in a rat after oral administration:

Materials and Methods:
1. Method Used to Pool Compounds ("Cassette Selection"):

The selection of compounds to be pooled into a "cassette" was based on their structural similarity and physicochemical properties. A solid phase extraction method applicable to all the selected compounds was established. Based on the initial testing where each compound was spiked into rat plasma and run through HPLC or HPLC/MS at a concentration of 0.5 μM, the retention time, ionic mass, and the possible separation among compounds by HPLC and/or HPLC/MS were used as basis for pooling 3-4 compounds into one "cassette".

2. Oral Vehicle and Compound Preparation:

Each "cassette" contains 3-4 compounds at 5 or 4 mg/kg for each compound. The cassettes were prepared as an oral suspension in 0.5% aqueous methylcellulose and 0.3% of polyoxyethylene (20) sorbitan monooleate (Tween-80). The dosing volume was 10 mL/kg via oral gavage.

3. Dosing and Plasma Sampling:

Male Sprague Dawley rats were fasted overnight in individual cages, with access to aqueous 10% dextrose. Two rats were dosed with each "cassette". Plasma samples (~1 mL) were collected at 1 and 2 h post-dosing from the 2 rats and pooled for extraction and analysis.

4. Compound Extraction and Analysis:

From each cassette, plasma samples at 1 and 2 h, blank plasma, blank plasma spiked with all the compounds at 0.5 µM of each, are extracted by the solid phase extraction method. Samples were analyzed by HPLC and HPLC/MS for comparison purpose. Plasma concentrations are estimated based on the single concentration of 0.5 µM standard.

Results

When assayed in the preceding screen, some compounds of this invention are found in the plasma at the 1 hour and 2 hour intervals following oral administration, with blood plasma levels up to 1.5 µM.

Tables of Compounds

In the following examples of compounds according to this invention are listed in the Tables 1 to 7, wherein Me defines methyl, Et defines ethyl and tBu defines tert-butyl. Compounds according to this invention usually show $IC_{50}$ values lower than about 200 nM and $EC_{50}$ values lower than about 300 nM.

TABLE 1

| Cpd. | B | $L^0$ | $L^1$ | $R^2$ | m/z $(M + H)^+$ $(MH + 2)^+$ |
|---|---|---|---|---|---|
| 1001 | tert-butyl | MeO— | MeO— | NHC(O)CH$_2$C(CH$_3$)$_3$ | 837.3 |
| 1002 | cyclobutyl | MeO— | MeO— | NHC(O)CH$_2$C(CH$_3$)$_3$ | 835.3 |
| 1003 | cyclopentyl | MeO— | MeO— | NHC(O)CH$_2$C(CH$_3$)$_3$ | 849.3 |
| 1004 | cyclohexyl | MeO— | MeO— | NHC(O)CH$_2$C(CH$_3$)$_3$ | 863.4 |
| 1005 | cyclobutylmethyl | MeO— | Me— | NHC(O)CH$_2$-cyclopentyl | 831.4 |
| 1006 | cyclobutylmethyl | MeO— | Me— | NHC(O)CH$_2$C(CH$_3$)$_3$ | 819.5 |

TABLE 1-continued
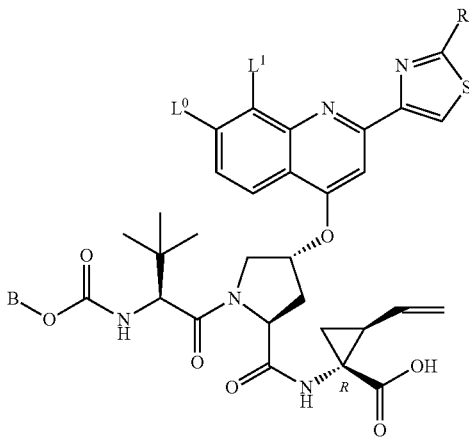
| Cpd. | B | L⁰ | L¹ | R² | m/z (M + H)⁺ (MH + 2)⁺ |
|---|---|---|---|---|---|
| 1007 | 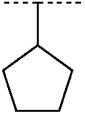 | MeO— | Me— | 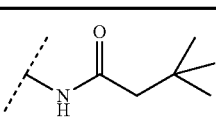 | 833.5 |
| 1008 |  | MeO— | Me— | 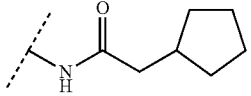 | 845.5 |
| 1009 |  | Me₂N— | Me— | 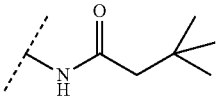 | 846.5 |
| 1010 |  | Me₂N— | Me— | 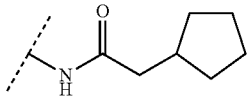 | 858.5 |
| 1011 |  | Me₂N— | Me— | 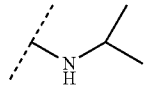 | 790.5 |
| 1012 |  | Me₂N— | Me— | 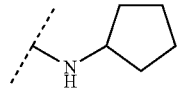 | 816.5 |
| 1013 |  | MeO— | Me— | 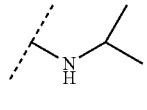 | 777.5 |
| 1014 |  | MeO— | Me— | 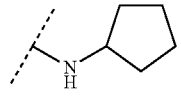 | 803.5 |

TABLE 1-continued
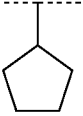
| Cpd. | B | L⁰ | L¹ | R² | m/z (M + H)⁺ (MH + 2)⁺ |
|---|---|---|---|---|---|
| 1015 | 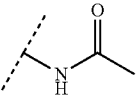 | MeO— | Me— |  | 777.5 |
| 1016 | 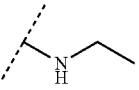 | MeO— | Me— |  | 763.5 |
| 1017 | 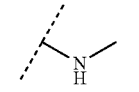 | MeO— | Me— |  | 749.5 |
| 1018 | 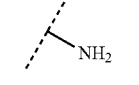 | MeO— | Me— |  | 735.4 |
| 1019 | 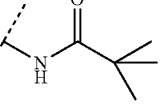 | MeO— | Me— |  | 819.4 |
| 1020 | 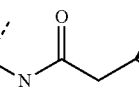 | MeO— | Et— |  | 847.5 |
| 1021 | 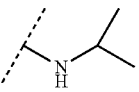 | MeO— | Et— |  | 791.4 |
| 1022 | 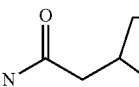 | MeO— | Et— | | 859.5 |

TABLE 1-continued
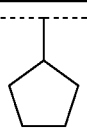
| Cpd. | B | L⁰ | L¹ | R² | m/z (M + H)⁺ (MH + 2)⁺ |
|---|---|---|---|---|---|
| 1023 | 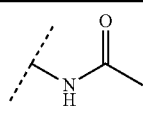 | MeO— | Et— | 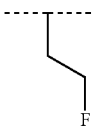 | 791.4 |
| 1024 | 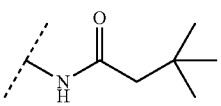 | MeO— | Me— | 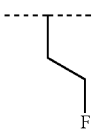 | 811.4 |
| 1025 | 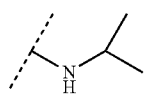 | MeO— | Me— | 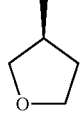 | 755.5 |
| 1026 | 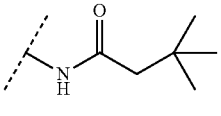 | MeO— | Me— | 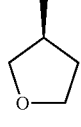 | 835.4 |
| 1027 | 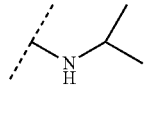 | MeO— | Me— | 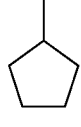 | 779.3 |
| 1028 | 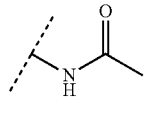 | MeO— | Br— | 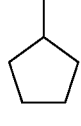 | 841.3 843.2 |
| 1029 | 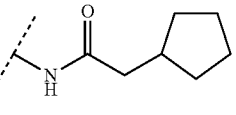 | MeO— | Br— | 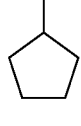 | 911.3 909.3 |
| 1030 | 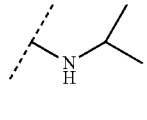 | MeO— | Br— | | 841.3 843.3 |

TABLE 1-continued

| Cpd. | B | L⁰ | L¹ | R² | m/z (M + H)⁺ (MH + 2)⁺ |
|---|---|---|---|---|---|
| 1031 | cyclopentyl | MeO— | Br— | NHC(O)CH₂C(CH₃)₃ | 897.3 899.3 |
| 1032 | cyclopentyl | tBuO— | Me— | NH-iPr | 819.4 |
| 1033 | cyclopentyl | tBuO— | Me— | NHC(O)CH₃ | 819.4 |
| 1034 | cyclopentyl | HO— | Me— | NH-iPr | 763.4 |
| 1035 | cyclopentyl | HO— | Me— | NHC(O)CH₃ | 763.3 |
| 1036 | 1-methylcyclopentyl | MeO— | Me— | NHC(O)CH₃ | 791.4 |
| 1037 | 1-methylcyclopentyl | MeO— | Me— | NHC(O)CH₂C(CH₃)₃ | 847.5 |
| 1038 | 1-methylcyclopentyl | MeO— | Me— | NH-iPr | 791.5 |

TABLE 1-continued
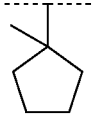
| Cpd. | B | L⁰ | L¹ | R² | m/z (M + H)⁺ (MH + 2)⁺ |
|---|---|---|---|---|---|
| 1039 | 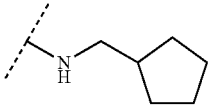 | MeO— | Me— |  | 859.5 |
| 1040 | 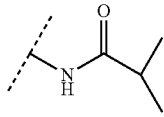 | MeO— | Me— |  | 805.4 |
| 1041 | 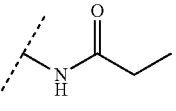 | MeO— | Me— |  | 791.4 |
| 1042 | 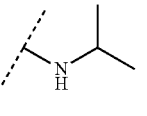 | MeO— | Cl |  | 797.4 799.3 |
| 1043 | 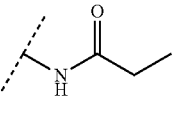 | MeO— | Br |  | 855.2 857.2 |
| 1044 | 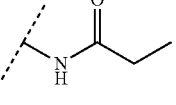 | MeO— | Cl |  | 811.3 813.3 |
| 1045 | 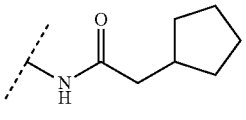 | MeO— | Cl |  | 865.4 867.4 |
| 1046 | 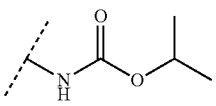 | MeO— | Me— |  | 821.4 |

TABLE 1-continued

| Cpd. | B | L⁰ | L¹ | R² | m/z (M + H)⁺ (MH + 2)⁺ |
|---|---|---|---|---|---|
| 1047 | cyclopentyl | MeO— | Me— | NHC(O)OMe | 793.4 |
| 1048 | cyclopentyl | MeO— | Cl | NHC(O)propyl | 825.3 827.3 |
| 1049 | cyclopentyl | MeO— | Br | NHC(O)OiPr | 885.3 887.3 |
| 1050 | cyclopentyl | MeO— | Cl | NHC(O)OiPr | 841.3 843.3 |
| 1051 | cyclopentyl | MeO— | F | NHC(O)Et | 795.3 |
| 1052 | cyclopentyl | MeO— | F | NH-iPr | 781.3 |
| 1053 | cyclopentyl | MeO— | Cl | NHC(O)OMe | 813.2 815.2 |
| 1054 | cyclopentyl | MeO— | Br | NHC(O)OMe | 857.2 859.2 |

TABLE 1-continued
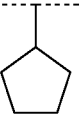
| Cpd. | B | L⁰ | L¹ | R² | m/z (M + H)⁺ (MH + 2)⁺ |
|---|---|---|---|---|---|
| 1055 | 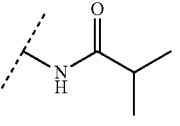 | MeO— | Br |  | 869<br>871.1 |
| 1056 | 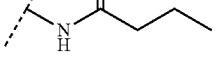 | MeO— | Br |  | 869<br>817.1 |
| 1057 | 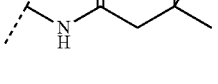 | HO | Me |  | 819.2 |
| 1058 | 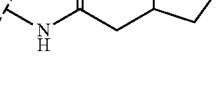 | HO | Me |  | 831.2 |
| 1059 | 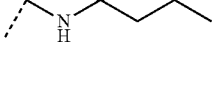 | H | Br |  | 867<br>869 |
| 1060 | 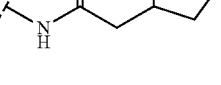 | H | Br |  | 879<br>881 |
| 1061 | 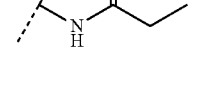 | H | Br |  | 825<br>827 |
| 1062 | 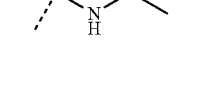 | H | Br | | 811<br>813 |

TABLE 1-continued

| Cpd. | B | L⁰ | L¹ | R² | m/z (M + H)⁺ (MH + 2)⁺ |
|---|---|---|---|---|---|
| 1063 | cyclopentyl-CH | F | Me | -NH-C(=O)-CH2-C(CH3)3 | 821.3 |
| 1064 | -CH(CH3)-CH2-CH2-CF3 | MeO— | Br | -NH-C(=O)-CH2CH3 | 883.2 885.2 |
| 1065 | cyclobutyl-CH | MeO— | Br | -NH-C(=O)-CH2CH3 | 869.3 871.3 |
| 1066 | -CH(CH3)-CH2CH3 | MeO— | Br | -NH-C(=O)-CH2CH3 | 815.2 817.2 |
| 1067 | -CH2-CH(CH3)2 with extra | MeO— | Br | -NH-C(=O)-CH2CH3 | 843.3 845.3 |
| 1068 | 4-methyl-1,3-dioxane-CH2 | MeO— | Br | -NH-C(=O)-CH2-cyclopentyl | 955.3 957.3 |
| 1069 | CF3-CH2-CH2-CH | MeO— | Br | -NH-C(=O)-CH2-cyclopentyl | 937.3 939.3 |
| 1070 | -CH(CH3)-CH2CH3 | MeO— | Br | -NH-C(=O)-CH2-cyclopentyl | 869.3 871.3 |

TABLE 1-continued

| Cpd. | B | L⁰ | L¹ | R² | m/z (M + H)⁺ (MH + 2)⁺ |
|---|---|---|---|---|---|
| 1071 | isobutyl | MeO— | Br | cyclopentylacetamide | 897.3 / 899.3 |
| 1072 | 4-methyl-1,3-dioxane-methyl | MeO— | Br | isopropyl carbamate | 931.3 / 933.3 |
| 1073 | CF₃-propyl | MeO— | Br | isopropyl carbamate | 913.2 / 915.2 |
| 1074 | cyclopentylmethyl | MeO— | Br | isopropyl carbamate | 899.3 / 901.3 |
| 1075 | propyl | MeO— | Br | isopropyl carbamate | 845.2 / 847.2 |
| 1076 | isobutyl | MeO— | Br | isopropyl carbamate | 873.3 / 875.3 |
| 1077 | 4-methyl-1,3-dioxane-methyl | MeO— | Br | isopropylamine | 887.2 / 889.2 |

TABLE 1-continued
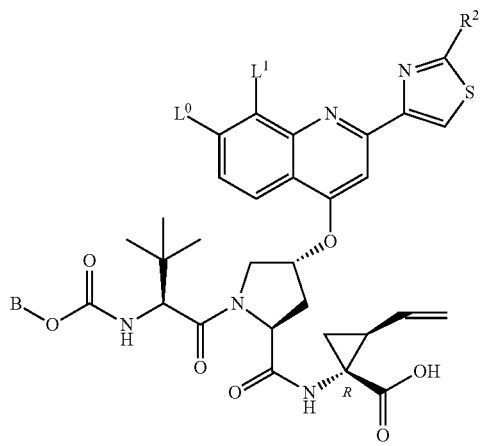
| Cpd. | B | L⁰ | L¹ | R² | m/z (M + H)⁺ (MH + 2)⁺ |
|---|---|---|---|---|---|
| 1078 | cyclopentyl-methyl | MeO— | Br | NH-iPr | 855.2 857.2 |
| 1079 | sec-butyl | MeO— | Br | NH-iPr | 801.2 803.2 |
| 1080 | isobutyl | MeO | Br | NH-iPr | 829.2 831.2 |
| 1081 | (1,3-dioxan-5-yl-methyl) | MeO | Br | NHC(O)Et | 901.3 903.3 |
| 1082 | cyclopentyl-methyl | H | Cl | NHC(O)CH₂C(CH₃)₃ | 823.3 825.3 |
| 1083 | cyclopentyl-methyl | H | Cl | NHC(O)CH₂-cyclopentyl | 835.3 837.3 |
| 1084 | cyclopentyl-methyl | H | Cl | NHC(O)Et | 781.2 783.2 |

TABLE 1-continued

| Cpd. | B | L⁰ | L¹ | R² | m/z (M + H)⁺ (MH + 2)⁺ |
|---|---|---|---|---|---|
| 1085 | cyclopentyl-CH2- | H | Cl | -NH-iPr | 767.2 769.2 |
| 1086 | cyclopentyl-CH2- | H | Cl | -NH-C(O)-CH2CH2CH3 | 795.2 797.2 |
| 1087 | cyclopentyl-CH2- | H | Cl | -NH-C(O)-CH(CH3)2 | 795.2 797.2 |
| 1088 | cyclopentyl-CH2- | H | Cl | -NH-C(O)-O-iPr | 811.2 813.2 |
| 1089 | cyclopentyl-CH2- | H | Cl | -NH-C(O)-O-Me | 783.2 |
| 1090 | cyclopentyl-CH2- | EtO— | Br | -NH-C(O)-CH2CH3 | 869.2 871.2 |
| 1091 | cyclopentyl-CH2- | EtO— | Br | -NH-C(O)-CH(CH3)2 | 883.2 885.2 |
| 1092 | cyclopentyl-CH2- | EtO— | Br | -NH-iPr | 855.2 857.2 |

TABLE 1-continued
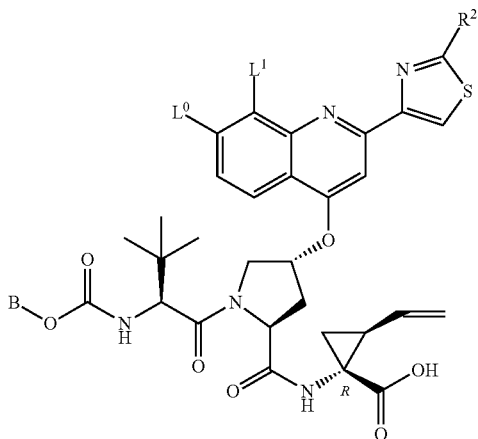
| Cpd. | B | L⁰ | L¹ | R² | m/z (M + H)⁺ (MH + 2)⁺ |
|---|---|---|---|---|---|
| 1093 | cyclopentylmethyl | EtO— | Br | NH-C(O)-O-iPr | 899.2 / 901.2 |
| 1094 | cyclopentylmethyl | PrO— | Br | NH-C(O)-Et | 883.2 / 885.2 |
| 1095 | cyclopentylmethyl | PrO— | Br | NH-C(O)-iPr | 897.2 / 899.2 |
| 1096 | cyclopentylmethyl | PrO— | Br | NH-iPr | 869.2 / 871.2 |
| 1097 | cyclopentylmethyl | PrO— | Br | NH-C(O)-O-iPr | 913.2 / 915.2 |
| 1098 | cyclopentylmethyl | H | Br | NH-C(O)-Me | 811 / 813 |
| 1099 | CF₃-(CH₂)₂- | MeO— | Br | NH-iPr | 869.2 / 871.1 |
| 1100 | cyclopentylmethyl | MeO— | Cl | NH-C(O)-iPr | 825.2 / 827.2 |

TABLE 1-continued
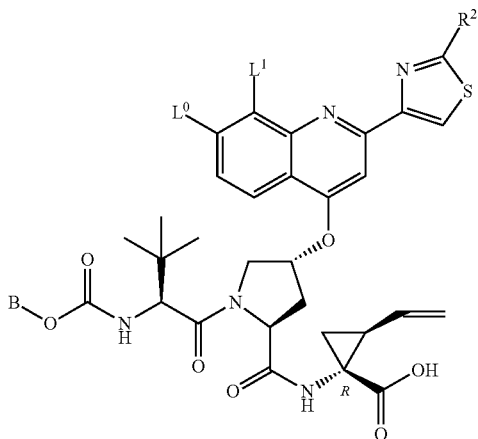
| Cpd. | B | L⁰ | L¹ | R² | m/z (M + H)⁺ (MH + 2)⁺ |
|---|---|---|---|---|---|
| 1101 | cyclopentyl-CH2- | EtO— | Me | -NHC(O)CH3 | 791.2 |
| 1102 | cyclopentyl-CH2- | EtO— | Me | -NHC(O)Et | 805.2 |
| 1103 | cyclopentyl-CH2- | EtO— | Me | -NH-iPr | 791.2 |
| 1104 | cyclopentyl-CH2- | EtO— | Me | -NHC(O)O-iPr | 835.3 |
| 1105 | cyclopentyl-CH2- | MeO— | CN | -NH-iPr | 786.2 |
| 1106 | cyclopentyl-CH2- | Br | MeO— | -NH-iPr | 841.2 843.2 |
| 1107 | cyclopentyl-CH2- | MeO— | CN | -NHC(O)Et | 800.2 |
| 1108 | F-CH2CH2CH2- | MeO— | Br | -NH-iPr | 819.1 821.1 |

TABLE 1-continued

| Cpd. | B | L⁰ | L¹ | R² | m/z (M + H)⁺ (MH + 2)⁺ |
|---|---|---|---|---|---|
| 1109 | F-CH₂CH₂CH₂-CH(CH₃)- | MeO | Br | -NH-iPr | 833.1 / 835.2 |
| 1110 | (S)-tetrahydrofuran-3-yl | MeO— | Br | -NH-iPr | 843.2 / 845.2 |
| 1111 | n-butyl (sec) | MeO— | Br | -NH-iPr | 815.2 / 817.2 |
| 1112 | 3-methylbut-2-yl | MeO— | Br | -NH-iPr | 843.2 / 845.2 |
| 1113 | F-CH₂CH₂-CH(CH₃)- | MeO— | Br | -NH-C(O)Et | 833.1 / 835.1 |
| 1114 | F-CH₂CH₂CH₂-CH(CH₃)- | MeO | Br | -NH-C(O)Et | 847.2 / 849.2 |
| 1115 | (S)-tetrahydrofuran-3-yl | MeO— | Br | -NH-C(O)Et | 857.2 / 859.2 |
| 1116 | n-butyl (sec) | MeO | Br | -NH-C(O)Et | 829.2 / 831.2 |
| 1117 | 3-methylbut-2-yl | MeO | Br | -NH-C(O)Et | 857.2 / 859.2 |

TABLE 1-continued

| Cpd. | B | L⁰ | L¹ | R² | m/z (M + H)⁺ (MH + 2)⁺ |
|---|---|---|---|---|---|
| 1118 | F-(CH₂)₂- | MeO | Br | -NHC(O)O-iPr | 863.2 / 865.2 |
| 1119 | F-(CH₂)₃- | MeO | Br | -NHC(O)O-iPr | 877.2 / 879.2 |
| 1120 | 3-isopropyl-tetrahydrofuran-3-yl | MeO | Br | -NHC(O)O-iPr | 887.2 / 889.2 |
| 1121 | sec-butyl | MeO | Br | -NHC(O)O-iPr | 859.2 / 861.2 |
| 1122 | 2,3-dimethylbut-2-yl | MeO | Br | -NHC(O)O-iPr | 887.2 / 889.2 |
| 1123 | cyclopentylmethyl | MeO | CN | -NHC(O)CH₂C(CH₃)₃ | 842.2 |
| 1124 | cyclopentylmethyl | MeO | CN | -NHC(O)CH₃ | 786.2 |
| 1125 | F-(CH₂)₂- | MeO— | Cl | -NH-iPr | 775.4 / 777.3 |
| 1126 | CF₃-(CH₂)₂- | MeO— | Cl | -NH-iPr | 825.4 / 827.4 |

TABLE 1-continued

| Cpd. | B | L⁰ | L¹ | R² | m/z (M + H)⁺ (MH + 2)⁺ |
|---|---|---|---|---|---|
| 1127 | ethyl(sec-butyl) | MeO | Cl | NH-iPr | 757.4 / 759.4 |
| 1128 | isobutyl-CH | MeO | Cl | NH-iPr | 785.4 / 787.4 |
| 1129 | tetrahydrofuran-3-yl | MeO | Cl | NH-iPr | 799.3 / 801.3 |
| 1130 | sec-pentyl | MeO | Cl | NH-iPr | 771.3 / 773.3 |
| 1131 | F-(CH₂)₃-CH | MeO | Cl | NH-iPr | 789.3 / 791.3 |
| 1132 | 2,3-dimethylbutyl | MeO | Cl | NH-iPr | 799.5 / 801.4 |
| 1133 | F-CH₂CH₂-CH | MeO | Cl | NHC(O)Et | 789.4 / 791.4 |
| 1134 | CF₃-(CH₂)₂-CH | MeO | Cl | NHC(O)Et | 839.4 / 841.4 |
| 1135 | sec-butyl | MeO | Cl | NHC(O)Et | 771.4 / 773.4 |

TABLE 1-continued

| Cpd. | B | L⁰ | L¹ | R² | m/z (M + H)⁺ (MH + 2)⁺ |
|---|---|---|---|---|---|
| 1136 | isobutyl | MeO | Cl | -CH₂NHC(O)Et | 799.4 / 801.4 |
| 1137 | tetrahydrofuran-3-yl | MeO | Cl | -CH₂NHC(O)Et | 813.3 / 815.3 |
| 1138 | sec-butyl | MeO | Cl | -CH₂NHC(O)Et | 785.3 / 787.3 |
| 1139 | 4-fluorobutyl | MeO | Cl | -CH₂NHC(O)Et | 803.3 / 805.3 |
| 1140 | 3-methylbut-2-yl | MeO | Cl | -CH₂NHC(O)Et | 813.5 / 815.4 |
| 1141 | 3-fluoropropyl | MeO | Cl | -CH₂NHC(O)OiPr | 819.4 / 821.4 |
| 1142 | 4,4,4-trifluorobutyl | MeO | Cl | -CH₂NHC(O)OiPr | 869.4 / 871.4 |
| 1143 | propyl | MeO | Cl | -CH₂NHC(O)OiPr | 801.4 / 803.4 |
| 1144 | isobutyl | MeO | Cl | -CH₂NHC(O)OiPr | 829.5 / 831.5 |

TABLE 1-continued

| Cpd. | B | L⁰ | L¹ | R² | m/z (M + H)⁺ (MH + 2)⁺ |
|---|---|---|---|---|---|
| 1145 | (3-tetrahydrofuranyl) | MeO | Cl | -NHC(O)OiPr | 843.4 / 845.3 |
| 1146 | sec-butyl | MeO | Cl | -NHC(O)OiPr | 815.3 / 817.3 |
| 1147 | 3-fluoropropyl | MeO | Cl | -NHC(O)OiPr | 833.3 / 835.3 |
| 1148 | 3-methylbut-2-yl | MeO | Cl | -NHC(O)OiPr | 843.5 / 845.5 |
| 1149 | 2-fluoroethyl-methyl | MeO | Cl | -NHC(O)iPr | 803.2 / 805.2 |
| 1150 | 3,3,3-trifluoropropyl | MeO | Cl | -NHC(O)iPr | 853.2 / 855.2 |
| 1151 | ethyl | MeO | Cl | -NHC(O)iPr | 785.2 |
| 1152 | isobutyl | MeO | Cl | -NHC(O)iPr | 813.3 |

TABLE 1-continued
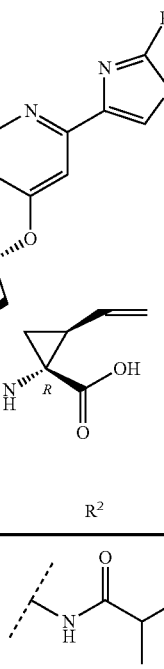
| Cpd. | B | L⁰ | L¹ | R² | m/z (M + H)⁺ (MH + 2)⁺ |
|---|---|---|---|---|---|
| 1153 | 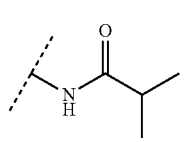 | MeO | Cl |  | 817.2 |
| 1154 | 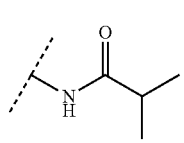 | MeO | Br | 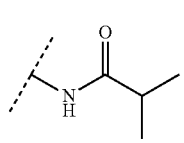 | 897.3 899.2 |
| 1155 | 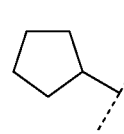 | MeO | Br | 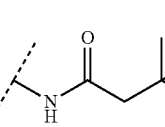 | 829.2 831.2 |
| 1156 | 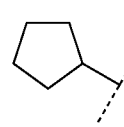 | MeO | Br | 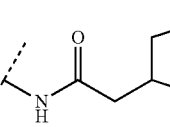 | 847.3 849.2 |
| 1157 | 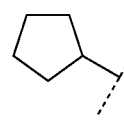 | H | —SMe | 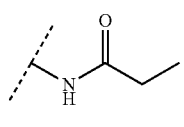 | 835.4 |
| 1158 | 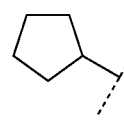 | H | —SMe | 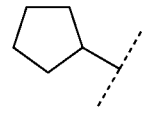 | 847.4 |
| 1159 | 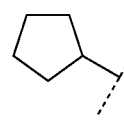 | H | —SMe | 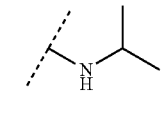 | 79.3. |
| 1160 | 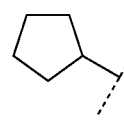 | H | —SMe | 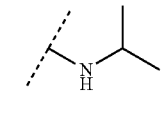 | 779.3 |

TABLE 1-continued

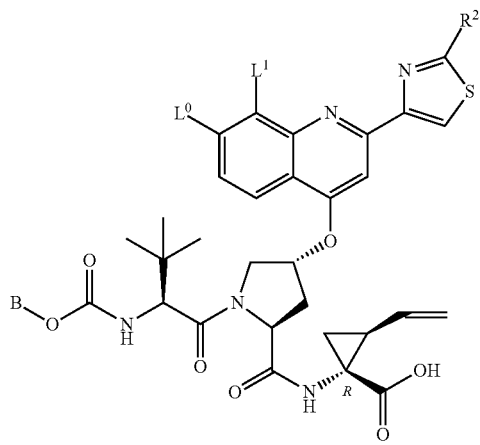

| Cpd. | B | L⁰ | L¹ | R² | m/z (M + H)⁺ (MH + 2)⁺ |
|---|---|---|---|---|---|
| 1161 | cyclopentylmethyl | H | —SMe | -NHC(O)CH₂CH₂CH₃ | 807.3 |
| 1162 | cyclopentylmethyl | H | —SMe | -NHC(O)CH(CH₃)₂ | 807.3 |
| 1163 | cyclopentylmethyl | H | —SMe | -NHC(O)OCH(CH₃)₂ | 823.3 |
| 1164 | cyclopentylmethyl | H | —CF₃ | -NHCH(CH₃)₂ | 801.4 |
| 1165 | cyclopentylmethyl | H | —CF₃ | -NHC(O)OCH(CH₃)₂ | 845.4 |
| 1166 | cyclopentylmethyl | H | —CF₃ | -NHC(O)CH₂CH₃ | 815.4 |
| 1167 | cyclopentylmethyl | Cl | Cl | -NHC(O)CH₃ | 801.3 803.3 805.3 |
| 1168 | cyclopentylmethyl | Cl | Cl | -NHC(O)CH₂C(CH₃)₃ | 857.2 |
| 1169 | cyclopentylmethyl | Cl | Cl | -NHCH(CH₃)₂ | 801.3 |

TABLE 1-continued
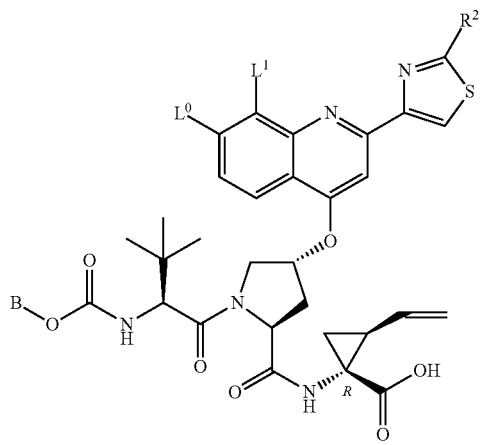
| Cpd. | B | L⁰ | L¹ | R² | m/z (M + H)⁺ (MH + 2)⁺ |
|---|---|---|---|---|---|
| 1170 | cyclopentylmethyl | Cl | Cl | -NHC(O)Et | 815.3 817.3 819.3 |
| 1171 | cyclopentylmethyl | H | —SO₂Me | -NH-iPr | 811.3 |
| 1172 | cyclopentylmethyl | H | —SO₂Me | -NHC(O)iPr | 839.3 |
| 1173 | cyclopentylmethyl | H | Me— | -NHC(O)Me | 747.3 |
| 1174 | cyclopentylmethyl | H | Me— | -NHC(O)Et | 761.4 |
| 1175 | cyclopentylmethyl | H | Me— | -NHC(O)CH₂C(CH₃)₃ | 803.4 |
| 1176 | cyclopentylmethyl | H | Me— | -NH-iPr | 747.4 |
| 1177 | cyclopentylmethyl | H | Me— | -NHC(O)iPr | 775.4 |
| 1178 | cyclopentylmethyl | H | Me— | -NHC(O)OiPr | 791.4 |

TABLE 1-continued

| Cpd. | B | L⁰ | L¹ | R² | m/z (M + H)⁺ (MH + 2)⁺ |
|---|---|---|---|---|---|
| 1179 | cyclopentylmethyl | H | —SO₂Me | NHC(O)O-iPr | 855.3 |
| 1180 | cyclopentylmethyl | H | —SO₂Me | NHC(O)Et | 825.2 |
| 1181 | cyclopentylmethyl | H | —OMe | NH-iPr | 763.4 |

TABLE 2

| Cpd. # | B | L⁰ | L¹ | R² | m/z (M + H)⁺ (MH + 2)⁺ |
|---|---|---|---|---|---|
| 2001 | cyclopentylmethyl | MeO— | Me— | NHC(O)CH₂C(CH₃)₃ | 832.6 |

TABLE 2-continued
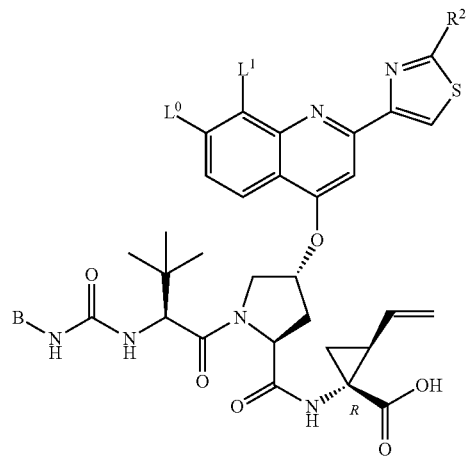
| Cpd. # | B | L⁰ | L¹ | R² | m/z (M + H)⁺ (MH + 2)⁺ |
|---|---|---|---|---|---|
| 2002 | cyclopentyl | MeO— | Me— | —NH-iPr | 776.5 |
| 2003 | cyclopentyl | MeO— | Me— | —NH₂ | 734.4 |
| 2004 | cyclopentyl | MeO— | Me— | —NHMe | 748.5 |
| 2005 | cyclopentyl | MeO— | Me— | —NHEt | 762.5 |
| 2006 | cyclopentyl | MeO— | Me— | —NH-cyclopentyl | 802.5 |
| 2007 | cyclopentyl | MeO— | Me— | —NHC(O)Me | 776.4 |
| 2008 | cyclopentyl | MeO— | Me— | —NHC(O)CH₂-cyclopentyl | 844.5 |

TABLE 2-continued
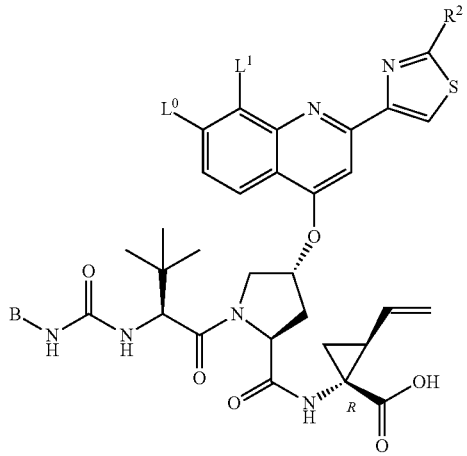
| Cpd. # | B | L⁰ | L¹ | R² | m/z (M + H)⁺ (MH + 2)⁺ |
|---|---|---|---|---|---|
| 2009 | cyclopentyl | MeO— | Me— | —CH(CH₃)— | 733.4 |
| 2010 | cyclopentyl | MeO— | Me— | —CH(Et)— | 747.4 |
| 2011 | cyclopentyl | MeO— | Me— | —CH(iPr)— | 761.4 |
| 2012 | 1-methylcyclopentyl | MeO— | Me— | —CH(NHC(O)CH₂C(CH₃)₃)— | 846.5 |
| 2013 | tert-butyl | MeO— | Me— | —CH(NHC(O)CH₃)— | 764.4 |
| 2014 | tert-butyl | MeO— | Me— | —CH(NHC(O)CH₂-cyclopentyl)— | 832.5 |
| 2015 | 1-methylcyclopentyl | MeO— | Me— | —CH(NHC(O)CH₃)— | 790.4 |

TABLE 2-continued
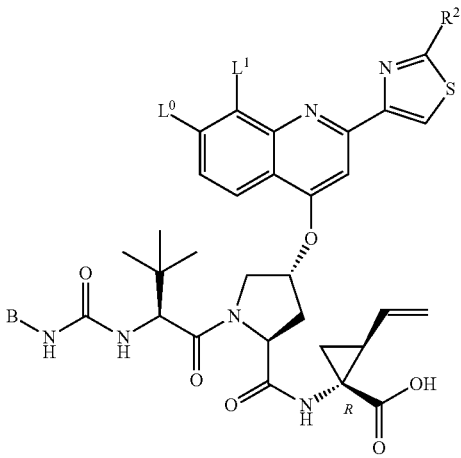
| Cpd. # | B | $L^0$ | $L^1$ | $R^2$ | m/z (M + H)$^+$ (MH + 2)$^+$ |
|---|---|---|---|---|---|
| 2016 | 1-methylcyclopentyl | MeO— | Me— | —NHC(O)CH$_2$-cyclopentyl | 858.5 |
| 2017 | cyclopentylmethyl | MeO— | Br— | —NHC(O)Et | 854.3 856.3 |
| 2018 | 3,3-dimethyl-2-butyl | MeO— | Me— | —NHC(O)Me | 792.4 |
| 2019 | 2-isopropyl-3-methoxypropyl | MeO— | Me | —NHC(O)CH$_2$-cyclopentyl | 876.5 |
| 2020 | 2,2-dimethyl-3-methoxypropyl | MeO— | Me | —NHC(O)CH$_2$-cyclopentyl | 890.5 |

TABLE 3

| Cpd. # | B | W¹ | W² | R² | m/z (M + H)⁺ (MH + 2)⁺ |
|---|---|---|---|---|---|
| 3001 | cyclopentyl | —O— | —O— | isopropylamino | 777.6 |
| 3002 | cyclopentyl | —O— | —O— | 3,3-dimethylbutanoylamino | 833.6 |
| 3003 | cyclopentyl | —CH₂— | —O— | acetylamino | 775.4 |
| 3004 | cyclopentyl | —CH₂— | —O— | isopropylamino | 775.4 |
| 3005 | cyclopentyl | —CH₂— | —O— | cyclopentylamino | 801.4 |
| 3006 | cyclopentyl | —CH₂— | —O— | methylamino | 747.3 |
| 3007 | cyclopentyl | —CH₂— | —O— | NH₂ | 733.3 |

TABLE 3-continued
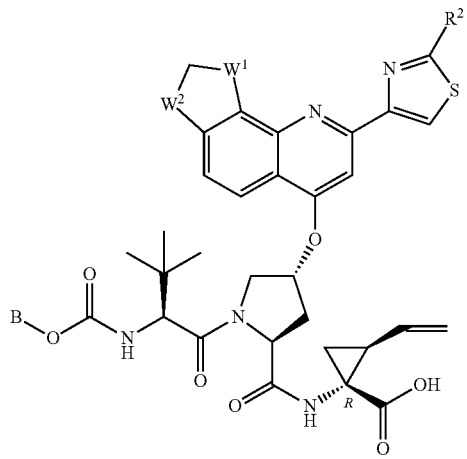
| Cpd. # | B | W¹ | W² | R² | m/z (M + H)⁺ (MH + 2)⁺ |
|---|---|---|---|---|---|
| 3008 | cyclopentyl | —CH₂— | —O— | NHC(O)CH₂C(CH₃)₃ | 831.5 |
| 3009 | cyclopentyl | —CH₂— | —O— | NHEt | 761.5 |
| 3010 | cyclopentyl | —CH₂— | —O— | NHC(O)CH₂-cyclopentyl | 843.3 |
| 3011 | cyclopentyl | —CH₂— | —CH₂— | NHC(O)CH(CH₃)₂ | 801.5 |
| 3012 | cyclopentyl | —CH₂— | —CH₂— | NHMe | 745.4 |
| 3013 | cyclopentyl | —CH₂— | —CH₂— | NHC(O)CH₃ | 773.4 |

TABLE 4
| Cpd. # | B | L⁰ | L² | R² | m/z (M + H)⁺ (MH + 2)⁺ |
|---|---|---|---|---|---|
| 4001 | 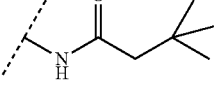 | MeO— | Me— |  | 833.5 |
| 4002 | 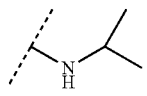 | MeO— | Me— |  | 777.5 |
| 4003 | 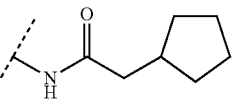 | MeO— | Me— |  | 845.5 |
| 4004 | 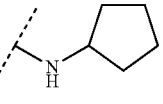 | MeO— | Me— |  | 803.5 |
| 4005 | 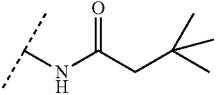 | Me₂N— | Me— |  | 846.5 |
| 4006 | 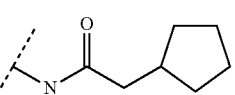 | Me₂N— | Me— |  | 858.5 |
| 4007 | 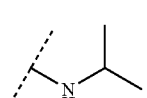 | Me₂N— | Me— |  | 790.5 |
| 4008 | 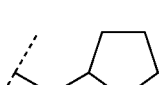 | Me₂N— | Me— | | 816.5 |

TABLE 4-continued
| Cpd. # | B | L⁰ | L² | R² | m/z (M + H)⁺ (MH + 2)⁺ |
|---|---|---|---|---|---|
| 4009 | cyclopentyl | MeO— | Me— | NHAc | 777.4 |
| 4010 | cyclopentyl | MeO— | Me— | NHMe | 749.4 |
| 4011 | cyclopentyl | MeO— | Me— | NHEt | 763.4 |
| 4012 | cyclopentyl | MeO— | MeO— | NHAc | 793.3 |
| 4013 | cyclopentyl | MeO— | MeO— | NHC(O)CH₂-cyclopentyl | 861.4 |
| 4014 | cyclopentyl | MeO— | MeO— | NHiPr | 793.4 |
| 4015 | cyclopentyl | MeO— | MeO— | NHC(O)CH₂C(CH₃)₃ | 849.4 |
| 4016 | cyclopentyl | Me— | MeO— | NHAc | 777.4 |

TABLE 4-continued
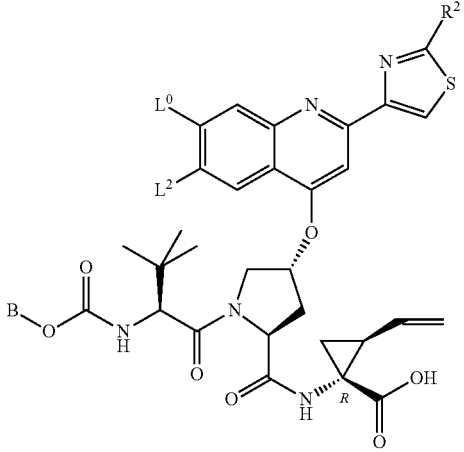
| Cpd. # | B | L⁰ | L² | R² | m/z (M + H)⁺ (MH + 2)⁺ |
|---|---|---|---|---|---|
| 4017 | cyclopentyl | Me— | MeO— | isopropylamino | 777.5 |
TABLE 5
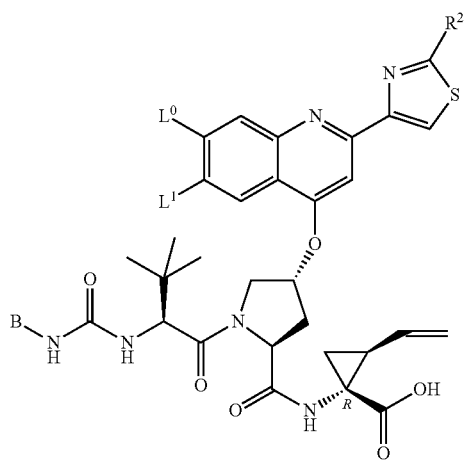
| Cpd. # | B | L⁰ | L² | R² | m/z (M + H)⁺ (MH + 2)⁺ |
|---|---|---|---|---|---|
| 5001 | cyclopentyl | MeO— | Me— | methylamino | 748.4 |
| 5002 | cyclopentyl | MeO— | Me— | acetamido | 776 |

TABLE 5-continued
| Cpd. # | B | L⁰ | L² | R² | m/z (M + H)⁺ (MH + 2)⁺ |
|---|---|---|---|---|---|
| 5003 | 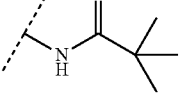 | MeO— | Me— |  | 832.5 |
| 5004 | 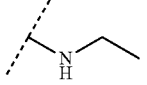 | MeO— | Me— |  | 762 |
| 5005 | 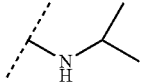 | MeO— | Me— |  | 776.5 |
| 5006 | 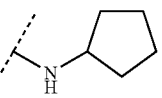 | MeO— | Me— |  | 802.5 |
| 5007 | 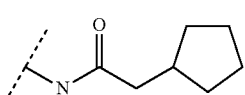 | MeO— | Me— | | 844.5 |

TABLE 6
| Cpd. # | B | L² | L⁰ | L¹ | R² | m/z (M + H)⁺ (MH + 2)⁺ |
|---|---|---|---|---|---|---|
| 6001 | 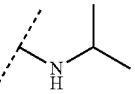 | MeO— | H | Me |  | 777.3 |
| 6002 | 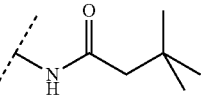 | MeO— | H | Me |  | 833.4 |
| 6003 | 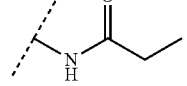 | MeO— | H | Me |  | 791.3 |
| 6004 | 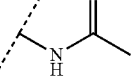 | MeO— | H | Me |  | 777.2 |
| 6005 | 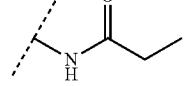 | Me | H | Br |  | 839.2 841.2 |
| 6006 | 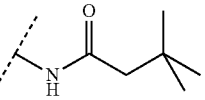 | Me | H | Br |  | 881.2 883.2 |
| 6007 | 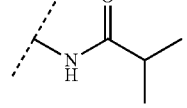 | Me | H | Br | | 853.2 855.2 |

TABLE 6-continued
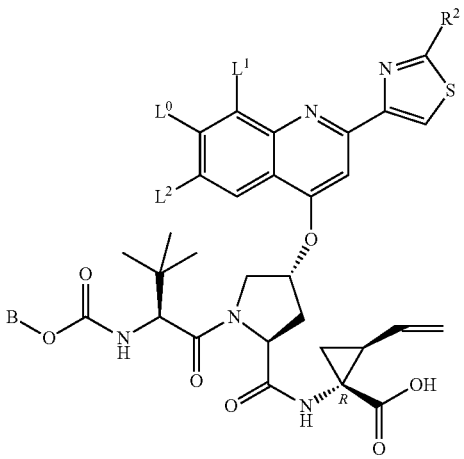
| Cpd. # | B | L² | L⁰ | L¹ | R² | m/z (M + H)⁺ (MH + 2)⁺ |
|---|---|---|---|---|---|---|
| 6008 | cyclopentyl | Me | H | Br | -NHC(O)O-iPr | 869.2 / 871.2 |
| 6009 | cyclopentyl | Me | H | Br | -NHC(O)CH₂-cyclopentyl | 893.2 / 895.2 |
| 6010 | cyclopentyl | Me | H | Br | -NHC(O)CH₂CH₂CH₃ | 853.2 / 855.2 |
| 6011 | cyclopentyl | Me | H | Me | -NHC(O)CH₂CH₃ | 775.3 |
| 6012 | cyclopentyl | Me | H | Me | -NHC(O)CH₂C(CH₃)₃ | 817.3 |
| 6013 | cyclopentyl | Me | H | Me | -NHC(O)CH₃ | 761.3 |
| 6014 | cyclopentyl | Me | H | Me | -NHCH(CH₃)₂ | 761.4 |

TABLE 6-continued
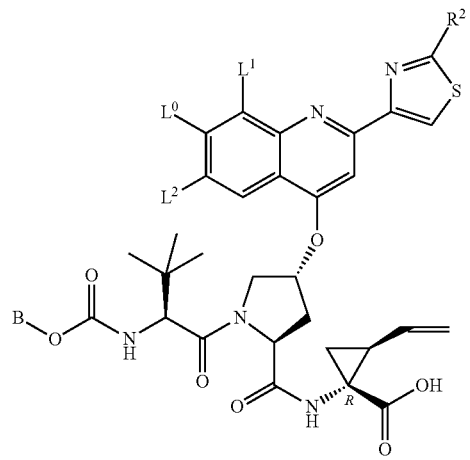
| Cpd. # | B | L² | L⁰ | L¹ | R² | m/z (M + H)⁺ (MH + 2)⁺ |
|---|---|---|---|---|---|---|
| 6015 | cyclopentyl | Me | MeO— | Me | -NHC(O)CH₂-cyclopentyl | 859.5 |
| 6016 | cyclopentyl | Me | MeO— | Me | -NHC(O)CH₂C(CH₃)₃ | 847.5 |
| 6017 | cyclopentyl | Br | H | Br | -NHC(O)CH₂CH₃ | 905.2 |
| 6018 | cyclopentyl | Br | H | Br | -NHC(O)CH(CH₃)₂ | 919.2 |
| 6019 | cyclopentyl | Br | H | Cl | -NHC(O)CH₂CH₃ | 861.2 |
| 6020 | cyclopentyl | Br | H | Cl | -NHC(O)CH(CH₃)₂ | 875.2 |

TABLE 7

| Cpd. # | B | R^Q | R^S | m/z (M + H)+ (MH + 2)+ |
|---|---|---|---|---|
| 7001 | cyclopentylmethyl | 2-(2-(isopropylamino)thiazol-4-yl)-8,9-dihydrofuro[2,3-h]quinolin-4-yl | cyclopropylmethyl | 878.8 |
| 7002 | 1-cyclopentyl-1-methylethyl | 2-(2-(3,3-dimethylbutanamido)thiazol-4-yl)-7-methoxy-6,8-dimethylquinolin-4-yl | cyclopropylmethyl | 950.4 |
| 7003 | (tetrahydrofuran-3-yl)methyl | 2-(2-(isopropylamino)thiazol-4-yl)-7-methoxy-8-methylquinolin-4-yl | 2-(dimethylamino)ethyl | 885.4 |

What is claimed is:

1. A racemate, diastereoisomer, or optical isomer of a compound of formula (I):

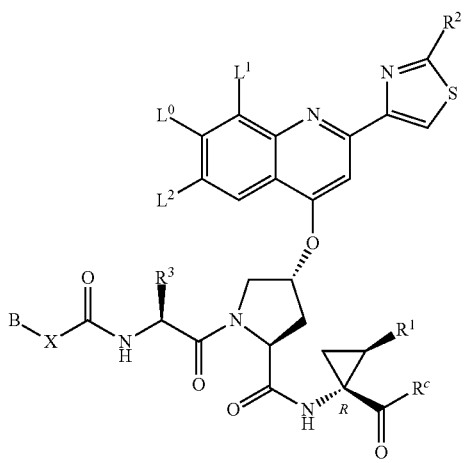

wherein:
B is $(C_{2-8})$alkyl, $(C_{3-7})$cycloalkyl or $(C_{1-3})$alkyl-$(C_{3-7})$cycloalkyl,
   a) wherein said alkyl, cycloalkyl, and alkyl-cycloalkyl may be mono-, di- or tri-substituted with $(C_{1-3})$alkyl; and
   b) wherein said alkyl, cycloalkyl, and alkyl-cycloalkyl may be mono- or di-substituted with substituents selected from hydroxy and O—$(C_{1-4})$alkyl; and
   c) wherein each of said alkyl groups may be mono-, di- or tri-substituted with fluorine or mono-substituted with chlorine or bromine; and
   d) wherein in each of said cycloalkyl groups being 5-, 6- or 7-membered, one or two —$CH_2$-groups not being directly linked to each other may be replaced by —O— such that the O-atom is linked to the group X via at least two C-atoms;

X is O or NH;

$R^3$ is $(C_{2-6})$alkyl or $(C_{3-7})$cycloalkyl, both of which being optionally substituted with 1 to 3 substituents selected from $(C_{1-4})$alkyl;

$L^0$ is —OH, —$OCH_3$, halogen or —$N(CH_3)_2$;

$L^1$ and $L^2$ are each independently selected from: halogen, —$CH_3$, —$C_2H_5$, —$OCH_3$, —$OC_2H_5$, —$OC_3H_7$, —$OCH(CH_3)_2$, $CF_3$, —SMe, —SOMe, and $SO_2Me$, whereby either $L^1$ or $L^2$ may be H;

$R^2$ is $R^{20}$, —$NHCOR^{20}$, —$NHCOOR^{20}$, —$NHR^{21}$ and —$NHCONR^{21}R^{23}$,
   wherein
   $R^{20}$ is selected from $(C_{1-8})$alkyl, $(C_{3-7})$cycloalkyl, $(C_{1-3})$alkyl-$(C_{3-7})$cycloalkyl, wherein said cycloalkyl and alkyl-cycloalkyl may be mono-, di- or tri-substituted with $(C_{1-3})$alkyl; and
   $R^{21}$ is H or $R^{20}$ as defined above; and
   $R^{23}$ is H or methyl;

$R^1$ is ethyl or vinyl; and $R^C$ is hydroxy;

or a pharmaceutically acceptable salt or ester thereof.

2. The compound according to claim 1 wherein

B is selected from: ethyl, n-propyl, tert-butyl, 2-methyl-propyl, 1,2-dimethylpropyl, 1,2,2-trimethylpropyl, 2-fluoroethyl, 3-fluoropropyl, 3,3,3-trifluoropropyl, cyclopropyl, cyclobutyl, cyclopentyl, cyclohexyl, 1-methylcyclopentyl and 1-methylcyclohexyl, and a group selected from:

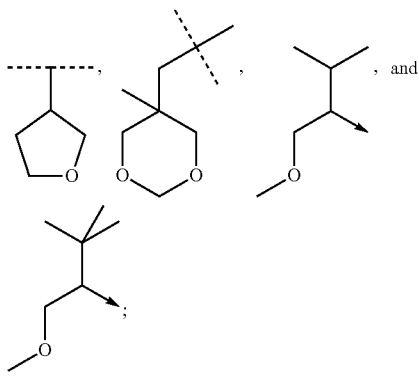

$R^3$ is selected from 1,1-dimethylethyl, cyclopentyl, cyclohexyl and 1-methylcyclohexyl; $L^0$ is —OH or —OCH$_3$; $L^1$ is CH$_3$, —F, —Cl, —Br, —OMe, —SMe, or —SO$_2$Me; $L^2$ is H;

$R^2$ is —NHCOR$^{20}$, —NHCOOR$^{20}$ or —NHR$^{21}$, wherein $R^{20}$ and $R^{21}$ are independently selected from methyl, ethyl, n-propyl, i-propyl, 2,2-dimethylpropyl, cyclopentyl and cyclopentylmethyl;

$R^1$ is vinyl; and $R^C$ is hydroxy;

or a pharmaceutically acceptable salt or ester thereof.

3. The compound according to claim 2 wherein B is selected from ethyl, n-propyl, tert-butyl, cyclopentyl, 1-methylcyclopentyl, 2-fluoroethyl and 3-fluoropropyl; $R^3$ is selected from 1,1-dimethylethyl and cyclohexyl; $L^0$ is —OCH$_3$; $L^1$ is —CH$_3$, —Cl, or —Br; $L^2$ is H; and $R^C$ is hydroxy;

or a pharmaceutically acceptable salt or ester thereof.

4. The compound according to claim 1 of the formula

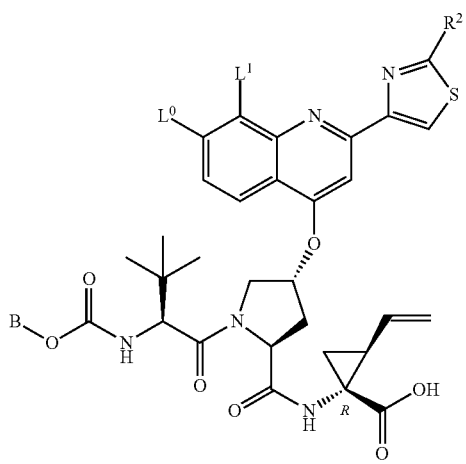

wherein B, $L^0$, $L^1$ and $R^2$ are defined as in the table below

| Cpd. | B | $L^0$ | $L^1$ | $R^2$ |
|---|---|---|---|---|
| 1001 | tert-butyl | MeO— | MeO— | —NHC(O)CH₂C(CH₃)₃ |
| 1002 | cyclobutyl | MeO— | MeO— | —NHC(O)CH₂C(CH₃)₃ |
| 1003 | cyclopentyl | MeO— | MeO— | —NHC(O)CH₂C(CH₃)₃ |
| 1004 | cyclohexyl | MeO— | MeO— | —NHC(O)CH₂C(CH₃)₃ |

-continued

| Cpd. | B | L⁰ | L¹ | R² |
|---|---|---|---|---|
| 1005 | cyclobutyl | MeO— | Me— | -NHC(O)CH₂-cyclopentyl |
| 1006 | cyclobutyl | MeO— | Me— | -NHC(O)CH₂C(CH₃)₃ |
| 1007 | cyclopentyl | MeO— | Me— | -NHC(O)CH₂C(CH₃)₃ |
| 1008 | cyclopentyl | MeO— | Me— | -NHC(O)CH₂-cyclopentyl |
| 1009 | cyclopentyl | Me₂N— | Me— | -NHC(O)CH₂C(CH₃)₃ |
| 1010 | cyclopentyl | Me₂N— | Me— | -NHC(O)CH₂-cyclopentyl |
| 1011 | cyclopentyl | Me₂N— | Me— | -NH-iPr |
| 1012 | cyclopentyl | Me₂N— | Me— | -NH-cyclopentyl |
| 1013 | cyclopentyl | MeO— | Me— | -NH-iPr |

-continued
| Cpd. | B | L⁰ | L¹ | R² |
|---|---|---|---|---|
| 1014 | 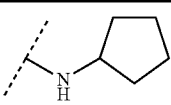 | MeO— | Me— | 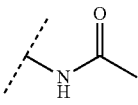 |
| 1015 | 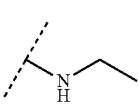 | MeO— | Me— | 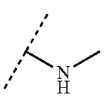 |
| 1016 | 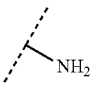 | MeO— | Me— | 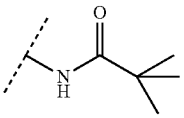 |
| 1017 | 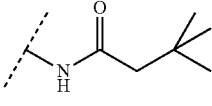 | MeO— | Me— | 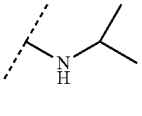 |
| 1018 | 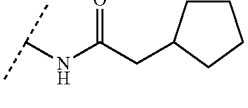 | MeO— | Me— | |
| 1019 | | MeO— | Me— | |
| 1020 | | MeO— | Et— | |
| 1021 | | MeO— | Et— | |
| 1022 | | MeO— | Et— | |

-continued

| Cpd. | B | L⁰ | L¹ | R² |
|---|---|---|---|---|
| 1023 | cyclopentyl | MeO— | Et— | —NHC(O)CH₃ |
| 1024 | —CH₂CH₂CH₂F | MeO— | Me— | —NHC(O)CH₂C(CH₃)₃ |
| 1025 | —CH₂CH₂CH₂F | MeO— | Me— | —NHCH(CH₃)₂ |
| 1026 | tetrahydrofuran-3-yl | MeO— | Me— | —NHC(O)CH₂C(CH₃)₃ |
| 1027 | tetrahydrofuran-3-yl | MeO— | Me— | —NHCH(CH₃)₂ |
| 1028 | cyclopentyl | MeO— | Br— | —NHC(O)CH₃ |
| 1029 | cyclopentyl | MeO— | Br— | —NHC(O)CH₂-cyclopentyl |
| 1030 | cyclopentyl | MeO— | Br— | —NHCH(CH₃)₂ |
| 1031 | cyclopentyl | MeO— | Br— | —NHC(O)CH₂C(CH₃)₃ |

| Cpd. | B | L⁰ | L¹ | R² |
|---|---|---|---|---|
| 1034 | 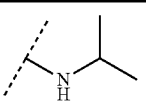 | HO— | Me— | 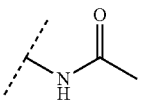 |
| 1035 | 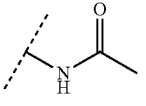 | HO— | Me— | 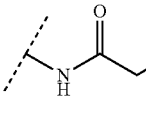 |
| 1036 | 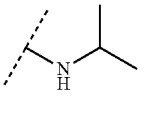 | MeO— | Me— | 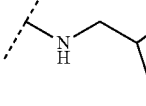 |
| 1037 | 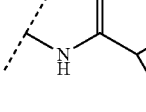 | MeO— | Me— | 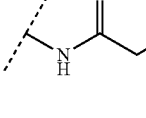 |
| 1038 | 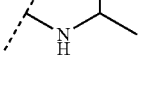 | MeO— | Me— | |
| 1039 | | MeO— | Me— | |
| 1040 | | MeO— | Me— | |
| 1041 | | MeO— | Me— | |
| 1042 | | MeO— | Cl | |

-continued

| Cpd. | B | L⁰ | L¹ | R² |
|---|---|---|---|---|
| 1043 | cyclopentyl | MeO— | Br | -NH-C(O)-CH₂CH₃ (propionamide) |
| 1044 | cyclopentyl | MeO— | Cl | -NH-C(O)-CH₂CH₃ (propionamide) |
| 1045 | cyclopentyl | MeO— | Cl | -NH-C(O)-CH₂-cyclopentyl |
| 1046 | cyclopentyl | MeO— | Me— | -NH-C(O)-O-CH(CH₃)₂ (isopropyl carbamate) |
| 1047 | cyclopentyl | MeO— | Me— | -NH-C(O)-O-CH₃ (methyl carbamate) |
| 1048 | cyclopentyl | MeO— | Cl | -NH-C(O)-CH₂CH₂CH₃ (butyramide) |
| 1049 | cyclopentyl | MeO— | Br | -NH-C(O)-O-CH(CH₃)₂ (isopropyl carbamate) |
| 1050 | cyclopentyl | MeO— | Cl | -NH-C(O)-O-CH(CH₃)₂ (isopropyl carbamate) |
| 1051 | cyclopentyl | MeO— | F | -NH-C(O)-CH₂CH₃ (propionamide) |

-continued

| Cpd. | B | L⁰ | L¹ | R² |
|---|---|---|---|---|
| 1052 | cyclopentyl-CH< | MeO— | F | —NH-iPr |
| 1053 | cyclopentyl-CH< | MeO— | Cl | —NH-C(O)-OMe |
| 1054 | cyclopentyl-CH< | MeO— | Br | —NH-C(O)-OMe |
| 1055 | cyclopentyl-CH< | MeO— | Br | —NH-C(O)-iPr |
| 1056 | cyclopentyl-CH< | MeO— | Br | —NH-C(O)-CH₂CH₂CH₃ |
| 1057 | cyclopentyl-CH< | HO | Me | —NH-C(O)-CH₂-C(CH₃)₃ |
| 1058 | cyclopentyl-CH< | HO | Me | —NH-C(O)-CH₂-cyclopentyl |
| 1063 | cyclopentyl-CH< | F | Me | —NH-C(O)-CH₂-C(CH₃)₃ |
| 1064 | CH₃CH(—)CH₂CH₂CF₃ | MeO— | Br | —NH-C(O)-CH₂CH₃ |

-continued

| Cpd. | B | L⁰ | L¹ | R² |
|---|---|---|---|---|
| 1065 | cyclopentyl(methyl) | MeO— | Br | NHC(O)Et |
| 1066 | ethyl | MeO— | Br | NHC(O)Et |
| 1067 | isobutyl | MeO— | Br | NHC(O)Et |
| 1068 | (1,3-dioxan-5-yl)methyl | MeO— | Br | NHC(O)CH₂-cyclopentyl |
| 1069 | CF₃(CH₂)₂ | MeO— | Br | NHC(O)CH₂-cyclopentyl |
| 1070 | ethyl | MeO— | Br | NHC(O)CH₂-cyclopentyl |
| 1071 | isobutyl | MeO— | Br | NHC(O)CH₂-cyclopentyl |
| 1072 | (1,3-dioxan-5-yl)methyl | MeO— | Br | NHC(O)OiPr |
| 1073 | CF₃(CH₂)₂ | MeO— | Br | NHC(O)OiPr |
| 1074 | cyclopentyl(methyl) | MeO— | Br | NHC(O)OiPr |
| 1075 | ethyl | MeO— | Br | NHC(O)OiPr |

-continued

| Cpd. | B | L⁰ | L¹ | R² |
|---|---|---|---|---|
| 1076 | isobutyl group | MeO— | Br | -NH-C(O)-O-iPr (isopropyl carbamate) |
| 1077 | 1,3-dioxane with methyl and propyl linker | MeO— | Br | -NH-iPr |
| 1078 | 1-methylcyclopentyl | MeO— | Br | -NH-iPr |
| 1079 | ethyl | MeO— | Br | -NH-iPr |
| 1080 | isobutyl | MeO | Br | -NH-iPr |
| 1081 | 1,3-dioxane with methyl and propyl linker | MeO | Br | -NH-C(O)-Et |
| 1099 | CF₃-propyl | MeO— | Br | -NH-iPr |
| 1100 | cyclopentylmethyl | MeO— | Cl | -NH-C(O)-iPr |
| 1106 | tetrahydrofuran-3-yl | Br | MeO— | -NH-iPr |
| 1108 | F-propyl | MeO— | Br | -NH-iPr |
| 1109 | F-butyl | MeO | Br | -NH-iPr |

-continued

| Cpd. | B | L⁰ | L¹ | R² |
|---|---|---|---|---|
| 1110 | (S)-tetrahydrofuran-3-yl | MeO— | Br | -NH-iPr |
| 1111 | n-propyl | MeO— | Br | -NH-iPr |
| 1112 | 3-methylbutan-2-yl | MeO— | Br | -NH-iPr |
| 1113 | 3-fluoropropyl | MeO— | Br | -NHC(O)Et |
| 1114 | 4-fluorobutyl | MeO | Br | -NHC(O)Et |
| 1115 | (S)-tetrahydrofuran-3-yl | MeO— | Br | -NHC(O)Et |
| 1116 | n-propyl | MeO | Br | -NHC(O)Et |
| 1117 | 3-methylbutan-2-yl | MeO | Br | -NHC(O)Et |
| 1118 | 3-fluoropropyl | MeO | Br | -NHC(O)O-iPr |
| 1119 | 4-fluorobutyl | MeO | Br | -NHC(O)O-iPr |
| 1120 | tetrahydrofuran-3-yl | MeO | Br | -NHC(O)O-iPr |
| 1121 | n-propyl | MeO | Br | -NHC(O)O-iPr |
| 1122 | 3-methylbutan-2-yl | MeO | Br | -NHC(O)O-iPr |

-continued
| Cpd. | B | L⁰ | L¹ | R² |
|---|---|---|---|---|
| 1125 | 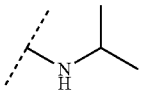 | MeO— | Cl | 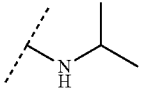 |
| 1126 | 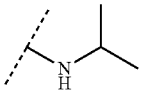 | MeO— | Cl | 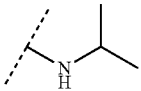 |
| 1127 | 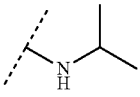 | MeO | Cl | 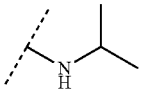 |
| 1128 | 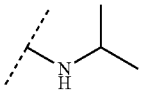 | MeO | Cl | 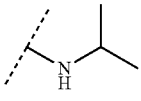 |
| 1129 | 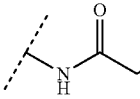 | MeO | Cl | 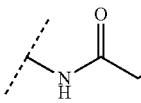 |
| 1130 | 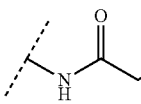 | MeO | Cl | 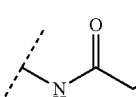 |
| 1131 | F─\─\─/ | MeO | Cl | ─\N(H)─/ |
| 1132 | ─\─/ (isopropyl branched) | MeO | Cl | ─\N(H)─/ |
| 1133 | F─\─\─/ | MeO | Cl | ─\NH─C(=O)─Et |
| 1134 | CF₃─\─\─/ | MeO | Cl | ─\NH─C(=O)─Et |
| 1135 | ─\─/ | MeO | Cl | ─\NH─C(=O)─Et |
| 1136 | ─\─\─/ | MeO | Cl | ─\NH─C(=O)─Et |

-continued
| Cpd. | B | L⁰ | L¹ | R² |
|---|---|---|---|---|
| 1137 | 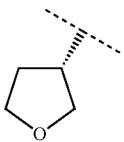 | MeO | Cl | 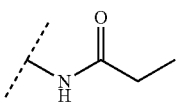 |
| 1138 | 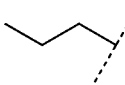 | MeO | Cl | 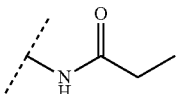 |
| 1139 | 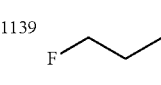 | MeO | Cl | 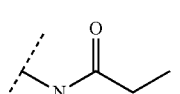 |
| 1140 | 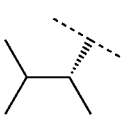 | MeO | Cl | 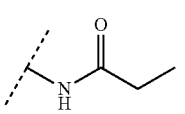 |
| 1141 | 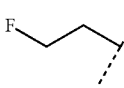 | MeO | Cl | 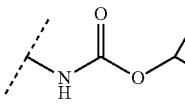 |
| 1142 | 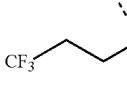 | MeO | Cl | 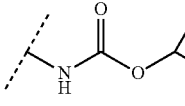 |
| 1143 |  | MeO | Cl | 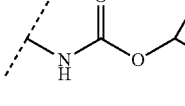 |
| 1144 | 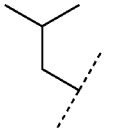 | MeO | Cl | 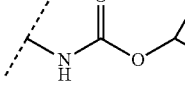 |
| 1145 | 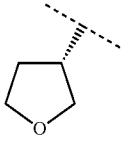 | MeO | Cl | 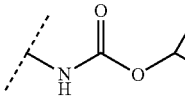 |
| 1146 | 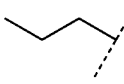 | MeO | Cl | 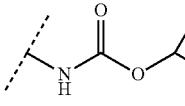 |
| 1147 | 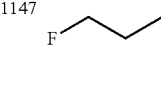 | MeO | Cl | 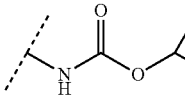 |
| 1148 | 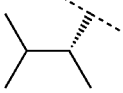 | MeO | Cl | 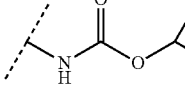 |

-continued
| Cpd. | B | L⁰ | L¹ | R² |
|---|---|---|---|---|
| 1149 |  | MeO | Cl |  |
| 1150 |  | MeO | Cl |  |
| 1151 |  | MeO | Cl |  |
| 1152 |  | MeO | Cl |  |
| 1153 |  | MeO | Cl |  |
| 1154 |  | MeO | Br |  |
| 1155 |  | MeO | Br |  |
| 1156 |  | MeO | Br |  |
| 1167 |  | Cl | Cl |  |
| 1168 |  | Cl | Cl |  |
| 1169 |  | Cl | Cl |  |

-continued
| Cpd. | B | L⁰ | L¹ | R² |
|---|---|---|---|---|
| 1170 | 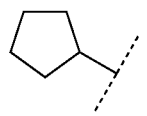 | Cl | Cl | 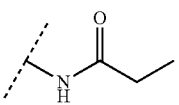 |
or a pharmaceutically acceptable salt or ester thereof.
5. The compound according to claim 1 of the formula
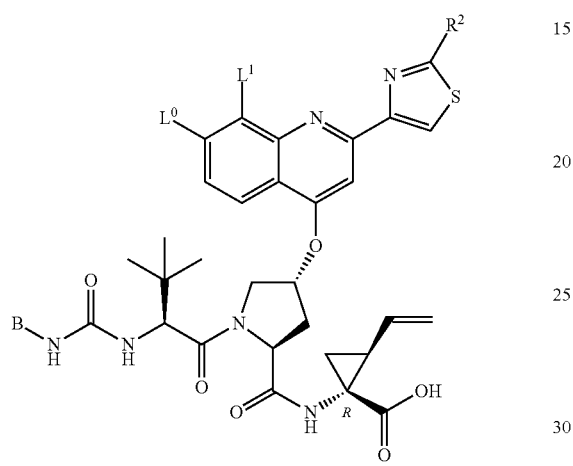
wherein B, L⁰, L¹ and R² are defined as in the table below
| Cpd. # | B | L⁰ | L¹ | R² |
|---|---|---|---|---|
| 2001 | 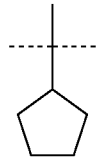 | MeO— | Me— | 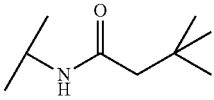 |
| 2002 | 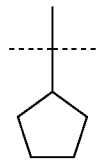 | MeO— | Me— | 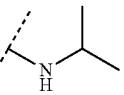 |
| 2003 | 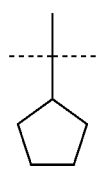 | MeO— | Me— | 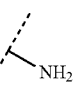 |
| 2004 | 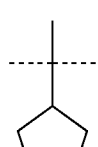 | MeO— | Me— |  |

-continued

| Cpd. # | B | L⁰ | L¹ | R² |
|---|---|---|---|---|
| 2005 | cyclopentyl | MeO— | Me— | -NH-ethyl |
| 2006 | cyclopentyl | MeO— | Me— | -NH-cyclopentyl |
| 2007 | cyclopentyl | MeO— | Me— | -NH-C(=O)-CH₃ |
| 2008 | cyclopentyl | MeO— | Me— | -NH-C(=O)-CH₂-cyclopentyl |
| 2009 | cyclopentyl | MeO— | Me— | -CH(CH₃)- |
| 2010 | cyclopentyl | MeO— | Me— | -CH(Et)- |
| 2011 | cyclopentyl | MeO— | Me— | -CH(iPr)- |
| 2012 | cyclopentyl | MeO— | Me— | -NH-C(=O)-CH₂-C(CH₃)₃ |

-continued

| Cpd. # | B | L⁰ | L¹ | R² |
|---|---|---|---|---|
| 2013 | (tert-butyl, dashed bond) | MeO— | Me— | (NHC(O)CH₃) |
| 2014 | (tert-butyl, dashed bond) | MeO— | Me— | (NHC(O)CH₂-cyclopentyl) |
| 2015 | (1-methylcyclopentyl, dashed bond) | MeO— | Me— | (NHC(O)CH₃) |
| 2016 | (1-methylcyclopentyl, dashed bond) | MeO— | Me— | (NHC(O)CH₂-cyclopentyl) |
| 2017 | (cyclopentylmethyl) | MeO— | Br— | (NHC(O)CH₂CH₃) |
| 2018 | (branched alkyl with stereochem) | MeO— | Me— | (NHC(O)CH₃) |
| 2019 | (MeOCH₂-CH(iPr)-) | MeO— | Me | (NHC(O)CH₂-cyclopentyl) |
| 2020 | (MeOCH₂-C(tBu)(Me)-) | MeO— | Me | (NHC(O)CH₂-cyclopentyl); | or a pharmaceutically acceptable salt or ester thereof.

6. The compound according to claim 1 of the formula

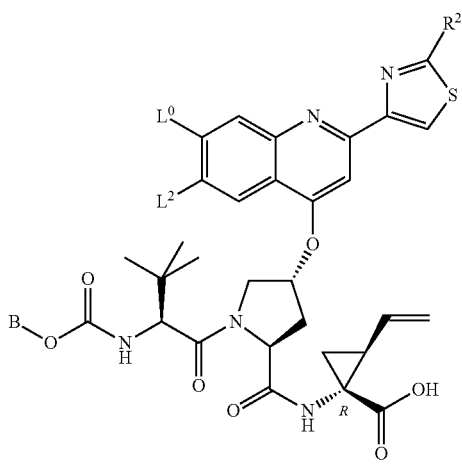

wherein B, L⁰, L² and R² are defined as in the table below

| Cpd. # | B | L⁰ | L¹ | R² |
|---|---|---|---|---|
| 4001 | cyclopentyl | MeO— | Me— | —NH—C(O)—CH₂—C(CH₃)₃ |
| 4002 | cyclopentyl | MeO— | Me— | —NH—CH(CH₃)₂ |
| 4003 | cyclopentyl | MeO— | Me— | —NH—C(O)—CH₂—cyclopentyl |
| 4004 | cyclopentyl | MeO— | Me— | —NH—cyclopentyl |
| 4005 | cyclopentyl | Me₂N— | Me— | —NH—C(O)—CH₂—C(CH₃)₃ |
| 4006 | cyclopentyl | Me₂N— | Me— | —NH—C(O)—CH₂—cyclopentyl |
| 4007 | cyclopentyl | Me₂N— | Me— | —NH—CH(CH₃)₂ |
| 4008 | cyclopentyl | Me₂N— | Me— | —NH—cyclopentyl |
| 4009 | cyclopentyl | MeO— | Me— | —NH—C(O)—CH₃ |
| 4010 | cyclopentyl | MeO— | Me— | —NH—CH₃ |
| 4011 | cyclopentyl | MeO— | Me— | —NH—CH₂CH₃ |
| 4012 | cyclopentyl | MeO— | MeO— | —NH—C(O)—CH₃ |
| 4013 | cyclopentyl | MeO— | MeO— | —NH—C(O)—CH₂—cyclopentyl |
| 4014 | cyclopentyl | MeO— | MeO— | —NH—CH(CH₃)₂ |
| 4015 | cyclopentyl | MeO— | MeO— | —NH—C(O)—CH₂—C(CH₃)₃ | or a pharmaceutically acceptable salt or ester thereof.

7. The compound according to claim 1 of the formula

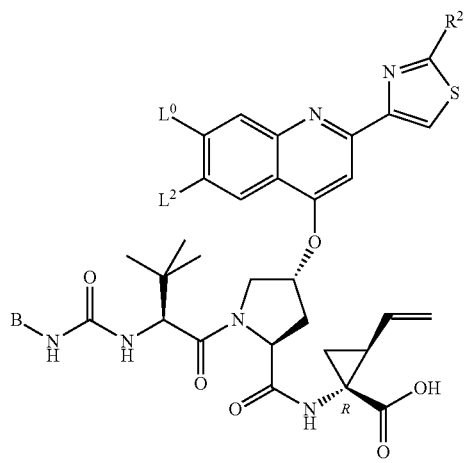

wherein B, $L^0$, $L^2$ and $R^2$ are defined as in the table below

| Cpd. # | B | $L^0$ | $L^1$ | $R^2$ |
|---|---|---|---|---|
| 5001 | cyclopentylmethyl | MeO— | Me— | —NHMe |
| 5002 | cyclopentylmethyl | MeO— | Me— | —NHC(O)Me |
| 5003 | cyclopentylmethyl | MeO— | Me— | —NHC(O)CH₂C(Me)₃ |
| 5004 | cyclopentylmethyl | MeO— | Me— | —NHEt |
| 5005 | cyclopentylmethyl | MeO— | Me— | —NHiPr |
| 5006 | cyclopentylmethyl | MeO— | Me— | —NH-cyclopentyl |
| 5007 | cyclopentylmethyl | MeO— | Me— | —NHC(O)CH₂-cyclopentyl | or a pharmaceutically acceptable salt or ester thereof.

8. The compound according to claim 1 of the formula wherein B, $L^0$, $L^1$, $L^2$ and $R^2$ are defined as in the table below

| Cpd. # | B | $L^2$ | $L^0$ | $L^1$ | $R^2$ |
|---|---|---|---|---|---|
| 6015 | cyclopentylmethyl | Me | MeO— | Me | —NHC(O)CH₂-cyclopentyl |
| 6016 | cyclopentylmethyl | Me | MeO— | Me | —NHC(O)CH₂C(Me)₃ | or a pharmaceutically acceptable salt or ester thereof.

9. A pharmaceutical composition comprising an anti-hepatitis C virally effective amount of a compound of formula I according to claim 1 or a pharmaceutically acceptable salt or ester thereof, in admixture with a pharmaceutically acceptable carrier medium or auxiliary agent.

10. The pharmaceutical composition according to claim 9 further comprising a therapeutically effective amount of at least one other antiviral agent.

11. The pharmaceutical composition according to claim 10, wherein said antiviral agent is ribavirin (1-β-D-ribofuranosyl-1H-1,2,4-triazole-3-carboxamide).

12. The pharmaceutical composition according to claim 10, wherein said antiviral agent is selected from α-interferon and pegylated α-interferon.

13. A method for the treatment of a hepatitis C viral infection in a mammal comprising administering to the mammal an anti-hepatitis C virally effective amount of a compound of formula I according to claim 1, or a pharmaceutically acceptable salt or ester thereof.

14. A method for the treatment of a hepatitis C viral infection in a mammal comprising administering thereto an anti-hepatitis C virally effective amount of a compound of formula I according to claim 1, or a pharmaceutically acceptable salt or ester thereof in combination with at least one other antiviral agent.

15. The method according to claim 14, wherein said antiviral agent is ribavirin (1-β-D-ribofuranosyl-1H-1,2,4-triazole-3-carboxamide).

16. The method according to claim 14, wherein said antiviral agent is selected from α-interferon and pegylated α-interferon.

17. The method according to claim 14, wherein said antiviral agent is selected from inhibitors of: helicase, NS2/3 protease and internal ribosome entry site (IRES).

18. An article of manufacture comprising packaging material contained within which is a composition effective to treat an HCV infection and the packaging material comprises a label which indicates that the composition can be used to treat infection by the hepatitis C virus, and wherein said composition comprises a compound of formula (I) according to claim 1 or a pharmaceutically acceptable salt or ester thereof, in admixture with a pharmaceutically acceptable carrier medium or auxiliary agent.

19. A compound of the following formula:

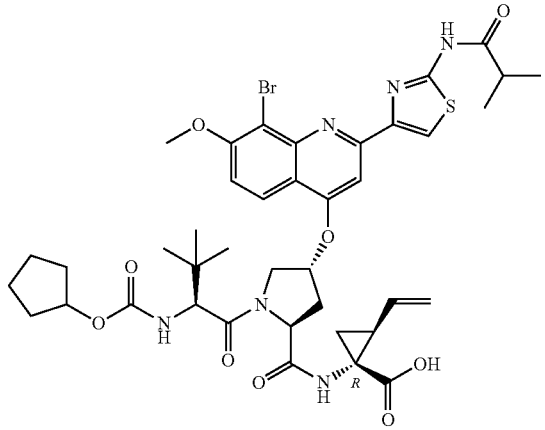

or a pharmaceutically acceptable salt or ester thereof.

20. A pharmaceutical composition comprising an anti-hepatitis C virally effective amount of a compound of the following formula:

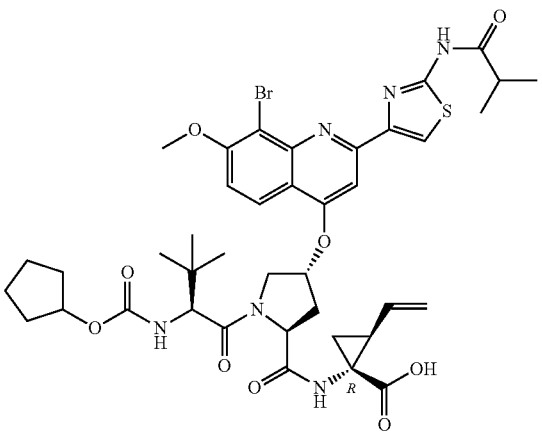

or a pharmaceutically acceptable salt or ester thereof, in admixture with a pharmaceutically acceptable carrier medium or auxiliary agent.

21. A method for the treatment of a hepatitis C viral infection in a mammal comprising administering to the mammal an anti-hepatitis C virally effective amount of a compound of the following formula:

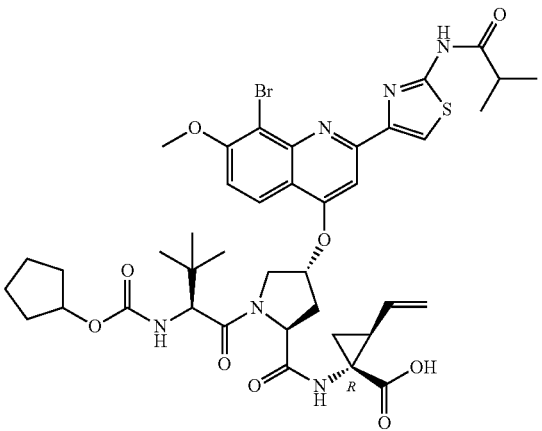

or a pharmaceutically acceptable salt or ester thereof.

* * * * *